(12) United States Patent
Naftalovitz et al.

(10) Patent No.: US 11,065,381 B2
(45) Date of Patent: Jul. 20, 2021

(54) INFUSION PUMP DEVICE AND METHOD FOR USE THEREOF

(71) Applicant: E3D AGRICULTURAL COOPERATIVE ASSOCIATION LTD., Merom Hagalil (IL)

(72) Inventors: Ziv Naftalovitz, D.N. West Galilee (IL); Ilan Shopen, Zefat (IL); Tsachi Shaked, Merom Hagalil (IL)

(73) Assignee: E3D A.C.A.L., Merom Hagalil (IL)

( * ) Notice: Subject to any disclaimer, the term of this patent is extended or adjusted under 35 U.S.C. 154(b) by 449 days.

(21) Appl. No.: 15/755,117

(22) PCT Filed: Oct. 5, 2016

(86) PCT No.: PCT/IL2016/051076
§ 371 (c)(1),
(2) Date: Feb. 26, 2018

(87) PCT Pub. No.: WO2017/060899
PCT Pub. Date: Apr. 13, 2017

(65) Prior Publication Data
US 2019/0015582 A1    Jan. 17, 2019

Related U.S. Application Data

(60) Provisional application No. 62/261,908, filed on Dec. 2, 2015, provisional application No. 62/237,008, filed on Oct. 5, 2015.

(51) Int. Cl.
*A61M 5/142* (2006.01)
*A61M 5/145* (2006.01)
(Continued)

(52) U.S. Cl.
CPC ...... *A61M 5/14248* (2013.01); *A61M 5/1452* (2013.01); *A61M 2005/1402* (2013.01);
(Continued)

(58) Field of Classification Search
CPC ............ A61M 5/14248; A61M 5/1452; A61M 2005/1402; A61M 2005/14252;
(Continued)

(56) References Cited

U.S. PATENT DOCUMENTS

| 6,362,591 B1 | 3/2002 | Moberg |
| 6,555,986 B2 | 4/2003 | Moberg |

(Continued)

FOREIGN PATENT DOCUMENTS

| EP | 921828 | 2/2003 |
| EP | 0999864 | 2/2004 |

(Continued)

*Primary Examiner* — Brandy S Lee
*Assistant Examiner* — Nidah M Hussain
(74) *Attorney, Agent, or Firm* — Sughrue Mion, PLLC

(57) ABSTRACT

A patch pump including a medicament reservoir having an inner surface defining an elongate piston engagement pathway, an electric motor having a rotary drive output element, a piston replaceably axially fixed to the electric motor. The piston having an outer surface arranged for sealing engagement with the inner surface of the medicament reservoir, the piston also including a rotary to longitudinal drive converter receiving a rotary drive input from the rotary drive output element of the electric motor and providing a longitudinal drive to the reservoir, thereby driving the medicament reservoir in longitudinal motion relative to the piston in which the elongate piston engagement pathway defined by the inner surface of the medicament reservoir is displaced axially and in sealing engagement with the outer surface of said piston.

14 Claims, 96 Drawing Sheets

(51) Int. Cl.
   *A61M 5/14* (2006.01)
   *A61M 5/158* (2006.01)
(52) U.S. Cl.
   CPC ............. *A61M 2005/14252* (2013.01); *A61M 2005/14268* (2013.01); *A61M 2005/1581* (2013.01); *A61M 2205/3306* (2013.01)
(58) Field of Classification Search
   CPC ........... A61M 2005/14268; A61M 2005/1581; A61M 2205/3306; A61M 5/00; A61M 5/142; A61M 5/14244; A61M 5/145; A61M 5/1456
   USPC ........................................................ 604/151
   See application file for complete search history.

(56) References Cited

U.S. PATENT DOCUMENTS

| | | | |
|---|---|---|---|
| 6,589,229 B1 | 7/2003 | Connelly | |
| 6,669,669 B2 | 12/2003 | Flaherty | |
| 6,740,059 B2 | 5/2004 | Flaherty | |
| 6,808,506 B2 | 10/2004 | Lastovich | |
| 6,854,620 B2 | 2/2005 | Ramey | |
| 6,878,132 B2 | 4/2005 | Kipfer | |
| 6,929,619 B2 | 8/2005 | Fago | |
| 6,997,906 B2 | 2/2006 | Langley | |
| 7,025,226 B2 | 4/2006 | Ramey | |
| 7,029,455 B2 | 4/2006 | Flaherty | |
| 7,137,964 B2 | 11/2006 | Flaherty | |
| 7,416,540 B2 | 8/2008 | Edwards | |
| 7,455,663 B2 | 11/2008 | Bikovsky | |
| 7,569,050 B2 | 8/2009 | Moberg | |
| 7,648,483 B2 | 1/2010 | Edwards | |
| 7,713,238 B2 | 5/2010 | Mernoe | |
| 7,766,873 B2 | 8/2010 | Moberg | |
| 7,789,857 B2 | 9/2010 | Moberg | |
| 7,789,859 B2 | 9/2010 | Estes | |
| 7,811,262 B2 | 10/2010 | Moberg | |
| 7,828,764 B2 | 11/2010 | Moberg | |
| 7,905,868 B2 | 3/2011 | Moberg | |
| 7,922,708 B2 | 4/2011 | Estes | |
| 7,927,306 B2 | 4/2011 | Cross | |
| 7,935,104 B2 | 5/2011 | Yodfat | |
| 7,935,105 B2 | 5/2011 | Miller | |
| 7,938,801 B2 | 5/2011 | Hawkins | |
| 7,955,305 B2 | 6/2011 | Moberg | |
| 7,963,954 B2 | 6/2011 | Kavazov | |
| 7,976,493 B2 | 7/2011 | Carter | |
| 7,976,500 B2 | 7/2011 | Adams | |
| 7,993,300 B2 | 8/2011 | Nyholm | |
| 7,998,111 B2 | 8/2011 | Moberg | |
| 8,002,752 B2 | 8/2011 | Yodfat | |
| 8,034,026 B2 | 10/2011 | Grant | |
| 8,062,253 B2 | 11/2011 | Nielsen | |
| 8,062,257 B2 | 11/2011 | Moberg | |
| 8,065,096 B2 | 11/2011 | Moberg | |
| 8,066,672 B2 | 11/2011 | Mandro | |
| 8,128,597 B2 | 3/2012 | Cross | |
| 8,162,923 B2 | 4/2012 | Adams | |
| 8,167,841 B2 | 5/2012 | Teisen-Simony | |
| 8,172,804 B2 | 5/2012 | Bikovsky | |
| 8,187,228 B2 | 5/2012 | Bikovsky | |
| 8,211,093 B2 | 7/2012 | Miller | |
| 8,223,028 B2 | 7/2012 | Mandro | |
| 8,226,615 B2 | 7/2012 | Bikovsky | |
| 8,231,577 B2 | 7/2012 | Carter | |
| 8,246,581 B2 | 8/2012 | Adams | |
| 8,267,892 B2 | 9/2012 | Spencer | |
| 8,267,893 B2 | 9/2012 | Moberg | |
| 8,267,921 B2 | 9/2012 | Yodfat | |
| 8,277,415 B2 | 10/2012 | Mounce | |
| 8,282,366 B2 | 10/2012 | Hilber | |
| 8,285,328 B2 | 10/2012 | Caffey | |
| 8,298,172 B2 | 10/2012 | Nielsen | |
| 8,303,574 B2 | 11/2012 | Gray | |
| 8,361,030 B2 | 1/2013 | Carter | |
| 8,382,701 B2 | 2/2013 | Nyholm | |
| 8,409,151 B2 | 4/2013 | Hawkins | |
| 8,483,980 B2 | 7/2013 | Moberg | |
| 8,486,018 B2 | 7/2013 | Kamen | |
| 8,491,570 B2 | 7/2013 | Kamen | |
| 8,500,692 B2 | 8/2013 | Yodfat | |
| 8,562,590 B2 | 10/2013 | Yodfat | |
| 8,597,270 B2 | 12/2013 | Kavazov | |
| 8,608,698 B2 | 12/2013 | Edward | |
| 8,617,110 B2 | 12/2013 | Moberg | |
| 8,632,499 B2 | 1/2014 | Grant | |
| 8,647,074 B2 | 2/2014 | Moberg | |
| 8,647,296 B2 | 2/2014 | Moberg | |
| 8,668,672 B2 | 3/2014 | Moberg | |
| 8,684,972 B2 | 4/2014 | Mandro | |
| 8,685,002 B2 | 4/2014 | Miller | |
| 8,696,633 B2 | 4/2014 | Estes | |
| 8,702,656 B2 | 4/2014 | Kamen | |
| 8,708,960 B2 | 4/2014 | Spencer | |
| 8,708,961 B2 | 4/2014 | Field | |
| 8,708,994 B2 | 4/2014 | Pettis | |
| 8,728,024 B2 | 5/2014 | Kamen | |
| 8,728,034 B2 | 5/2014 | Yodfat | |
| 8,773,257 B2 | 7/2014 | Yodfat | |
| 8,777,901 B2 | 7/2014 | Smith | |
| 8,784,364 B2 | 7/2014 | Kamen | |
| 8,827,962 B2 | 9/2014 | Giambattista | |
| 8,845,587 B2 | 9/2014 | Lanigan | |
| 8,852,152 B2 | 10/2014 | Tverskoy | |
| 8,881,774 B2 | 11/2014 | Lanier, Jr. | |
| 8,905,972 B2 | 12/2014 | Smith | |
| 8,905,995 B2 | 12/2014 | Mernoe | |
| 8,915,879 B2 | 12/2014 | Smith | |
| 8,961,467 B2 | 2/2015 | Lanigan | |
| 8,979,799 B1 | 3/2015 | Askarinya | |
| 9,011,371 B2 | 4/2015 | Moberg | |
| 9,033,922 B2 | 5/2015 | Kamen | |
| 9,039,679 B2 | 5/2015 | Yodfat | |
| 9,061,097 B2 | 6/2015 | Holt | |
| 2008/0051698 A1 | 2/2008 | Mounce | |
| 2008/0051709 A1* | 2/2008 | Mounce | A61M 5/1413 604/131 |
| 2010/0049128 A1 | 2/2010 | McKenzie | |
| 2010/0094261 A1 | 4/2010 | Bryant | |
| 2010/0241065 A1 | 9/2010 | Moberg | |
| 2011/0060280 A1 | 3/2011 | Caffey | |
| 2011/0137255 A1 | 6/2011 | Nielsen | |
| 2011/0144574 A1 | 6/2011 | Kamen | |
| 2011/0152770 A1 | 6/2011 | DiPerna | |
| 2011/0166512 A1* | 7/2011 | Both | A61M 5/14248 604/67 |
| 2011/0196337 A1* | 8/2011 | Brandt | A61M 5/1413 604/506 |
| 2011/0270188 A1* | 11/2011 | Caffey | A61M 5/14593 604/151 |
| 2012/0022499 A1 | 1/2012 | Anderson | |
| 2012/0078181 A1 | 3/2012 | Smith | |
| 2012/0078182 A1 | 3/2012 | Smith | |
| 2012/0078184 A1 | 3/2012 | Smith | |
| 2012/0078185 A1 | 3/2012 | Smith | |
| 2012/0078217 A1 | 3/2012 | Smith | |
| 2012/0078222 A1 | 3/2012 | Smith | |
| 2012/0116311 A1 | 5/2012 | Brueggemann | |
| 2012/0118138 A1 | 5/2012 | Navarro | |
| 2012/0209179 A1 | 8/2012 | Kamen | |
| 2012/0209185 A1 | 8/2012 | Kamen | |
| 2012/0209186 A1 | 8/2012 | Kamen | |
| 2012/0209188 A1 | 8/2012 | Gray | |
| 2012/0209204 A1 | 8/2012 | Gray | |
| 2013/0226093 A1 | 8/2013 | Grant | |
| 2013/0231608 A1 | 9/2013 | Kamen | |
| 2013/0249687 A1 | 9/2013 | Kamen | |
| 2013/0281974 A1 | 10/2013 | Kamen | |
| 2013/0289485 A1 | 10/2013 | Lanigan | |
| 2013/0300565 A1 | 11/2013 | Kamen | |
| 2013/0303991 A1 | 11/2013 | Kamen | |
| 2013/0319576 A1 | 12/2013 | Kavazov | |
| 2013/0319577 A1 | 12/2013 | Kavazov | |

(56) References Cited

U.S. PATENT DOCUMENTS

| | | |
|---|---|---|
| 2014/0048174 A1 | 2/2014 | Lanigan |
| 2014/0052055 A1 | 2/2014 | Yodfat |
| 2014/0088557 A1 | 3/2014 | Mernoe |
| 2014/0114282 A1 | 4/2014 | Gray |
| 2014/0142498 A1 | 5/2014 | Lanier, Jr. |
| 2014/0148784 A1 | 5/2014 | Anderson |
| 2014/0148785 A1 | 5/2014 | Moberg |
| 2014/0163469 A1 | 6/2014 | Mandro |
| 2014/0163521 A1 | 6/2014 | O'Connor |
| 2014/0221929 A1 | 8/2014 | Kamen |
| 2014/0228761 A1 | 8/2014 | Spencer |
| 2014/0257237 A1 | 9/2014 | Kamen |
| 2014/0296785 A1 | 10/2014 | Hutchinson |
| 2014/0343495 A1 | 11/2014 | Chiang |
| 2015/0005711 A1 | 1/2015 | Grant |
| 2015/0025457 A1 | 1/2015 | Moberg |
| 2015/0025463 A1 | 1/2015 | Tverskoy |
| 2015/0025503 A1 | 1/2015 | Searle |
| 2015/0051571 A1 | 2/2015 | Lanigan |
| 2015/0057615 A1 | 2/2015 | Mernoe |
| 2015/0073386 A1 | 3/2015 | Smith |
| 2015/0133855 A1 | 5/2015 | Smith |
| 2015/0265768 A1 | 9/2015 | Vazquez |
| 2019/0009019 A1* | 1/2019 | Shor .................. A61M 5/1723 |

FOREIGN PATENT DOCUMENTS

| | | |
|---|---|---|
| EP | 1335764 | 6/2007 |
| EP | 1221992 | 1/2008 |
| EP | 1971381 | 9/2008 |
| EP | 1853332 | 11/2008 |
| EP | 2029200 | 3/2009 |
| EP | 2099434 | 9/2009 |
| EP | 2198380 | 6/2010 |
| EP | 2206062 | 7/2010 |
| EP | 2289580 | 3/2011 |
| EP | 2326365 | 6/2011 |
| EP | 2343093 | 7/2011 |
| EP | 2349400 | 8/2011 |
| EP | 2349401 | 8/2011 |
| EP | 2349407 | 8/2011 |
| EP | 2370125 | 10/2011 |
| EP | 2370126 | 10/2011 |
| EP | 2379133 | 10/2011 |
| EP | 2391408 | 12/2011 |
| EP | 2473215 | 7/2012 |
| EP | 2488233 | 8/2012 |
| EP | 2407192 | 10/2012 |
| EP | 2506896 | 10/2012 |
| EP | 2560727 | 2/2013 |
| EP | 2283882 | 6/2013 |
| EP | 2324872 | 7/2013 |
| EP | 2618867 | 7/2013 |
| EP | 2453972 | 1/2014 |
| EP | 2258420 | 4/2014 |
| EP | 2719410 | 6/2014 |
| EP | 1461099 | 8/2014 |
| EP | 2268253 | 10/2014 |
| EP | 2785396 | 10/2014 |
| EP | 2793979 | 10/2014 |
| EP | 2822543 | 1/2015 |
| EP | 2385851 | 2/2015 |
| EP | 2453948 | 2/2015 |
| EP | 1349591 | 3/2016 |
| EP | 2285360 | 4/2016 |
| EP | 2519288 | 4/2016 |
| EP | 2179754 | 6/2016 |
| EP | 2699286 | 8/2016 |
| EP | 2532377 | 11/2016 |
| EP | 2695627 | 1/2017 |
| EP | 2384207 | 3/2017 |
| EP | 2101845 | 5/2017 |
| EP | 2185223 | 7/2017 |
| EP | 2224977 | 7/2017 |
| EP | 2300077 | 7/2017 |
| EP | 2061543 | 10/2017 |
| EP | 2865325 | 11/2017 |
| EP | 2821049 | 1/2018 |
| EP | 2044544 | 4/2018 |
| EP | 2125077 | 4/2018 |
| EP | 2271384 | 4/2018 |
| JP | 2013099579 | 5/2013 |
| JP | 2014000432 | 1/2014 |
| WO | 2006077263 | 7/2006 |
| WO | 2008024812 | 7/2008 |
| WO | 2010078207 | 7/2010 |
| WO | 2011010198 | 12/2011 |
| WO | 2014147025 | 9/2014 |
| WO | 2014158425 | 10/2014 |
| WO | 2015003145 | 1/2015 |

* cited by examiner

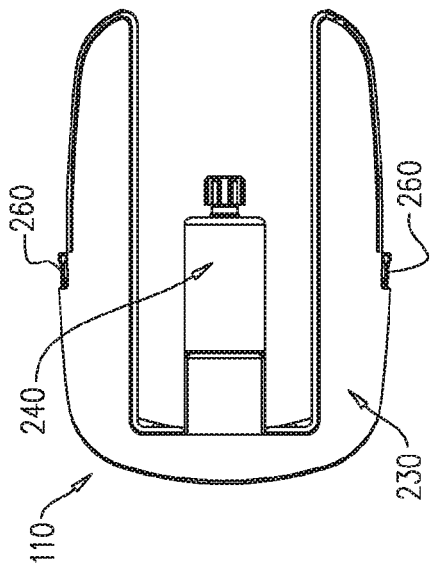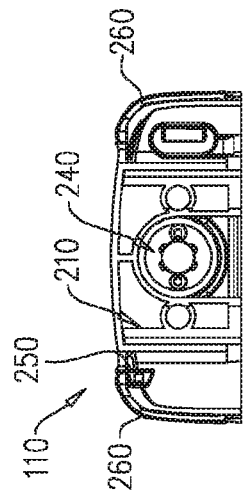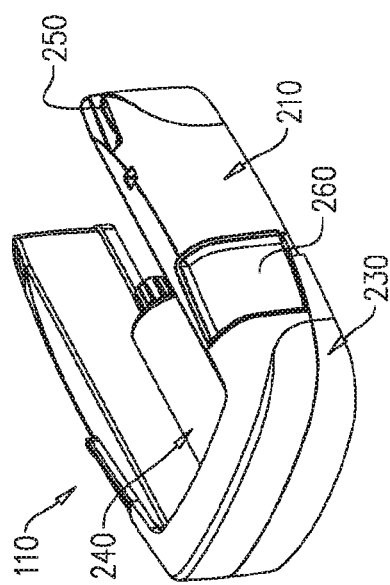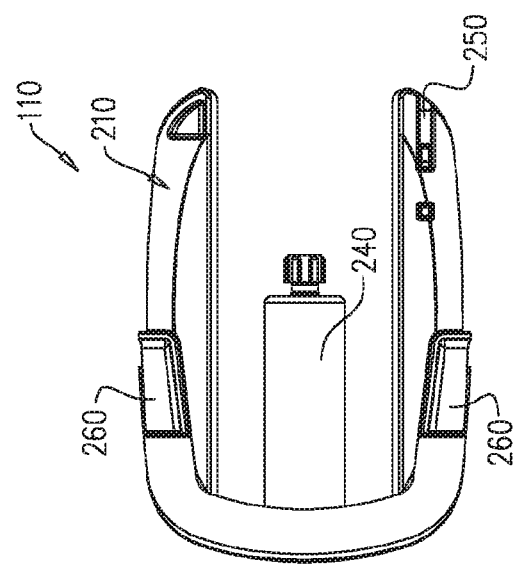

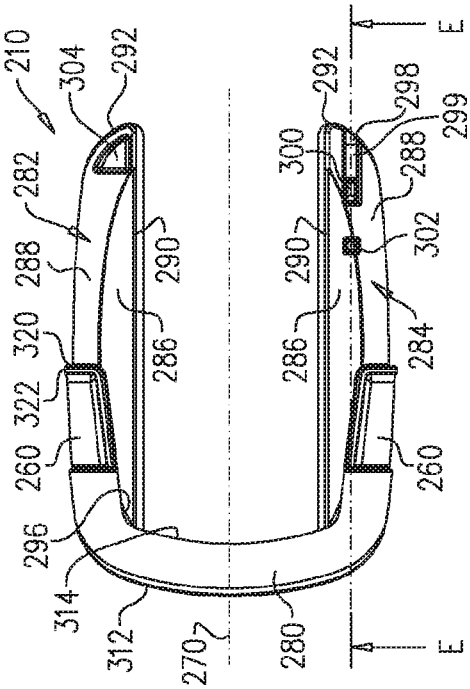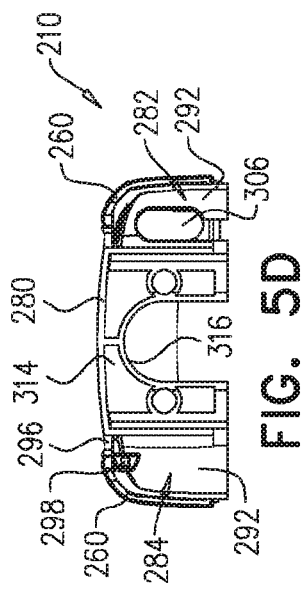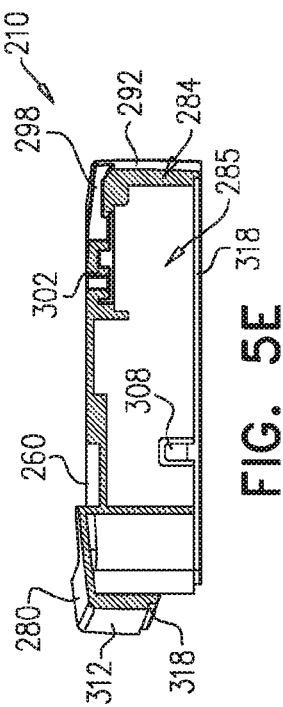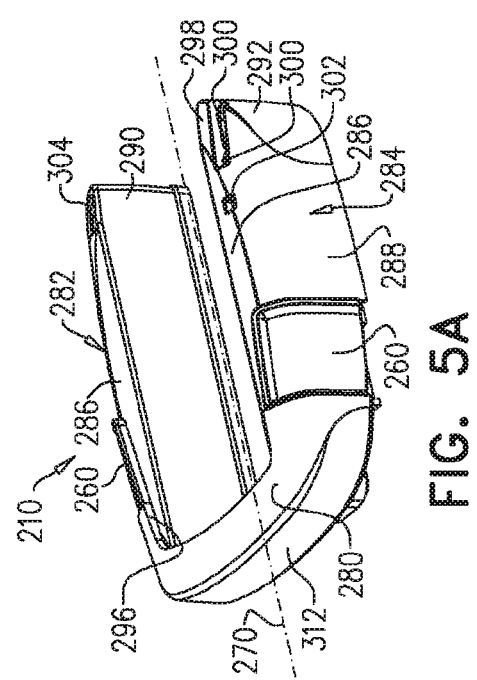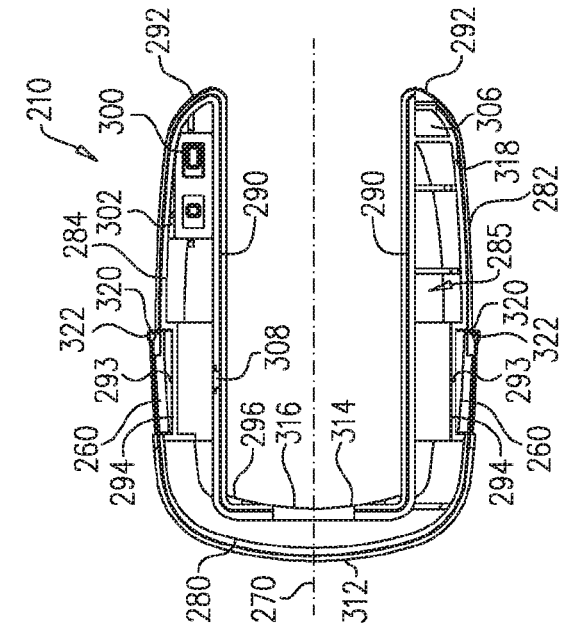

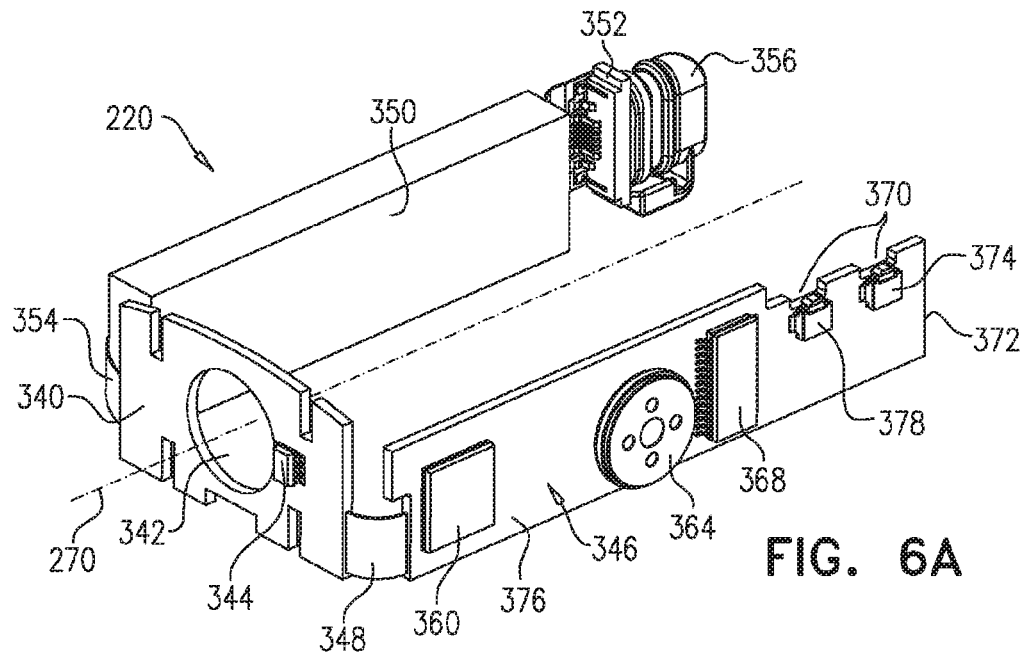
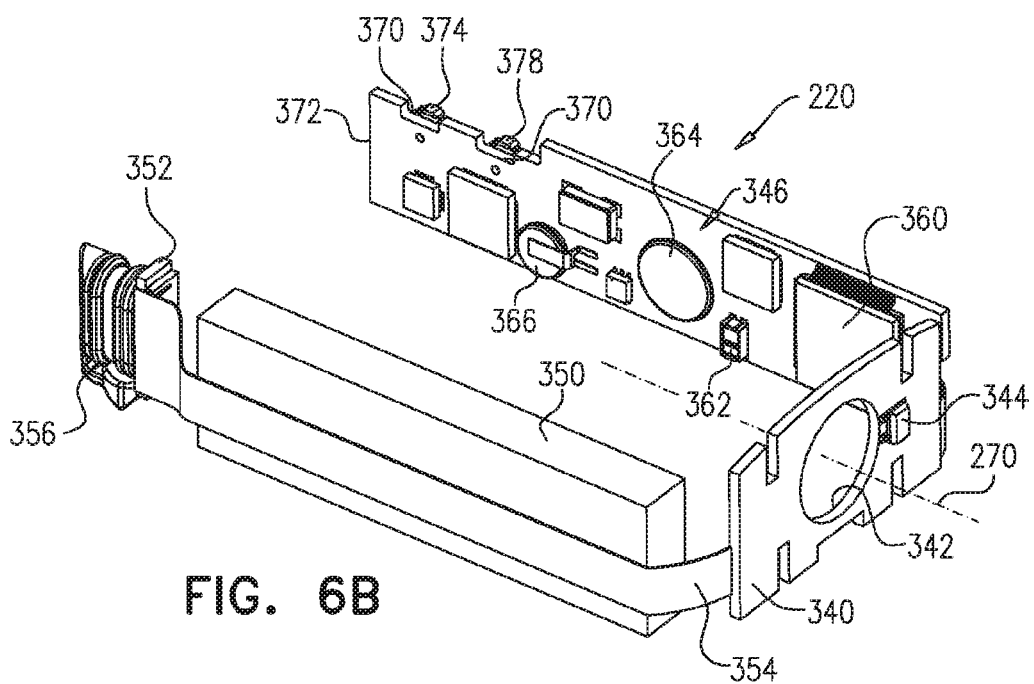

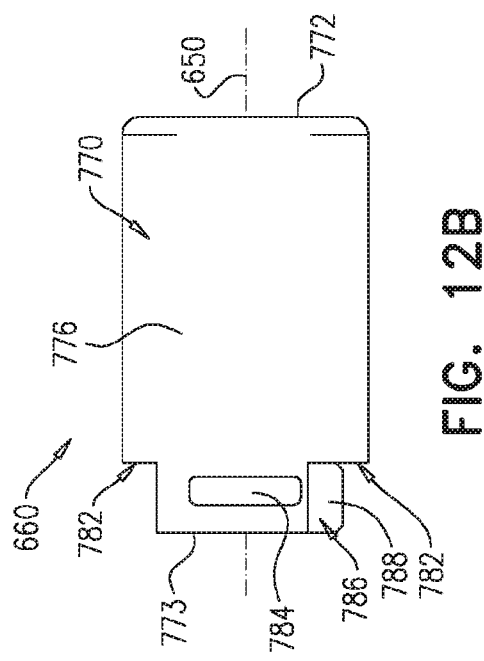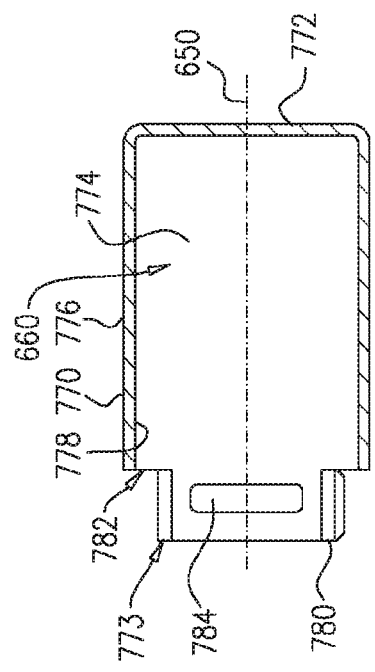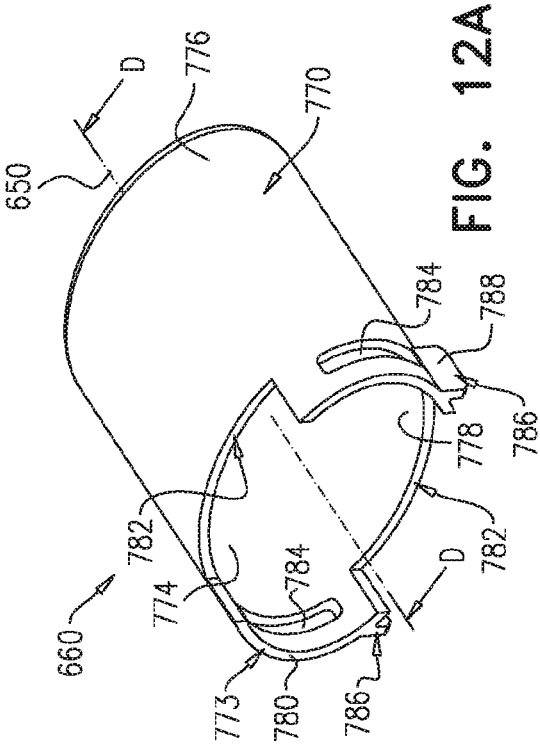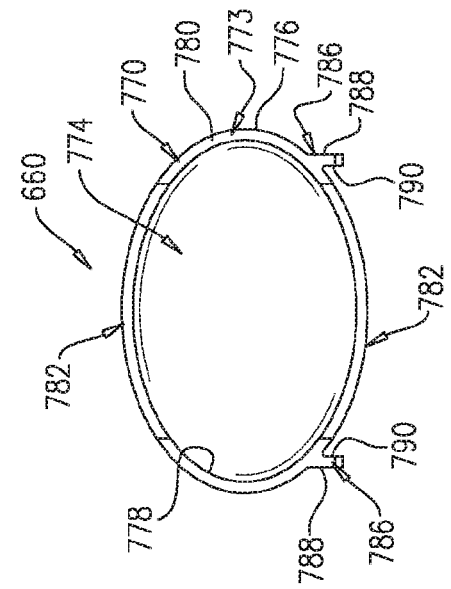

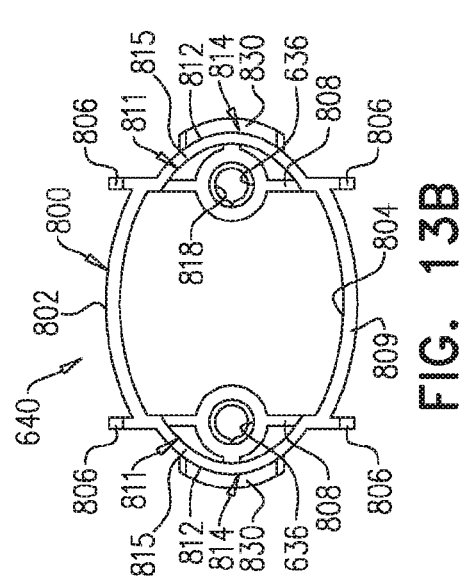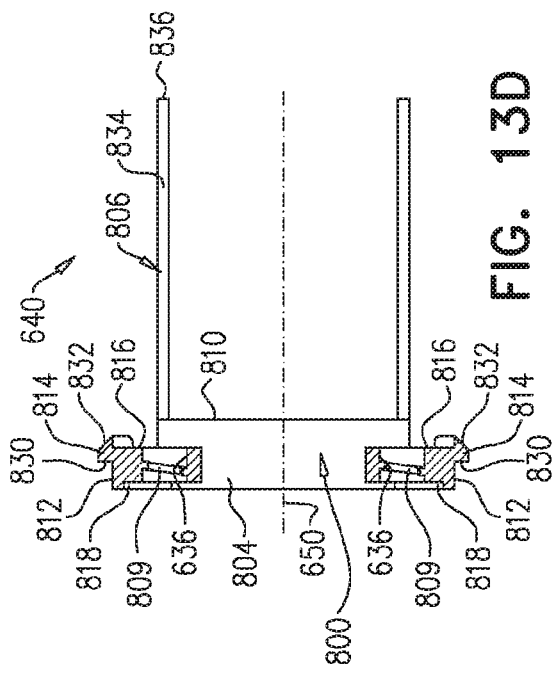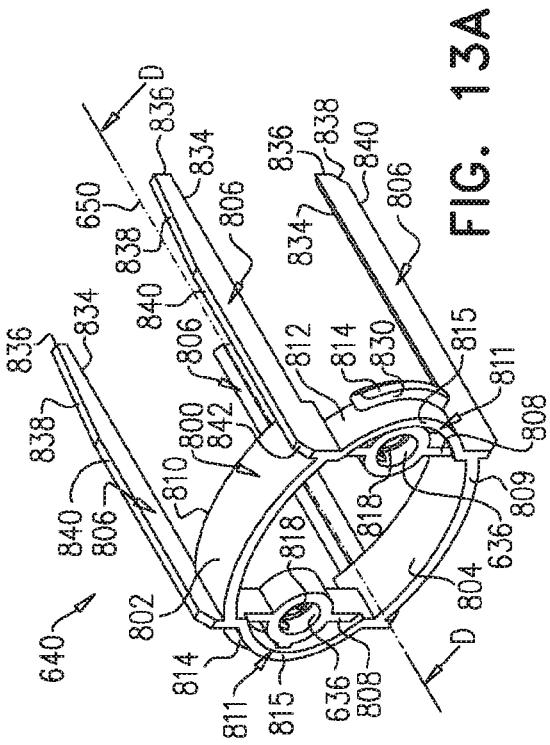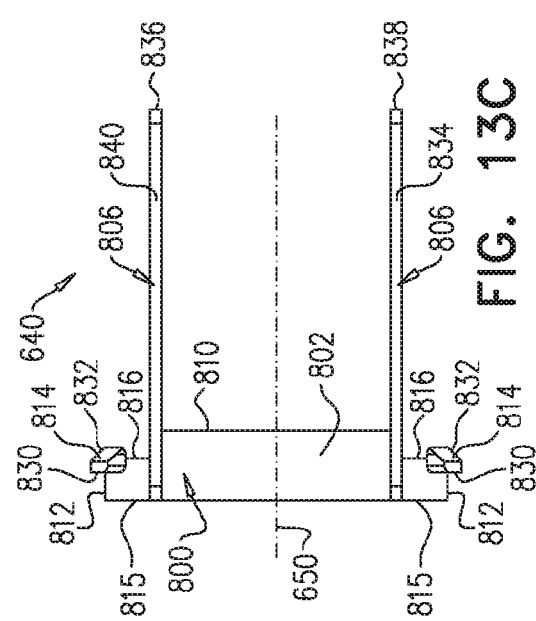

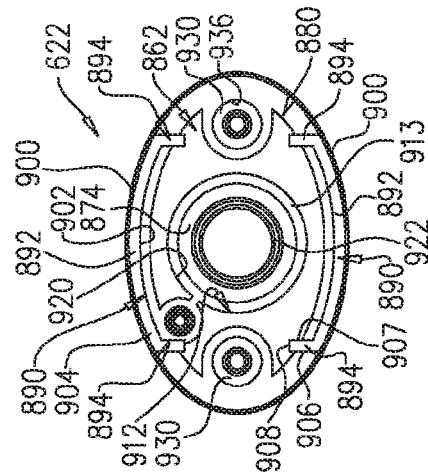
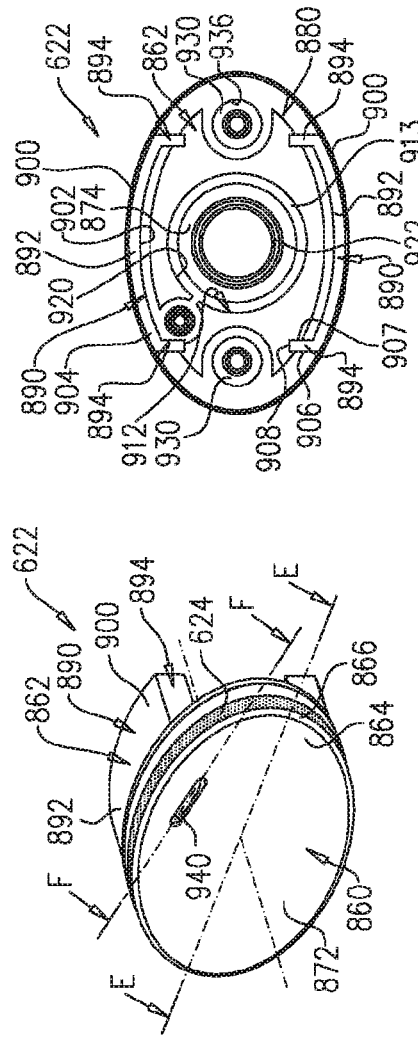
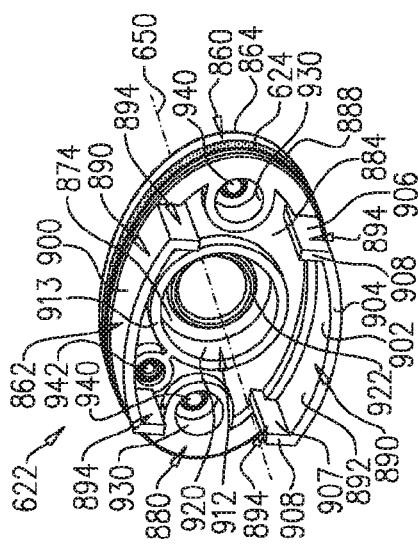
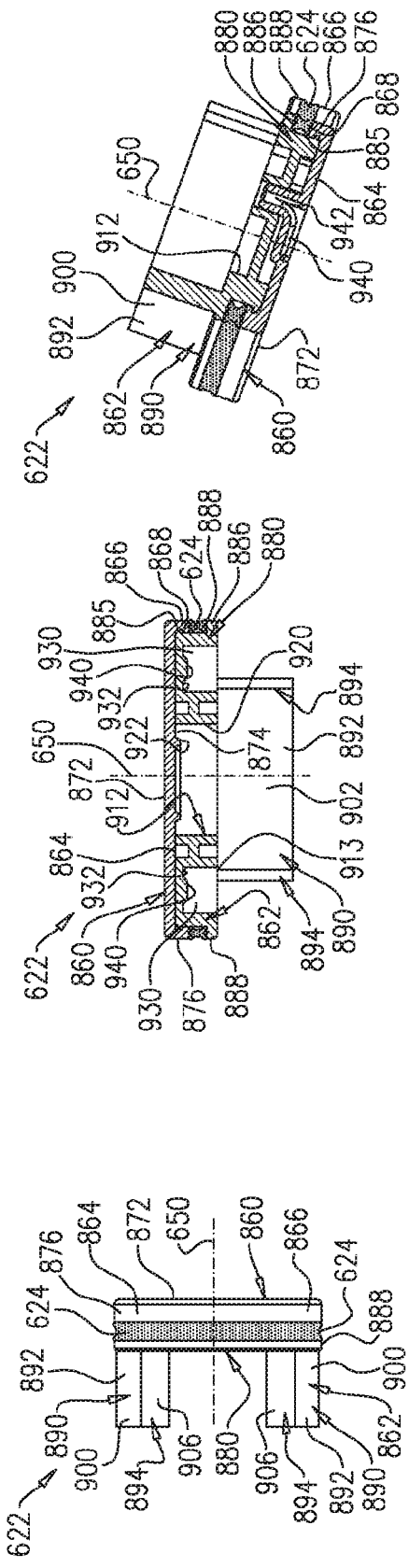

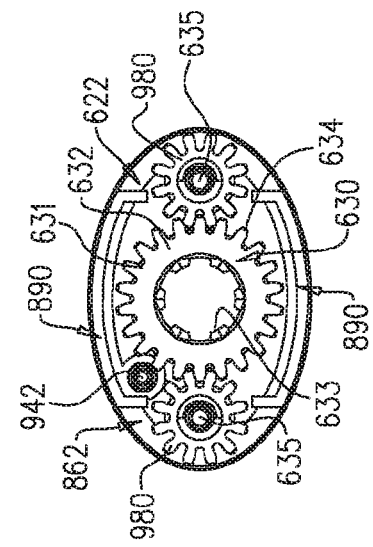
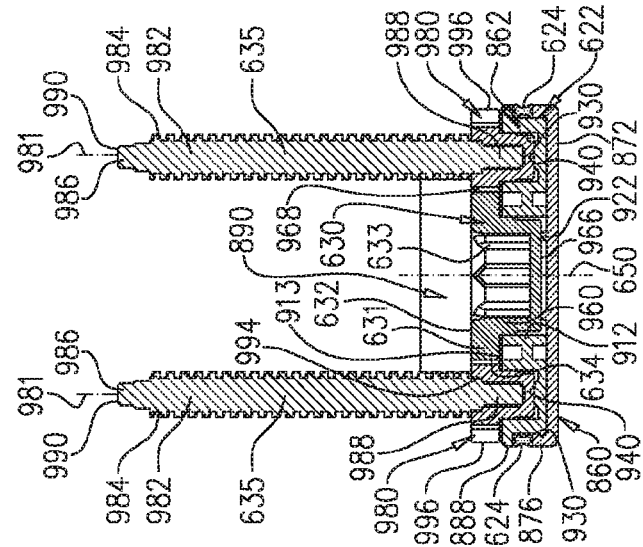
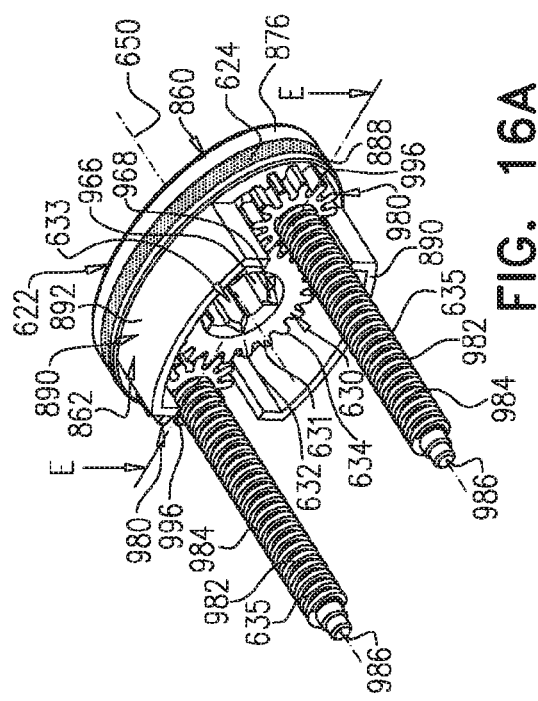
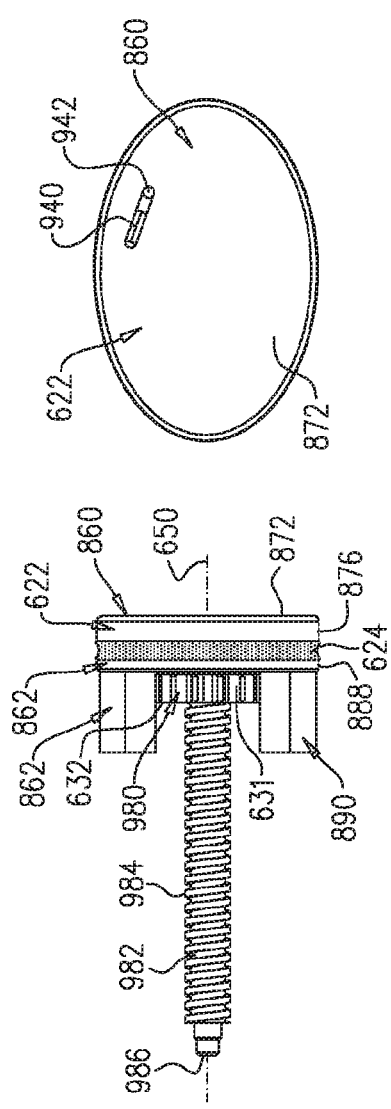
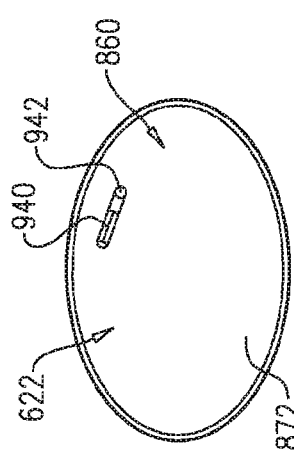

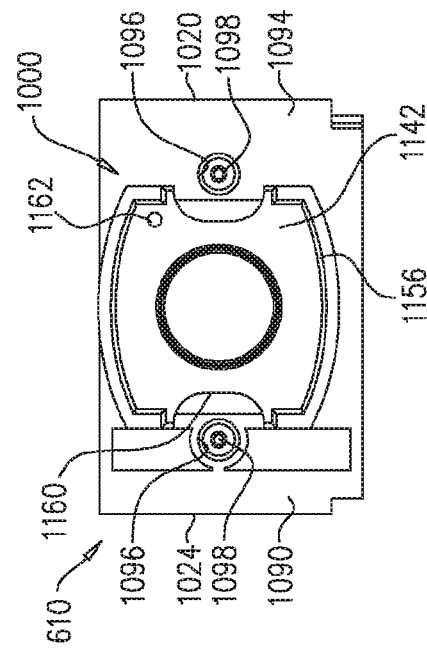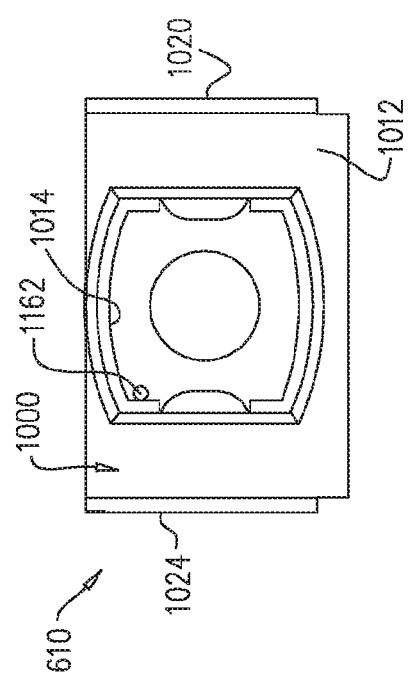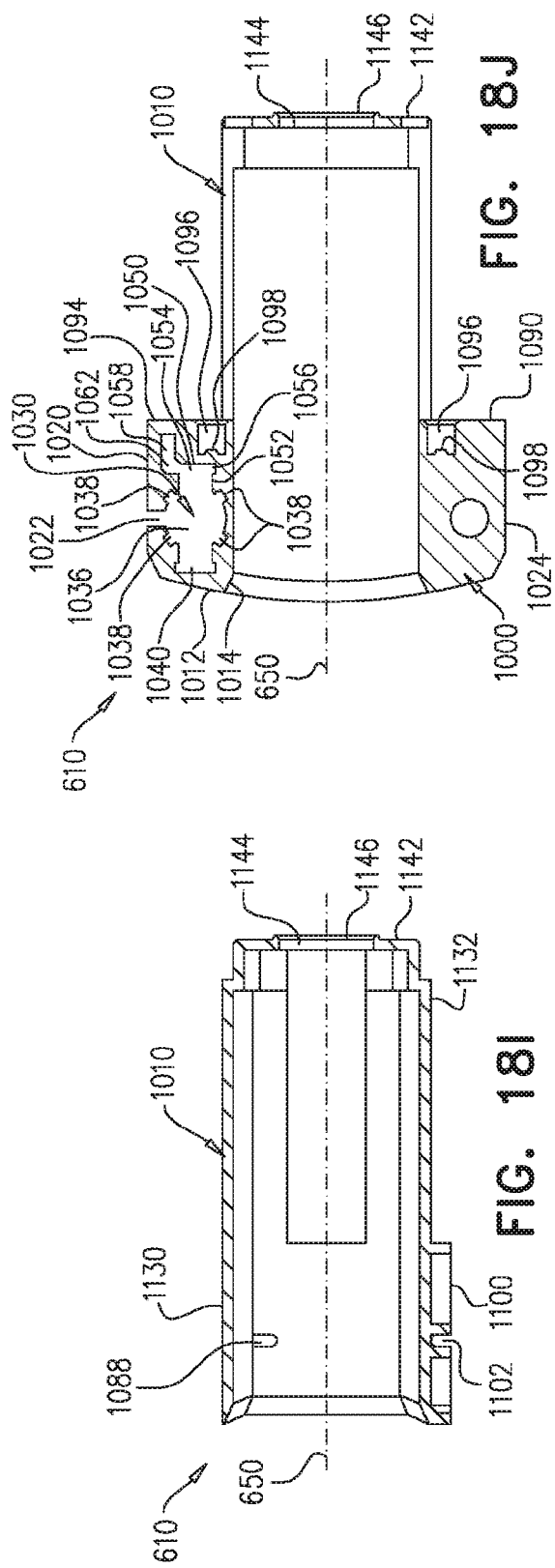

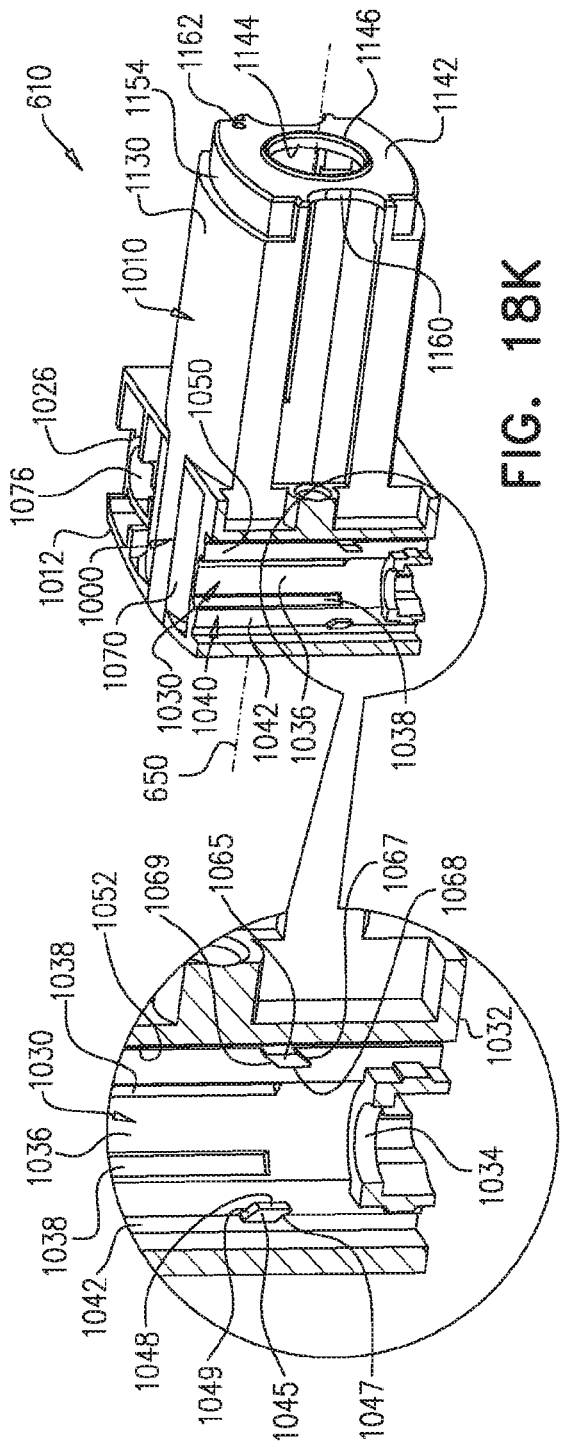
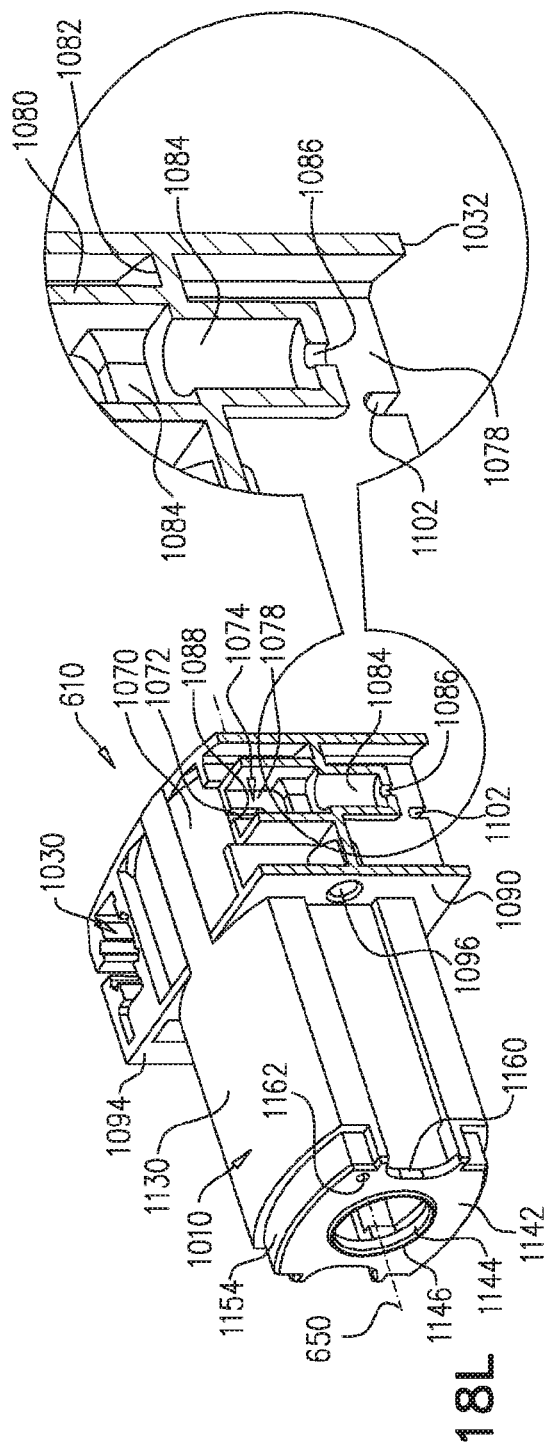
FIG. 18K
FIG. 18L

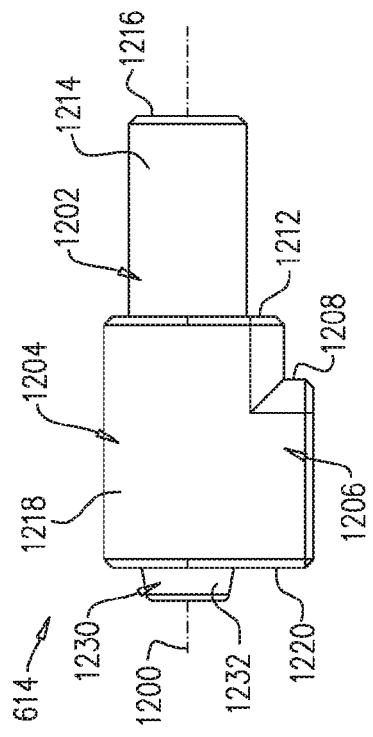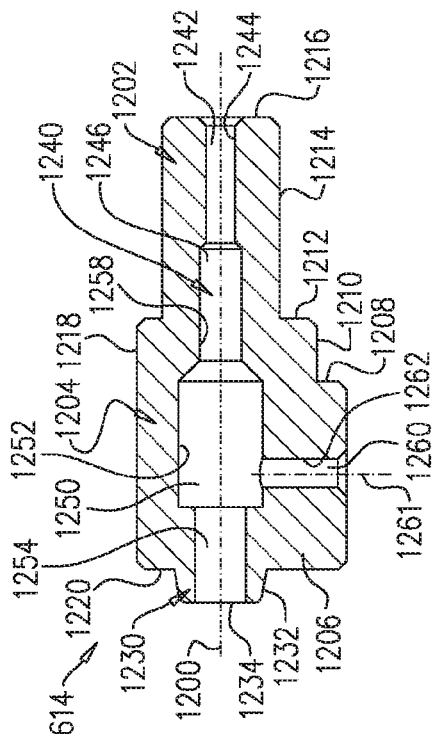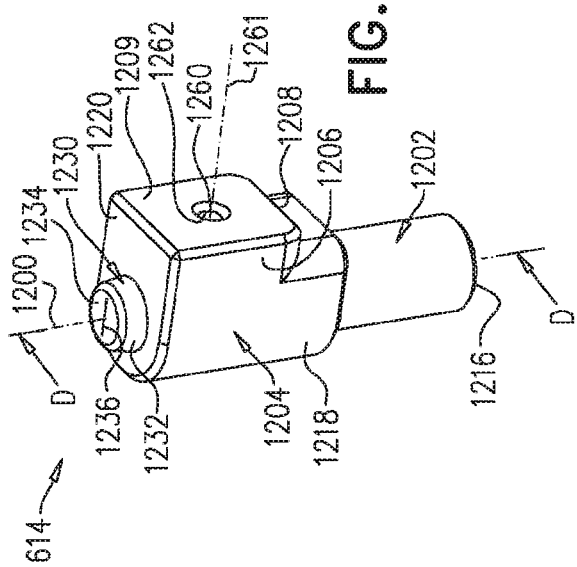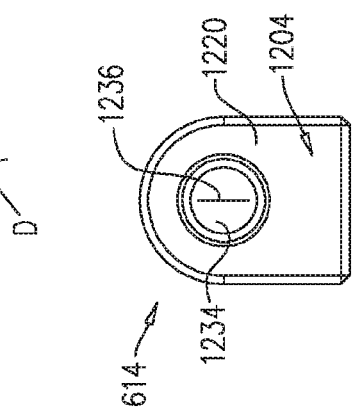

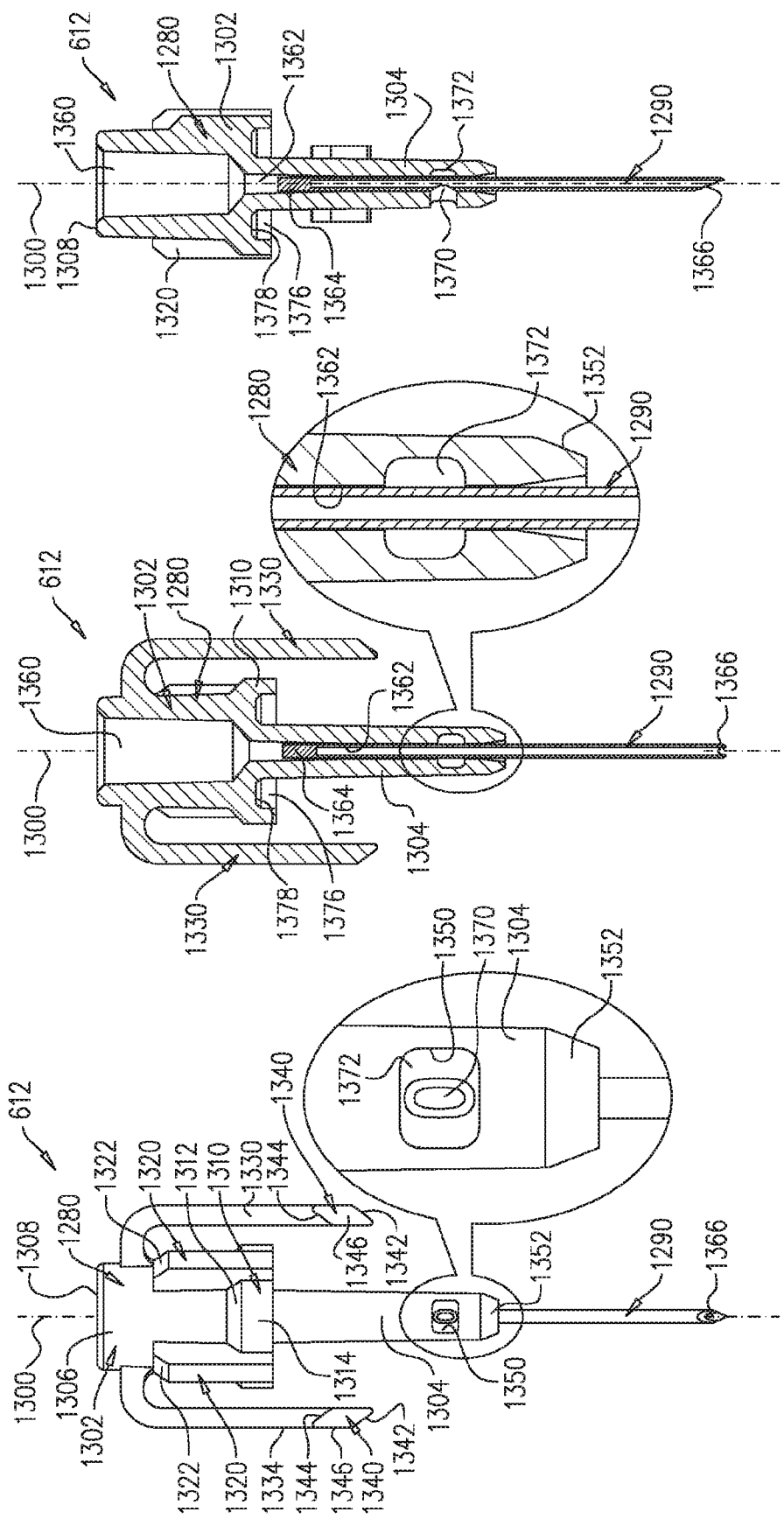

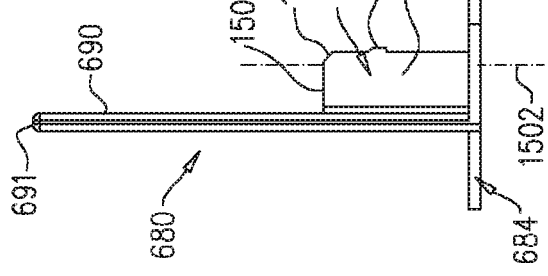
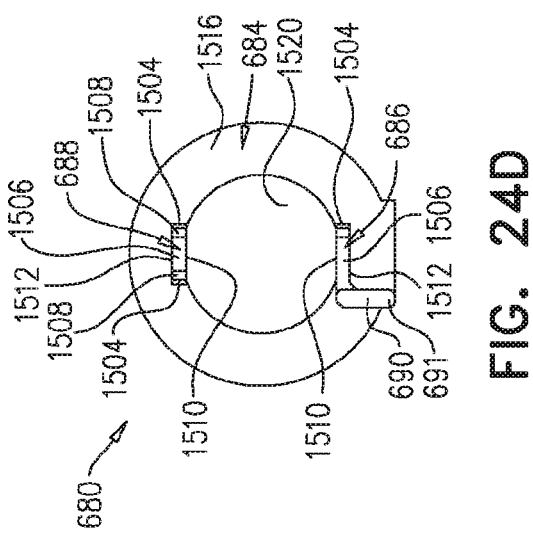
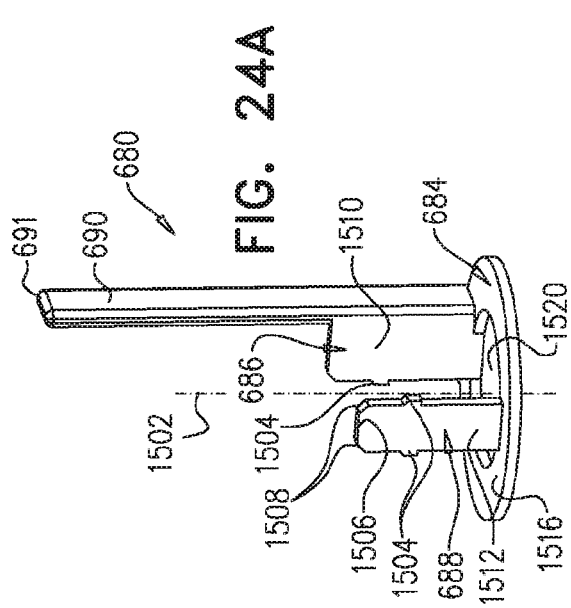
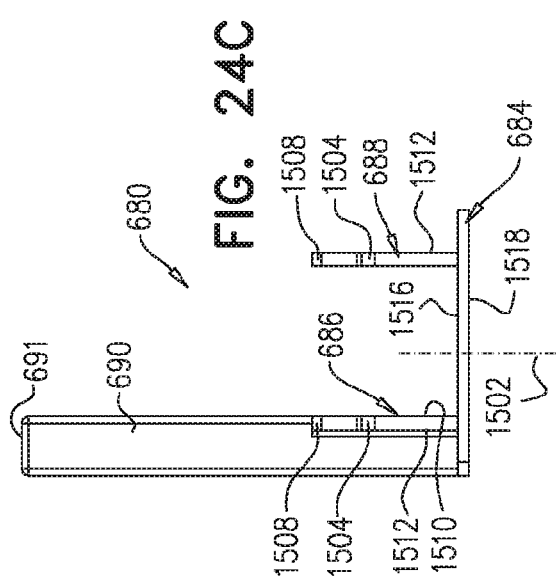

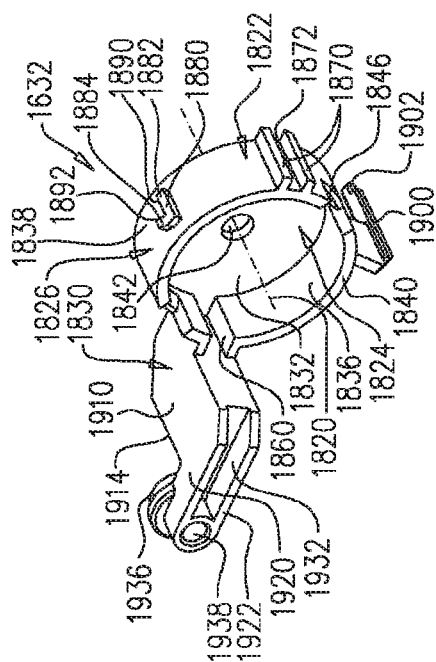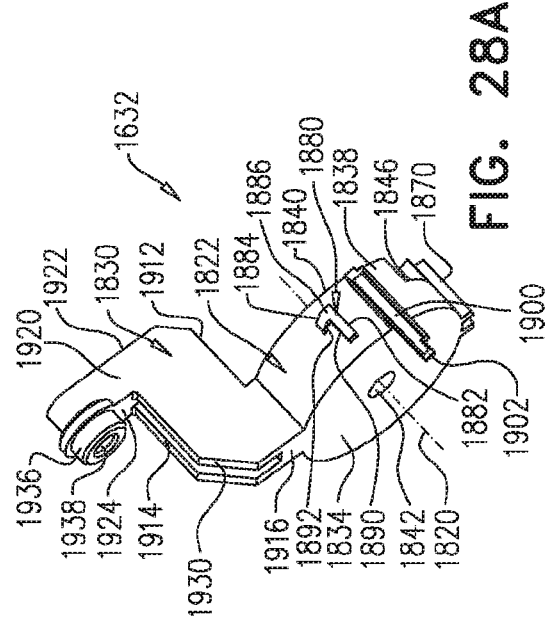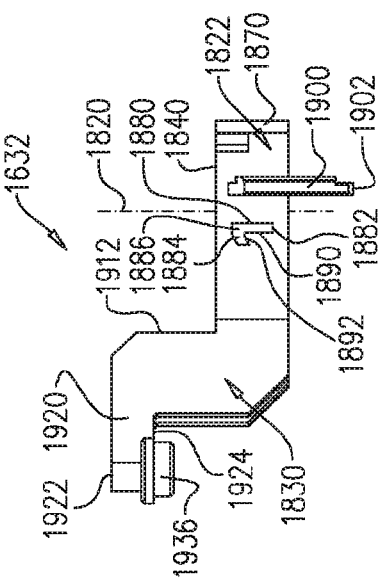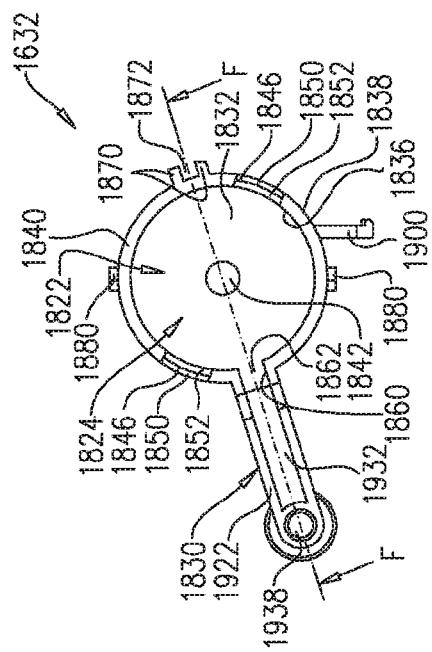

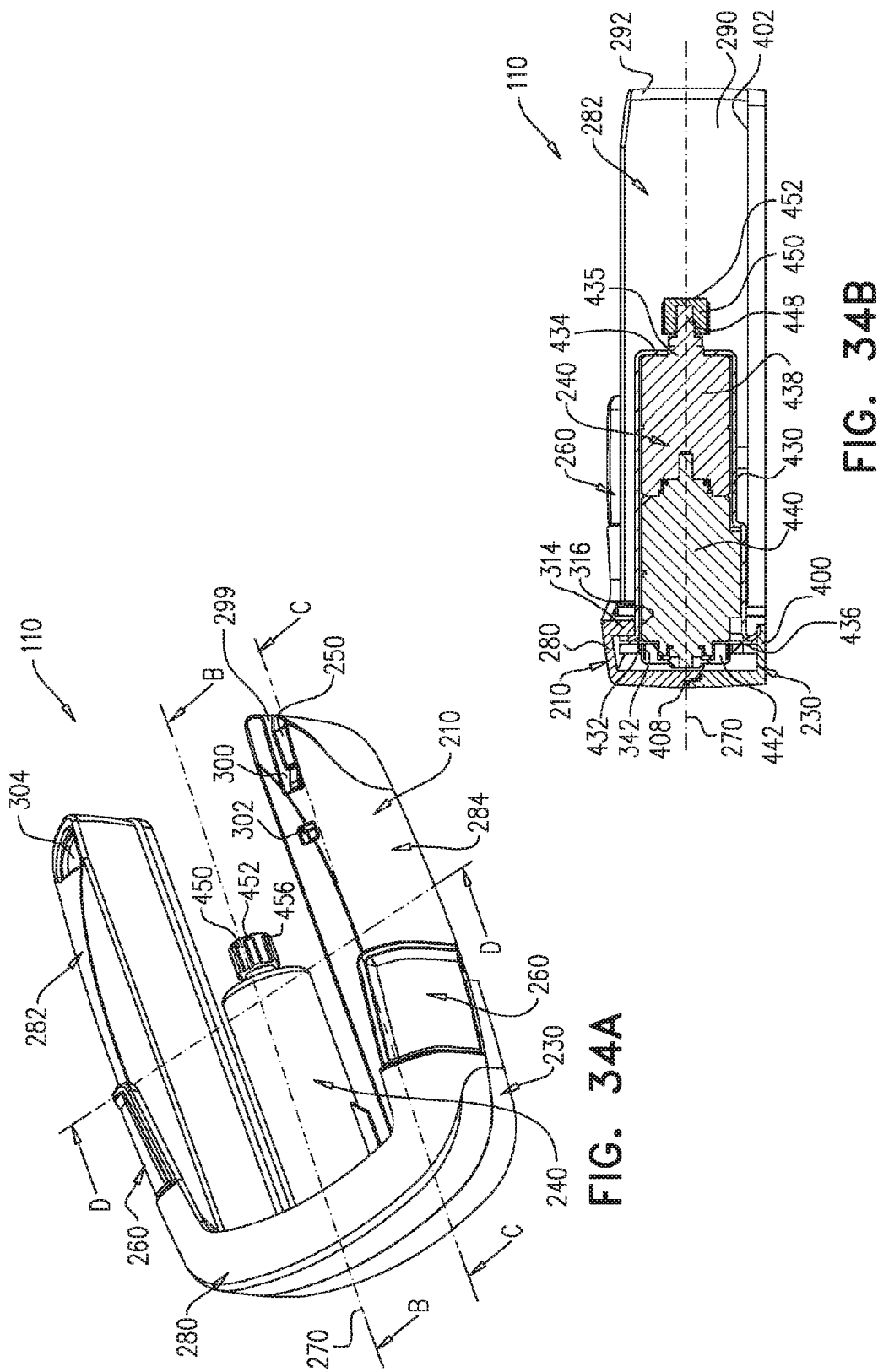

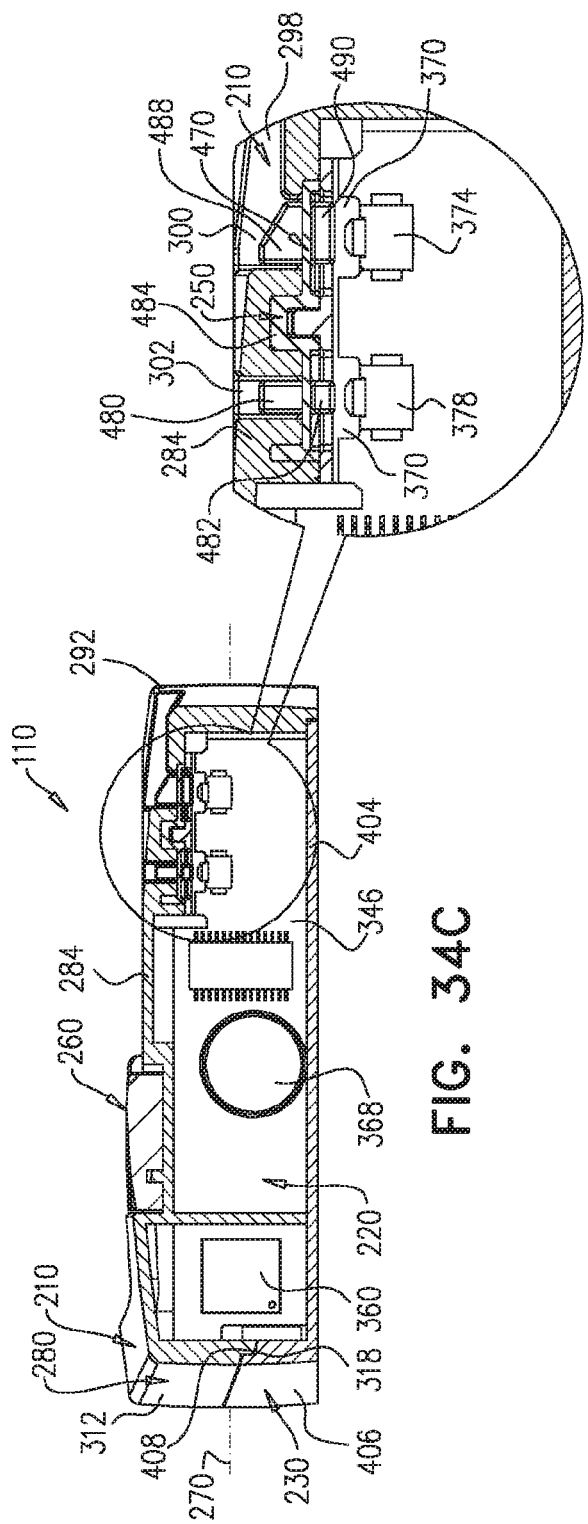
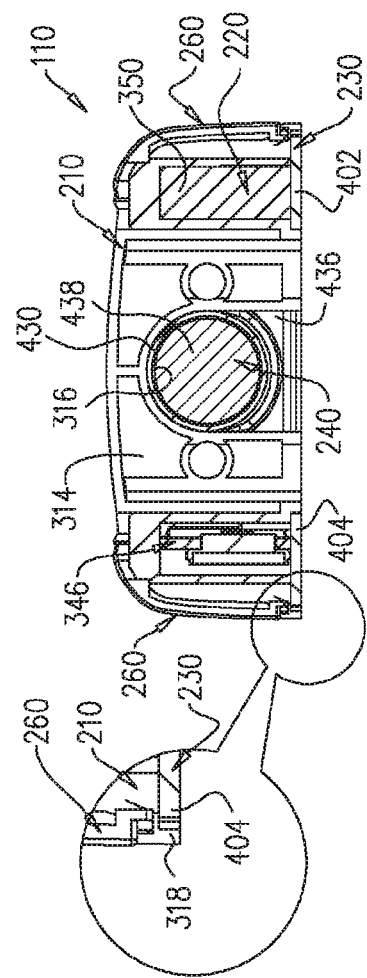
FIG. 34C
FIG. 34D

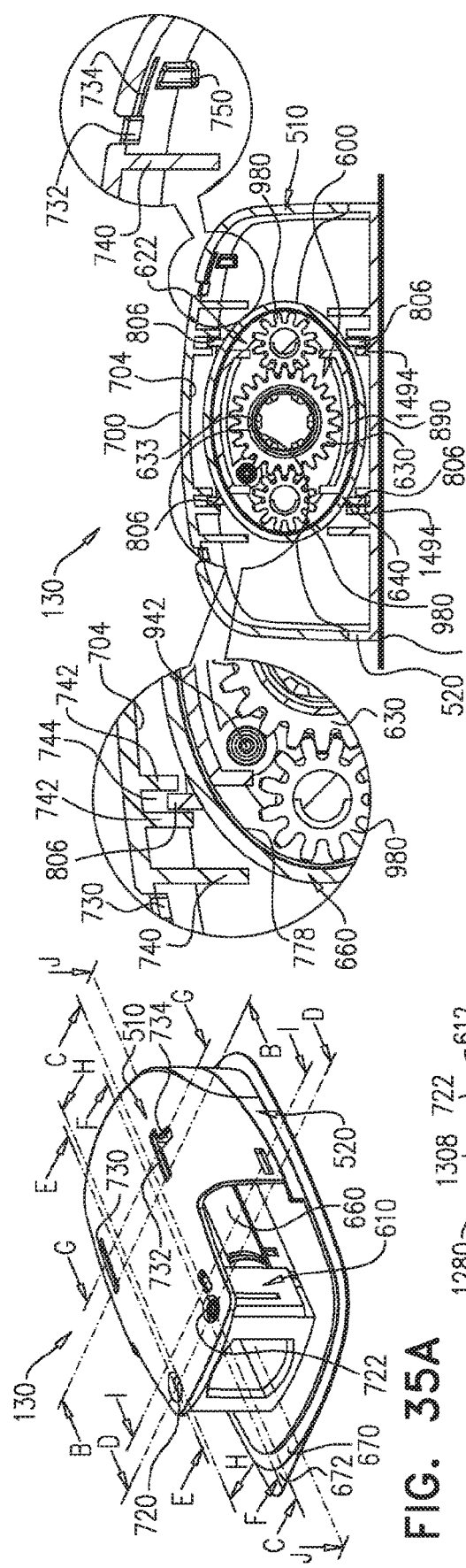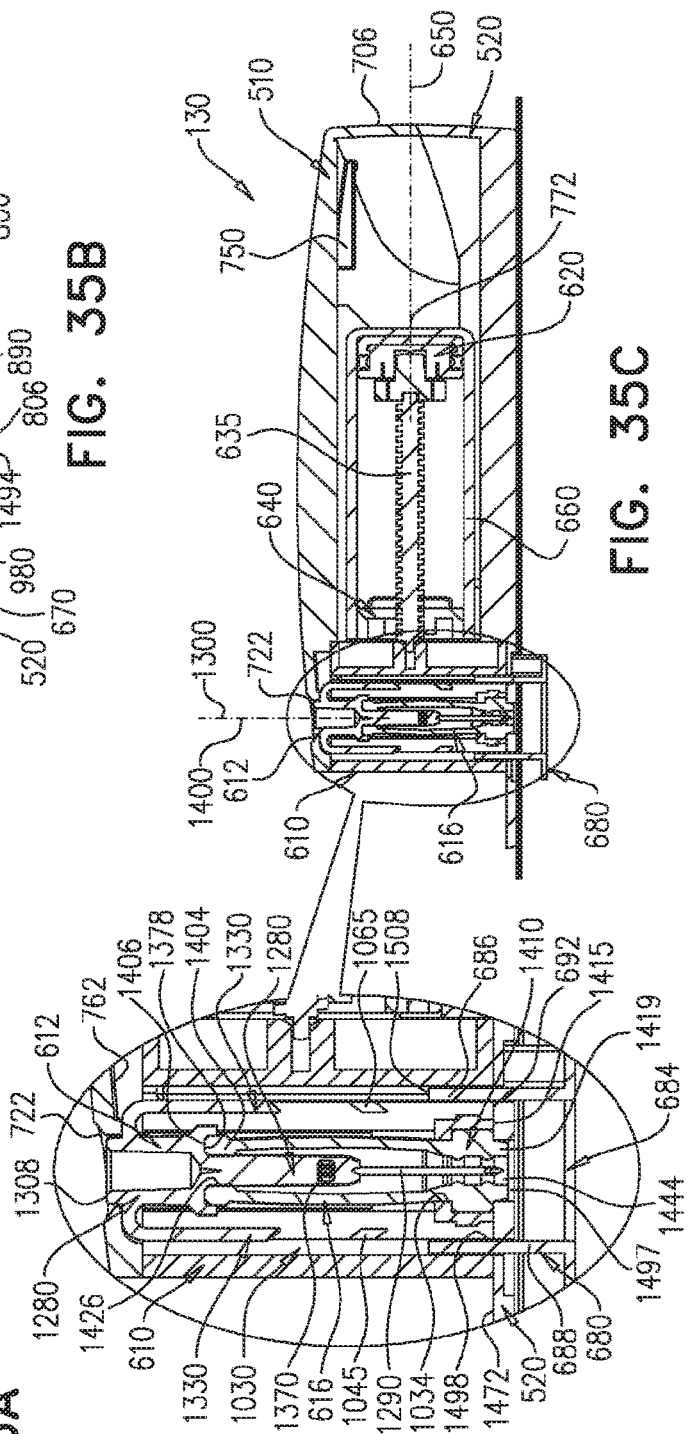

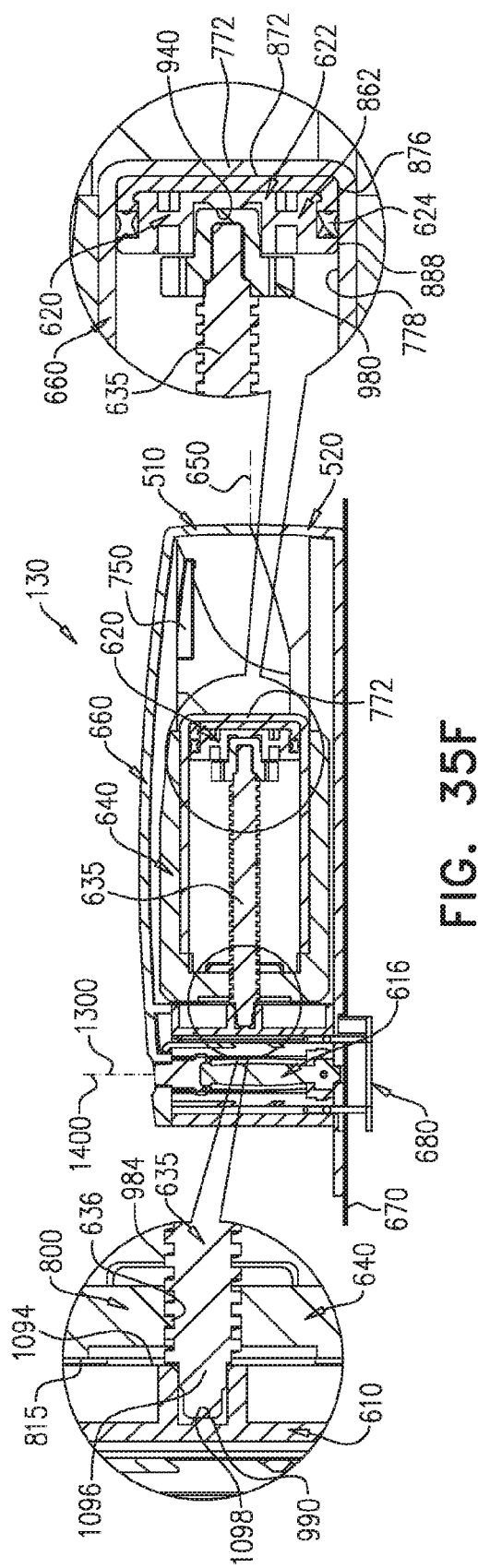
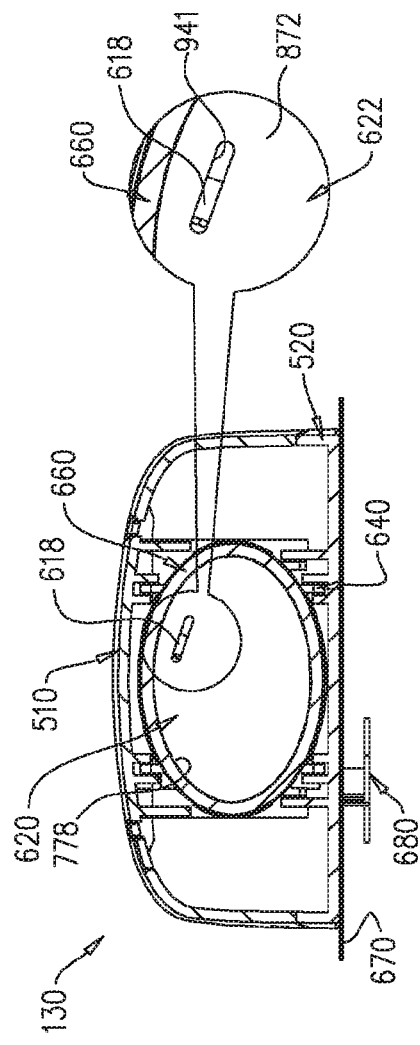
FIG. 35F
FIG. 35G

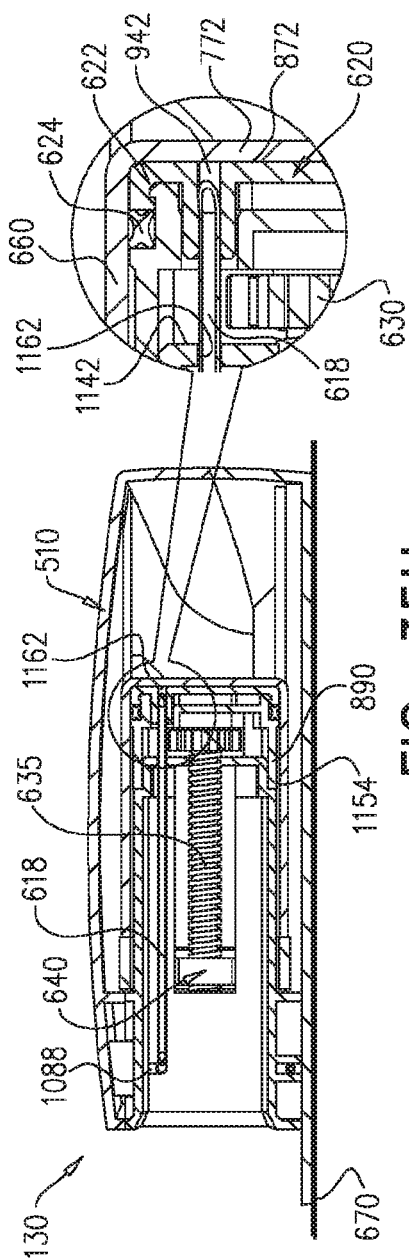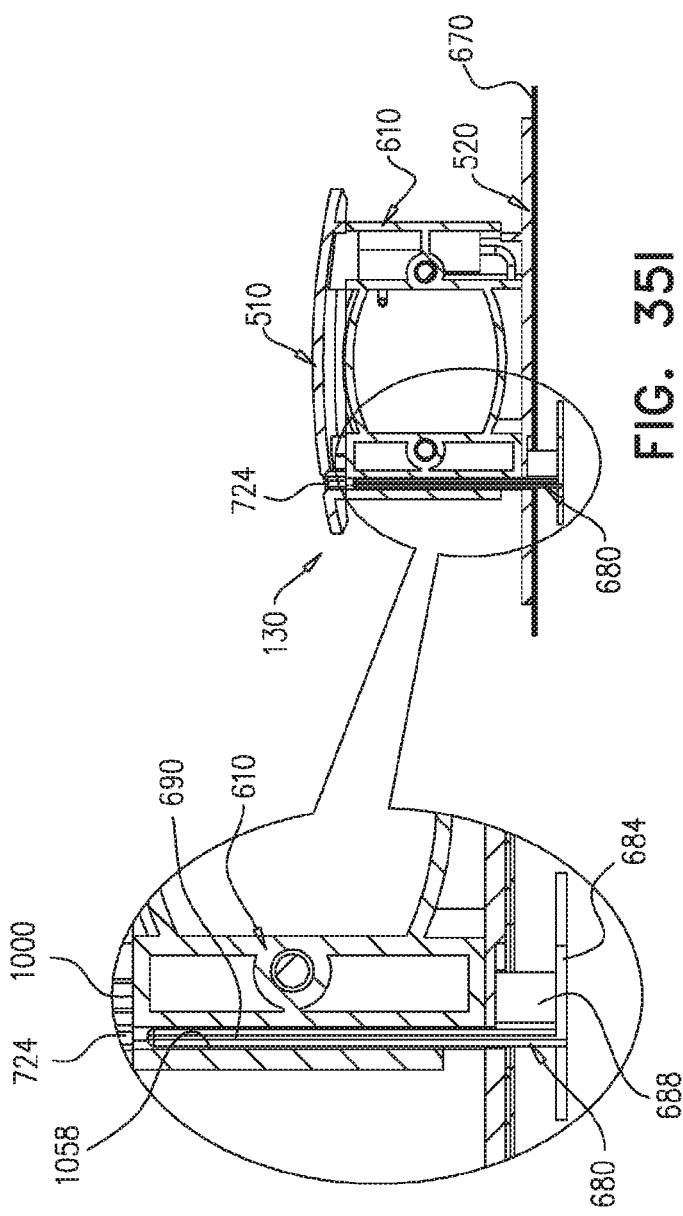
FIG. 35H
FIG. 35I

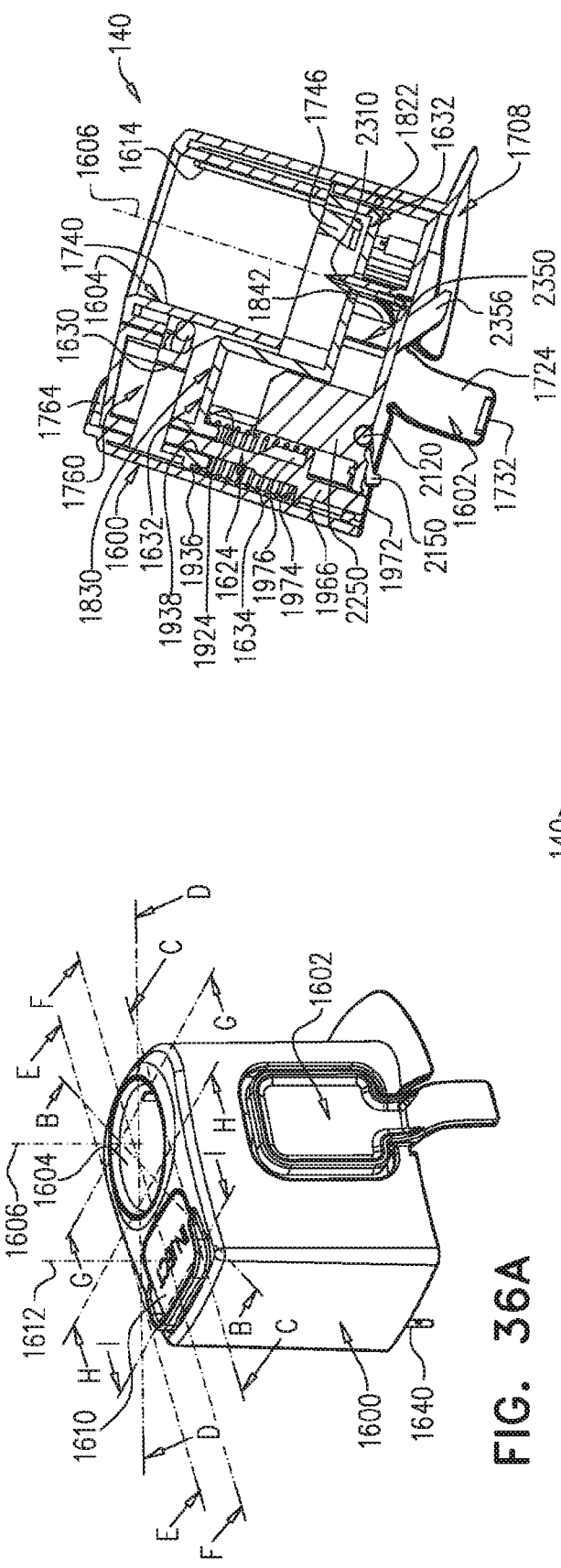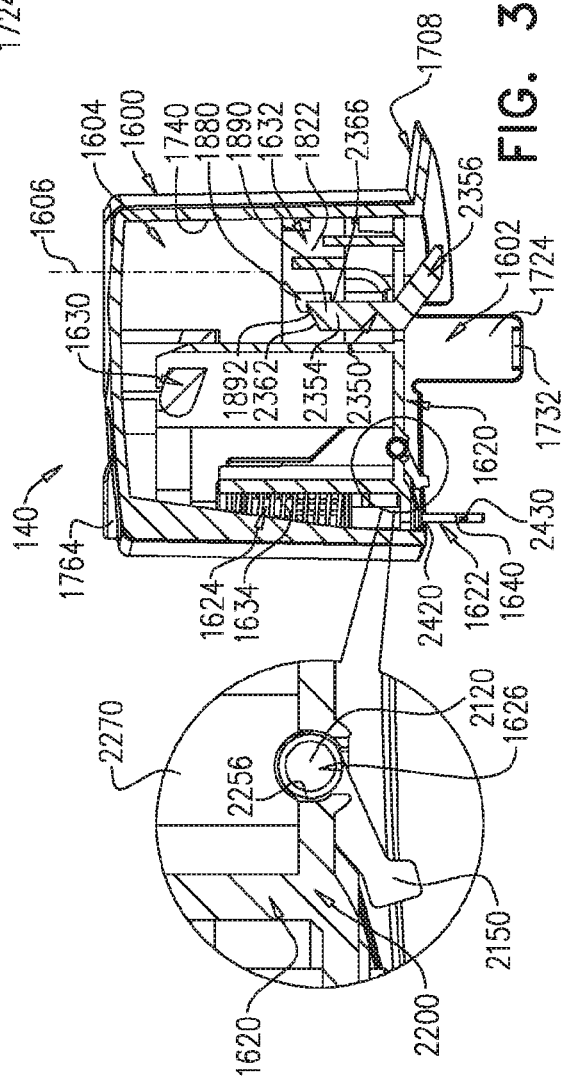

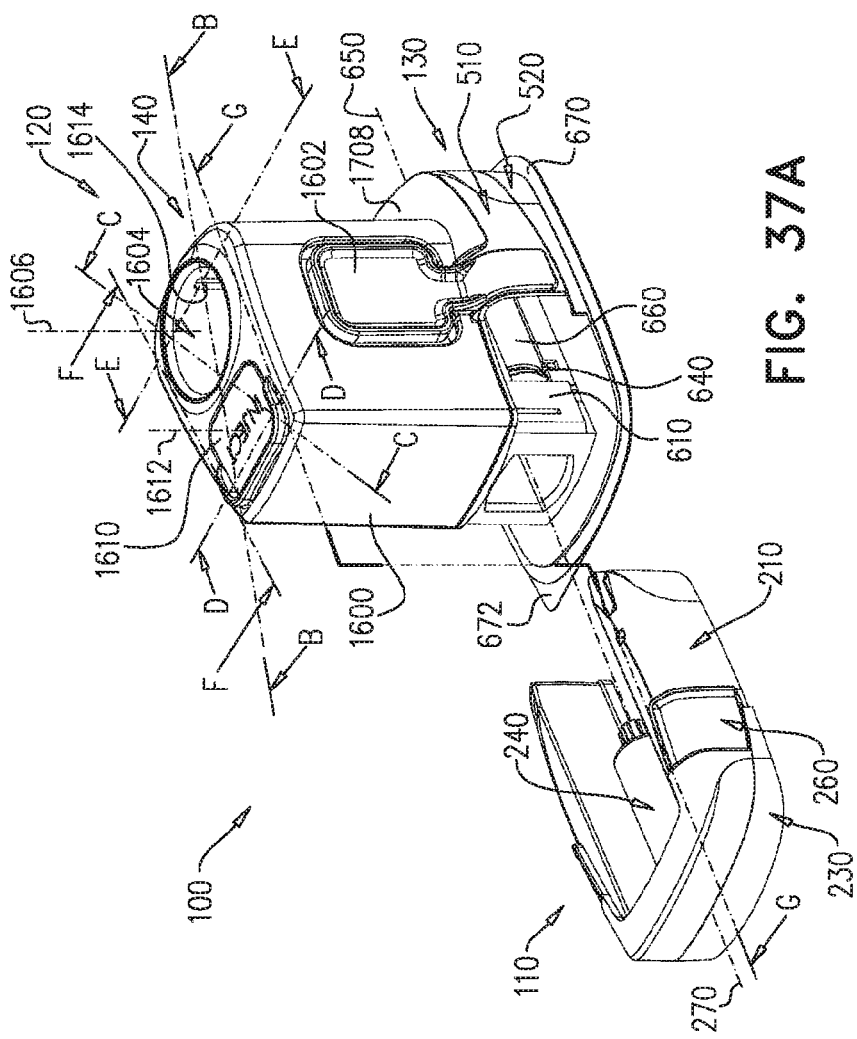

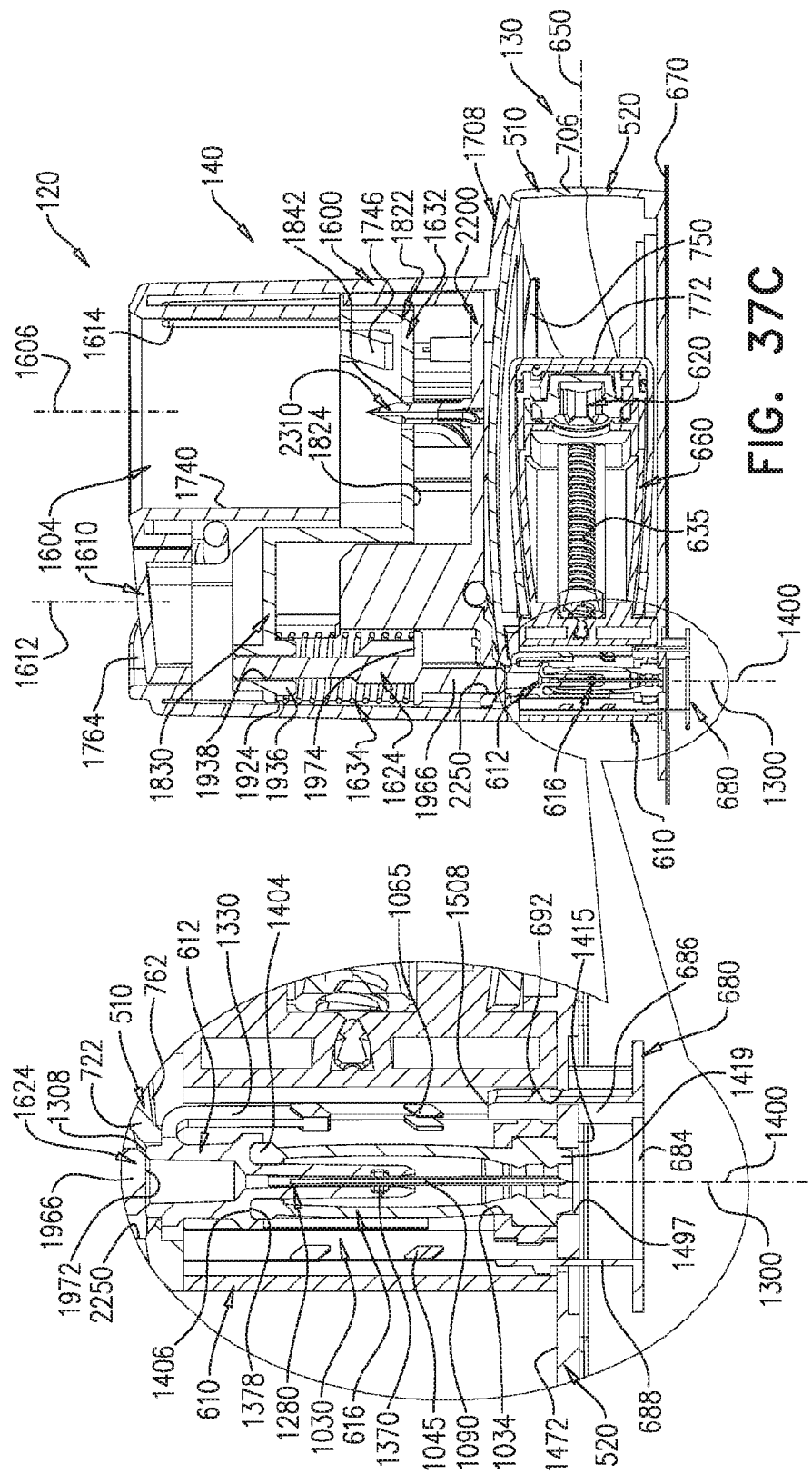

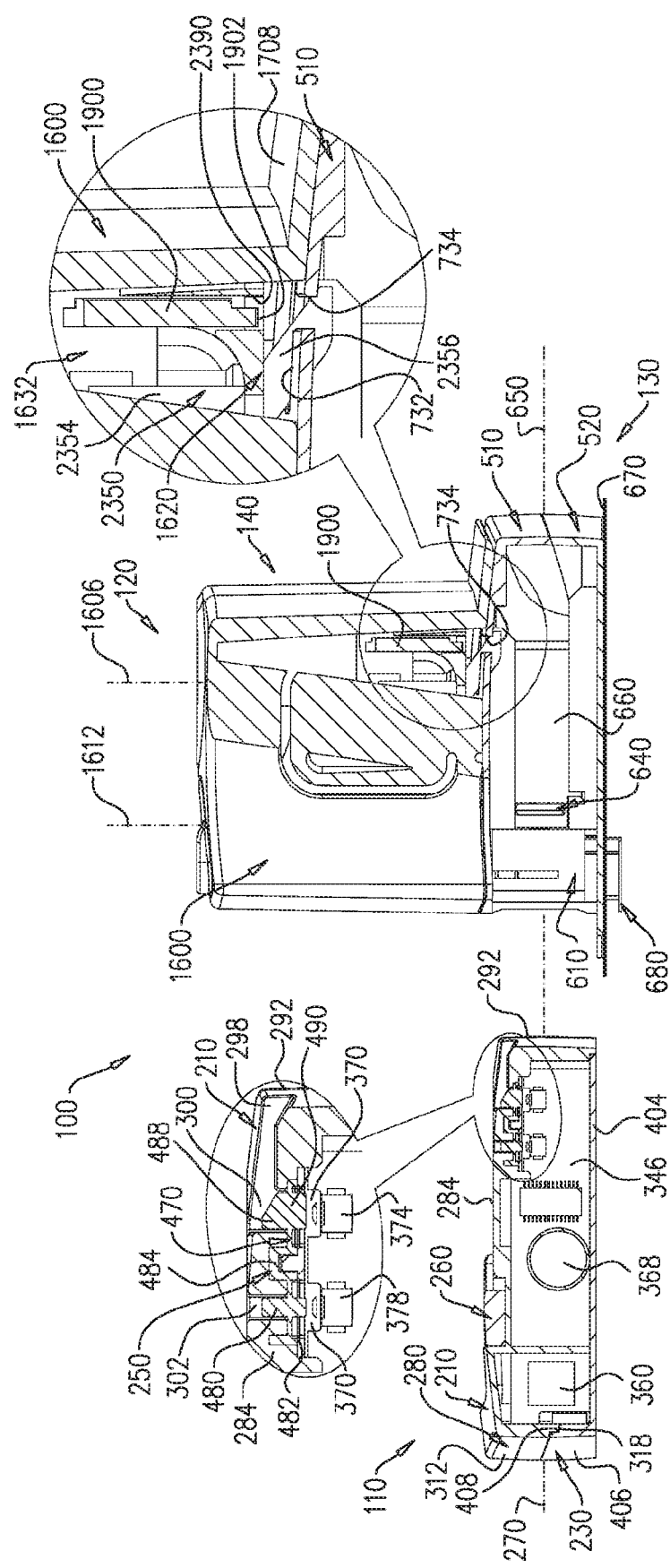

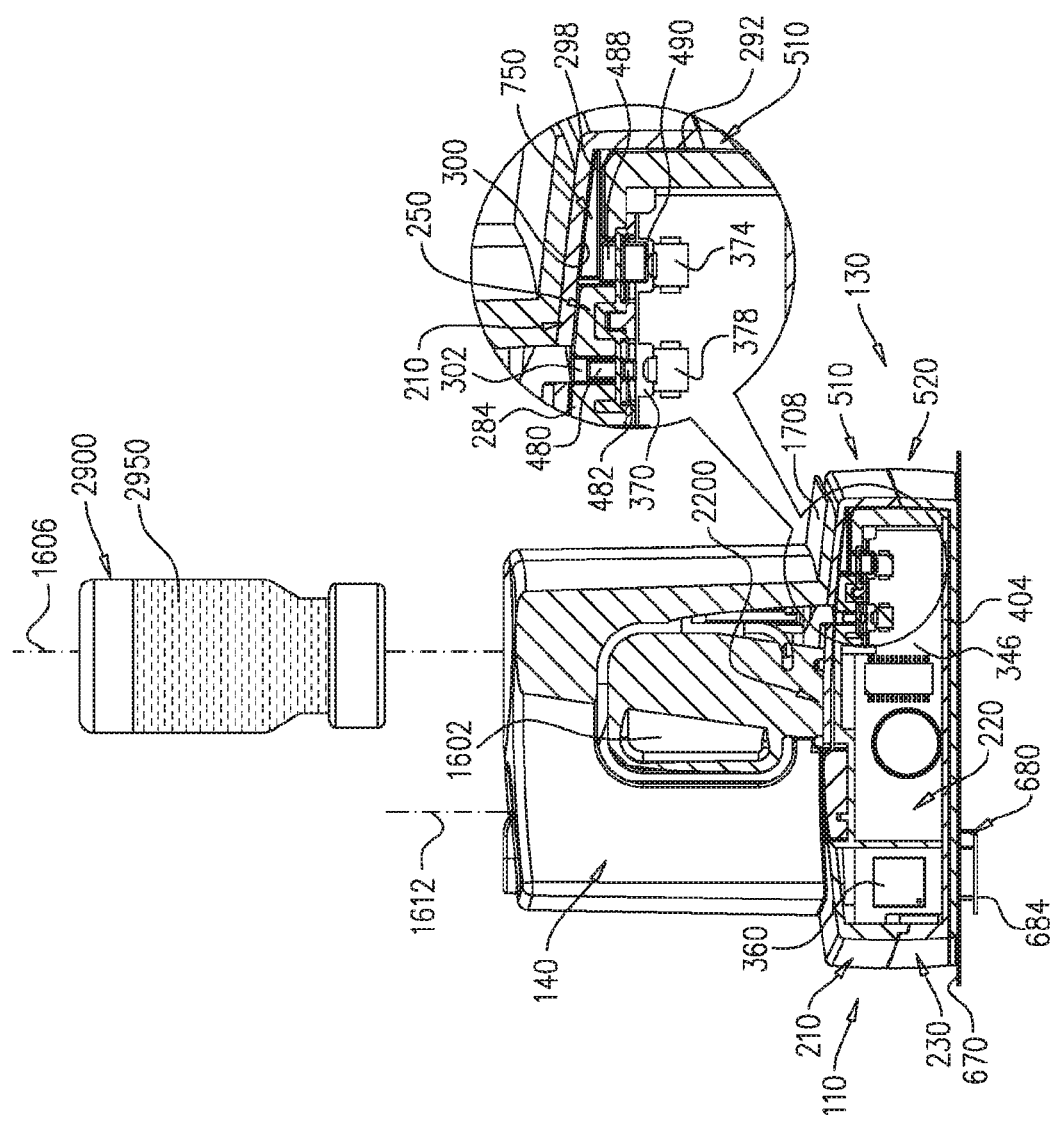

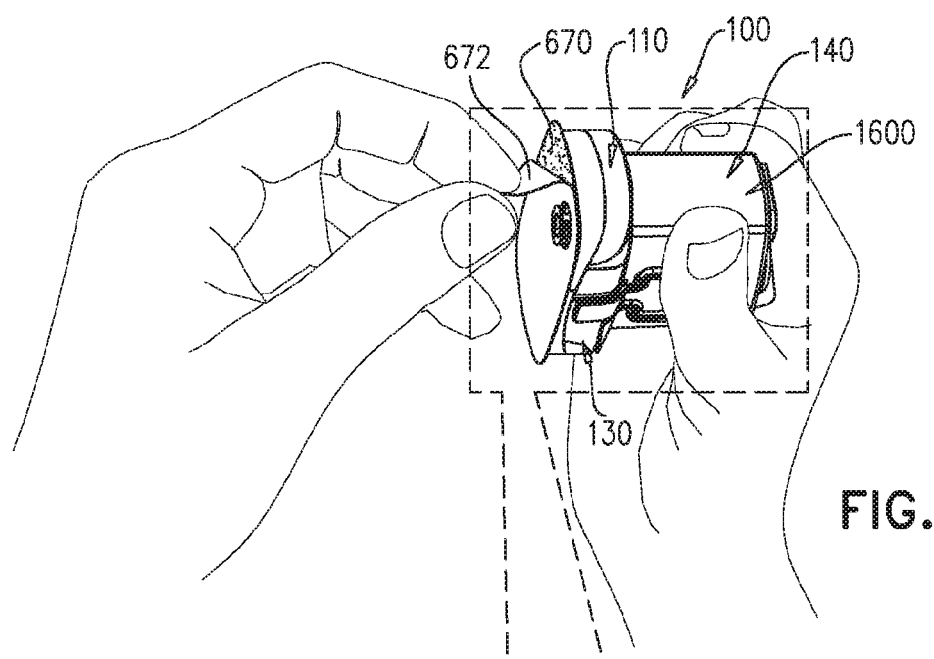
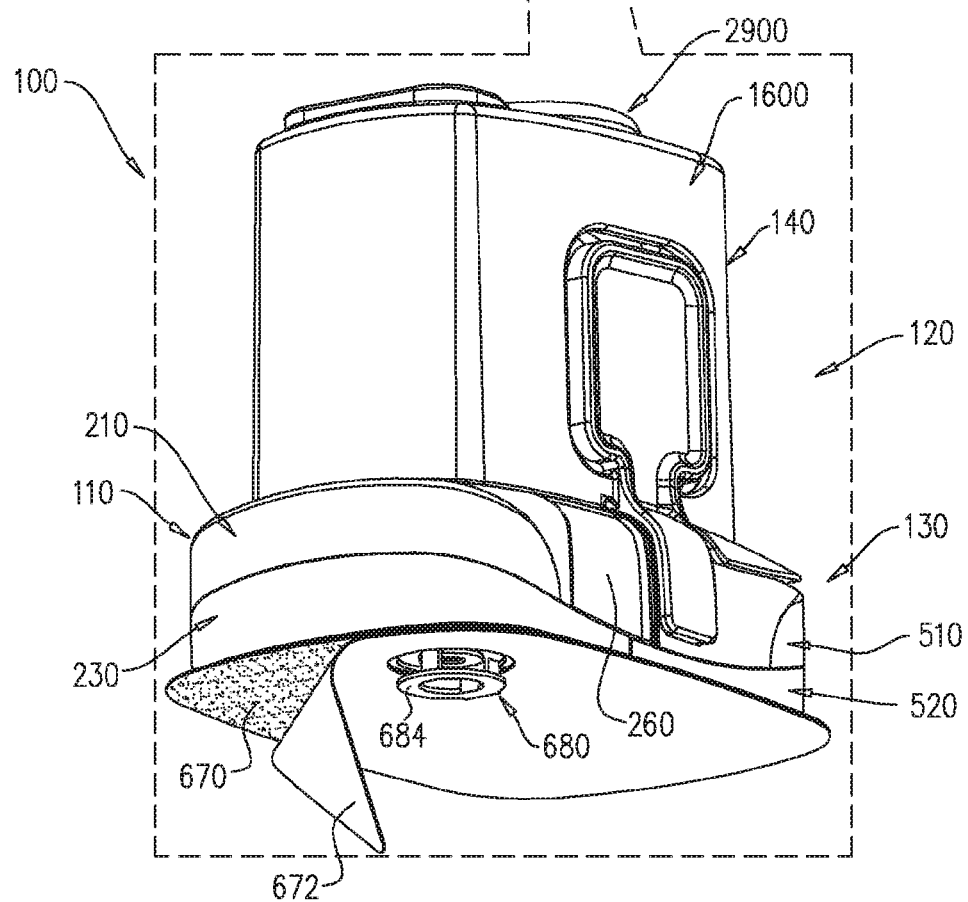
FIG. 41

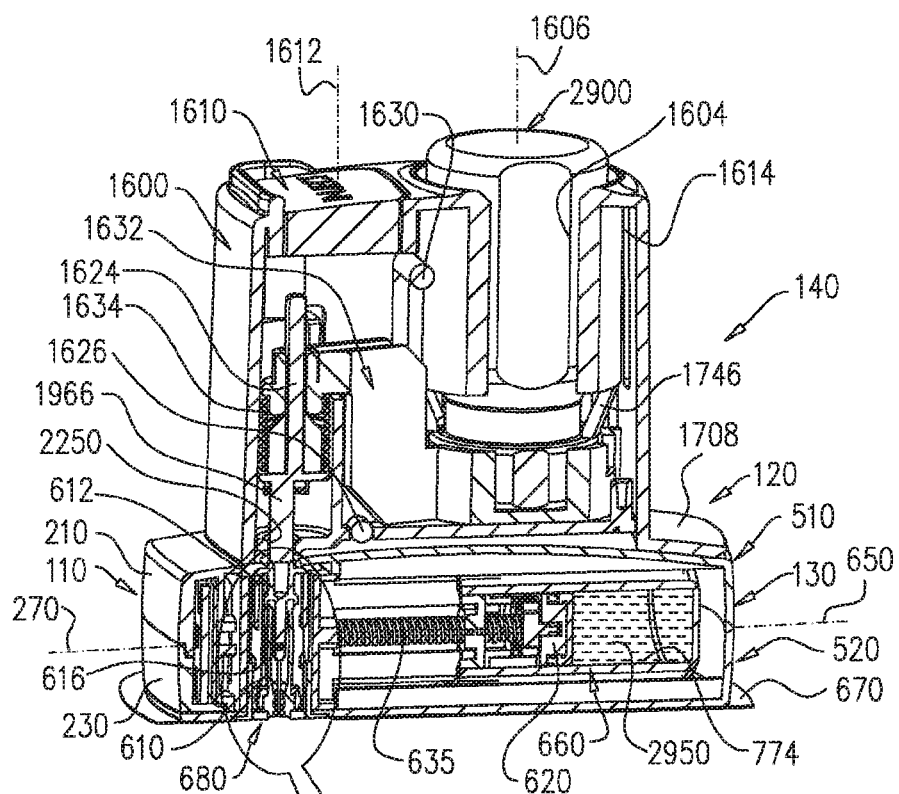
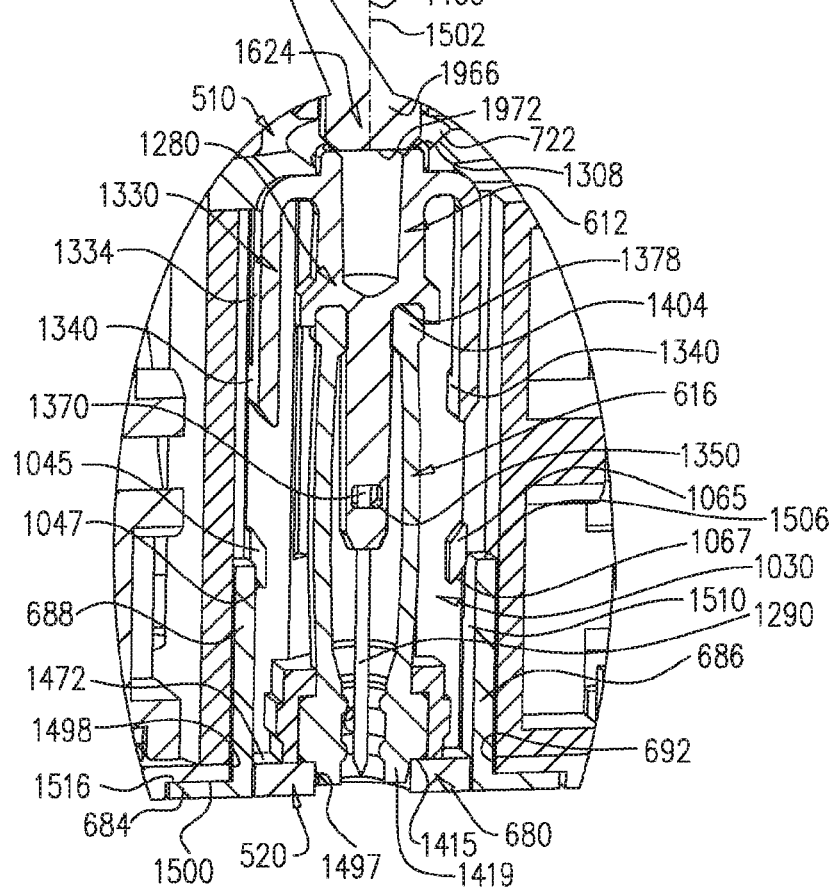
FIG. 42B

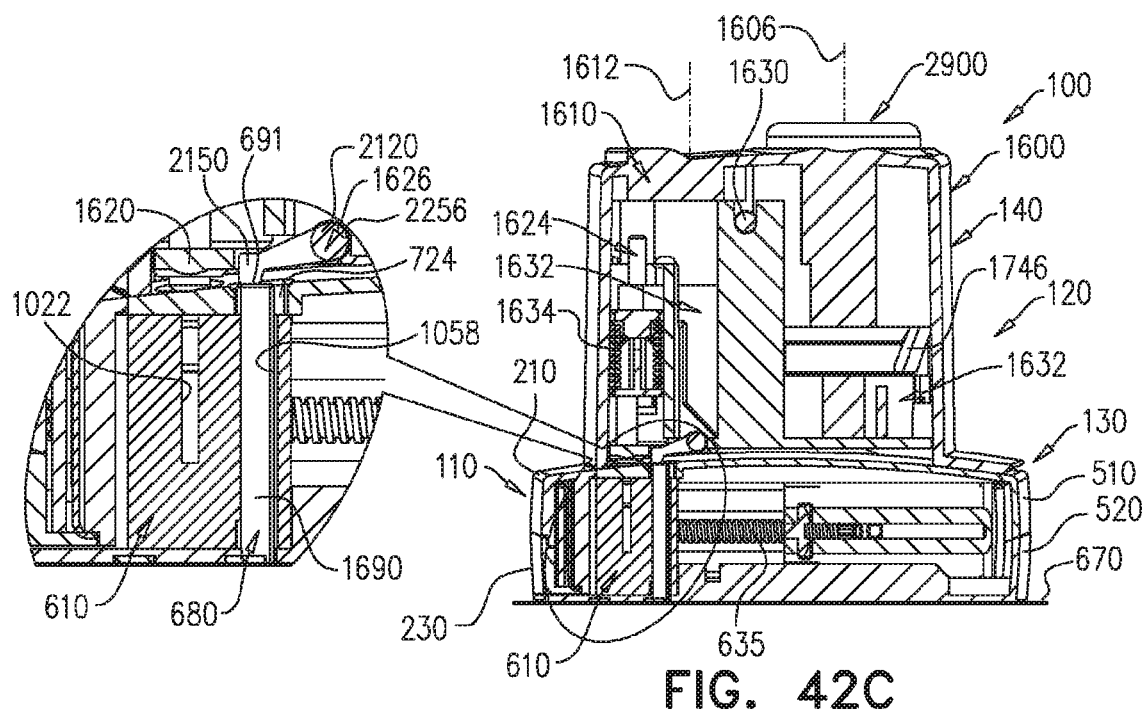
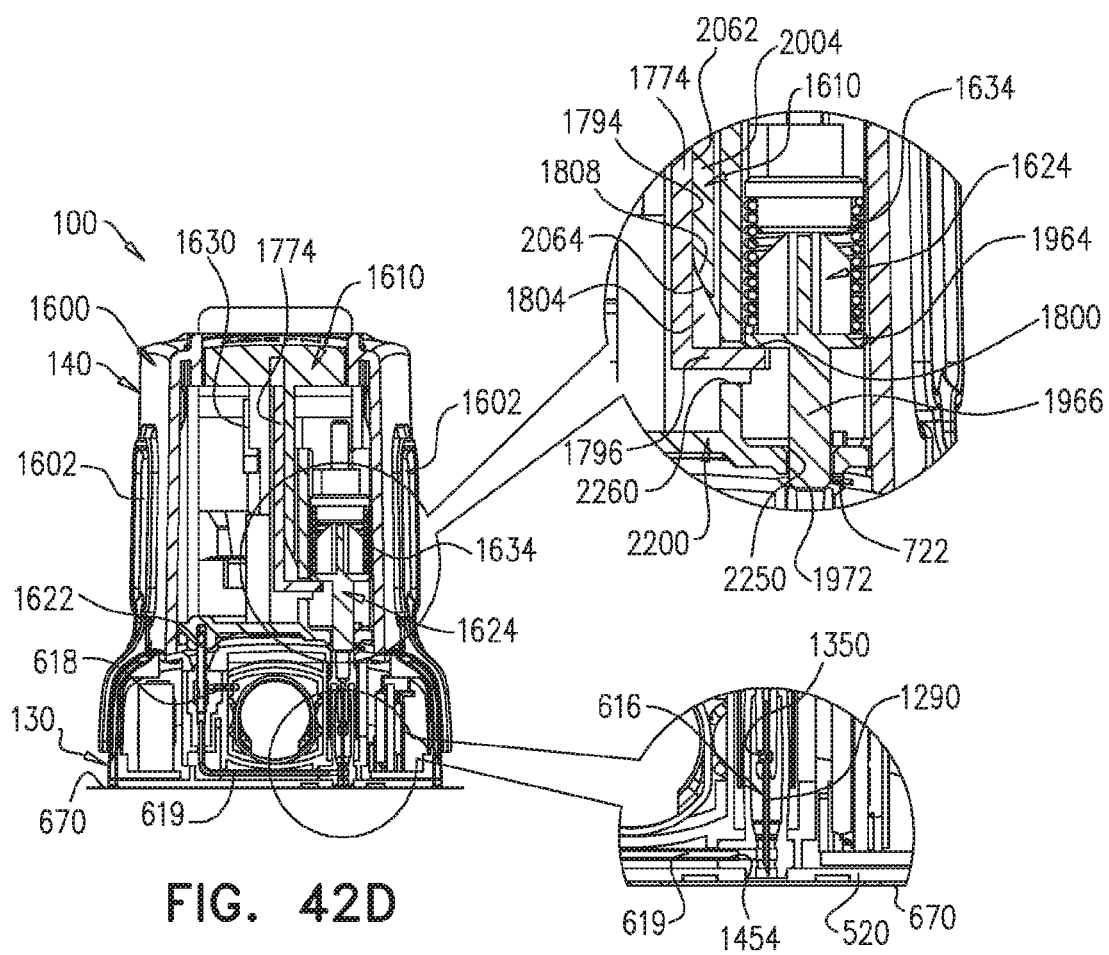
FIG. 42C
FIG. 42D

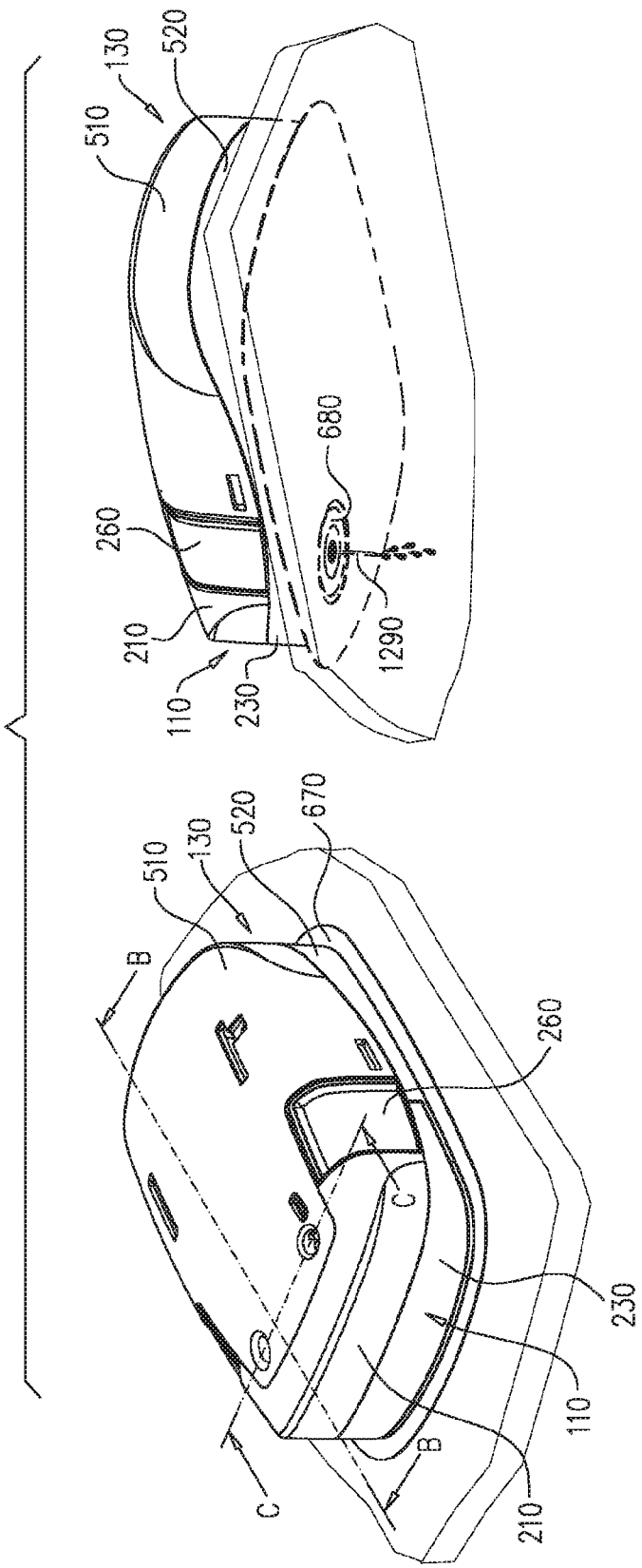

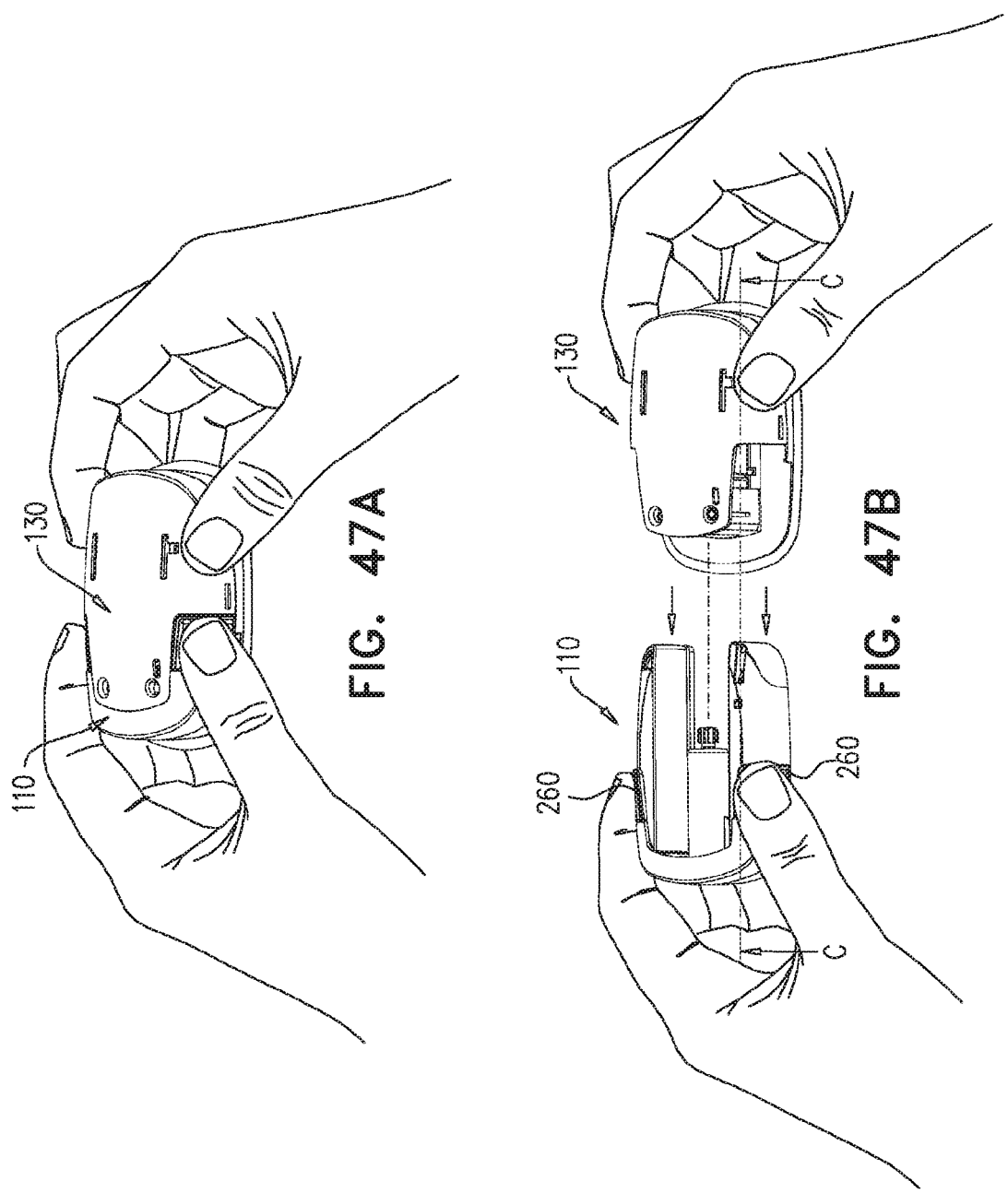

INFUSION PUMP DEVICE AND METHOD FOR USE THEREOF

SUMMARY OF THE INVENTION

The present invention seeks to provide improved infusion and injection devices.

There is thus provided in accordance with an embodiment of the present invention a patch pump including a medicament reservoir having an inner surface defining an elongate piston engagement pathway, an electric motor having a rotary drive output element, a piston replaceably axially fixed to the electric motor, the piston having an outer surface arranged for scaling engagement with the inner surface of the medicament reservoir, the piston also including a rotary to longitudinal drive converter receiving a rotary drive input from the rotary drive output element of the electric motor and providing a longitudinal drive to the reservoir, thereby driving the medicament reservoir in longitudinal motion relative to the piston in which the elongate piston engagement pathway defined by the inner surface of the medicament reservoir is displaced axially and in sealing engagement with the outer surface of said piston.

Preferably, the piston defines at least one medicament passageway and wherein the medicament passageway defines at least one of a medicament inlet and a medicament outlet. Alternatively, the medicament passageway defines both a medicament inlet and a medicament outlet.

Further preferably, electric motor is operative in a first mode of operation in a first rotational direction to draw a medicament into the medicament reservoir via the medicament passageway and is operative in a second mode of operation in a second rotational direction to force medicament out of the medicament reservoir via the medicament passageway.

Still preferably, the patch pump includes a disposable portion and a reusable portion, which are adapted to be selectably operatively coupled to each other.

In accordance with an embodiment of the present invention, the electric motor is operative in the first mode of operation automatically in response to operative engagement of a medicament containing vial therewith. Preferably, patch pump also including a plunger assembly, which is adapted to be part of the reusable portion and to replaceably engage the piston, wherein the piston and the medicament reservoir are adapted to be part of the disposable portion.

Preferably, the rotary to longitudinal drive converter includes a gear, having interior gear teeth and exterior gear teeth, which exterior gear teeth drive a pair of linear driving screws. Further preferably, the medicament reservoir is fixedly attached to a linear displacer, which threadably receives the linear driving screws, wherein rotation of the linear driving screws enables displacement of the linear displacer relative to the piston.

Still preferably, the medicament reservoir includes a portion that is adapted to be detected by an optical sensor, which is adapted to provide a signal to a control system of the patch pump indicating position reference point of the medicament reservoir.

In accordance with an embodiment of the present invention, the patch pump also includes an infusion needle assembly attached to a needle biasing and sealing element, and wherein the infusion needle assembly is adapted to be fluidly coupled to the medicament passageway. Preferably, the infusion needle assembly is adapted to be disposed in a needle retracted operative orientation prior to engagement of the patch pump to an injection site and is adapted to be disposed in a needle penetration operative orientation upon activating needle penetration actuation element, thus driving the infusion needle assembly into the injection site.

Preferably, needle biasing and sealing element is disposed in at rest operative orientation when the infusion needle assembly is disposed in the needle retracted operative orientation, and the needle biasing and sealing element is compressed when the infusion needle assembly is disposed in the needle penetration operative orientation. Further preferably, patch pump also includes a filling septum, which includes a first fluid flow path operatively coupling a medicament containing vial and the medicament reservoir and a second fluid flow path operatively coupling the medicament reservoir and the infusion needle assembly.

Still preferably, the first fluid flow path is operative for aspiration of a medicament into the medicament reservoir and the second fluid flow path is operative for injection of the medicament into the injection site. Yet preferably, the disposable portion includes a needle penetration prevention element, which is configured to lock the needle penetration actuation element prior to the selectable connection of the disposable portion and the reusable portion.

In accordance with an embodiment of the present invention, the disposable portion includes a vial adaptor, which is adapted to be displaced downwardly for operatively receiving a medicament containing vial, only upon connection of the reusable portion to the disposable portion. Preferably, the disposable portion includes a needle actuation penetration pin, which is prevented from driving the infusion needle assembly into an injection site prior to attachment of the patch pump to the injection site.

Preferably, the disposable portion includes a disposable base portion and a disposable interface and control module, which is adapted to be selectably released from the disposable base portion following driving of the infusion needle assembly into the injection site. Further preferably, a medicament containing vial is irremovably locked to the disposable interface and control module upon insertion of the medicament containing vial thereinto.

Yet preferably, aspiration of medicament into the medicament reservoir is initiated upon connection of the reusable portion to the disposable portion and insertion of a medicament containing vial into the disposable portion. Still preferably, a microswitch is activated upon connection of the reusable portion to the disposable portion.

In accordance with an embodiment of the present invention, the medicament containing vial is disposed at a right angle with respect to an injection site during medicament aspiration into the medicament reservoir, thereby providing for automatic priming of the medicament passageway upon initiation of medicament aspiration. Preferably, the disposable portion includes an injection site engagement element which is operative to retain the infusion needle assembly in the needle penetration operative orientation following attachment of the patch pump to an injection site.

Further preferably, the needle biasing and sealing element is sealingly disposed over the infusion needle assembly when the infusion needle assembly is disposed in the needle penetration operative orientation.

Yet further preferably, an optical sensor is provided to detect a reference position of the medicament reservoir. Still preferably, an optical sensor is provided to detect an operative orientation of the infusion needle assembly.

In accordance with an embodiment of the present invention, ejection of medicament from the medicament reservoir is permitted upon removal of the disposable interface and control module from the disposable base portion. Preferably, a microswitch is provided to detect the removal of the disposable interface and control module from the disposable base portion. Further preferably, upon connection of the reusable portion to the disposable portion, the interior gear teeth of the rotary to longitudinal drive converter engage a plurality of exterior teeth of the rotary drive output element. Still further preferably, disengagement of the plurality of exterior teeth from the interior gear teeth is permitted at any point of time during the use of the patch pump.

In accordance with an embodiment of the present invention, a patch pump including an electric motor adapted to be fixedly located with respect to an injection site during injection of a medicament, the electric motor having a drive output element; and a medicament reservoir, the medicament reservoir being displaceable with respect to the electric motor and to the injection site in response to driving thereof by the drive output element. Preferably, the electric motor is adapted to be reusable and the medicament reservoir is adapted to be replaceably coupled to the drive output element and to be disposable.

Preferably, the patch pump also includes a piston arranged in scaling engagement with an interior of the medicament reservoir, the piston being adapted to be fixedly located with respect to the injection site during injection of a medicament, whereby the displacement of the medicament reservoir relative to the piston changes an internal volume of the medicament reservoir. Further preferably, the displacement of the medicament reservoir relative to the piston in a first direction causes the medicament to be dispensed from the medicament reservoir. Still preferably, the displacement of the medicament reservoir relative to the piston in a second direction causes the medicament to be received in the medicament reservoir.

In accordance with an embodiment of the present invention, the piston defines at least one medicament passageway. Preferably, the medicament passageway defines at least one of a medicament inlet and a medicament outlet. Alternatively, the medicament passageway defines both a medicament inlet and a medicament outlet.

Preferably, the patch pump includes a disposable portion and a reusable portion, which are adapted to be selectably operatively coupled to each other. Preferably, the electric motor is operative to initiate rotation in a first direction automatically in response to operative engagement of a medicament containing vial therewith. Further preferably, the patch pump also includes a plunger assembly, which is adapted to be part of the reusable portion and to replaceably engage the piston, wherein the piston and the medicament reservoir are adapted to be part of the disposable portion.

Yet preferably, the piston includes a rotary to longitudinal drive converter, which has a gear, having interior gear teeth and exterior gear teeth, which exterior gear teeth drive a pair of linear driving screws. Still preferably, the medicament reservoir is fixedly attached to a linear displacer, which threadably receives the linear driving screws, wherein rotation of the linear driving screws enables displacement of the linear displacer relative to the piston.

In accordance with an embodiment of the present invention, the medicament reservoir includes a portion that is adapted to be detected by an optical sensor, which is adapted to provide a signal to a control system of the patch pump indicating position reference point of the medicament reservoir. Preferably, the patch pump also includes an infusion needle assembly attached to a needle biasing and sealing element, and wherein the infusion needle assembly is adapted to be fluidly coupled to the medicament passageway. Further preferably, the infusion needle assembly is adapted to be disposed in a needle retracted operative orientation prior to engagement of the patch pump to the injection site and is adapted to be disposed in a needle penetration operative orientation upon activating needle penetration actuation element, thus driving the infusion needle assembly into the injection site.

Still preferably, the needle biasing and sealing element is disposed in at rest operative orientation when the infusion needle assembly is disposed in the needle retracted operative orientation, and the needle biasing and sealing element is compressed when the infusion needle assembly is disposed in the needle penetration operative orientation.

In accordance with an embodiment of the present invention, the patch pump also includes a filling septum, which includes a first fluid flow path operatively coupling a medicament containing vial and the medicament reservoir and a second fluid flow path operatively coupling the medicament reservoir and the infusion needle assembly.

Preferably, the first fluid flow path is operative for aspiration of a medicament into the medicament reservoir and the second fluid flow path is operative for injection of the medicament into the injection site. Further preferably, the disposable portion includes a needle penetration prevention element, which is configured to lock the needle penetration actuation element prior to the selectable connection of the disposable portion and the reusable portion.

Still preferably, aspiration of medicament into the medicament reservoir is initiated upon connection of the reusable portion to the disposable portion and insertion of a medicament containing vial into the disposable portion. Preferably, a microswitch is activated upon connection of the reusable portion to the disposable portion.

Preferably, an optical sensor is provided to detect a reference position of the medicament reservoir. Further preferably, an optical sensor is provided to detect an operative orientation of the infusion needle assembly.

In accordance with an embodiment of the present invention, a patch pump including a base which is removably mountable onto an injection site; an electric motor having a drive output element, the electric motor being fixed with respect to the base; and a medicament reservoir, the medicament reservoir being linearly displaceable with respect to the base in response to driving thereof by the drive output element. Preferably, the patch pump also includes a piston, which is fixed with respect to the base, and which cooperates with the medicament reservoir, whereby linear displacement of the medicament reservoir relative to the base and to the piston causes medicament to be forced out of the medicament reservoir. Further preferably, the piston includes a medicament passageway, the pump also including an infusion needle assembly which is displaceable relative to the base and which is coupled to the medicament passageway.

Further preferably, the base and the electric motor are adapted to be reusable and the medicament reservoir is adapted to be replaceably coupled to the drive output element.

Preferably, the medicament passageway defines at least one of a medicament inlet and a medicament outlet. Alternatively, the medicament passageway defines both a medicament inlet and a medicament outlet.

In accordance with an embodiment of the present invention, and wherein the electric motor is operative in a first mode of operation in a first rotational direction to draw a medicament into the medicament reservoir via the medicament passageway and is operative in a second mode of operation in a second rotational direction to force medicament out of the medicament reservoir via the medicament passageway.

Preferably, the patch pump includes a disposable portion and a reusable portion, which are adapted to be selectably operatively coupled to each other. Further preferably, the electric motor is operative in the first mode of operation automatically in response to operative engagement of a medicament containing vial therewith.

Further preferably, the medicament reservoir includes a portion that is adapted to be detected by an optical sensor, which is adapted to provide a signal to a control system of the patch pump indicating position reference point of the medicament reservoir.

Still preferably, the infusion needle assembly is adapted to be disposed in a needle retracted operative orientation prior to engagement of the patch pump to the injection site and is adapted to be disposed in a needle penetration operative orientation upon activating needle penetration actuation element, thus driving the infusion needle assembly into the injection site.

In accordance with an embodiment of the present invention, the patch pump also includes a filling septum, which includes a first fluid flow path operatively coupling a medicament containing vial and the medicament reservoir and a second fluid flow path operatively coupling the medicament reservoir and the infusion needle assembly. Preferably, the first fluid flow path is operative for aspiration of a medicament into the medicament reservoir and the second fluid flow path is operative for injection of the medicament into the injection site.

Preferably, the disposable portion includes a needle penetration prevention element, which is configured to lock the needle penetration actuation element prior to the selectable connection of the disposable portion and the reusable portion. Further preferably, the disposable portion includes a vial adaptor, which is adapted to be displaced downwardly for operatively receiving a medicament containing vial, only upon connection of the reusable portion to the disposable portion.

Further preferably, the disposable portion includes a needle actuation penetration pin, which is prevented from driving the infusion needle assembly into the injection site prior to attachment of the patch pump to the injection site.

In accordance with an embodiment of the present invention, aspiration of medicament into the medicament reservoir is initiated upon connection of the reusable portion to the disposable portion and insertion of a medicament containing vial into the disposable portion.

Preferably, a microswitch is activated upon connection of the reusable portion to the disposable portion.

Further preferably, the medicament containing vial is disposed at a right angle with respect to the injection site during medicament aspiration into the medicament reservoir, thereby providing for automatic priming of the medicament passageway upon initiation of medicament aspiration.

Still preferably, the disposable portion includes an injection site engagement element which is operative to retain the infusion needle assembly in the needle penetration operative orientation following attachment of the patch pump to the injection site.

Yet preferably, an optical sensor is provided to detect a reference position of the medicament reservoir. Still preferably, an optical sensor is provided to detect an operative orientation of the infusion needle assembly.

Preferably, upon connection of the reusable portion to the disposable portion, the piston is operatively engaged with the drive output element. Further preferably, disengagement of the drive output element and the piston is permitted at any point of time during the use of the patch pump.

In accordance with an embodiment of the present invention, a patch pump including an electric motor having a rotary drive output element; a medicament reservoir; and a piston having an outer surface arranged for sealing mutually linearly displaceable engagement with the medicament reservoir for dispensing medicament therefrom, the piston also comprising a rotary to longitudinal drive converter receiving a rotary drive input from the rotary drive output element and providing a linear driving output producing linear displacement between the piston and the reservoir.

Preferably, the piston defines at least one medicament passageway. Further preferably, the medicament passageway defines at least one of a medicament inlet and a medicament outlet. Alternatively, the medicament passageway defines both a medicament inlet and a medicament outlet.

Still preferably, the electric motor is operative in a first mode of operation in a first rotational direction to draw a medicament into the medicament reservoir via the medicament passageway and is operative in a second mode of operation in a second rotational direction to force medicament out of the medicament reservoir via the medicament passageway.

In accordance with an embodiment of the present invention, the patch pump includes a disposable portion and a reusable portion, which are adapted to be selectably operatively coupled to each other. Preferably, the electric motor is operative in the first mode of operation automatically in response to operative engagement of a medicament containing vial therewith.

Further preferably, the rotary to longitudinal drive converter includes a gear, having interior gear teeth and exterior gear teeth, which exterior gear teeth drive a pair of linear driving screws. Still preferably, the medicament reservoir is fixedly attached to a linear displacer, which threadably receives the linear driving screws, wherein rotation of the linear driving screws enables displacement of the linear displacement relative to the piston.

Preferably, the medicament reservoir includes a portion that is adapted to be detected by an optical sensor, which is adapted to provide a signal to a control system of the patch pump indicating position reference point of the medicament reservoir. Further preferably, patch pump also includes an infusion needle assembly attached to a needle biasing and sealing element, and wherein the infusion needle assembly is adapted to be fluidly coupled to the medicament passageway.

Still preferably, the infusion needle assembly is adapted to be disposed in a needle retracted operative orientation prior to engagement of the patch pump to an injection site and is adapted to be disposed in a needle penetration operative orientation upon activating needle penetration actuation element, thus driving the infusion needle assembly into the injection site.

Yet preferably, the needle biasing and sealing element is disposed in at rest operative orientation when the infusion needle assembly is disposed in the needle retracted operative orientation, and the needle biasing and sealing element is compressed when the infusion needle assembly is disposed in the needle penetration operative orientation.

In accordance with an embodiment of the present invention, the patch pump also includes a filling septum, which includes a first fluid flow path operatively coupling a medicament containing vial and the medicament reservoir and a second fluid flow path operatively coupling the medicament reservoir and the infusion needle assembly.

Preferably, the first fluid flow path is operative for aspiration of a medicament into the medicament reservoir and the second fluid flow path is operative for injection of the medicament into the injection site. Further preferably, aspiration of medicament into the medicament reservoir is initiated upon connection of the reusable portion to the disposable portion and insertion of a medicament containing vial into the disposable portion.

Still preferably, a microswitch is activated upon connection of the reusable portion to the disposable portion. Yet preferably, the medicament containing vial is disposed at a right angle with respect to an injection site during medicament aspiration into the medicament reservoir, thereby providing for automatic priming of the medicament passageway upon initiation of medicament aspiration.

Preferably, the disposable portion includes an injection site engagement element which is operative to retain the infusion needle assembly in the needle penetration operative orientation following attachment of the patch pump to an injection site. Further preferably, the needle biasing and sealing element is sealingly disposed over the infusion needle assembly when the infusion needle assembly is disposed in the needle penetration operative orientation.

In accordance with an embodiment of the present invention, an optical sensor is provided to detect a reference position of the medicament reservoir. Preferably, an optical sensor is provided to detect an operative orientation of the infusion needle assembly. Further preferably, upon connection of the reusable portion to the disposable portion, the interior gear teeth of the rotary to longitudinal drive converter engage a plurality of exterior teeth of the rotary drive output element. Still preferably, disengagement of the plurality of exterior teeth from the interior gear teeth is permitted at any point of time during the use of the patch pump.

In accordance with an embodiment of the present invention, the patch pump includes a medicament reservoir, and an electric motor having a rotary drive output element and being operative in a first mode of operation in a first rotational direction to draw a medicament into the medicament reservoir and in a second mode of operation in a second rotational direction to dispense medicament from the medicament reservoir, the electric motor being operative in the first mode of operation automatically in response to operative engagement of a medicament-containing vial therewith.

Preferably, the patch pump also includes a piston, which is fixed with respect to the electric motor, and which cooperates with the medicament reservoir, whereby linear displacement of the medicament reservoir relative to the electric motor and to the piston causes medicament to be forced out of the medicament reservoir. Further preferably, the piston includes a medicament passageway, the pump also includes an infusion needle assembly which is coupled to the medicament passageway.

Preferably, the electric motor is adapted to be reusable and the medicament reservoir is adapted to be replaceably coupled to the drive output element. Further preferably, the medicament passageway defines at least one of a medicament inlet and a medicament outlet. Alternatively, the medicament passageway defines both a medicament inlet and a medicament outlet.

In accordance with an embodiment of the present invention, the patch pump includes a disposable portion and a reusable portion, which are adapted to be selectably operatively coupled to each other.

Preferably, the piston having an outer surface arranged for sealing mutually linearly displaceable engagement with the medicament reservoir for dispensing medicament therefrom, the piston also including a rotary to longitudinal drive converter receiving a rotary drive input from the rotary drive output element and providing a linear driving output producing linear displacement between the piston and the reservoir.

Further preferably, the medicament reservoir includes a portion that is adapted to be detected by an optical sensor, which is adapted to provide a signal to a control system of the patch pump indicating position reference point of the medicament reservoir.

Still preferably, the infusion needle assembly is adapted to be disposed in a needle retracted operative orientation prior to engagement of the patch pump to the injection site and is adapted to be disposed in a needle penetration operative orientation upon activating needle penetration actuation element, thus driving the infusion needle assembly into the injection site.

In accordance with an embodiment of the present invention, the patch pump also includes a filling septum, which includes a first fluid flow path operatively coupling a medicament containing vial and the medicament reservoir and a second fluid flow path operatively coupling the medicament reservoir and the infusion needle assembly. Preferably, the first fluid flow path is operative for aspiration of a medicament into the medicament reservoir and the second fluid flow path is operative for injection of the medicament into the injection site.

Further preferably, the disposable portion includes a vial adaptor, which is adapted to be displaced downwardly for operatively receiving a medicament containing vial, only upon connection of the reusable portion to the disposable portion.

Still preferably, a microswitch is activated upon connection of the reusable portion to the disposable portion. Yet preferably, the disposable portion includes an injection site engagement element which is operative to retain the infusion needle assembly in the needle penetration operative orientation following attachment of the patch pump to the injection site.

In accordance with an embodiment of the present invention, an optical sensor is provided to detect a reference position of the medicament reservoir. Preferably, an optical sensor is provided to detect an operative orientation of the infusion needle assembly. Further preferably, upon connection of the reusable portion to the disposable portion, the piston is operatively engaged with the drive output element. Yet preferably, disengagement of the drive output element and the piston is permitted at any point of time during the use of the patch pump.

BRIEF DESCRIPTION OF THE DRAWINGS

The present invention will be understood and appreciated more fully from the following detailed description, taken in conjunction with the drawings in which:

FIGS. 3A, 3B, 3C and 3D are simplified illustrations of a reusable portion of the patch pump assembly of FIG. 1;

FIGS. 5A, 5B, 5C, 5D & 5E are simplified illustrations of a main housing portion, forming part of the reusable portion of the patch pump assembly of FIGS. 1-4;

FIGS. 6A and 6B are simplified pictorial illustrations of an internal subassembly forming part of the reusable portion of the patch pump assembly of FIGS. 1-4;

FIGS. 12A, 12B, 12C & 12D are simplified pictorial illustrations of a medicament reservoir of the disposable base portion of the patch pump assembly of FIGS. 1 and 2;

FIGS. 13A, 13B, 13C & 13D are simplified pictorial illustrations of a linear displacer fixedly attached to the medicament reservoir of the disposable base portion of the patch pump assembly of FIGS. 1 and 2;

FIGS. 15A, 15B, 15C, 15D, 15E & 15F are simplified illustrations of a piston base element, forming part of the piston assembly of FIG. 14;

FIGS. 16A, 16B, 16C, 16D & 16E are simplified illustrations the piston assembly including the rotary to longitudinal drive converter as seen in FIG. 14;

FIGS. 18A, 18B, 18C, 18D, 18E, 18F, 18G, 18H, 18I, 18J, 18K and 18L are simplified illustrations of a housing element of the medicament supply and infusion assembly;

FIGS. 19A, 19B, 19C & 19D are simplified illustrations of a medicament filling septum, forming part of the medicament supply and infusion assembly of FIGS. 17A & 17B;

FIGS. 20A, 20B, 20C, 20D, 20E and 20F are simplified illustrations of a medicament infusion needle assembly, forming part of the medicament supply and infusion assembly of FIGS. 17A & 17B;

FIGS. 24A, 24B, 24C & 24D are simplified pictorial illustrations of an injection site engagement element of the disposable base portion of the patch pump assembly of FIGS. 1 and 2;

FIGS. 28A, 28B, 28C, 28D, 28E and 28F are simplified illustrations of a vial adaptor portion, forming part of the disposable interface and control module of FIGS. 25A-26;

FIGS. 34A-34D are simplified illustrations of an assembled reusable portion of the patch pump assembly of FIG. 1;

FIGS. 35A-35J are simplified illustrations of an assembled disposable base portion of the patch pump assembly of FIG. 1;

FIGS. 36A-36I are simplified illustrations of an assembled disposable interface and control module of the patch pump assembly of FIG. 1;

FIGS. 37A-37H are simplified illustrations of the patch pump assembly of FIGS. 1-36I in a storage operative orientation;

FIGS. 38A-38F are simplified illustrations of the patch pump assembly of FIGS. 1-36I in a pre-vial insertion operative orientation;

FIG. 41 is a simplified illustrations of the patch pump assembly of FIGS. 1-36I in a pre-injection site engagement operative orientation;

FIGS. 42A-42F are simplified illustrations of the patch pump assembly of FIGS. 1-36I in an injection site engagement operative orientation;

FIGS. 45A-45C are simplified illustrations of the patch pump assembly of FIGS. 1-36I in an intermediate injection operative orientation;

FIGS. 47A-47C are simplified illustrations of the patch pump assembly of FIGS. 1-36I in a reusable portion/disposable portion disengagement operative orientation.

DETAILED DESCRIPTION OF EMBODIMENTS OF THE INVENTION

Figure 1:
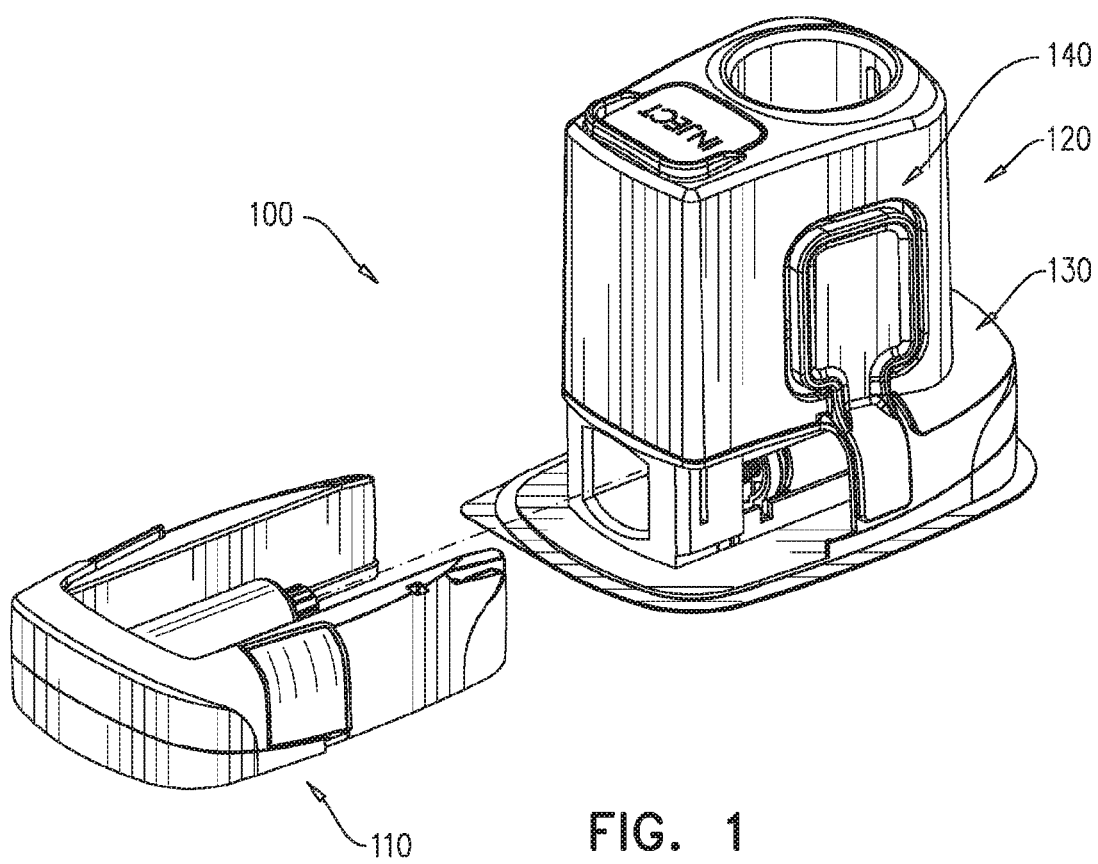
FIG. 1 is a simplified pictorial illustration of a patch pump assembly constructed and operative in accordance with a preferred embodiment of the present invention.
Figure 2:
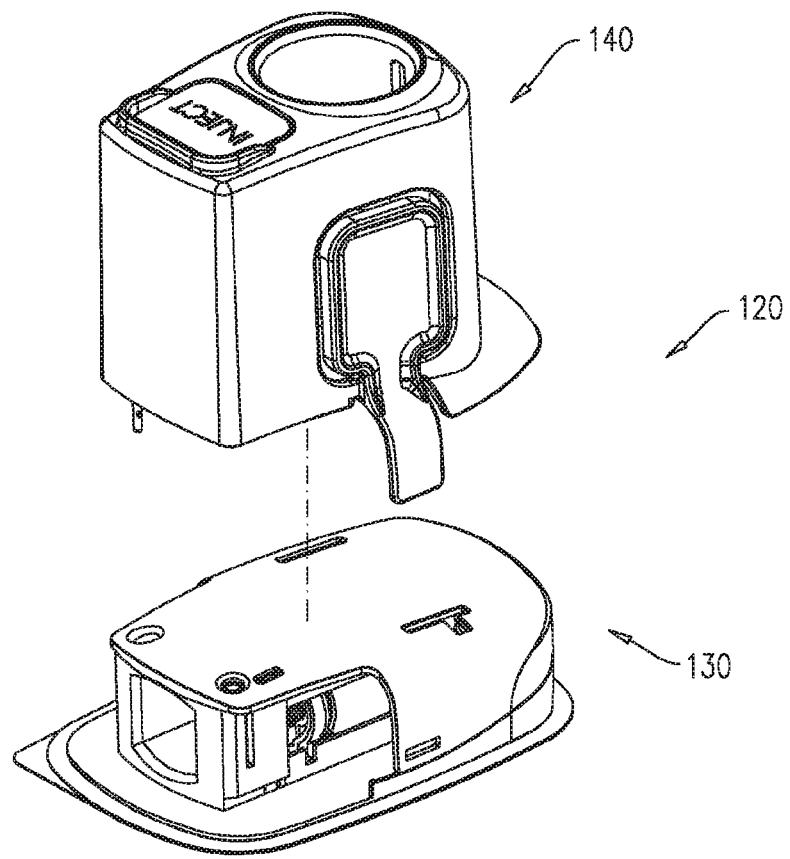
FIG. 2 is a simplified pictorial illustration of a disposable portion of the patch pump assembly of FIG. 1 in a disassembled operative orientation.

Reference is now made to FIGS. 1 and 2, which are simplified pictorial illustrations of a patch pump assembly constructed and operative in accordance with a preferred embodiment of the present invention.

As seen in FIG. 1, there is provided patch pump assembly 100 including a reusable portion 110, which is adapted for repeated use, and a disposable portion 120, which is not adapted for repeated use and is intended to be replaced upon each use. As seen in FIG. 2, the disposable portion 120 comprises a disposable base portion 130 and a disposable interface and a control module 140, which is removably mounted onto the disposable base portion 130.

Figure 4:
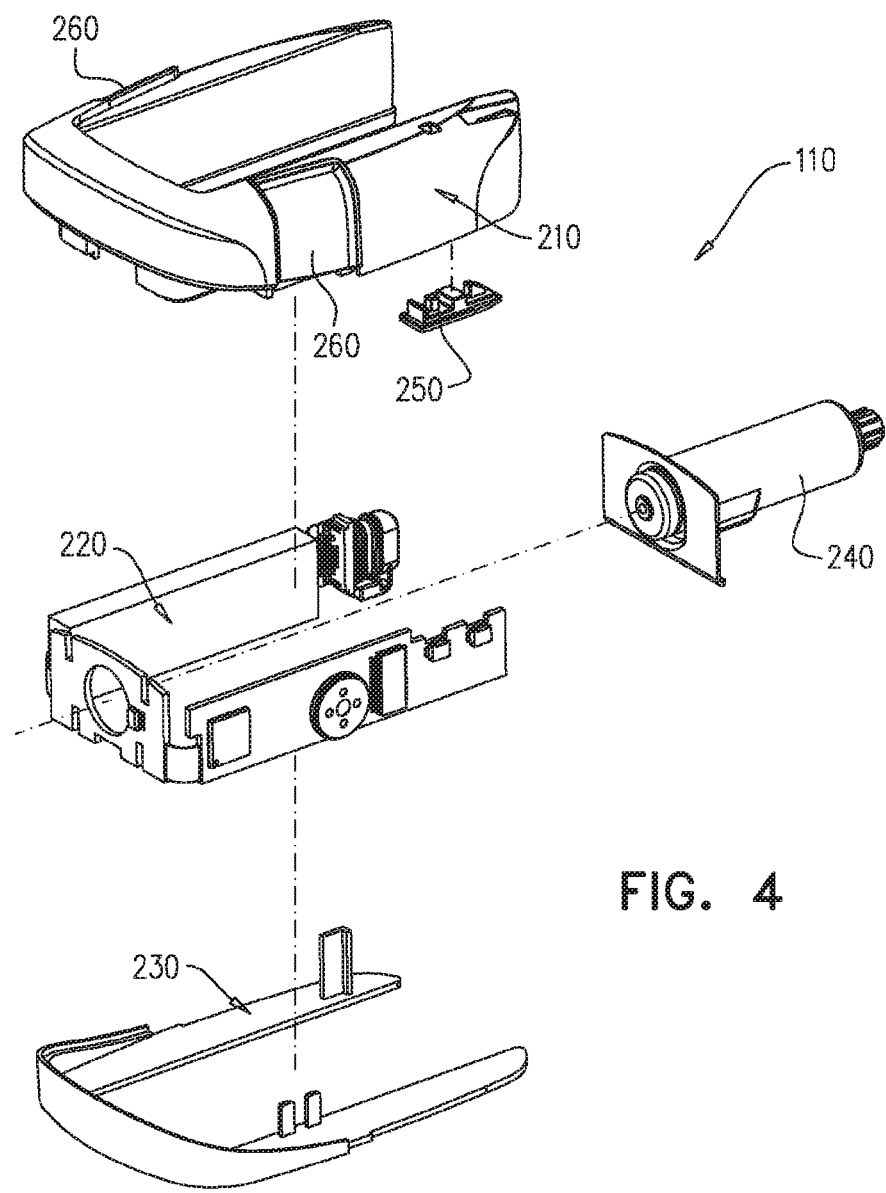
FIG. 4 is a simplified exploded view illustration of the reusable portion of the patch pump assembly as seen in FIGS. 3A-3D.

Reference is now made to FIGS. 3A, 3B, 3C and 3D, which are simplified illustrations of the reusable portion 110 (FIG. 1). FIG. 3A is a simplified pictorial illustration, FIGS. 3B & 3C are two different plan views, downwardly facing and upwardly facing respectively and FIG. 3D is a rearwardly facing end view of reusable portion 110. Reference is additionally made to FIG. 4, which is a simplified exploded view illustration of the reusable portion 110 of the patch pump assembly 100 as seen in FIGS. 3A-3D.

As seen in FIGS. 3A-4, the reusable portion 110 includes a main housing portion 210, an internal subassembly 220, a bottom housing portion 230, a plunger assembly 240 and a sealing element 250. A pair of manually actuable buttons 260 cooperate with main housing portion 210.

Reference is now made to FIGS. 5A, 5B, 5C, 5D & 5E, which are simplified illustrations of the main housing portion 210 (FIG. 4), forming part of the reusable portion 110 of the patch pump assembly 100 of FIGS. 1-4. FIGS. 5A-5E are simplified respective pictorial, top plan view, bottom plan view, planar rearward facing end view and a sectional illustration taken along lines E-E in FIG. 5A of the main housing portion 210.

As seen in FIGS. 5A-5E, main housing portion 210 preferably is an integrally formed element, preferably injection molded of plastic and is arranged along longitudinal axis of symmetry 270.

It is seen in FIGS. 5A-5E that main housing portion 210 is preferably U-shaped, having a base portion 280 and two generally hollow arm portions 282 and 284 generally extending rearwardly from base portion 280, and are preferably parallel to longitudinal axis 270. The underside of base portion 280 and arm portions 282 and 284 preferably defines an inner volume 285. It is appreciated that in accordance with one embodiment of the present invention, the manually actuable buttons 260 are attachable to each of arm portions 282 and 284 and cooperate therewith. In accordance with an alternative embodiment of the present invention, the manually actuable buttons 260 are integrally made with main housing portion 210 and cooperate therewith.

Each of arm portions 282 and 284 has an upwardly facing generally planar surface 286, an outwardly facing generally curved surface 288 and an inner facing generally planar surface 290, all joining at a generally curved rearward facing end surface 292.

It is particularly seen in FIG. 5C that a recess 293 is formed on each of arm portions 282 and 284 defining an outwardly facing wall portion 294, which stop the displacement of manually actuable buttons 260.

It is further seen in FIGS. 5A-5E that base portion 280 extends slightly upwardly with respect to arm portions 282 and 284, thus forming a generally curved rearwardly facing rim 296 adapted to serve as a stopper when connecting the main housing portion 210 of the reusable portion 110 with the compatible disposable base portion 130 of the disposable portion 110.

It is further seen in FIGS. 5A-5E that arm portion 284 has a cut-out 298 formed at its rearward facing end surface 292 and extending forwardly therefrom, defining an upwardly facing surface 299 and terminating in aperture 300. Aperture 300 extends along an axis, which is transversely disposed with respect to longitudinal axis 270. It is appreciated that aperture 300 communicates with inner volume 285 of the main housing portion 210 and is configured for insertion of a micro-switch or a sensor thereinto.

An additional aperture 302 is formed preferably slightly forwardly from aperture 300. It is appreciated that aperture 302 also communicates with inner volume 285 of the main housing portion 210 and is formed for insertion of a micro-switch or a sensor thereinto.

A recess 304 is formed adjacent rearward facing end surface 292 of arm portion 282. Additionally, a socket 306 is formed at rearward facing end surface 292 and extending forwardly therefrom along an axis, which is preferably parallel to longitudinal axis 270. It is appreciated that socket 306 serves for insertion of a USB connector thereinto. Socket 306 preferably communicates with the inner volume 285 defined by the underside of base portion 280 and arm portions 282 and 284. It is appreciated that the USB connector is adapted for recharging of a battery of the patch pump assembly 100 and upload/download data to/from a remote computing device through the USB connector.

A slot 308 is preferably formed on the inner facing planar surface 290 of arm portion 284 and communicates with inner volume 285.

It is seen in FIGS. 5A-5E that base portion 280 defines a forwardly facing wall 312 and additional wall 314 rearwardly spaced therefrom. A cut-out 316 is formed through wall 314, the cut out 316 communicates with inner volume 285 and is adapted for insertion of a portion of the plunger assembly 240 therethrough.

It is additionally seen in FIG. 5E that underside of base portion 280 and arm portions 282 and 284 define a downwardly facing circumferential edge 318 adapted for connection with bottom housing portion 230.

It is seen particularly in FIG. 5C that manually actuable buttons 260 include a rearwardly facing edge 320 and an outwardly extending protrusion 322 formed thereon and adapted to serve as a locking portion while connecting the reusable portion 110 with the disposable portion 120.

Reference is now made to FIGS. 6A and 6B, which are simplified pictorial illustrations of the internal subassembly 220 (FIG. 4) forming part of the reusable portion 110 of the patch pump assembly 100 of FIGS. 1-4 and are shown from two different perspectives, FIG. 6A is a pictorial forward-facing view illustration. FIG. 6B is a pictorial side-facing view illustration of the internal subassembly 220.

As seen in FIGS. 6A & 6B, the internal subassembly 220 is preferably arranged along longitudinal axis of symmetry 270.

It is seen in FIGS. 6A & 6B that internal subassembly 220 preferably includes a base PCB portion 340 having a bore 342 formed therein for insertion of a portion of the plunger assembly 240 therethrough. It is additionally seen that a sensor, such as a hall effect sensor 344 is positioned on the base PCB portion 340, preferably adjacent to bore 342. It is appreciated that sensor 344 provides an indication of angular displacement and rotation direction of the electric motor.

It is additionally seen in FIGS. 6A & 6B that a side PCB portion 346 is adapted to be coupled with the base PCB portion 340 by a flex cable 348. Base PCB portion 340 is additionally operatively coupled with a battery 350 and a USB connector 352 by flex cable 354.

It is seen in FIGS. 6A & 6B that a sealing element 356, preferably formed of rubber, is provided adjacent the USB connector 352 in order to fluidly seal connector 352.

It is appreciated that a plurality of electrical components is formed on the side PCB portion 346. In accordance with an embodiment of the present invention, a CPU 360, optical sensor 362, speaker 364, real time clock 366 and a motor driver 368 are all disposed on side PCB portion 346.

It is further appreciated that optical sensor 362 is adapted to detect the operative orientation of the needle of the patch pump assembly.

It is additionally seen that side PCB portion 346 also includes preferably two recesses 370 adjacent a rearward end 372 thereof. It is appreciated that an on/off microswitch 374 is positioned on an outer surface 376 of side PCB portion 346 and adjacent recess 370, such that the operative portion of the on/off microswitch 374 is exposed through recess 370. Additionally, a vial microswitch 378 is positioned on the outer surface 376 of side PCB portion 346 adjacent on/off microswitch 374 and adjacent second recess 370, such that the operative portion of the vial microswitch 378 is exposed through recess 370.

Figure 7A:
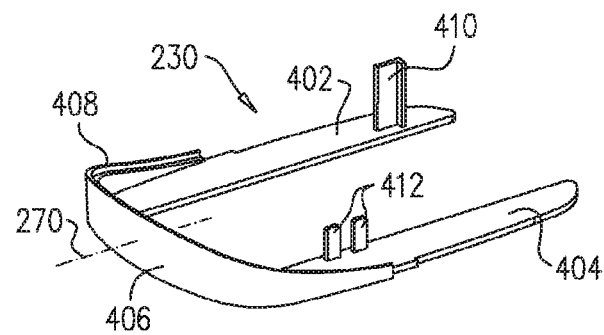
FIGS. 7A, 7B and 7C are simplified illustrations of a bottom housing portion, forming part of the reusable portion of the patch pump assembly of FIGS. 1-4.
Figure 7B:
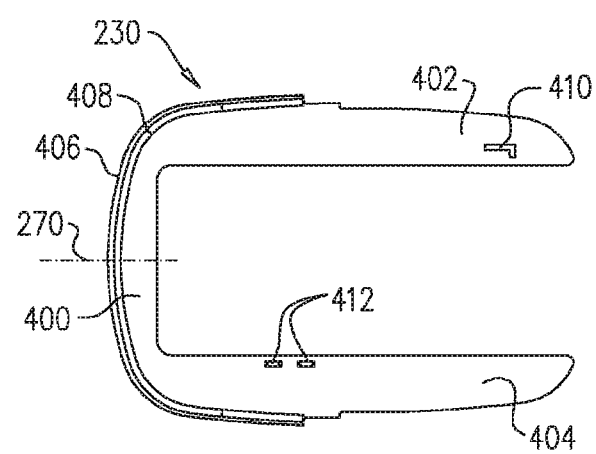
Figure 7C:
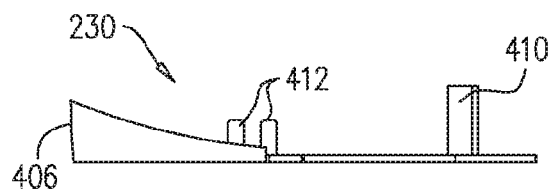

Reference is now made to FIGS. 7A, 7B and 7C, which are simplified illustrations of bottom housing portion 230 (FIG. 4), forming part of the reusable portion 110 of the patch pump assembly 100 of FIGS. 1-4. FIGS. 7A-7C are simplified respective pictorial, top and side plan view illustrations of the bottom housing portion 230.

As seen in FIGS. 7A-7C, bottom housing portion 230 preferably is an integrally formed element, preferably injection molded of plastic and is arranged along longitudinal axis of symmetry 270.

It is seen in FIGS. 7A-7C that bottom housing portion 230 is preferably U-shaped, having a base portion 400 and two generally planar arm portions 402 and 404 generally extending rearwardly from base portion 400, and are preferably parallel to longitudinal axis 270. Arm portions 402 and 404 are joined by the base portion 400. A generally curved wall portion 406 extends upwardly from base portion 400 and defines an upwardly facing rim 408 adapted for connection with the underside of main housing portion 210.

An upwardly extending protrusion 410 is formed adjacent to a rearward end of arm portion 402, and is adapted for retaining the USB connector 352 forming part of the internal subassembly 220.

It is additionally seen that two axially spaced upwardly extending protrusions 412 are formed adjacent base portion 400 and are adapted for operative engagement with optical sensor 362, forming part of the internal subassembly 220.

Figure 8A:
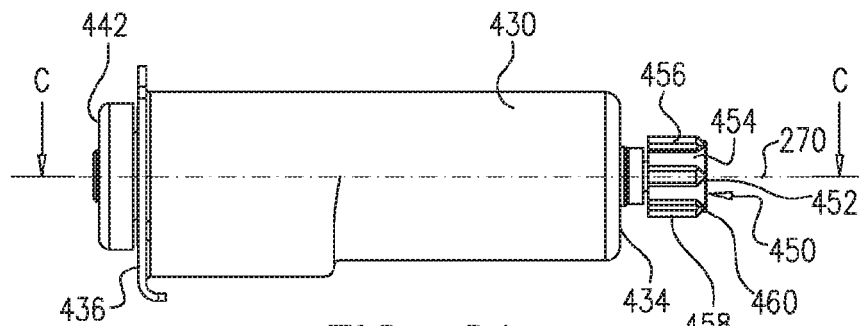
FIGS. 8A, 8B and 8C are simplified illustrations of a plunger assembly forming part of the reusable portion of the patch pump assembly of FIGS. 1-4.
Figure 8B:
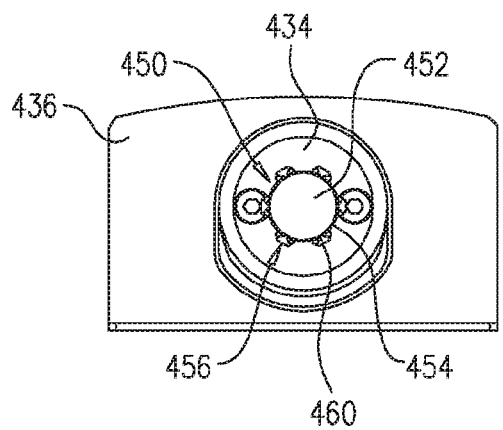
Figure 8C:
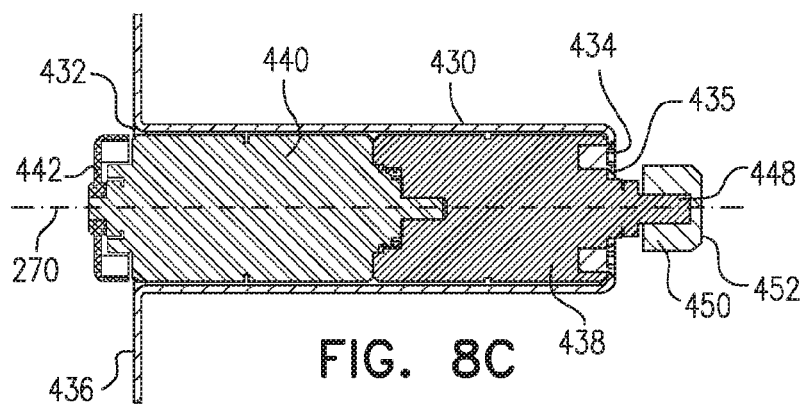

Reference is now made to FIGS. 8A, 8B and 8C, which are simplified illustrations of plunger assembly 240 (FIG. 4), forming part of the reusable portion 110 of the patch pump assembly 100 of FIGS. 1-4. FIGS. 8A-8C are simplified respective plan top view, rearward-facing end view and a sectional illustration taken along lines C-C in FIG. 8A of the plunger assembly 240.

Plunger assembly 240 is preferably arranged along longitudinal axis 270.

It is seen in FIGS. 8A-8C that plunger assembly 240 includes a hollow generally cylindrical container element 430 having an open forward end 432 and a partially closed rearward end 434 having an opening 435. An outwardly extending flange 436 extends from forward end 432.

It is particularly seen in FIG. 8C that a gear 438 and an electric motor 440 operatively connected thereto, are enclosed within container element 430. A magnetic element 442 is operatively coupled to motor 440 at its forward end for cooperation with hall effect sensor 344, which forms part of the internal subassembly 220.

The gear 438 has a protrusion 448 at its rearward end, which protrudes through opening 435 of the container element 430.

A drive element 450 is mounted onto protrusion 448 of gear 438. It is seen that drive element 450 has a rearwardly facing surface 452 and a circumferential outwardly facing surface 454 having a plurality of mutually azimuthally spaced teeth 456 formed thereon. The teeth 456 generally extend along an axis, which is parallel to longitudinal axis 270 and having a generally planar portion 458 and a generally rearwardly tapered portion 460 extending rearwardly therefrom and positioned preferably adjacent rearwardly facing surface 452.

Reference is now made to FIGS. 9A, 9B, 9C and 9D, which are simplified illustrations of the sealing element 250 (FIG. 4), forming part of the reusable portion 110 of the patch pump assembly 100 of FIGS. 1-4. FIGS. 9A-9D are simplified respective pictorial, top plan view, bottom plan view and side plan view illustrations of the sealing element 250.

As seen in FIGS. 9A-9D, sealing element 250 preferably is an integrally formed element, preferably made of rubber.

Sealing element 250 is adapted to be mounted between the main housing portion 210 and the internal subassembly 220 in order to seal and protect micro-switches 374 and 378.

Figure 9A:
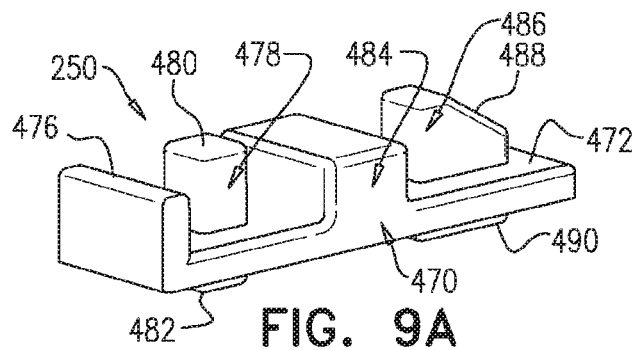
FIGS. 9A, 9B, 9C and 9D are simplified illustrations of a sealing element forming part of the reusable portion of the patch pump assembly of FIGS. 1-4.
Figure 9B:
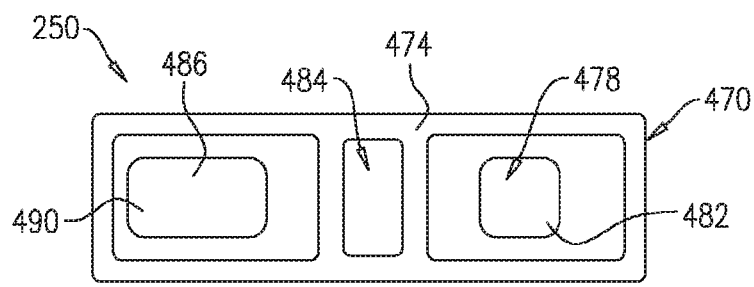
Figure 9C:
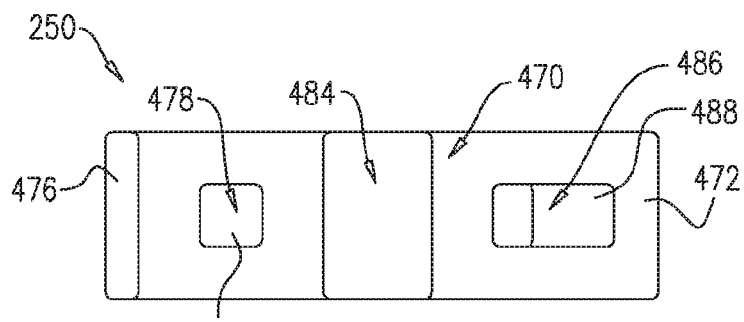
Figure 9D:
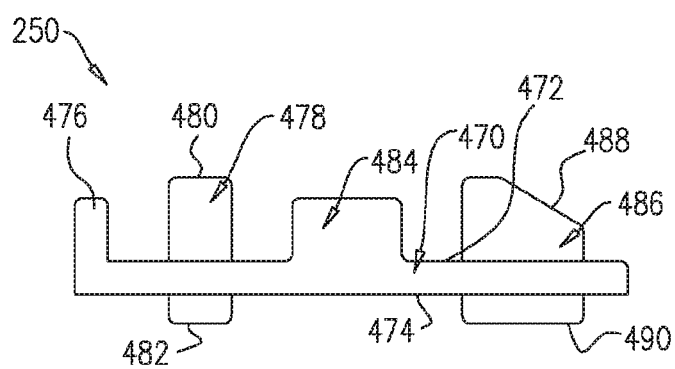

It is seen in FIGS. 9A-9C that sealing element 250 has a planar base portion 470 defining an upper surface 472 and a bottom surface 474. An upwardly extending forwardmost protrusion 476 is formed at the forward end of base portion 470, an upwardly and downwardly extending forward protrusion 478 is rearwardly spaced from protrusion 476 and is also formed on the base portion 470. Protrusion 478 defines upper engagement surface 480 and bottom engagement surface 482. It is additionally seen that an intermediate upwardly extending protrusion 484 is rearwardly spaced from protrusion 478 and is also formed on base portion 470. An upwardly and downwardly extending rearward protrusion 486 is rearwardly spaced from protrusion 484 and is also formed on the base portion 470. Protrusion 486 defines upper rearwardly tapered engagement surface 488 and bottom engagement surface 490.

Figure 10:
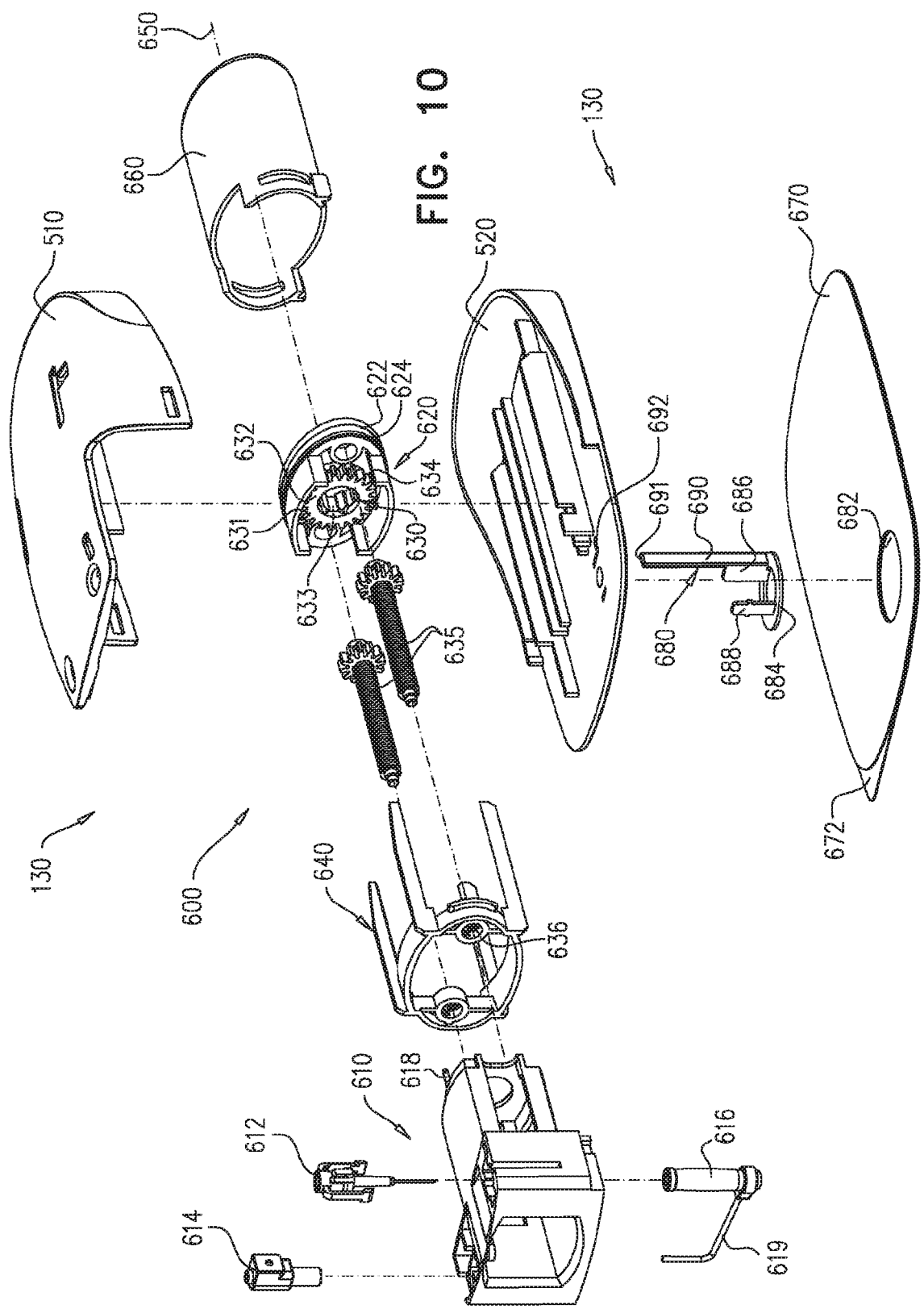
FIG. 10 is a simplified exploded view illustration of the disposable base portion of the patch pump assembly of FIGS. 1 and 2.

Reference is now made to FIG. 10, which is a simplified exploded view illustration of the disposable base portion 130 of the patch pump assembly 100 of FIGS. 1 and 2.

As seen in FIG. 10, the disposable base portion 130 preferably includes a top housing portion 510 and a bottom housing portion 520, which are adapted to be removably fixed to an injection site during administration of a medicament. It is a particular feature of an embodiment of the present invention that there is provided, disposed between the top housing portion 510 and the bottom housing portion 520 a movable medicament reservoir/fixed piston medicament storage and dispensing subassembly MMRFPMSDS 600.

In accordance with a preferred embodiment of the present invention, the MMRFPMSDS 600 comprises a housing element 610, which is fixed to the top housing portion 510 and the bottom housing portion 520 and thus adapted to be removably fixed to an injection site during administration of a medicament. Housing element 610 preferably supports a medicament infusion needle assembly 612, a medicament filling septum 614, a needle biasing and sealing element 616, a medicament coupling filling conduit 618 and a medicament coupling injecting conduit 619.

It is a further particular feature of an embodiment of the present invention that the MMRFPMSDS 600 comprises a piston assembly 620 which includes a piston base element 622 having a piston seal 624 and a rotary-to-longitudinal drive converter 630, which preferably includes a gear 631, which includes a circular bearing surface 632, interior gear teeth 633 and exterior gear teeth 634, which exterior gear teeth 634 drive a pair of linear driving screws 635. Piston base element 622 is preferably fixedly axially attached to housing element 610, which is fixed to the top housing portion 510 and the bottom housing portion 520 and thus adapted to be removably fixed to an injection site during administration of a medicament.

Linear drive screws 635, which rotate but are not displaced linearly relative to housing element 610, preferably drivingly engage suitably threaded sockets 636 formed in a linear displacer 640, thereby providing linear displacement thereof along an axis 650. Linear displacer 640 is preferably fixedly attached to a medicament reservoir 660. Accordingly, linear displacement of linear displacer 640 provides corresponding linear displacement along axis 650 of medicament reservoir 660 relative to piston assembly 620. More particularly, it is appreciated that preferably medicament reservoir 660 includes an inner surface which is sealingly engaged by piston seal 624 of piston base element 622 of piston assembly 620, such that linear displacement of the medicament reservoir 660 in a first direction along axis 650 effectively increases the interior volume of the medicament reservoir 660 and linear displacement of the medicament reservoir 660 in a second direction along axis 650, opposite to the first direction, effectively decreases the interior volume of the medicament reservoir 660.

An injection site adhesive sticker 670 is fixedly attached, preferably by ultrasonic welding, to an underside surface of bottom housing portion 520 and is provided with release sheet 672, which, when removed, exposes an adhesive surface for removably engagement with an injection site on a person.

An injection site engagement element 680, preferably formed of plastic, extends through an aperture 682 formed in injection site adhesive sticker 670 and includes an injection site engagement surface defining ring 684 and three upstanding shafts, 686, 688 and 690. Shafts 686 and 688 engage needle assembly 612 for retaining the needle assembly in a needle penetration operative orientation, as is described hereinbelow in detail. Shaft 690 defines an upwardly facing edge 691 and extends through an aperture 692 formed in bottom housing portion 520 and through an aperture (not shown in FIG. 10) in housing element 610 and serve to enable needle penetration to the injection site, as is described hereinbelow in detail.

Reference is now made to FIGS. 11A, 11B, 11C 11D & 11E, which are simplified pictorial illustrations of the top housing portion 510 (FIG. 10) of the disposable base portion 130 of the patch pump assembly 100 of FIGS. 1 and 2. FIGS. 11A-11E are simplified respective two pictorial illustration shown from two different perspectives, top plan view, first side plan view and bottom plan view illustrations of the top housing portion 510.

As seen in FIGS. 11A-11E, top housing portion 510 preferably is an integrally formed element, preferably injection molded from relatively rigid plastic, such as polycarbonate.

Top housing portion 510 has a generally curved cover portion 700 having an upper surface 702 and a bottom surface 704, a partially circumferential curved portion 706 extends downwardly from curved cover portion 700 and both define a forwardly facing edge 708, adapted to engage a corresponding edge of the reusable portion 110.

It is seen in FIGS. 11A-11E that an aperture 720 is formed adjacent forward end of the top housing portion 510, adapted for insertion of medicament filling septum 614 thereinto. Additional aperture 722 is formed adjacent forward end of the top housing portion 510 and spaced from aperture 720. A slot 724 is formed adjacent aperture 722 and adapted for insertion of shaft 690 of injection site engagement element 680 therethrough.

Typically, two generally longitudinal slots 730 and 732 are formed in an intermediate location of the curved cover portion 700 of top housing portion 510 and are spaced from each other. Slot 732 includes a lateral extension slot 734, extending preferably transversely thereto.

It is additionally seen in FIGS. 11A-11E that generally longitudinal slots 736, symmetric with respect to longitudinal axis 650, are formed on opposite sides of partially circumferential curved portion 706 and adapted for cooperating with disposable interface and control module 140 in order to retain it with respect to disposable base portion 130.

It is additionally seen on the underside of top housing portion 510 that preferably two downwardly protruding, preferably symmetric with respect to longitudinal axis 650, axially extending ribs 740 are formed on bottom surface 704 of top housing portion 510. Disposed inwardly with respect to each of ribs 740 is a pair of axially extending guiding track ribs 742, forming a guiding channel 744 therebetween for guiding axial displacement of linear displacer 640 relative to top housing portion 510.

Figure 11A:
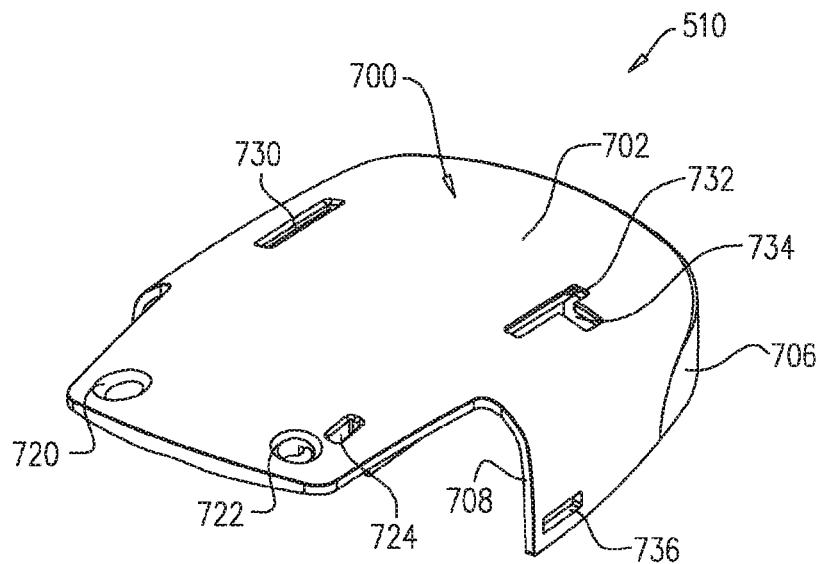
FIGS. 11A, 11B, 11C 11D & 11E are simplified pictorial illustrations of a top housing portion of the disposable base portion of the patch pump assembly of FIGS. 1 and 2.
Figure 11B:
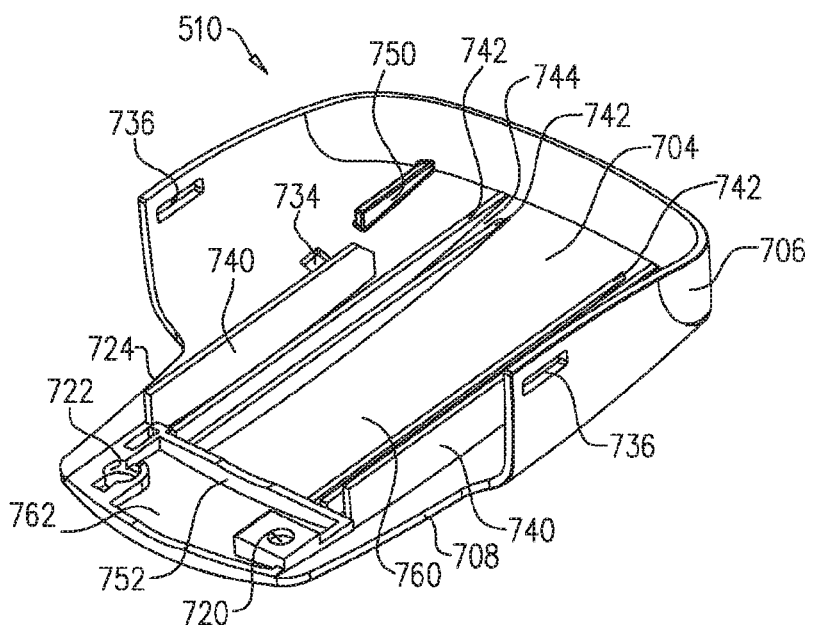
Figure 11C:
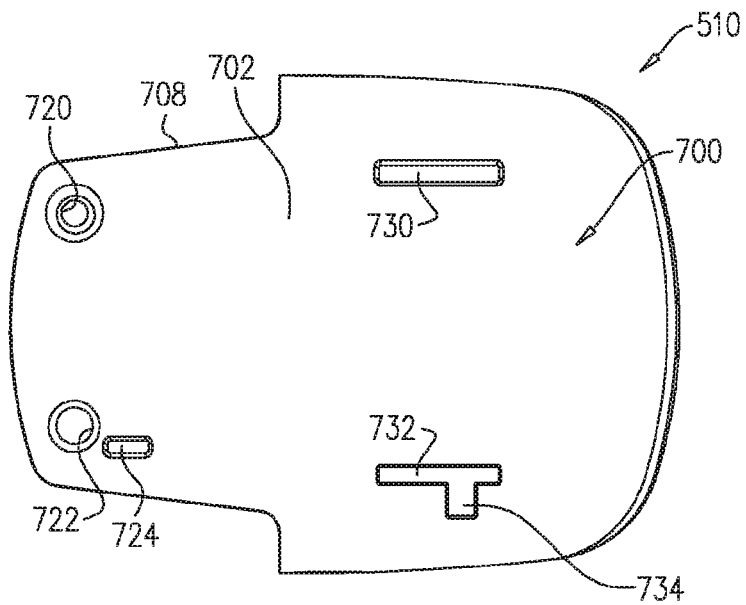
Figure 11D:
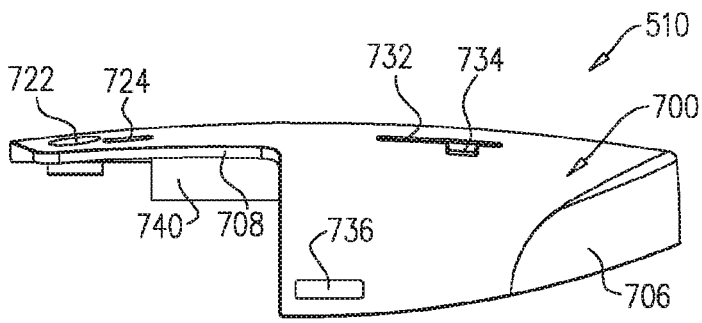
Figure 11E:
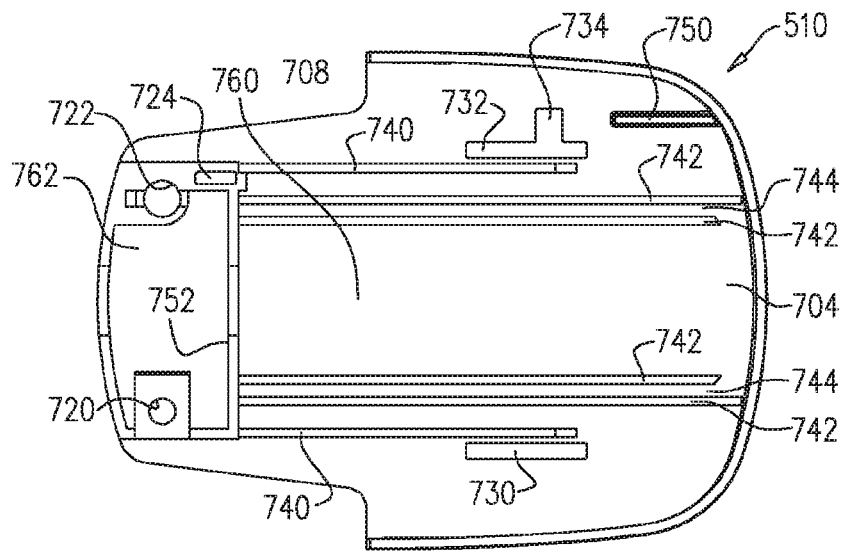

It is particularly seen in FIGS. 11B and 11E that an inwardly extending protrusion 750 is formed on bottom surface 704 and disposed adjacent and slightly rearwardly of lateral extension slot 734.

It is additionally particularly seen in FIGS. 11B and 11E that a downwardly protruding wall portion 752 extends transversely with respect to longitudinal axis 650 and is disposed between apertures 720, 722 and between forward ends of ribs 740. Wall portion 752 divides the bottom surface 704 to a rearward bottom surface 760 and a forward bottom surface 762.

Reference is now made to FIGS. 12A, 12B, 12C & 12D, which are simplified pictorial illustrations of the medicament reservoir 660 (FIG. 10) of the disposable base portion 130 of the patch pump assembly 100 of FIGS. 1 and 2. FIGS. 12A-12D are simplified respective pictorial view, side plan view, forward facing end plan view and a sectional view taken along lines D-D in FIG. 12A of medicament reservoir 660.

As seen in FIGS. 12A-12D, medicament reservoir 660 preferably is an integrally formed element, preferably injection molded from relatively resilient bio-compatible plastic, such as polypropylene. Medicament reservoir 660 is preferably arranged along longitudinal axis 650.

Medicament reservoir 660 is preferably a hollow longitudinal element 770 having an oval cross-section, a closed rearward end wall 772 and a forward open end 773, defining an interior volume 774. Longitudinal element 770 defines an outer surface 776 and an inner surface 778. Forward edge 780 is defined at the forward open end 773 of longitudinal element 770.

It is seen in FIGS. 12A-12D that generally two mutually opposed cut-outs 782 extend rearwardly from forward edge 780 and are adapted for engagement with linear displacer 640. Two mutually opposed apertures 784 are formed adjacent forward edge 780 and are also adapted for engagement with linear displacer 640.

It is additionally seen in FIGS. 12A-12D that preferably two mutually opposed protrusions 786 are formed adjacent each of apertures 784 and extend generally rearwardly from forward edge 780 and downwardly from outer surface 776. Protrusions 786 each have an outwardly facing surface 788 and an inwardly facing surface 790.

It is a particular feature of an embodiment of the present invention that the outwardly facing surface 788 is preferably covered by a reflective color in order to enable detection thereof by optical sensor 362 of internal subassembly 220.

Reference is now made to FIGS. 13A, 13B, 13C & 13D, which are simplified pictorial illustrations of the linear displacer 640 (FIG. 10) fixedly attached to the medicament reservoir 660 of the disposable base portion 130 of the patch pump assembly 100 of FIGS. 1 and 2. FIGS. 13A-13D are simplified respective pictorial view, forward facing end plan view, side plan view and a sectional view taken along lines D-D in FIG. 13A of linear displacer 640.

As seen in FIGS. 13A-13D, linear displacer 640 preferably is an integrally formed element arranged along longitudinal axis 650 and is preferably injection molded from a relatively rigid plastic, such as polycarbonate.

It is seen in FIGS. 13A-13D that linear displacer 640 includes a hollow enlarged base element 800 having a generally partially oval cross section, having an outer surface 802 and an inner surface 804. Generally, two pairs of mutually spaced arm portions 806 extend axially rearwardly and partially radially outwardly from enlarged base element 800 and extend along an axis parallel to longitudinal axis 650. Each pair of arm portions 806 is joined by a transversely disposed reinforcement portion 808. The enlarged base element 800 defines a forwardly facing edge 809 and a rearwardly facing edge 810.

A partially oval portion 811 extends radially outwardly from each reinforcement portion 808, defining an outer circumferential edge 812, on which a radially outwardly extending protrusion 814 is formed, adapted for engagement with medicament reservoir 660. Partially oval portion 811 has a forwardly facing edge 815, which is preferably coplanar with forwardly facing edge 809 of enlarged base element 800 and a rearwardly facing edge 816.

As seen in FIGS. 13A-13D, two generally internally threaded sockets 636 are formed in reinforcement portions 808. Internal threading 818 formed in sockets 636 is adapted for engagement with linear driving screws 635.

It is appreciated that outwardly extending protrusion 814 has a generally planar forwardly facing surface 830 and a rearwardly facing forwardly tapered surface 832.

It is further appreciated that each arm portion 806 has a planar elongate engagement surface 834, a rearwardmost planar surface 836, a forwardly tapered surface 838, a planar elongate surface 840 and a forwardly tapered surface 842 joining forwardly facing edge 809 of base element 800.

Figure 14:
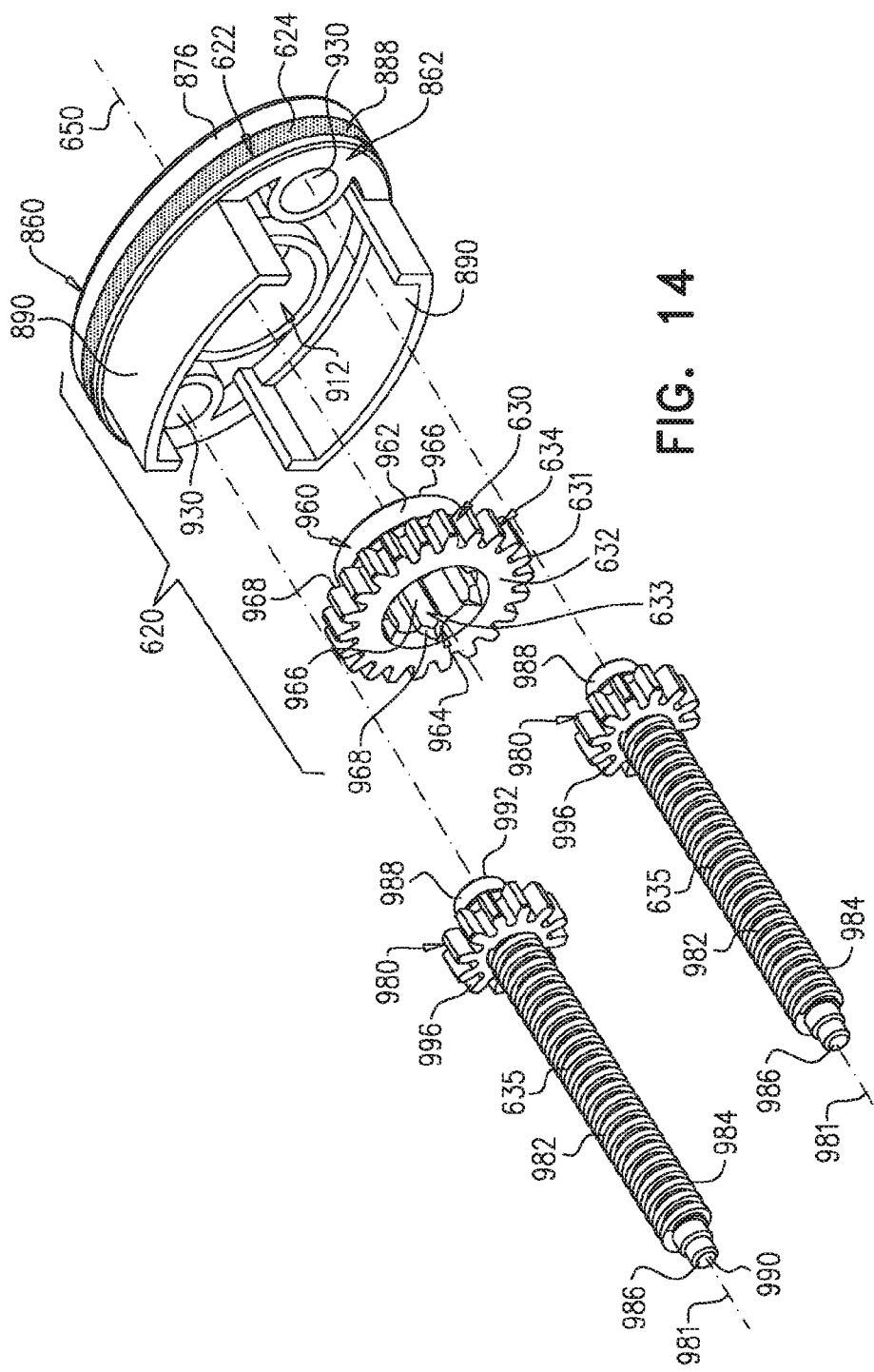
FIG. 14 is a simplified exploded view illustration of a piston assembly including a rotary to longitudinal drive converter operative to drive the linear displacer of FIGS. 13A, 13B, 13C & 13D in axial motion.

Reference is now made to FIG. 14 is a simplified exploded view illustration of the piston assembly 620 (FIG. 10) including the rotary to longitudinal drive converter 630 operative to drive the linear displacer 640 of FIGS. 13A, 13B, 13C & 13D in axial motion. Reference is now additionally made to FIGS. 15A, 15B, 15C, 15D, 15E & 15F, which are simplified illustrations of the piston base element 622 (FIG. 10), forming part of the piston assembly 620 of FIG. 14. FIGS. 15A-15F are simplified respective pictorial illustrations shown from two different perspectives, forward facing end plan view, side plan view, two sectional views taken along lines E-E and F-F in FIG. 15B of piston base element 622. Reference is now further made to FIGS. 16A, 16B, 16C, 16D & 16E, which are simplified illustrations of the piston assembly 620 including the rotary to longitudinal drive converter 630 as seen in FIG. 14. FIGS. 16A-16E are simplified respective pictorial illustration, forward facing end plan view, side plan view, rearward facing end plan view and a sectional view taken along lines E-E in FIG. 16A of piston assembly 620.

As noted hereinabove, the piston assembly 620 includes piston base element 622 having piston seal 624 and rotary-to-longitudinal drive converter 630, which preferably includes gear 631, which includes circular bearing surface 632, interior gear teeth 633 and exterior gear teeth 634, which exterior gear teeth 634 drive pair of linear driving screws 635.

It is particularly seen in FIGS. 15A-15F that piston base element 622 is preferably formed as an assembly of medicament engaging portion 860 and a base portion 862, both arranged along longitudinal axis 650. Medicament engaging portion 860 is preferably injection molded of a bio-compatible relatively resilient plastic, such as polypropylene. Base portion 862 is preferably injection molded from a relatively rigid plastic, such as polycarbonate. Piston base element 622 includes piston seal 624 integrally formed therewith and preferably made of rubber. Alternatively, piston seal 624 can be mounted onto piston base element 622.

Medicament engaging portion 860 includes a base portion 864 preferably having an oval cross-section and a circumferential forwardly extending rim 866 defining a radially inwardly extending circumferential flange 868. Medicament engaging portion 860 has a rearwardly facing surface 872, a forwardly facing surface 874 and a circumferential edge surface 876.

Base portion 862 includes an engagement portion 880 preferably having an oval cross-section having a rearwardly facing surface 882 adapted to engage the forwardly-facing surface 874 of medicament engaging portion 860. Engagement portion 880 further defines a forwardly-facing surface 884.

It is seen that an outwardly extending circumferential flange 885 extends from a rearward end of engagement portion 880 and is adapted to be fixedly snapped over flange 868 of medicament engaging portion 860.

It is further seen that an outwardly extending circumferential flange 886 extends from a forward end of engagement portion 880 and defines a circumferential outwardly facing edge surface 888.

It is appreciated that piston seal 624 is disposed between flange 886 and flange 868. Circumferential edge surface 876 of the medicament engaging portion 860, piston seal 624 and circumferential outwardly facing edge surface 888 are adapted to sealingly engage the inner surface 778 of the medicament reservoir 660.

It is further seen in FIGS. 15A-15F that generally two arm portions 890 extend forwardly from forwardly facing surface 884 of engagement portion 880. Each arm portion 890 has a curved portion 892 bounded by mutually opposite wall portions 894, which extend radially inwardly from curved portion 892. Each of curved portions 892 define an outer surface 900, an inner surface 902 and a forwardly facing end surface 904. Each of wall portions 894 define an outer surface 906, an inner surface 907 and a forwardly facing end surface 908, joining forwardly facing end surface 904 and coplanar therewith.

A hollow central socket 912 is formed in base portion 862 and adapted for receiving part of the rotary-to-longitudinal drive converter 630 therein. It is appreciated that the central socket 912 extends axially forwardly from forwardly facing surface 874 to forwardly facing edge 913. Central socket 912 defines an inner surface 920. It is further seen in FIGS. 15A-15F that central socket 912 has a bearing surface 922 that protrudes slightly forwardly from surface 874 and is disposed within central socket 912.

Generally, two symmetric sockets 930 are formed in base portion 862 and are disposed on diametrically opposed sides of central socket 912 and each socket is disposed between the two arm portions 890. Each of sockets 930 is adapted for receiving a rearward end of driving screw 635 therein. It is appreciated that sockets 930 extend axially forwardly from surface 932, which is disposed slightly forwardly of surface 874, to a surface that is generally coplanar with forwardly facing edge 913. Sockets 930 define an inner surface 936. It is further seen in FIGS. 15A-15F that sockets 930 each has a bearing surface 940 protruding slightly forwardly from surface 932 and is disposed within socket 930.

It is particularly seen in FIGS. 15B & 15F that a groove 941 is formed on rearwardly facing surface 872 of medicament engaging portion 860. Groove 941 proceeds to an axially extending aperture 942 formed in base portion 862, which extends preferably along an axis that is parallel to longitudinal axis 650 to a location disposed in vicinity of forwardly facing surface 884 and is adapted for providing a passage and sealingly engage medicament coupling filling conduit 618.

It is particularly seen in FIG. 14 that rotary-to-longitudinal drive converter 630 includes a generally cylindrical portion 960 having an outer surface 962 and an inner surface 964 and gear 631 disposed at the forward end thereof. Cylindrical portion 960 defines a rearwardly facing edge 966.

Gear 631 protrudes generally radially outwardly with respect to cylindrical portion 960 and having a forward facing circular bearing surface 632 and a rearwardly facing surface 968.

Gear 631 additionally includes radially outwardly extending exterior gear teeth 634, which exterior gear teeth 634 drive pair of linear driving screws 635.

It is further seen in FIG. 14. FIGS. 16A, 16B and 16E that gear 631 further includes interior gear teeth 633, which are disposed along longitudinal axis 650. Interior gear teeth 633 are disposed on inner surface 964 of cylindrical portion 960 and each preferably has a generally planar rearward portion 966 and a generally forwardly tapered portion 968.

It is further seen in FIG. 14 that each driving screw 635 has a nut 980 threadably engaged therewith. Each driving screw 635 is an integrally formed elongate element arranged along longitudinal axis 981, which is parallel to longitudinal axis 650. Each driving screw 635 has a cylindrical portion 982 with an external threading 984, having a forward end 986 and a rearward end 988. Forward end 986 defines a forwardly facing surface 990 and rearward end 988 defines a rearwardly facing surface 992.

Nuts 980 include an internal threading 994, which is threadably engageable with the external threading 984 of driving screws 635. Nuts 980 additionally include outwardly extending exterior gear teeth 996.

It is particularly seen in FIGS. 16A-16E that rotary-to-longitudinal drive converter 630 is received by piston base element 622, such that cylindrical portion 960 of rotary-to-longitudinal drive converter 630 is received within central socket 912 of base portion 862 and planar rearward portion 966 of cylindrical portion 960 is bearingly and rotatably supported by bearing surface 922 of central socket 912, thus reducing friction between piston base element 622 and rotary-to-longitudinal drive converter 630.

It is further seen in FIGS. 16A-16E that driving screws 635 are received by piston base element 622, such that the rearward end 988 of each driving screw 635 is inserted into the respective socket 930 of base portion 862 and rearwardly facing surface 992 of each driving screw 635 is bearingly and rotatably supported by bearing surface 940 of each socket 930, thus reducing friction between piston base element 622 and driving screws 635.

It is further seen that the outer nuts 980, which are mounted on driving screws 635, are each intermeshed with rotary-to-longitudinal drive converter 630, such that outwardly extending exterior gear teeth 996 of nuts 980 engage outwardly extending exterior gear teeth 634 of rotary-to-longitudinal drive converter 630.

Figure 17A:
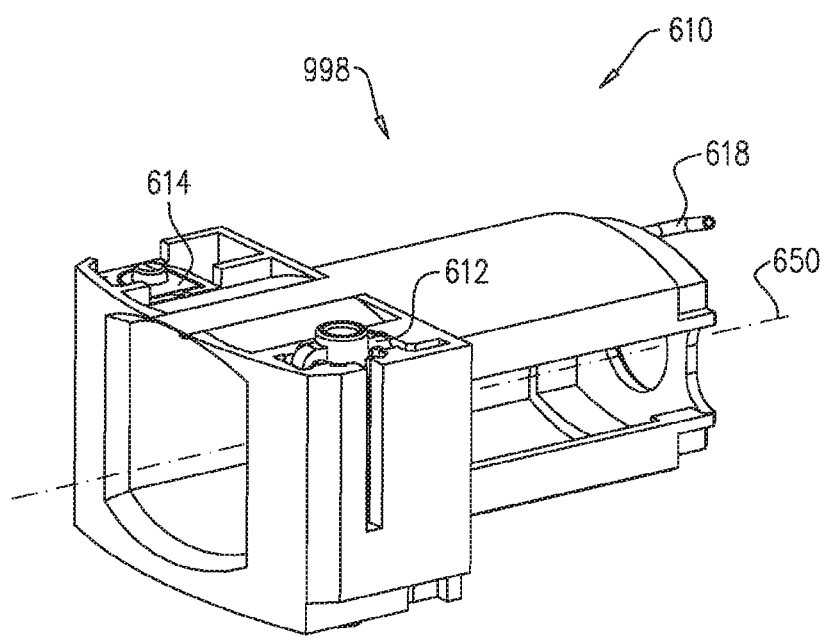
FIGS. 17A and 17B are simplified respective assembled and exploded view illustrations of a medicament supply and infusion assembly fixed to the piston assembly of FIG. 14.
Figure 17B:
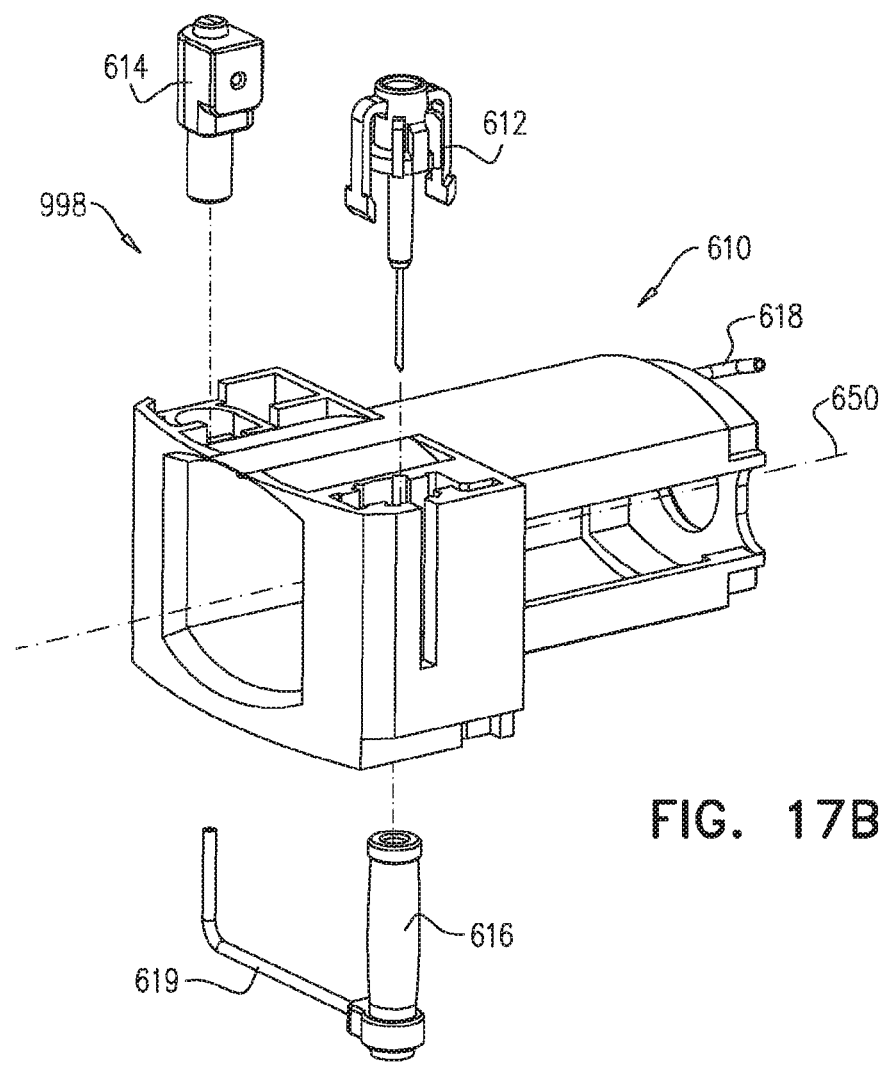

Reference is now made to FIGS. 17A and 17B, which are simplified respective assembled and exploded view illustrations of a medicament supply and infusion assembly 998 (FIG. 10) fixed to the piston assembly 620 of FIG. 14.

Medicament supply and infusion assembly 998, forming part of the MMRFPMSDS 600, includes a housing element 610, which preferably supports medicament infusion needle assembly 612, medicament filling septum 614, needle biasing and sealing element 616, medicament coupling filling conduit 618, fluidly connecting the filling septum 614 with the medicament reservoir 660, and medicament coupling injecting conduit 619, fluidly connecting the filling septum 614 and the infusion needle assembly 612, through needle biasing and sealing element 616.

Figure 18A:
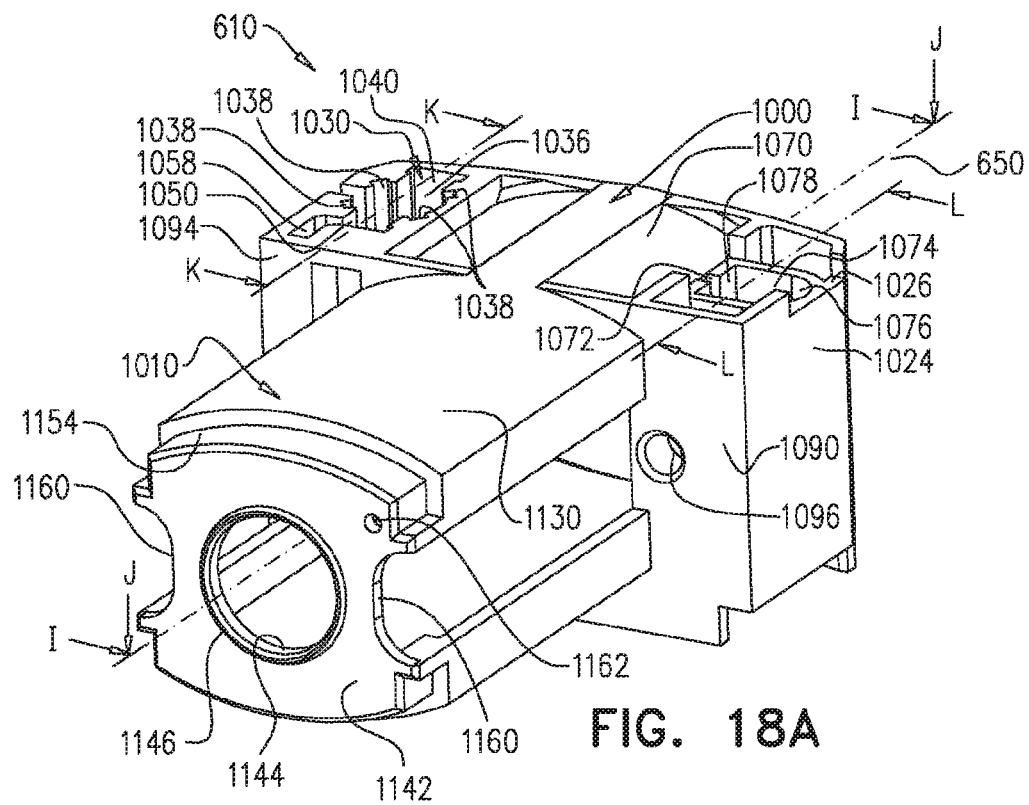
Figure 18B:
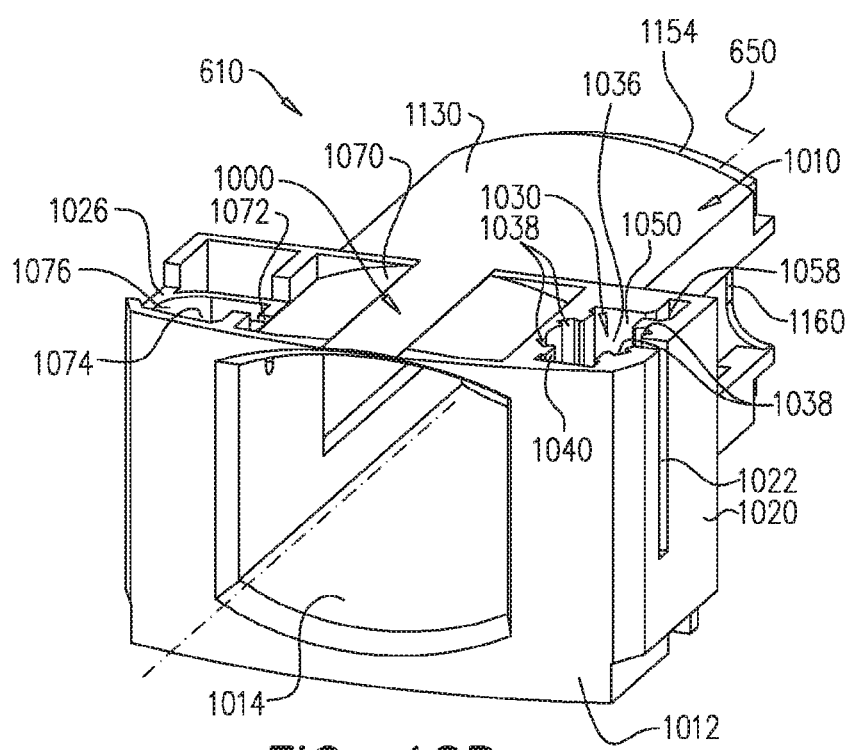
Figure 18C:
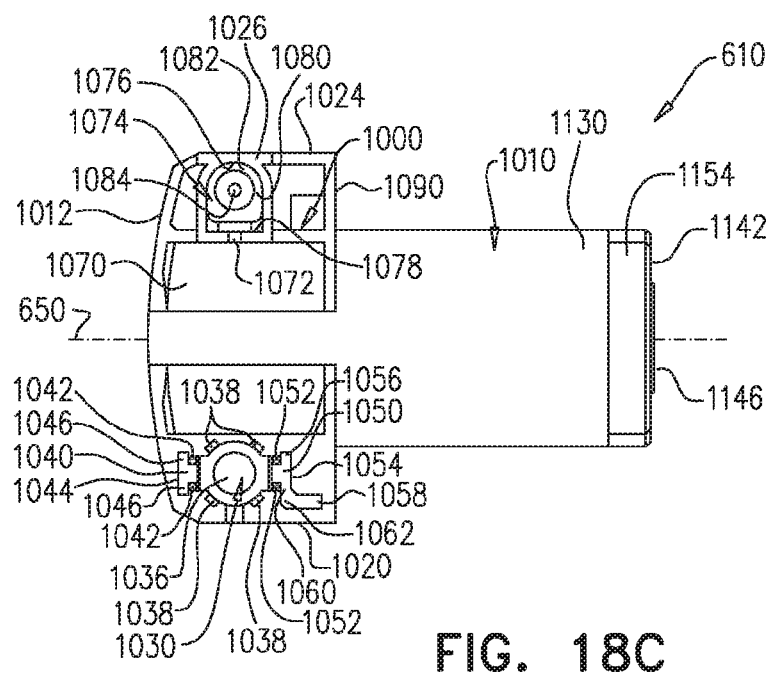
Figure 18D:
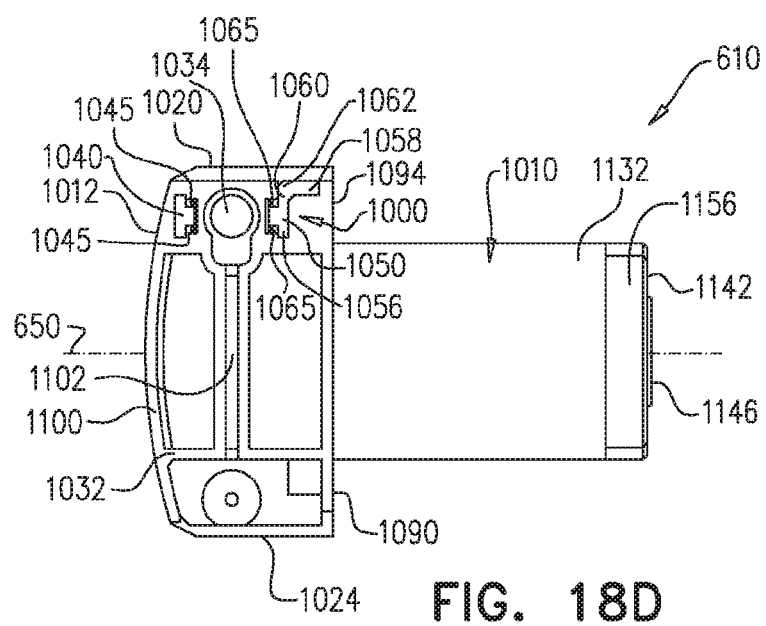
Figure 18E:
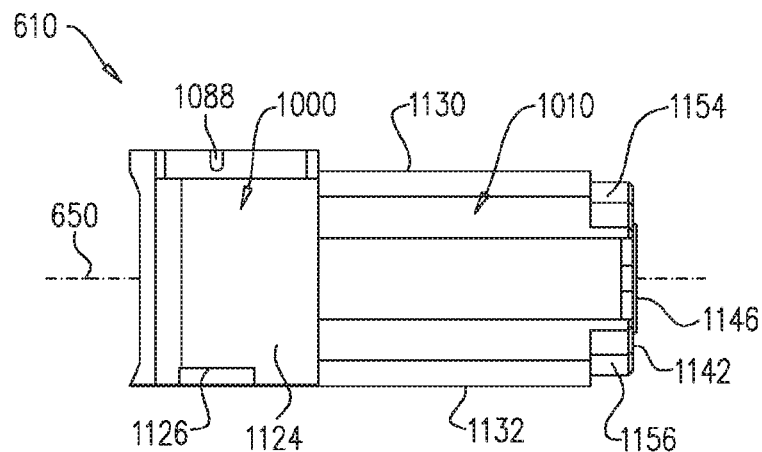
Figure 18F:
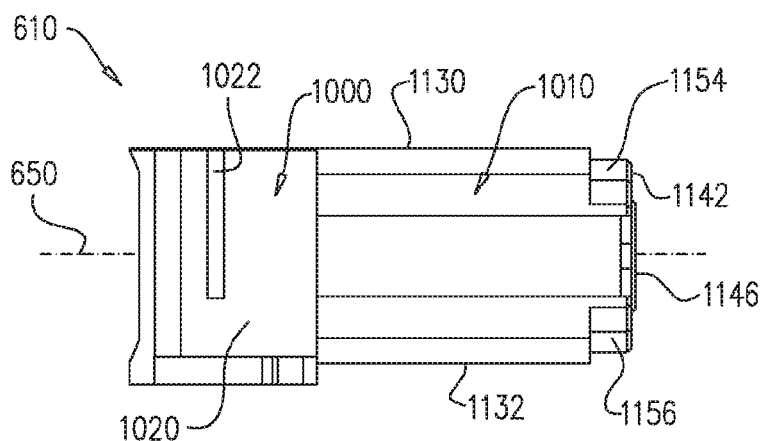
Figure 20A:
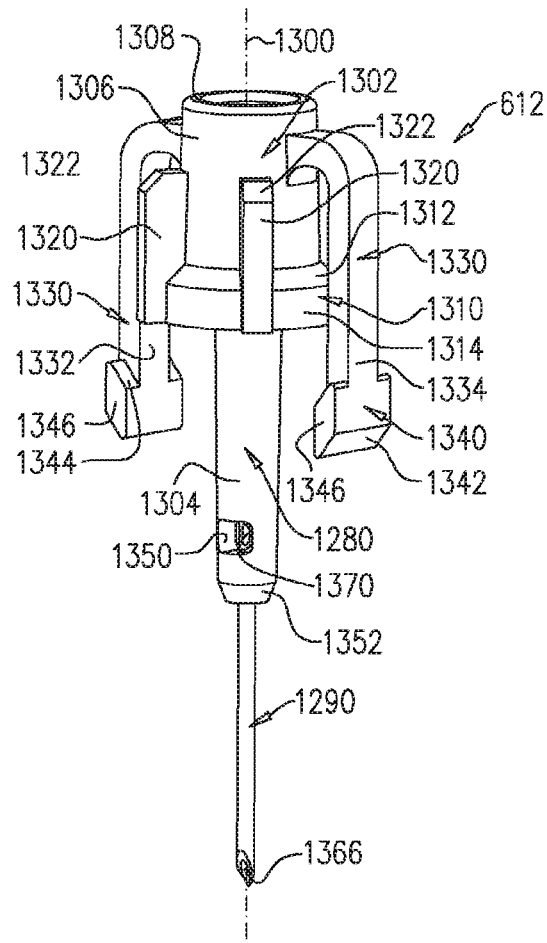
Figure 20B:
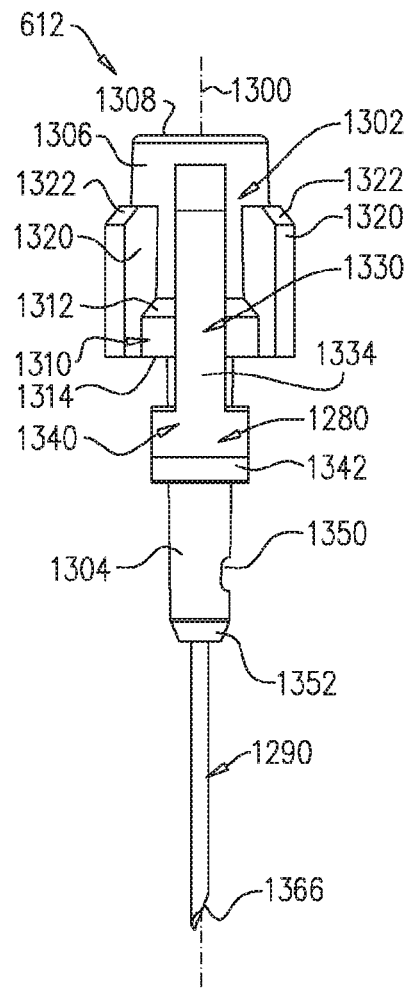
Figure 20C:
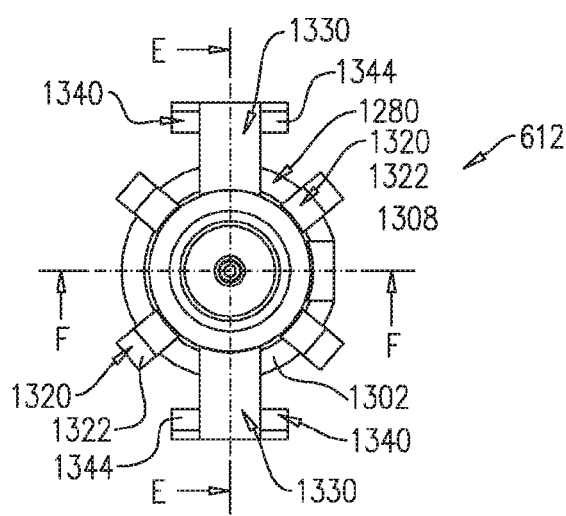

Reference is now made to FIGS. 18A, 18B, 18C, 18D, 18E, 18F, 18G, 18H, 18I, 18J, 18K and 18L, which are simplified illustrations of housing element 610 (FIG. 10). FIGS. 18A and 18B are simplified pictorial illustrations taken along opposite directions with respect to axis 650; FIGS. 18C and 18D are simplified respective top and bottom views of the housing element; FIGS. 18E and 18F are simplified side views of the housing element; FIGS. 18G and 18H are simplified plan views of opposite ends of the housing element along axis 650; and FIGS. 18I, 18J, 18K and 18L are simplified sectional illustrations taken along respective lines I-I, J-J, K-K and L-L in FIG. 18A.

As seen in FIGS. 18A-18L, housing element 610 is preferably a unitary element formed by injection molding of plastic and includes a generally rectangular portion 1000 and a generally cylindrical portion 1010 extending outwardly therefrom. The rectangular portion 1000 preferably includes an end wall 1012 having formed therein a central aperture 1014, as seen clearly in FIG. 18G, for receiving plunger assembly 240 of reusable portion 110. The rectangular portion 1000 also includes a first side wall 1020, as seen clearly in FIG. 18F, having formed therein a relatively narrow slit 1022 and a second side wall 1024 having formed therein an edge cut out 1026.

Disposed adjacent first side wall 1020 and communicating with slit 1022 is a needle assembly location bore 1030. Needle assembly location bore 1030 preferably has a uniform cross section and terminates in a bottom wall 1032 having a circular aperture 1034, as seen most clearly in FIG. 18D. The cross-sectional configuration of bore 1030 is seen most clearly in FIGS. 18A, 18B, 18C, 18J and 18K and includes a central portion 1036, which communicates with slit 1022 and which accommodates the main portion of the medicament infusion needle assembly 612. Extending radially outwardly from central portion 1036 are preferably four relatively small elongate recesses 1038, which accommodate radial protrusions of the medicament infusion needle assembly 612.

Extending to one side of central portion 1036 is a first relatively large elongate recess 1040 having side walls 1042, an end wall 1044 and a pair of small elongate recesses 1046 located at the junctions of the end wall 1044 and side walls 1042.

It is seen particularly in FIGS. 18D & 18K that a downwardly tapered protrusion 1045 is formed on each of side walls 1042 and is preferably disposed adjacent bottom wall 1032 and adapted for retaining the medicament infusion needle assembly 612 in the needle penetration operative orientation. It is particularly seen in FIG. 18K that protrusion 1045 includes a downwardly facing tapered surface 1047, generally planar surface 1048 and an upwardly facing tapered surface 1049.

Extending to an opposite side of central portion 1036, opposite to first relatively large elongate recess 1040, is a second relatively large elongate recess 1050 having side walls 1052, an end wall 1054 and a small elongate recess 1056 located at the junctions of the end wall 1054 and of side walls 1052. Additionally, a generally rectangular recess 1058 extends from second relatively large elongate recess 1050 and includes a joining portion 1060 having a curved surface 1062.

It is seen particularly in FIGS. 18D & 18K that a downwardly tapered protrusion 1065 is formed on each of side walls 1052 and is preferably disposed adjacent bottom wall 1032 and adapted for retaining the medicament infusion needle assembly 612 in the needle penetration operative orientation. It is particularly seen in FIG. 18K that protrusion 1065 includes a downwardly facing tapered surface 1067, generally planar surface 1068 and an upwardly facing tapered surface 1069.

It is seen particularly in FIG. 18L that disposed adjacent second side wall 1024 is a top recess 1070, which communicates via a slit 1072 with a central bore 1074, having a generally square cross section including a curved wall 1076 and an oppositely facing generally flat wall 1078 having a protrusion 1080 and a bottom wall 1082, from which extends a relatively small bore 1084, preferably having a circular cross section and having a bottom aperture 1086. Top bore 1088 is formed through slit 1072.

It is noted that medicament coupling injecting conduit 619 is adapted to be inserted into filing septum 614, which is adapted to be received within at least the central bore 1074.

Extending generally perpendicularly to first and second end walls 1020 and 1024 are first and second back walls 1090 and 1094, each of which is formed with a screw end receiving recess 1096, preferably having a central protrusion 1098.

Generally rectangular portion 1000 is preferably formed with a bottom wall 1100 which defines a recess 1102 arranged to accommodate a portion of injecting conduit 619.

Generally cylindrical portion 1010 is preferably formed with top and bottom elongate wall portions 1130 and 1132, each of which preferably has an outer wall surface having a generally elliptical cross section. Top and bottom elongate wall portions 1130 and 1132 preferably terminate in an end wall 1142 which is formed with a circular aperture 1144 surrounded by an outwardly-facing circular protrusion 1146 defining an inner-facing bearing surface which bearingly and rotatably supports circular bearing surface 632 of gear 631, which forms part of rotary-to-longitudinal drive converter 630.

Top and bottom elongate wall portions 1130 and 1132 terminate at a stepped forward portion defining top and bottom stepped surface 1154 and 1156.

Cylindrical portion 1010 has two elongate side cut-outs 1160 extending from end wall 1142 to back walls 1090 and 1094.

It is additionally seen that an aperture 1162 is formed in end wall 1142.

Reference is now made to FIGS. 19A, 19B, 19C & 19D, which are simplified illustrations of medicament filling septum 614 (FIG. 10), forming part of the medicament supply and infusion assembly 998 of FIGS. 17A & 17B. FIGS. 19A-19D are simplified respective pictorial illustration, side plan view, forward facing end plan view and a sectional view taken along lines D-D in FIG. 19A of medicament filling septum 614.

It is seen in FIGS. 19A-19D that medicament filling septum 614 is an integrally formed element, preferably made of rubber, and is generally arranged along longitudinal axis 1200, which extends generally transversely with respect to longitudinal axis 650.

Medicament filling septum 614 generally includes a bottom cylindrical portion 1202 and an enlarged upper portion 1204. Radially outwardly extending portion 1206 is formed along a portion of the length of the enlarged upper portion 1204. A downwardly facing shoulder 1208 is defined between an outwardly facing surface 1209 of outwardly extending portion 1206 and enlarged upper portion 1204, joining with an outwardly facing wall surface 1210 of upper portion 1204.

It is seen in FIGS. 19A-19D that a downwardly facing circumferential surface 1212 is formed between upper portion 1204 and bottom portion 1202. Bottom portion 1202 defines an outer circumferential surface 1214 and a downwardly facing end surface 1216. Upper portion 1204 defines an outer circumferential surface 1218 and an upwardly facing end surface 1220.

It is further seen in FIGS. 19A-19D that an upwardly extending protrusion 1230 is formed on upper portion 1204 and extends upwardly from end surface 1220. Upwardly extending protrusion 1230 has a tapered portion 1232 and a planar portion 1234 having a selectively openable slit 1236 formed therein.

It is seen particularly in FIG. 19D that a central varying diameter fluid conduit 1240 is arranged along axis 1200 and extends within bottom portion 1202 and upper portion 1204 from downwardly facing end surface 1216 up to planar portion 1234. It is appreciated that fluid conduit 1240 has a bottom conduit portion 1242 of a first diameter defining a first inner surface 1244; an intermediate narrow portion 1246 having a second diameter, which is preferably greater than the first diameter and defining a second inner surface 1248; an intermediate enlarged portion 1250 having a third diameter, which is preferably greater than the second diameter and defining a third inner surface 1252; and an upper portion 1254, which defines the inner surface of slit 1236.

It is further seen particularly in FIGS. 19A & 19D that a side fluid conduit 1260 is preferably arranged along axis 1261, which extends transversely with respect to axis 1200. Side fluid conduit 1260 is formed in upper portion 1204 and extends through outwardly extending portion 1206 and is adapted to be fluidly coupled with varying diameter fluid conduit 1240, and particularly connected to intermediate enlarged portion 1250 according to an embodiment of the present invention. Side fluid conduit 1260 defines an inner surface 1262.

Reference is now made to FIGS. 20A, 20B, 20C, 20D, 20E and 20F are simplified illustrations of a medicament infusion needle assembly 612 (FIG. 10), forming part of the medicament supply and infusion assembly 998 of FIGS. 17A & 17B. FIGS. 20A-20F are simplified respective pictorial illustration, first side plan view, upwardly facing end plan view, second side plan view, and two sectional views taken along lines E-E and F-F in FIG. 20C of medicament infusion needle assembly 612.

It is seen in FIGS. 20A-20F that medicament infusion needle assembly 612 preferably has a needle hub 1280, which is an integrally formed element preferably injection molded of plastic and a needle 1290 mounted onto needle hub 1280 preferably using an adhesive. Needle hub 1280 and needle 1290 are generally arranged along longitudinal axis 1300, which extends generally transversely with respect to longitudinal axis 650.

The needle hub 1280 includes an upward generally enlarged cylindrical portion 1302 and a downward generally elongate tapered portion 1304, both arranged along mutual longitudinal axis 1300. Cylindrical portion 1302 defines an outer generally circular surface 1306 having an upward edge 1308 and a downward end terminating at an outwardly radially extending generally circumferential skirt 1310, defining a downwardly tapered circumferential surface 1312 and a planar circumferential surface 1314.

Typically, four elongate ribs 1320 extend radially outwardly from surface 1306 of cylindrical portion 1302 and adapted for positioning the needle hub 1280 with respect to disposable portion 120. Each of the ribs 1320 preferably defines an upward end having a downwardly tapered surface 1322.

It is seen in FIGS. 20A-20F that typically two lever portions 1330 extend generally outwardly and downwardly from cylindrical portion 1302. Each lever portion 1330 is preferably positioned between two ribs 1320. Lever portions 1330 preferably define an inner surface 1332, an outer surface 1334 and a T-shaped extension 1340 at the downward end of lever portion 1330. T-shaped extension 1340 preferably defines a downwardly tapered end surface 1342, an upwardly tapered surface 1344, which is generally upwardly spaced from end surface 1342 and two side wall portions 1346 joining the end surface 1342 and the tapered surface 1344.

It is further seen in FIGS. 20A-20F that an aperture 1350 is formed in tapered portion 1304 and adapted for communication with medicament coupling injecting conduit 619. It is also seen that tapered portion 1304 defines a downward tapered edge surface 1352.

It is particularly seen in FIGS. 20E & 20F that a longitudinal bore 1360 of a first diameter is formed through cylindrical portion 1302 fluidly communicating with a longitudinal channel 1362 of a second diameter, which is smaller than a first diameter, formed in tapered portion 1304. It is particularly seen that needle 1290 having an upward end 1364 and a sharp downward end 1366 is mounted into channel 1362 of needle hub 1280, preferably by means of adhesive. It is appreciated that the upward end 1364 of needle 1290 is sealingly disposed within channel 1362.

It is further seen that an aperture 1370 is formed in an intermediate location on needle 1290. It is also seen that a radially extending socket 1372 is formed as an extension of aperture 1350 in tapered portion 1304. Socket 1372 preferably extends transversely with respect to longitudinal axis 1300 and preferably intersects channel 1362.

It is a particular feature of an embodiment of the present invention that the dimensions of aperture 1350 formed in tapered portion 1304 are larger than the dimensions of aperture 1370 formed in needle 1290 such that socket 1372 contains a portion of needle 1290 therewithin and fluid communication is permitted between aperture 1350, aperture 1370 and around the circumference of needle 1290 within socket 1372.

It is also seen in FIGS. 20E and 20F that a circumferential groove 1376 is formed within skirt 1310 defining a generally planar downwardly facing surface 1378 adapted for engagement with needle biasing and sealing element 616.

Figure 21B:
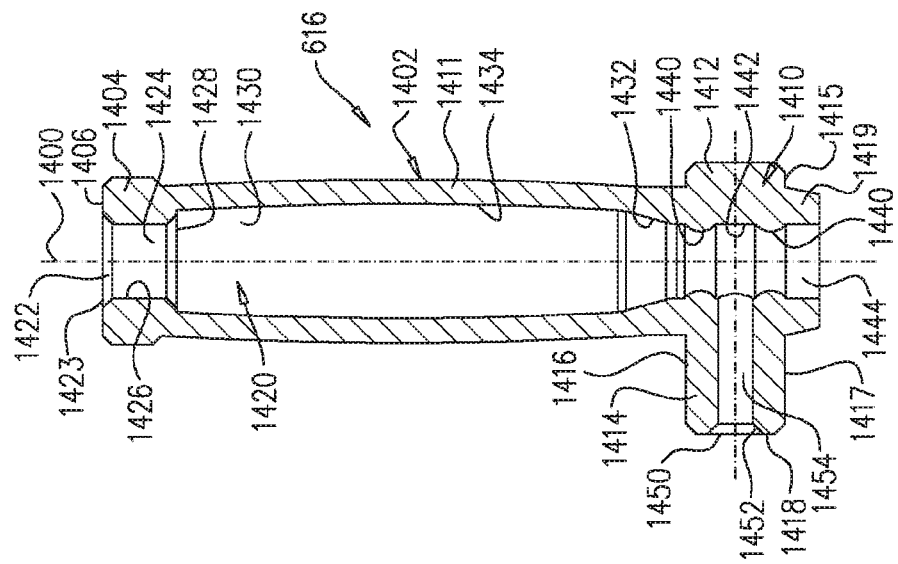
FIGS. 21A and 21B are respective pictorial and sectional illustrations of a needle biasing and sealing element, forming part of the medicament supply and infusion assembly of FIGS. 17A & 17B in a first operative state.
Figure 21A:
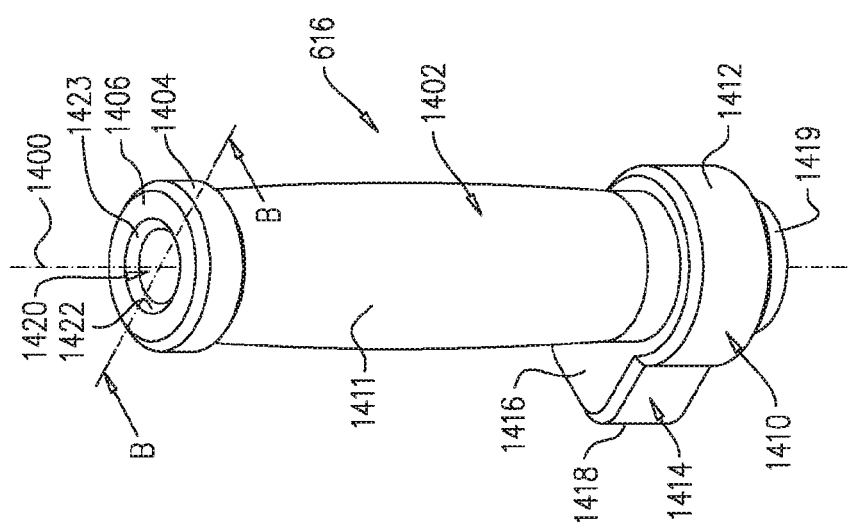

Reference is now made to FIGS. 21A and 21B, which are respective pictorial and sectional illustrations of the needle biasing and sealing element 616, forming part of the medicament supply and infusion assembly 998 of FIGS. 17A & 17B in a first operative state. FIGS. 21A & 21B are simplified respective pictorial illustration and a sectional view taken along lines B-B in FIG. 21A of needle biasing and sealing element 616.

It is seen in FIGS. 21A & 21B that needle biasing and sealing element 616 is an integrally formed element, preferably made of rubber, and is generally arranged along longitudinal axis 1400, which extends generally transversely with respect to longitudinal axis 650.

Needle biasing and sealing element 616 is shown in at rest operative orientation in FIGS. 21A & 21B. It is seen in FIGS. 21A & 21B that needle biasing and sealing element 616 is a generally longitudinal cylindrical element 1402 arranged along axis 1400 having an upward end having a radially outwardly extending upper circumferential flange 1404 formed thereon, which defines an upwardly facing surface 1406. It is also seen that needle biasing and sealing element 616 has a downward end having a radially extending portion 1410 formed preferably adjacent thereto. Cylindrical element 1402 further includes a resilient biasing portion 1411 disposed between circumferential flange 1404 and radially extending portion 1410 and is adapted to be compressed when positioned in a stressed operative orientation. Radially extending portion 1410 preferably includes a bottom circumferential flange 1412 encircling cylindrical element 1402 and a generally planar wall portion 1414 extending radially outwardly therefrom. Bottom circumferential flange 1412 defines a downwardly facing surface 1415. Planar wall portion 1414 defines an upwardly facing surface 1416, a downwardly facing surface 1417, which joins downwardly facing surface 1415 and a side facing surface 1418 which joins surfaces 1416 and 1417. Bottom cylindrical portion 1419 extends downwardly from radially extending portion 1410.

It is particularly seen in FIG. 21B that the cylindrical element 1402 is formed with a varying diameter througoing bore 1420 arranged along longitudinal axis 1400. An aperture 1422 is formed in upwardly facing surface 1406 having an inwardly tapered edge surface 1423 and communicating with an upward bore portion 1424 formed within upper circumferential flange 1404. Upward bore portion 1424, having a first diameter, extends downwardly from edge surface 1423 and defines inner surface 1426.

An outwardly tapered surface 1428 disposed adjacent inner surface 1426 and downwardly thereof. An intermediate longitudinal bore portion 1430, formed in resilient biasing portion 1411, extends downwardly from tapered surface 1428 to an inwardly tapered surface 1432. Longitudinal bore portion 1430 has a second diameter, relatively greater than the first diameter and defines an inner surface 1434.

Disposed downwardly of inwardly tapered surface 1432 and within bottom circumferential flange 1412 are typically two mutually spaced inwardly extending circumferential sealing protrusions 1440 defining an inwardly facing surface 1442 therebetween. A bottom bore portion 1444 is formed downwardly of sealing protrusions 1440 and communicates with intermediate bore portion 1430, upward bore portion 1424 and aperture 1422.

It is further particularly seen in FIG. 21B that an aperture 1450 is formed in surface 1418 of planar wall portion 1414 defining an outwardly tapered surface 1452 and communicating with a bore 1454 extending from aperture 1450 into througoing bore 1420. Bore 1454 is preferably disposed transversely with respect to througoing bore 1420 and fluidly communicates therewith. It is appreciated that bore 1454 partially intersects througoing bore 1420 in a location disposed between sealing protrusions 1440.

Figure 22A:
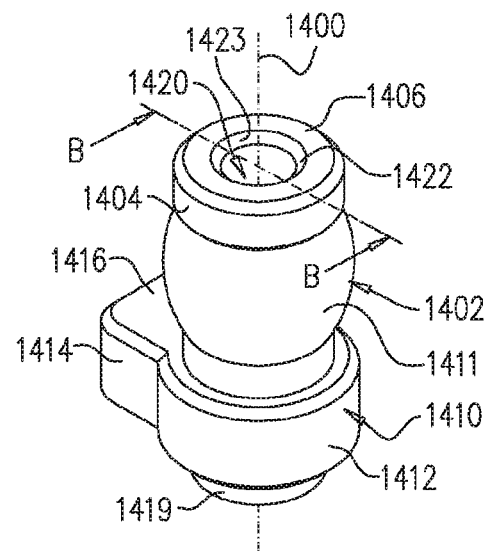
FIGS. 22A and 22B are respective pictorial and sectional illustrations of the needle biasing and sealing element, forming part of the medicament supply and infusion assembly of FIGS. 17A & 17B in a second operative state.
Figure 22B:
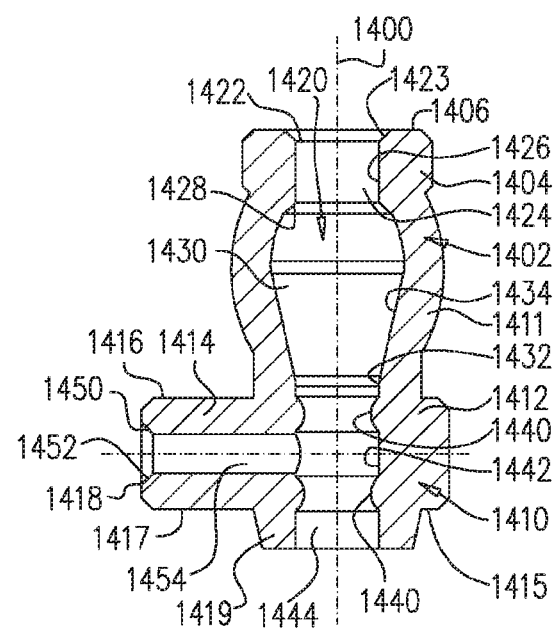

Reference is now made to FIGS. 22A and 22B, which are respective pictorial and sectional illustrations of the needle biasing and sealing element 616, forming part of the medicament supply and infusion assembly 998 of FIGS. 17A & 17B in a second operative state. FIGS. 22A & 22B are simplified respective pictorial illustration and a sectional view taken along lines B-B in FIG. 22A of needle biasing and sealing element 616.

It is particularly seen in FIGS. 22A & 22B that in a stressed operative orientation of the needle biasing and sealing element, as is described in detail hereinbelow, the resilient biasing portion 1411 is axially compressed along longitudinal axis 1400, such that upper circumferential flange 1404 is disposed closer to bottom circumferential flange 1412 in this stressed operative orientation than in at rest operative orientation.

Reference is now made to FIGS. 23A, 23B, 23C & 23D, which are simplified pictorial illustrations of the bottom housing portion 520 of the disposable base portion 130 of the patch pump assembly 100 of FIGS. 1 and 2. FIGS. 23A-23D are simplified respective two pictorial illustrations shown from two different perspectives, side plan view and top plan view illustrations of the bottom housing portion 520.

As seen in FIGS. 23A-23D, bottom housing portion 520 preferably is an integrally formed element, preferably injection molded from relatively rigid plastic, such as polycarbonate.

Bottom housing portion 520 has a generally planar floor portion 1470 having an upper surface 1472 and a bottom surface 1474, a partially circumferential curved portion 1476 extends upwardly from planar floor portion 1470 and defines an upwardly facing edge 1478, adapted to engage a corresponding edge of the upper housing portion 510 and two forwardly facing edges 1480. It is appreciated that bottom surface 1474 is adapted for engagement with injection site adhesive sticker 670.

Figure 23B:
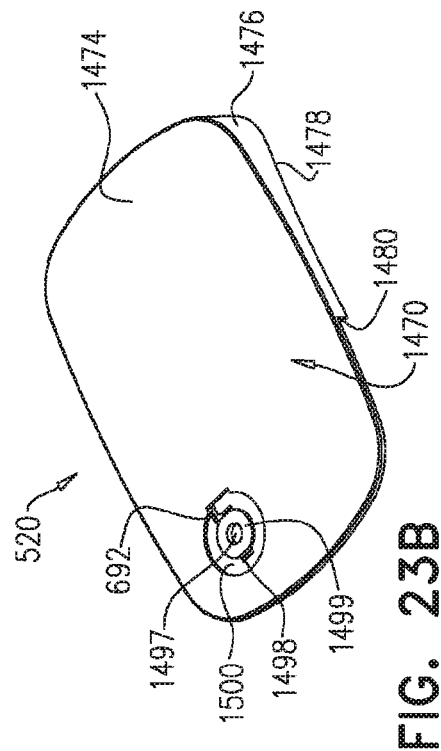
FIGS. 23A, 23B, 23C & 23D are simplified pictorial illustrations of a bottom housing portion of the disposable base portion of the patch pump assembly of FIGS. 1 and 2.
Figure 23D:
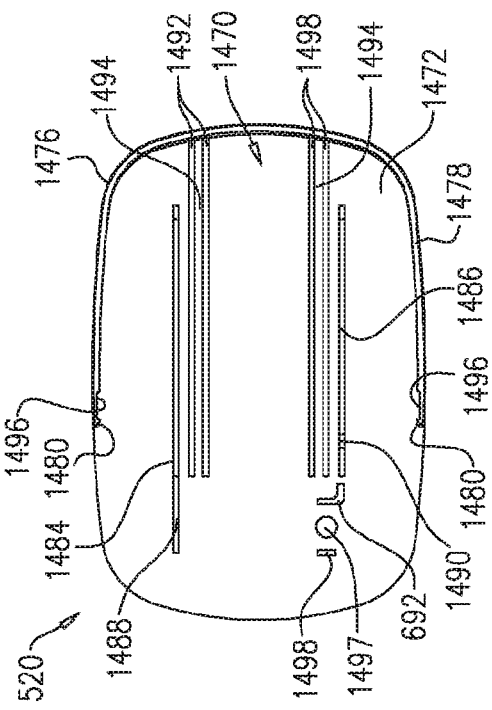
Figure 23A:
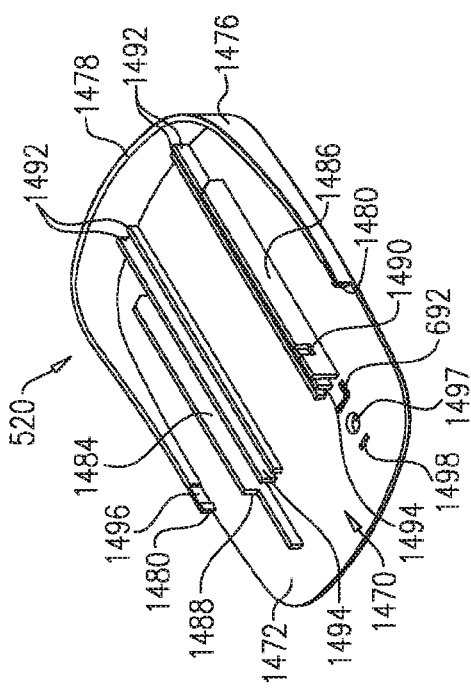
Figure 23C:
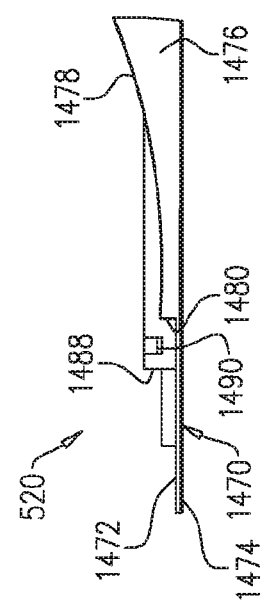

It is seen in FIGS. 23A and 23D that preferably two upwardly protruding, preferably symmetric with respect to longitudinal axis 650, axially extending ribs 1484 and 1486 are formed on upper surface 1472 of bottom housing portion 520. It is seen particularly in FIGS. 23A and 23C that a forwardly facing shoulder 1488 is defined on rib 1484. It is further seen in FIG. 23A that a cut-out 1490 is formed adjacent the forward end of rib 1486 adapted for cooperation with an optical sensor, forming part of the reusable portion 110 of the patch pump assembly 100.

Disposed inwardly with respect to each of ribs 1484 and 1486 is a pair of axially extending guiding track ribs 1492, forming a guiding channel 1494 therebetween for guiding axial displacement of linear displacer 640 relative to bottom housing portion 520.

It is seen in FIGS. 23A and 23D that a recess 1496 is formed adjacent each of the two forwardly facing edges 1480 of curved portion 1476, and adapted for cooperating with manually actuable buttons 260, forming part of the reusable portion 110.

It is seen in FIGS. 23A-23D that a central aperture 1497 is formed in planar portion 1470 adjacent forward end thereof, configured for insertion of needle 1290 therethrough. A generally L-shaped aperture 692 (FIG. 10) is formed slightly rearwardly of central aperture 1497 for insertion of shafts 686 and 690 of injection site engagement element 680 therethrough. An additional aperture 1498 is formed slightly forwardly of central aperture 1497 for insertion of shaft 688 of injection site engagement element 680 therethrough.

It is seen in FIG. 23B that an injection site engagement element seat 1499 is formed in a recess 1500 formed on the bottom surface 1474 of bottom housing portion 520.

Reference is now made to FIGS. 24A, 24B, 24C & 24D, which are simplified pictorial illustrations of injection site engagement element 680 of the disposable base portion of the patch pump assembly of FIGS. 1 and 2. FIGS. 24A-24D are simplified respective pictorial illustration, first side plan view, second side plan view and top plan view illustrations of the injection site engagement element 680.

It is seen in FIGS. 24A-24D that injection site engagement element 680 is an integrally formed element injection molded of plastic.

As previously noted, the injection site engagement element 680 includes engagement surface defining ring 684 arranged along longitudinal axis 1502, which extends transversely with respect to longitudinal axis 650. Injection site engagement element 680 also has three upstanding shafts, 686, 688 and 690, which are parallel to axis 1502.

It is seen that each of shafts 686 and 688 has two protrusions 1504 formed on the sides of the shafts, adapted to retain the injection site engagement element 680 from being released from bottom housing portion 520. It is further seen that each one of shafts 686 and 688 defines an upwardly facing edge 1506 having two generally tapered surfaces 1508 and shaft 690 defines upwardly facing edge 691. Shafts 686 and 688 further each define an inwardly facing surface 1510 and an outwardly facing surface 1512.

Engagement surface defining ring 684 defines an upwardly facing surface 1516, downwardly facing surface 1518 and a central aperture 1520.

Figure 25A:
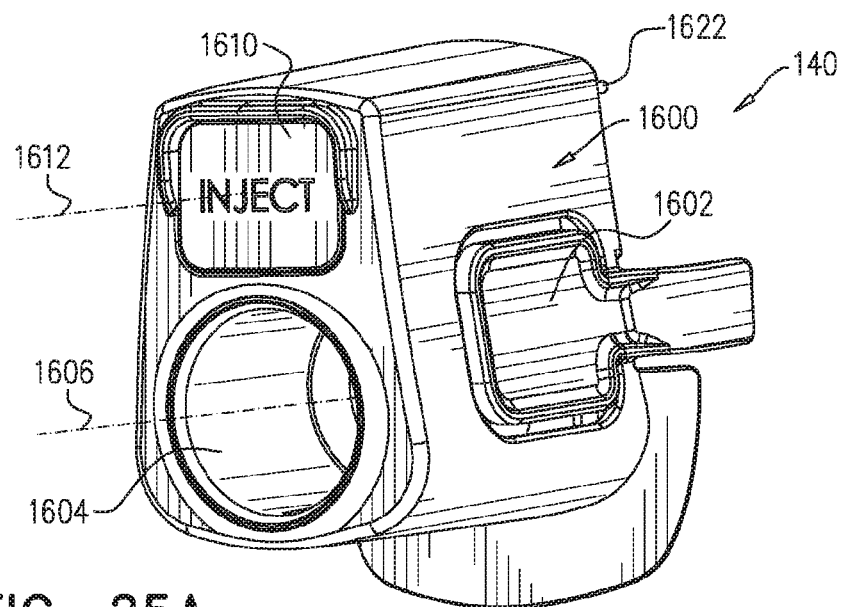
FIGS. 25A and 25B are simplified pictorial illustrations of a disposable interface and control module forming part of the patch pump assembly of FIGS. 1 and 2.
Figure 25B:
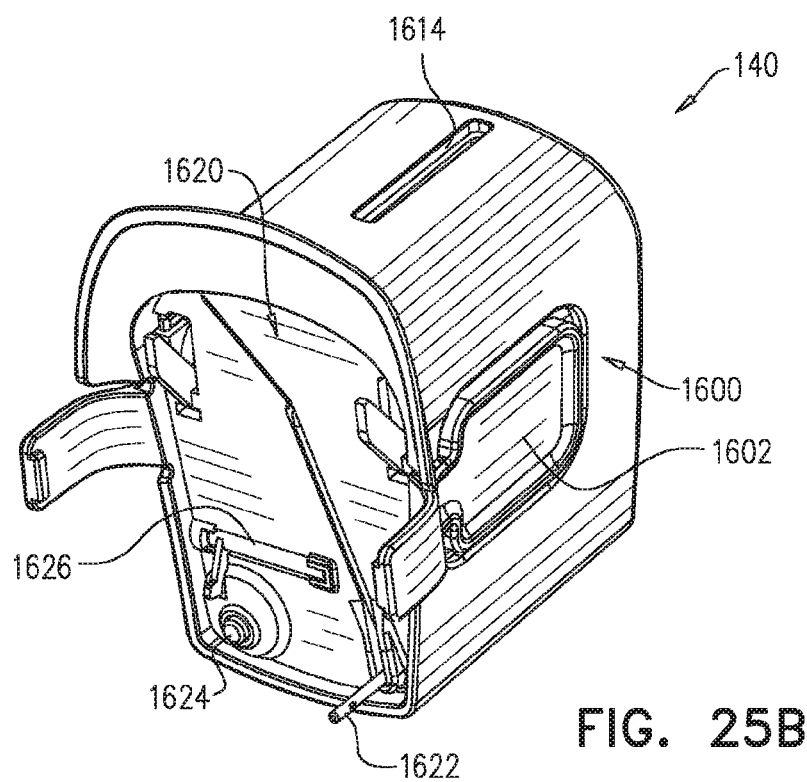

Reference is now made to FIGS. 25A and 25B, which are simplified pictorial illustrations of the disposable interface and control module 140 forming part of the patch pump assembly 100 of FIGS. 1 and 2.

It is seen in FIGS. 25A & 25B that the disposable interface and control module 140 is adapted to be selectably releasably mounted onto disposable base portion 130 to form the disposable portion 120. It is particularly seen that a housing portion 1600 is adapted to be mounted onto the disposable base portion 130, by means of manually actuable buttons 1602 forming part of the housing portion 1600 and adapted to operatively cooperate with top housing portion 510 of disposable base portion 130.

It is further seen in FIGS. 25A & 25B that housing portion 1600 includes a generally longitudinal cylindrical well 1604 arranged along longitudinal axis 1606 and configured for insertion of a vial containing a medicament, thereinto.

A needle penetration actuation element 1610 is disposed within the housing portion 1600 and is preferably arranged along a longitudinal axis 1612, which is preferably parallel to axis 1606.

It is further seen that an indication window 1614 is formed on a side wall of housing portion 1600, providing for inspection of the medicament vial contents.

It is seen particularly in FIG. 25B that a base portion 1620 is fixedly mounted to housing portion 1600 and various components of the disposable interface and control module 140 are contained between housing portion 1600 and base portion 1620. Base portion 1620 particularly contains at least part of a medicament conduit 1622, a needle penetration actuation pin 1624 and an inadvertent needle penetration prevention element 1626 all partially protruding generally downwardly therefrom.

Figure 26:
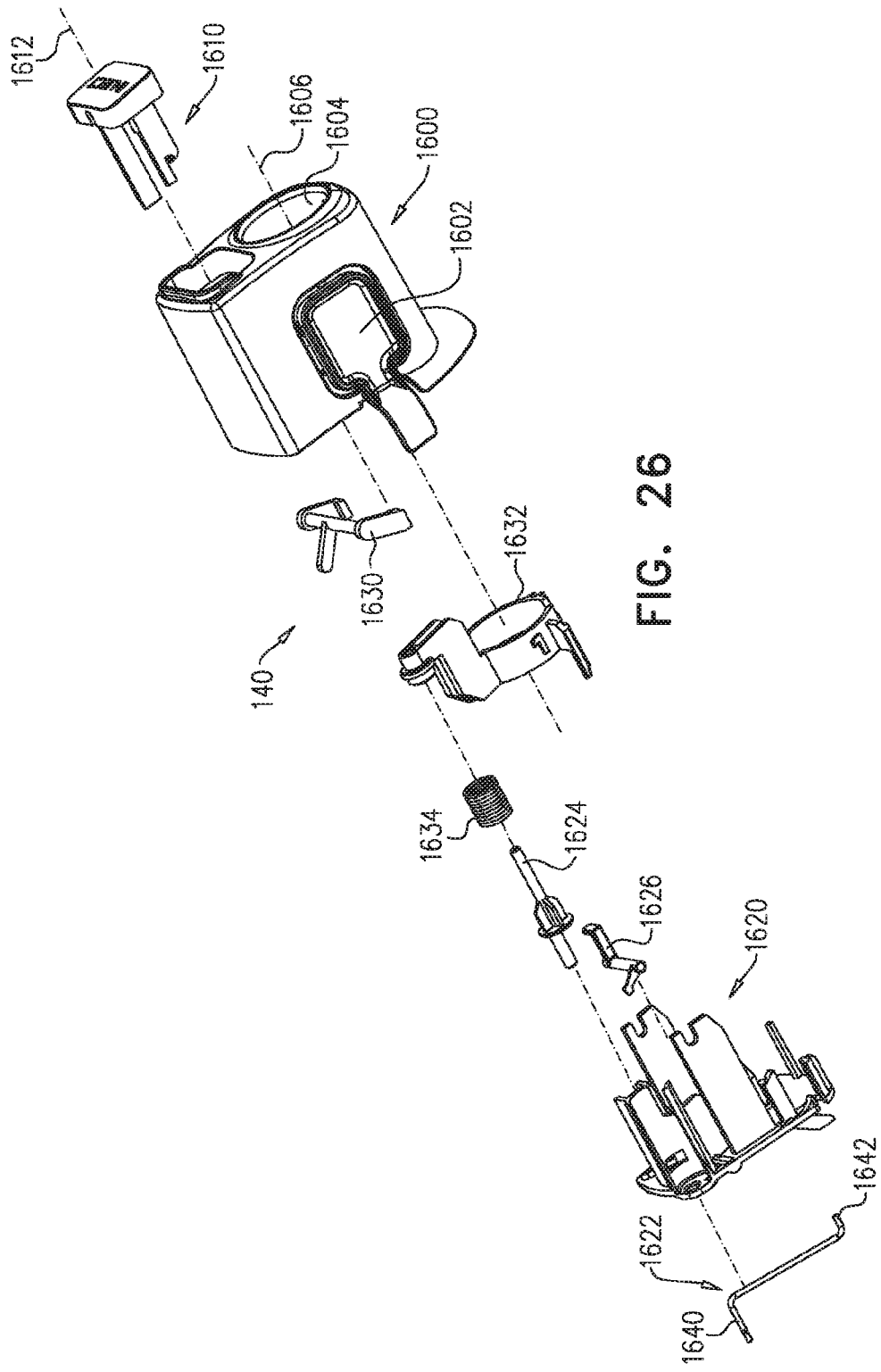
FIG. 26 is a simplified exploded view illustration of the disposable interface and control module of FIGS. 25A & 25B.

Reference is now made to FIG. 26, which is a simplified exploded view illustration of the disposable interface and control module 140 of FIGS. 25A & 25B.

As seen in FIG. 26, the disposable interface and control module 140 includes the housing portion 1600, and the needle penetration actuation element 1610 inserted therein along longitudinal axis 1612. Disposable interface and control module 140 further includes an inserter decoupling prevention element 1630 that is operatively engaged with needle penetration actuation element 1610, a vial adaptor portion 1632 adapted to be seated within well 1604 and arranged along longitudinal axis 1606 and is operatively engaged with both the base portion 1620 and the reusable portion 110 of patch pump assembly 100.

It is further seen in FIG. 26 that needle penetration actuation pin 1624 is contained within the disposable interface and control module 140 having a compression spring 1634 mounted thereon and adapted to be seated between needle penetration actuation pin 1624 and vial adaptor portion 1632. The inadvertent needle penetration prevention element 1626 and medicament conduit 1622 are adapted to be seated onto base portion 1620 and the medicament conduit 1622 has a first end 1640 adapted to be fluidly coupled with the filling septum 614 and a second end 1642 adapted to be fluidly coupled with the medicament vial.

Reference is now made to FIGS. 27A, 27B, 27C, 27D, 27E, 27F and 27G, which are simplified illustrations of the housing portion 1600, forming part of the disposable interface and control module 140 of FIGS. 25A-26. FIGS. 27A-27G are respective two pictorial illustrations shown from two different perspectives, top plan view and three different section views being taken along respective section lines D-D, E-E, F-F and G-G in FIG. 27C of the housing portion 1600.

It is seen in FIGS. 27A-27G that housing portion 1600 is an integrally formed hollow element having a generally rectangular cross section, defining a rearward wall portion 1700, a forward wall portion 1702, two side wall portions 1704 and a top wall portion 1706. Forward wall portion 1702, rearward wall portion 1700 and side wall portions 1704 together define an inner circumferential surface 1707. A generally curved cover extension 1708 extends rearwardly from rearward wall portion 1700.

Manually actuable buttons 1602 are formed on side wall portions 1704 by means of partially circumferential recesses 1720 formed in side wall portions 1704 around buttons 1602. Manually actuable buttons 1602 include a generally planar portion 1722 disposed in side wall portions 1704 and bounded by recess 1720, a generally curved portion 1724 extending downwardly and outwardly from side wall portions 1704 and an integral hinge portion 1726 joining the planar portion 1722 and the curved portion 1724 of buttons 1602 and adapted for providing pivotable displacement of the curved portion 1724 upon force exertion on the planar portion 1722. It is further seen that curved portion 1724 of each of manually actuable buttons 1602 defines an inner surface 1730. An inwardly extending retaining protrusion 1732 is formed at the downwardmost edge of curved portion 1724 of each of manually actuable buttons 1602, which extends inwardly from inner surface 1730 and is adapted for operative engagement with the top housing portion 510 of the disposable base portion 130.

It is further seen in FIGS. 27A-27G that cylindrical well 1604 extends from top wall portion 1706 and defines an inner surface 1740, an outer surface 1742 and a downwardly facing edge surface 1744. Typically, two undercut portions 1746 extend downwardly and generally inwardly with respect to longitudinal axis 1606 and are formed on downwardly facing edge surface 1744. Undercut portions 1746 are adapted to fixedly retain the medicament vial within the disposable interface and control module 140 upon insertion of the medicament vial thereinto.

A generally longitudinal window 1750 is formed in well 1604 and extends upwardly from downwardly facing edge surface 1744. It is appreciated that window 1750 is preferably aligned with window 1614 and thus inspection of medicament vial contents by the user is enabled.

A button receiving socket 1760 is formed in top wall portion 1706, forwardly of well 1604 and defining an inner circumferential surface 1761 and a downwardly facing edge surface 1762. A partially circumferential rim 1764 extends upwardly from top wall portion 1706 and disposed around socket 1760.

It is seen in FIGS. 27A-27G that a partition wall portion 1770 is formed within button receiving socket 1760, disposed between the inner surface 1707 of forward wall portion 1702 and outer surface 1742 of well 1604 and extends generally downwardly from downwardly facing edge 1762 of socket 1760.

The partition wall portion 1770 has an upwardly facing edge surface 1772 and includes a forward wall portion 1774 and a rearward wall portion 1776, generally downwardly extending therefrom. Rearward wall portion 1776 is spaced from well 1604 by a recess 1778 defining a downwardly facing curved surface 1780 disposed slightly downwardly of downwardly facing edge surface 1762 of socket 1760. Rearward wall portion 1776 defines a downwardly facing edge surface 1782.

Forward wall portion 1774 is spaced from rearward wall portion 1776 by a recess 1784 defining a downwardly facing curved surface 1786 disposed slightly downwardly of curved surface 1780. Forward wall portion 1774 is further spaced from inner surface 1707 of forward wall portion 1702 by a recess 1788 defining a downwardly facing curved surface 1790.

Figure 27A:
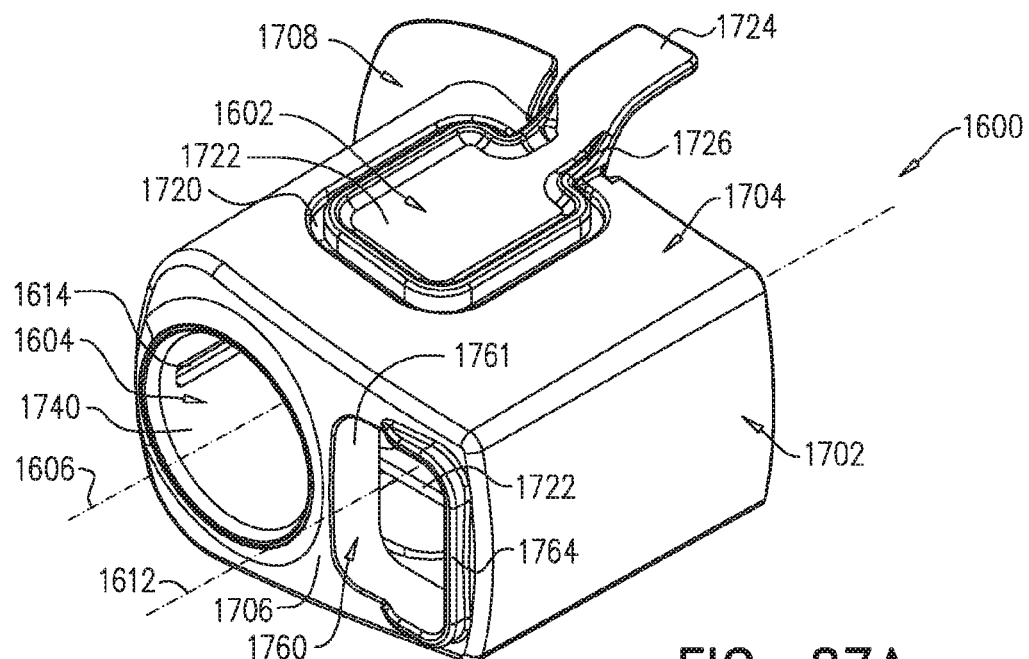
FIGS. 27A, 27B, 27C, 27D, 27E, 27F and 27G are simplified illustrations of a housing portion, forming part of the disposable interface and control module of FIGS. 25A-26.
Figure 27B:
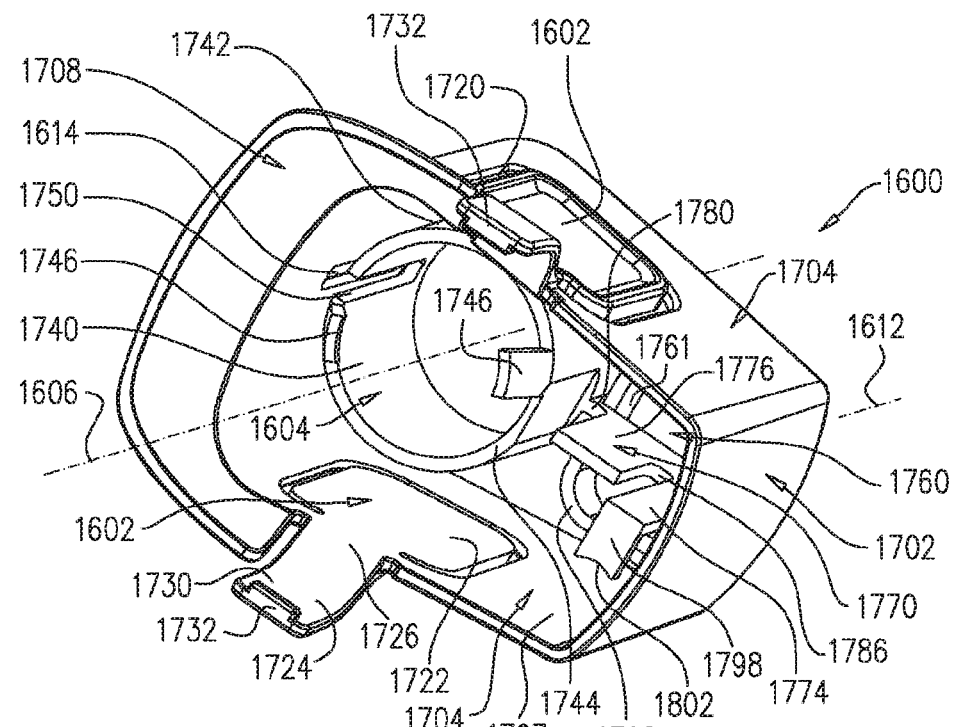
Figure 27C:
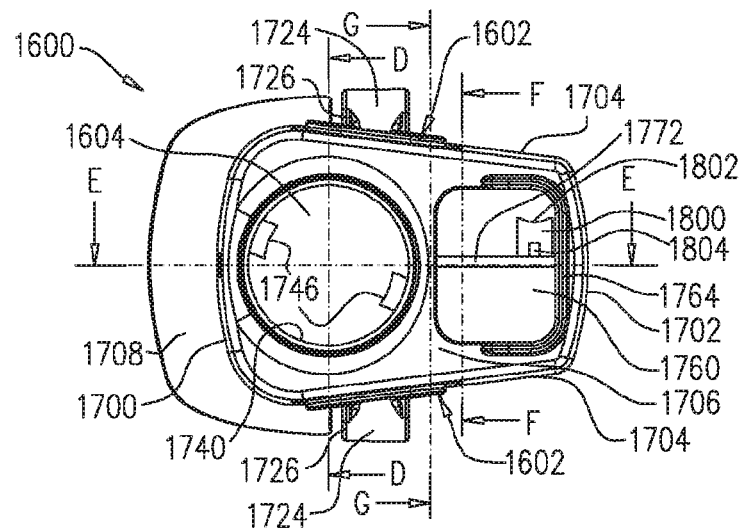
Figure 27D:
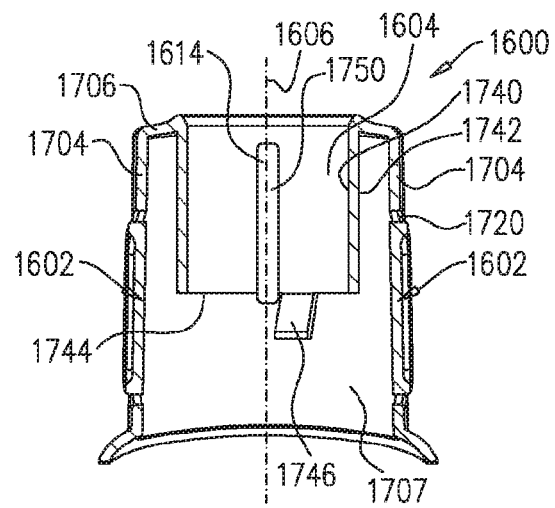
Figure 27E:
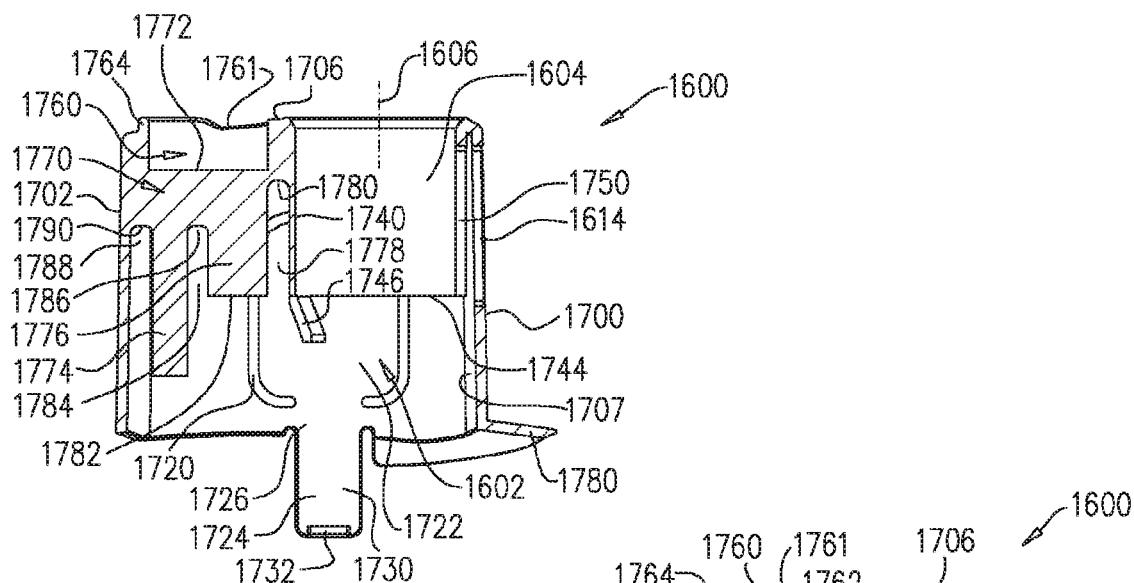
Figure 27F:
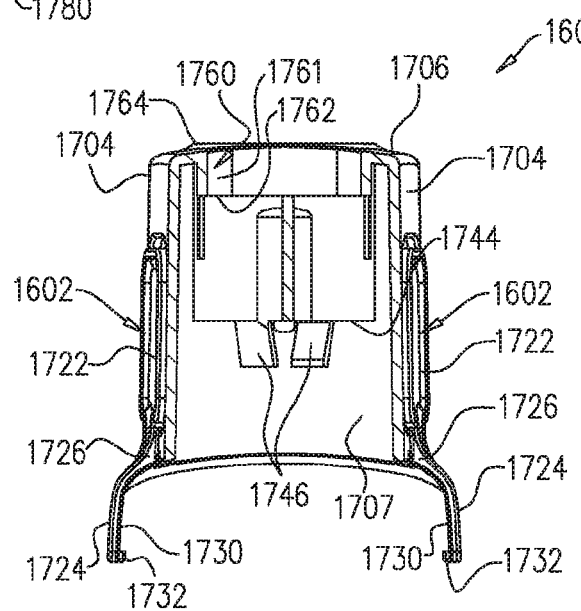
Figure 27G:
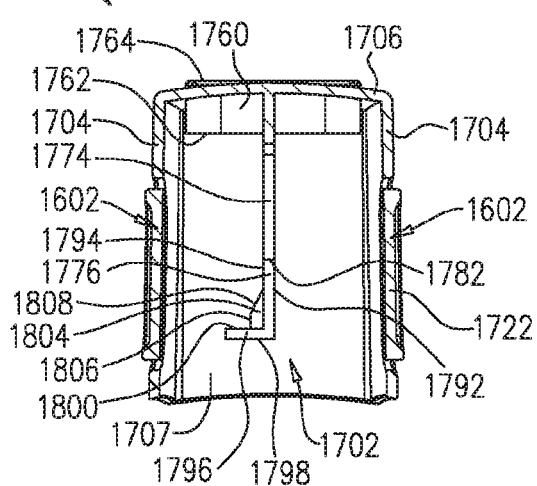
Figure 28F:
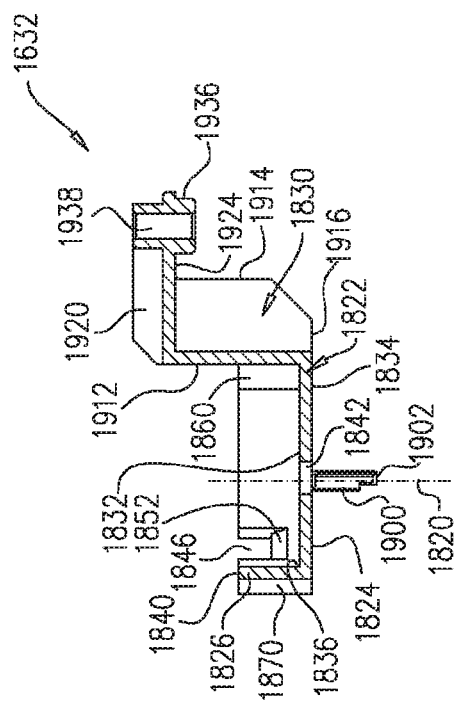
Figure 28E:
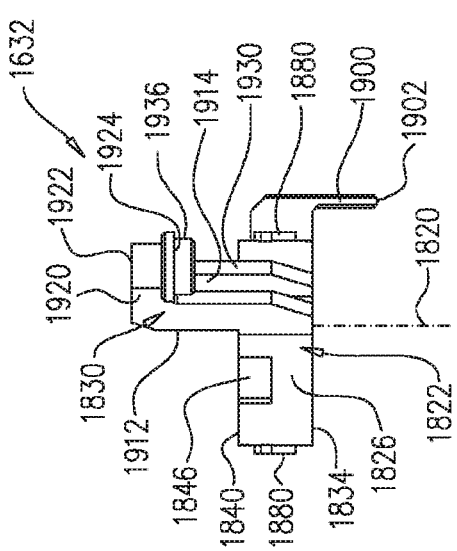

It is particularly seen in FIGS. 27B & 27G that forward wall portion 1774 defines a first side surface 1792, a second side surface 1794 and a transversely disposed wall portion 1796 disposed at the downward end of forward wall portion 1774. Transversely disposed wall portion 1796 defines a downwardly facing surface 1798, an upwardly facing surface 1800, and a generally concave edge surface 1802 facing side wall portion 1704. A protrusion 1804 is formed on second side surface 1794 of forward wall portion 1774, which joins second side surface 1794 and wall portion 1796. Protrusion 1804 defines a generally planar edge surface 1806 adjacent wall portion 1796 and a generally tapered edge surface 1808 upwardly thereof and joining second side surface 1794.

Reference is now made to FIGS. 28A, 28B, 28C, 28D, 28E and 28F are simplified illustrations of the vial adaptor portion 1632, forming part of the disposable interface and control module 140 of FIGS. 25A-26. FIGS. 28A-28F are respective two pictorial illustrations shown from two different perspectives, top plan view, first side plan view, second side plan view and a section views being taken along section lines F-F in FIG. 28C of the vial adaptor portion 1632.

It is seen in FIGS. 28A-28F that vial adaptor portion 1632 is an integrally formed element injection molded of plastic and arranged around longitudinal axis 1820.

Vial adaptor portion 1632 includes a vial seating portion 1822, which has a general planar circular wall portion 1824 and a circumferential rim 1826 extending generally upwardly from wall portion 1824 and generally transversely thereto. Vial adaptor portion 1632 further includes an L-shaped vial adaptor retaining portion 1830 generally extending upwardly from wall portion 1824.

It is seen in FIGS. 28A-28F that wall portion 1824 defines an upwardly facing surface 1832 and a downwardly facing surface 1834. The circumferential rim 1826 defines an inwardly facing surface 1836, an outwardly facing surface 1838 and an upwardly facing edge surface 1840. A central aperture 1842 is formed in wall portion 1824. Generally, two radially opposed cut-outs 1846 are formed in circumferential rim 1826 and extend downwardly from upwardly facing edge surface 1840 and defining an upwardly facing edge surface 1850, which is located downwardly of edge surface 1840, and a downwardly tapered surface 1852 extending from edge surface 1850. An additional cut-out 1860 is formed in circumferential rim 1826 and extends from upwardly facing edge surface 1840 to wall portion 1824 and forming a longitudinal groove 1862 facing vial adaptor retaining portion 1830.

It is seen in FIGS. 28A-28F that typically two radially outwardly extending guiding track protrusions 1870 are formed on the outer surface 1838 of circumferential rim 1826 and are disposed in a radially opposite location with respect to vial adaptor retaining portion 1830. Guiding track protrusions 1870 form a longitudinal groove 1872 therebetween.

It is further seen in FIGS. 28A-28F that typically two retaining protrusions 1880 are formed on the outer surface 1838 of circumferential rim 1826 and are disposed in a radially opposite location one with respect to another. Retaining protrusions 1880 generally extend radially outwardly from outer surface 1838 and include a generally planar longitudinal portion 1882 and a generally downwardly tapered portion 1884 connected thereto by an edge portion 1886. Planar longitudinal portion 1882 defines an inner facing edge surface 1890 connected to an inner facing tapered edge surface 1892 defined by tapered portion 1884.

It is further seen in FIGS. 28A-28F that a switch actuating protrusion 1900 is formed on the outer surface 1838 of circumferential rim 1826. It is noted that switch actuating protrusion 1900 extends generally outwardly and downwardly of wall portion 1824, defining a downwardly facing engaging edge 1902, disposed downwardly of wall portion 1824.

It is further seen in FIGS. 28A-28F that vial adaptor retaining portion 1830 includes a longitudinally extending portion 1910 defining an inwardly facing edge surface 1912, an outwardly facing edge surface 1914 and a downwardly facing edge surface 1916 joining downwardly facing surface 1834 of vial seating portion 1822, vial adaptor retaining portion 1830 further includes an extension portion 1920, extending generally transversely with respect to longitudinally extending portion 1910 and defining an upwardly facing edge surface 1922 and a downwardly facing edge surface 1924. It is seen that a guiding groove 1930 is formed in both outwardly facing edge surface 1914 and partially in downwardly facing edge surface 1916. It is further seen that a groove 1932 is formed in upwardly facing edge surface 1922.

A generally cylindrical spring seat 1936 is formed on downwardly facing edge surface 1924 and extending downwardly therefrom. A central bore 1938 is formed through spring seat 1936 and extends upwardly through extension portion 1920.

Figure 29A:
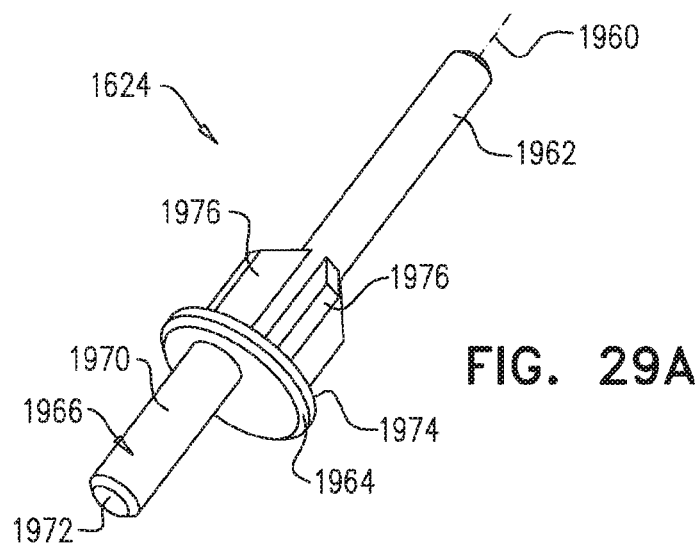
FIGS. 29A and 29B are simplified illustrations of a needle penetration actuation pin, forming part of the disposable interface and control module of FIGS. 25A-26.
Figure 29B:
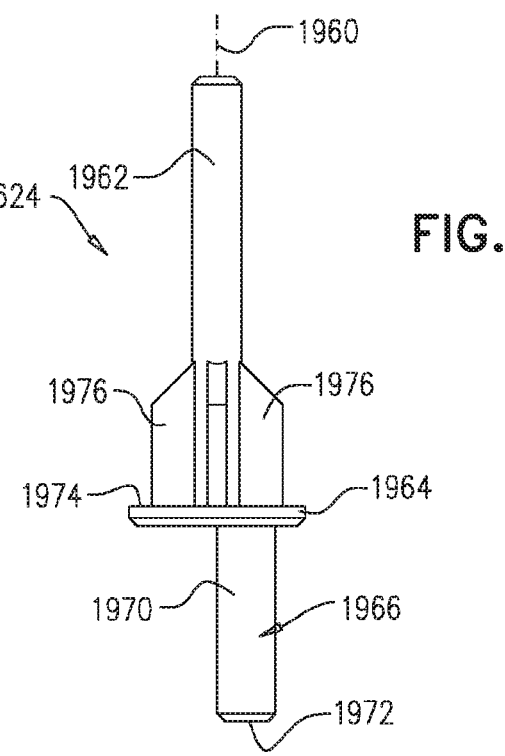
Figure 30B:
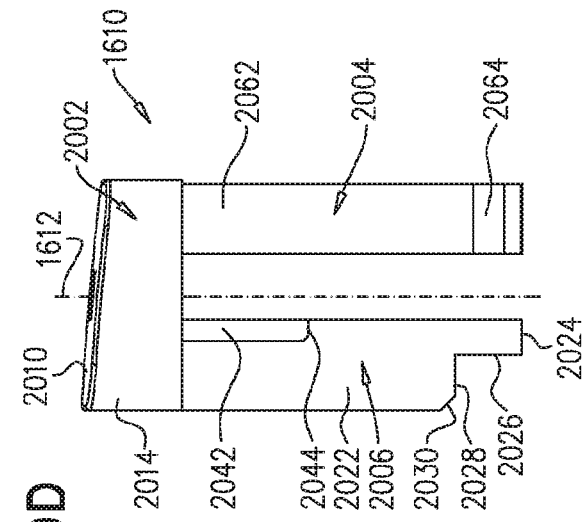
FIGS. 30A, 30B, 30C and 30D are simplified illustrations of a needle penetration actuation element, forming part of the disposable interface and control module of FIGS. 25A-26.
Figure 30A:
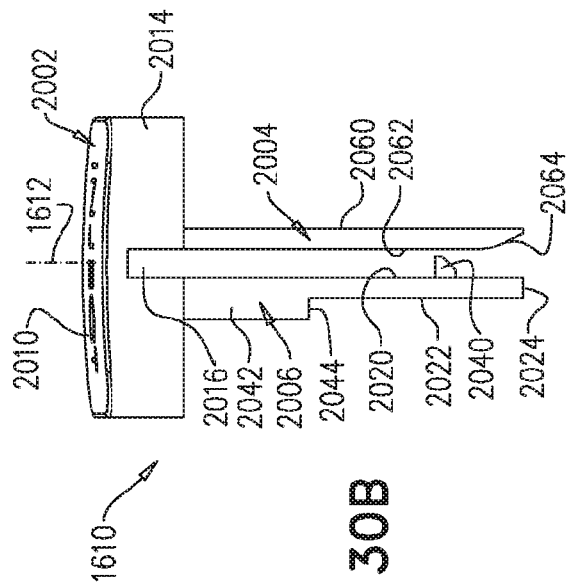
Figure 30D:
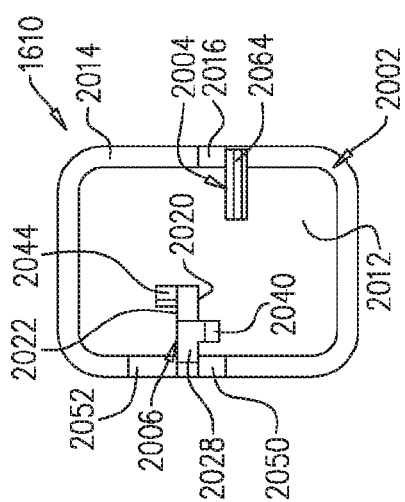
Figure 30C:
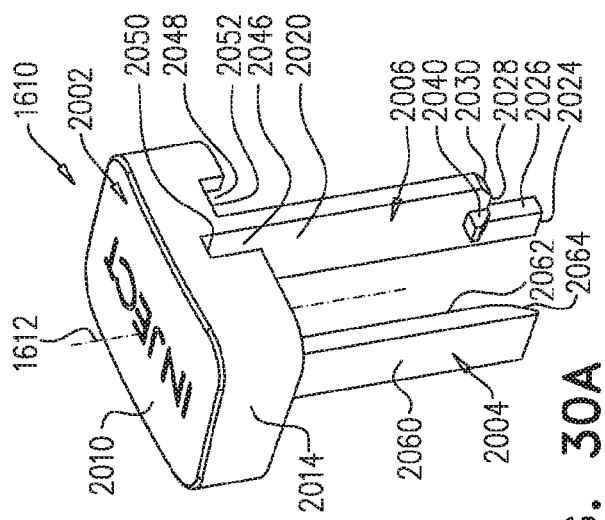

Reference is now made to FIGS. 29A and 29B, which are simplified illustrations of the needle penetration actuation pin 1624, forming part of the disposable interface and control module 140 of FIGS. 25A-26. FIGS. 29A & 29B are respective simplified pictorial illustration and a side plan view of the needle penetration actuation pin 1624.

It is seen in FIGS. 29A & 29B that needle penetration actuation pin 1624 is an integrally formed element injection molded of plastic and arranged around longitudinal axis 1960.

Needle penetration actuation pin 1624 includes a generally longitudinal cylindrical rod 1962 extending upwardly from a generally circular flange portion 1964 and a generally cylindrical activation rod 1966 extending downwardly from flange portion 1964. Cylindrical rod 1962 extends along longitudinal axis 1960. Cylindrical activation rod 1966 is offset from longitudinal axis 1960 and extends along an axis, which is parallel to longitudinal axis 1960. Cylindrical activation rod 1966 defines an outer surface 1970 and a downwardly facing end surface 1972.

Flange portion 1964 defines an upwardly facing surface 1974. Typically, four ribs 1976 extend generally radially outwardly from cylindrical rod 1962 and upwardly from upwardly facing surface 1974 of flange portion 1964. It is appreciated that ribs 1976 are adapted for positioning of spring 1634.

Reference is now made to FIGS. 30A, 30B, 30C and 30D, which are simplified illustrations of the needle penetration actuation element 1610, forming part of the disposable interface and control module 140 of FIGS. 25A-26. FIGS. 30A-30D are respective simplified pictorial illustration, first side plan view, top plan view and second side plan view of the needle penetration actuation element 1610.

It is seen in FIGS. 30A-30D that needle penetration actuation element 1610 is an integrally formed element injection molded of plastic and arranged around longitudinal axis 1612.

Needle penetration actuation element 1610 preferably includes a preferably rectangular finger engagement portion 2002, an activating shaft 2004 extending downwardly therefrom and extending along an axis parallel to longitudinal axis 1612 and a retaining shaft 2006 extending downwardly therefrom and extending along another axis parallel to longitudinal axis 1612.

Finger engagement portion 2002 defines an upwardly facing surface 2010, a downwardly facing surface 2012 and a circumferential rim 2014 extends downwardly therefrom. Activating shaft 2004 and retaining shaft 2006 are preferably formed on opposite side walls formed by rim 2014.

A cut-out 2016 is formed in rim 2014 adjacent activating shaft 2004 and defines a downwardly facing edge surface 2018. Retaining shaft 2006 defines a first side surface 2020, a second side surface 2022 and a downwardmost edge 2024. A stepped cut-out is formed adjacent the downwardmost edge 2024, forming a planar axially extending edge surface 2026, a downwardly facing edge 2028 disposed upwardly than downwardmost edge 2024 and an upwardly tapered edge surface 2030.

It is seen in FIGS. 30A-30D that a protrusion 2040 is formed on the first side surface 2020 and adapted for retaining the needle penetration actuation element 1610 within the disposable interface and control module 140. It is seen that protrusion 2040 is preferably disposed adjacent to downwardly facing edge 2028 and extends preferably radially outwardly.

It is further seen in FIGS. 30A-30D that a generally elongate rib 2042 is formed on the second side surface 2022 of retaining shaft 2006. Elongate rib 2042 extends generally downwardly from downwardly facing surface 2012 along portion of the longitudinal extent of retaining shaft 2006. It is appreciated that elongated rib 2042 defines a downwardly facing edge surface 2044.

It is seen that generally two cut-outs 2046 and 2048 are formed in circumferential rim 2014, from each side of retaining shaft 2006. Cut-out 2046 defines downwardly facing edge surface 2050, which is disposed upwardly from a downwardly facing edge surface 2052 defined by cut-out 2048.

It is appreciated that activating shaft 2004 defines an outwardly facing surface 2060, an inwardly facing surface 2062 and a downwardly tapered edge surface 2064.

Figure 31A:
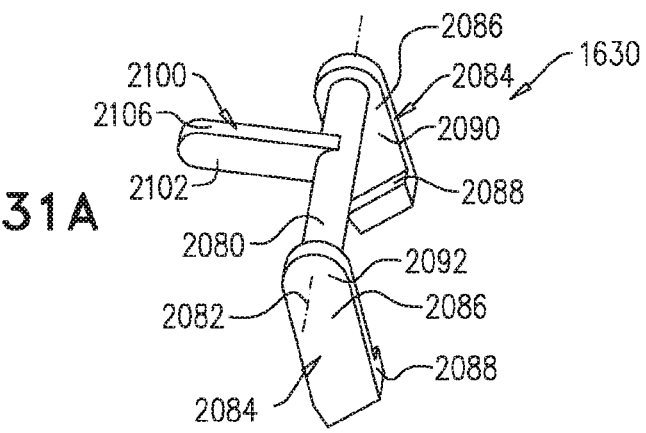
FIGS. 31A, 31B and 31C are simplified illustrations of an inserter decoupling prevention element, forming part of the disposable interface and control module of FIGS. 25A-26.
Figure 31B:
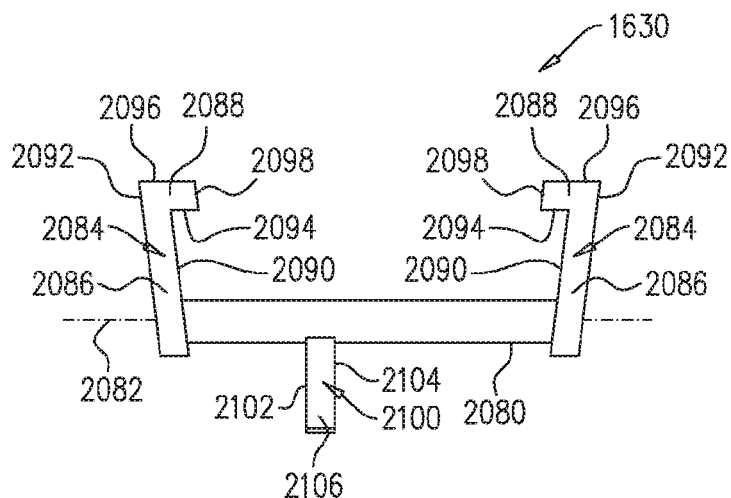
Figure 31C:
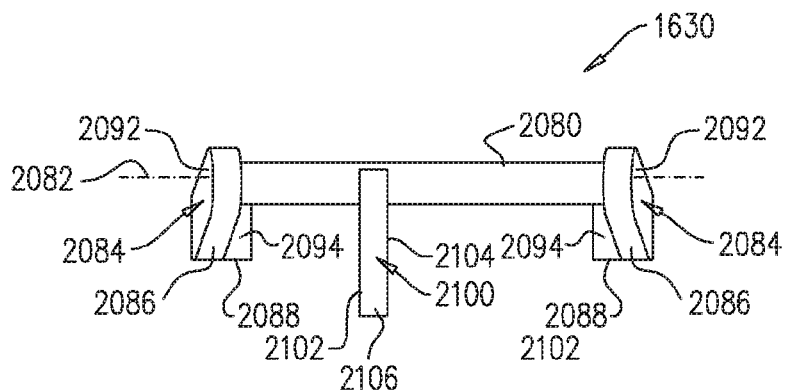
Figure 32A:
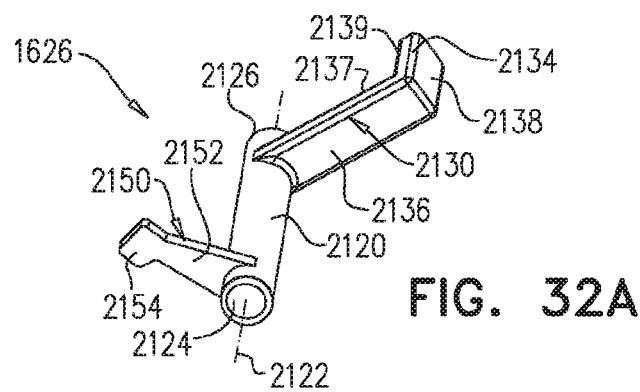
FIGS. 32A, 32B, 32C and 32D are simplified illustrations of an inadvertent needle penetration prevention element, forming part of the disposable interface and control module of FIGS. 25A-26.
Figure 32B:
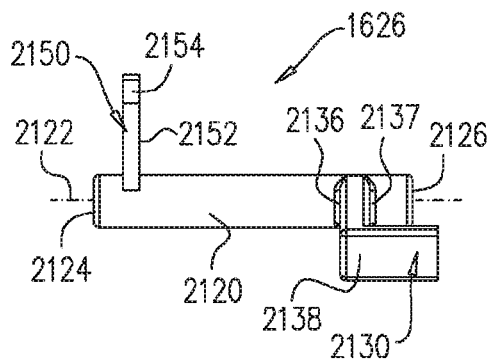
Figure 32C:
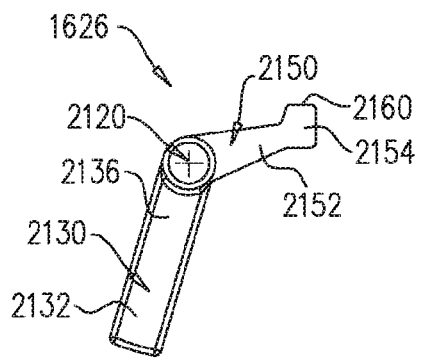
Figure 32D:
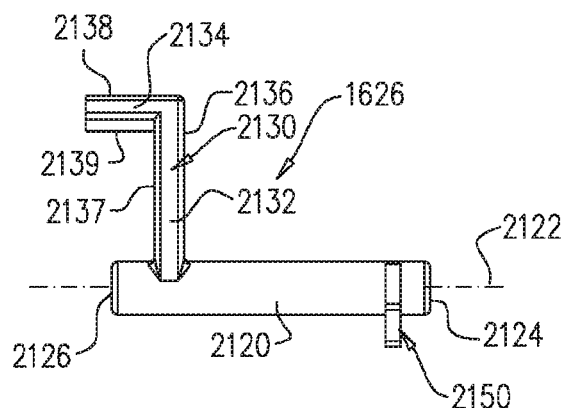
Figure 33A:
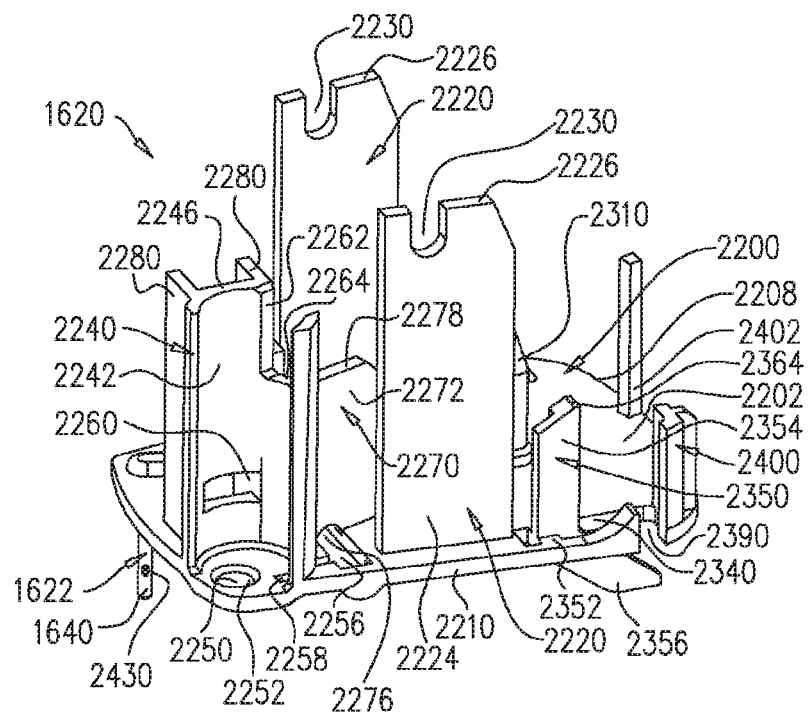
FIGS. 33A, 33B, 33C, 33D, 33E, 33F and 33G are simplified illustrations of a base element, forming part of the disposable interface and control module of FIGS. 25A-26.
Figure 33B:
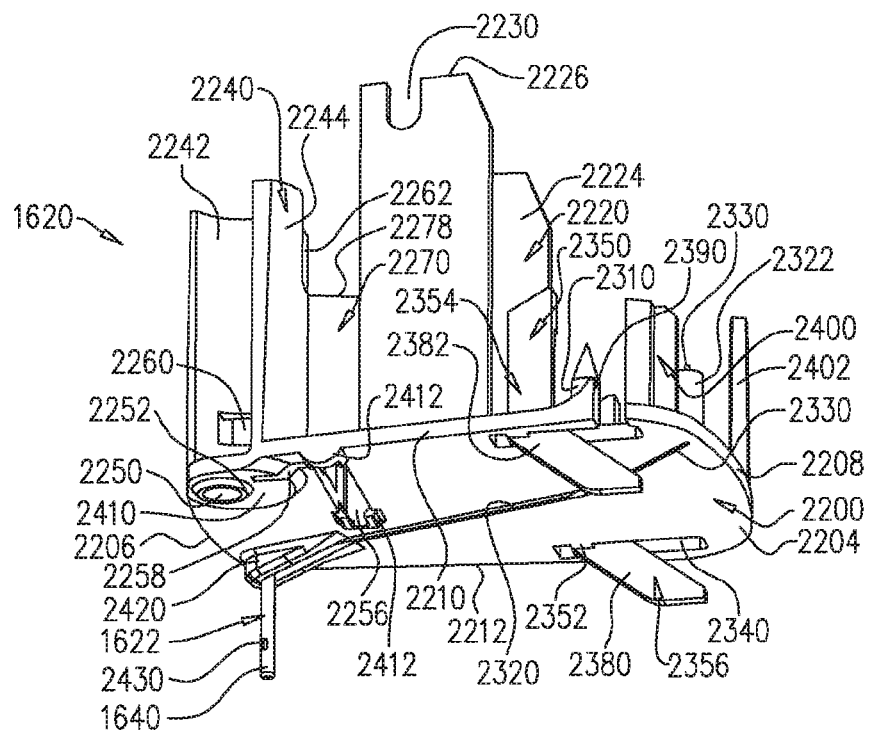
Figure 33C:
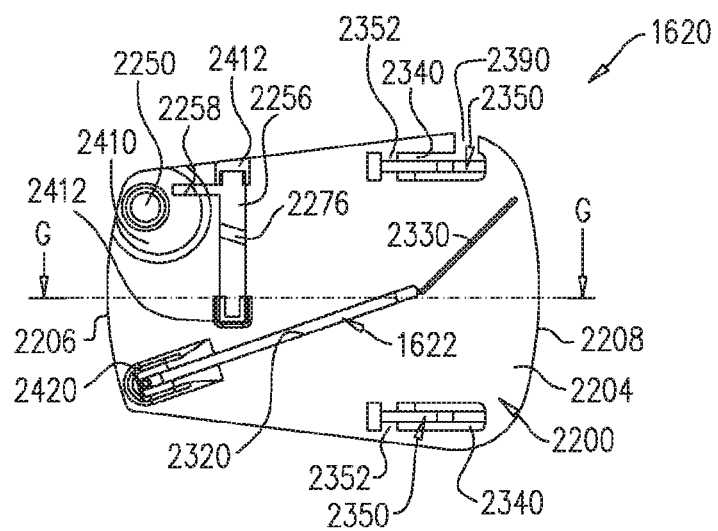
Figure 33D:
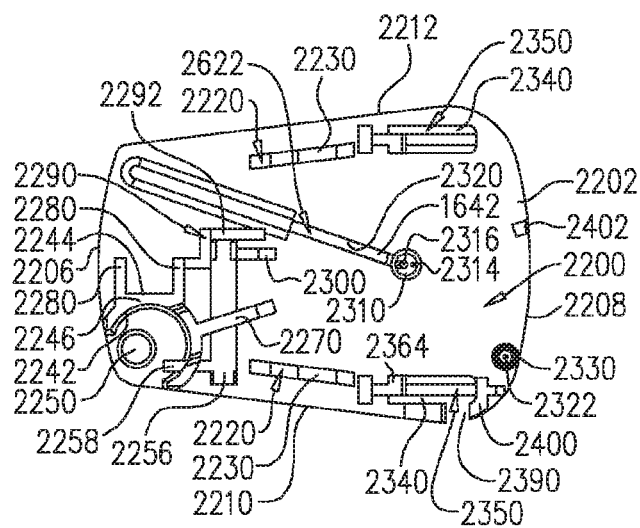
Figure 33E:
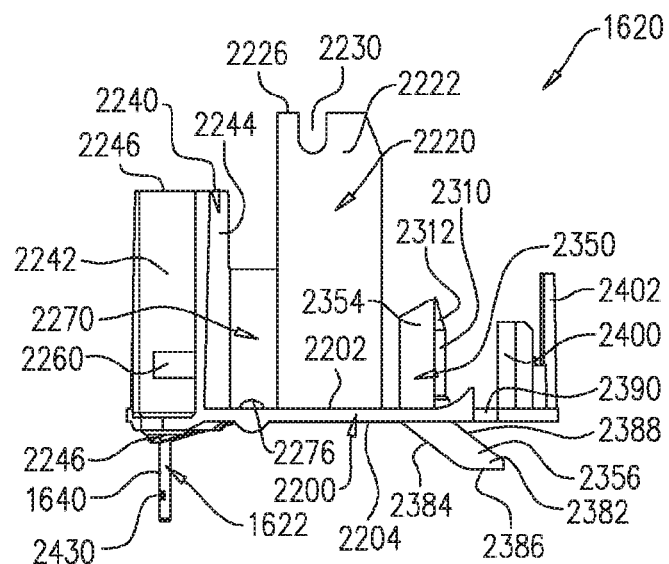
Figure 33F:
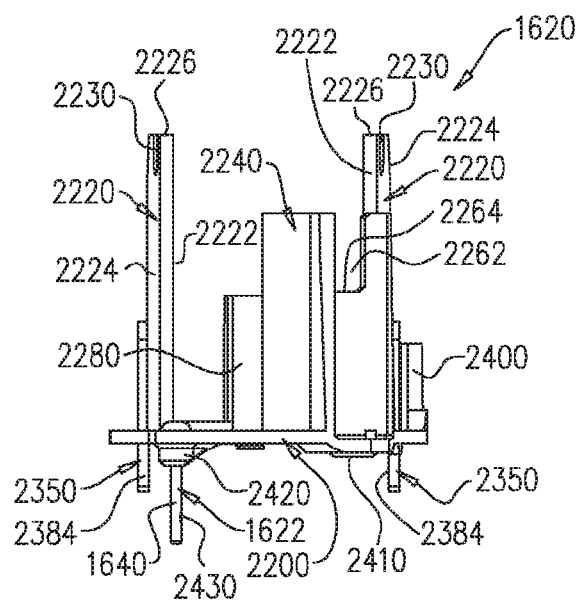
Figure 33G:
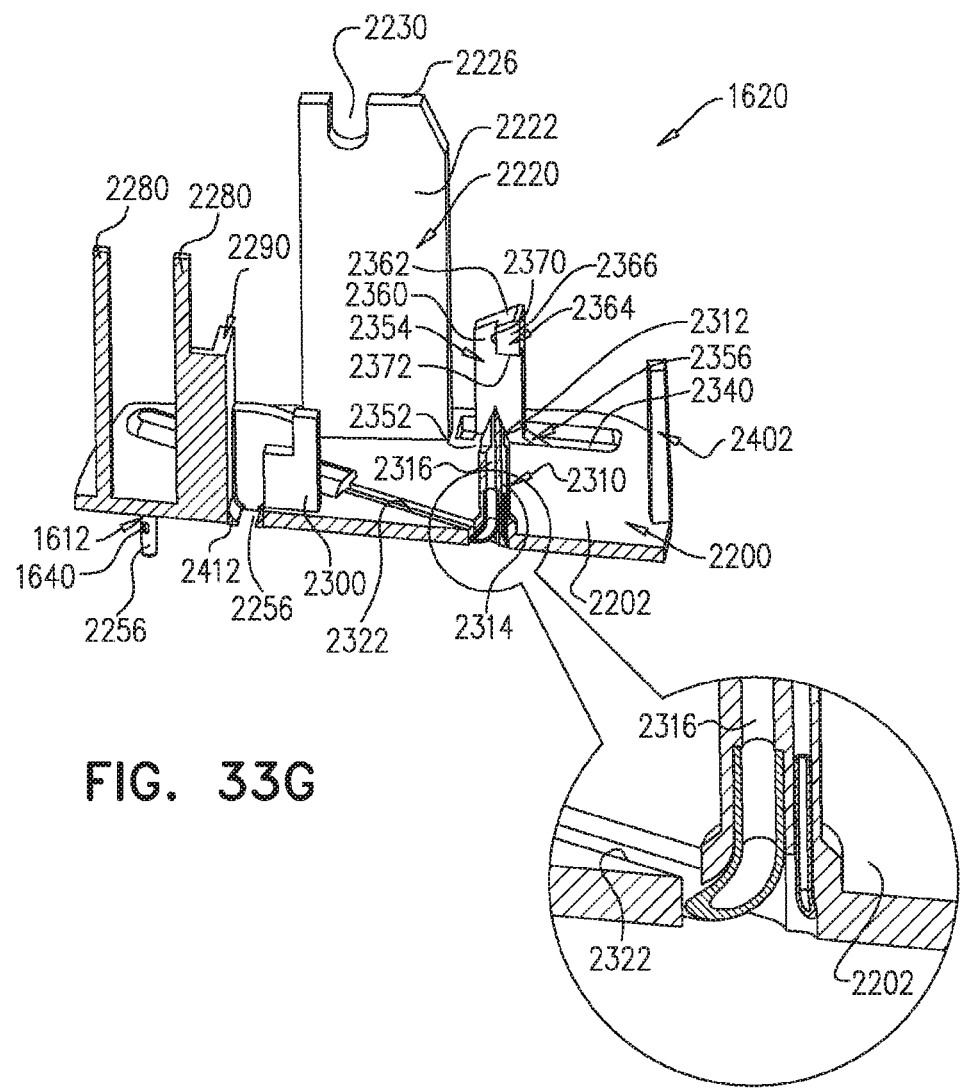

Reference is now made to FIGS. 31A, 31B and 31C, which are simplified illustrations of the inserter decoupling prevention element 1630, forming part of the disposable interface and control module 140 of FIGS. 25A-26. FIGS. 31A-31C are respective simplified pictorial view, top plan view and front plan view of the inserter decoupling prevention element 1630.

It is seen in FIGS. 31A-31C that inserter decoupling prevention element 1630 is an integrally formed element injection molded of plastic.

Inserter decoupling prevention element 1630 preferably includes a generally cylindrical elongate pivoting rod 2080 arranged along axis 2082 and having two arm portions 2084 disposed at each side of the pivoting rod 2080. It is appreciated that each of arm portions 2084 includes a generally planar portion 2086 extending at an obtuse angle with respect to axis 2082 and a retaining portion 2088 extending generally inwardly with respect to planar portion 2086 and transversely thereto.

It is appreciated that planar portions 2086 define an inwardly facing surface 2090 and an outwardly facing surface 2092. Retaining portions 2088 define an inwardly facing surface 2094, an outwardly facing surface 2096 and a side edge surface 2098 connecting therebetween.

It is further seen in FIGS. 31A-31C that engagement rod 2100 generally extends downwardly and at an angle to pivoting rod 2080 and is disposed between arm portions 2084. It is appreciated that engagement rod 2100 defines a first planar side surface 2102, a second planar side surface 2104 and a circumferential edge surface 2106.

Reference is now made to FIGS. 32A, 32B, 32C and 32D, which are simplified illustrations of the inadvertent needle penetration prevention element 1626, forming part of the disposable interface and control module 140 of FIGS. 25A-26. FIGS. 32A-32D are respective simplified pictorial view, top plan view, first side view and second side view of the inadvertent needle penetration prevention element 1626.

It is seen in FIGS. 32A-32D that inadvertent needle penetration prevention element 1626 is an integrally formed element injection molded of plastic.

The inadvertent needle penetration prevention element 1626 preferably includes a generally cylindrical elongate pivoting rod 2120 arranged along axis 2122 and defining a first end surface 2124 and a second end surface 2126.

It is seen in FIGS. 32A-32D that a retaining portion 2130 extend generally radially outwardly and upwardly from pivoting rod 2120 and is disposed generally adjacent second end surface 2126. Retaining portion 2130 includes a generally planar wall portion 2132 extending generally transversely with respect to axis 2122 and an extension portion 2134 integrally formed therewith and extends generally in parallel to axis 2122. Planar wall portion 2132 defines a first side surface 2136 and a second side surface 2137 and extension portion 2134 defines a first side surface 2138 and a second side surface 2139.

It is further seen in FIGS. 32A-32D that an engagement portion 2150 extend generally radially outwardly and downwardly from pivoting rod 2120 and disposed generally adjacent first end surface 2124. Engagement portion 2150 includes a generally planar wall portion 2152 and an end portion 2154, defining a side edge engaging surface 2160.

Reference is now made to FIGS. 33A, 33B, 33C, 33D, 33E, 33F and 33G, which are simplified illustrations of the base element 1620, forming part of the disposable interface and control module 140 of FIGS. 25A-26. FIGS. 33A-33G are respective simplified two pictorial views shown from different perspectives, bottom plan view, top plan view, first and second side views and a section view taken along lines G-G in FIG. 33C of the base element 1620 including the medicament conduit 1622 mounted thereon.

It is seen in FIGS. 33A-33G that base element 1620 is an integrally made injection molded element, having medicament conduit 1622 mounted thereon, having first end 1640 adapted to be fluidly coupled with the filling septum 614 and a second end 1642 adapted to be fluidly coupled with the medicament vial.

It is seen in FIGS. 33A-33G that base element 1620 includes a base wall portion 2200 defining an upwardly facing surface 2202 and a downwardly facing surface 2204. Base wall portion 2200 has a forward edge surface 2206, a rearward edge surface 2208, a first side edge surface 2210 and a second side edge surface 2212.

Typically, two longitudinal flat wall portions 2220 extend upwardly from base wall portion 2200 and transversely thereto. Wall portions 2220 are each disposed adjacent respective side edge surface 2210 and 2212 and in an intermediate location between forward edge surface 2206 and rearward edge surface 2208. Each wall portion 2220 defines an inwardly facing surface 2222, an outwardly facing surface 2224 and an upwardly facing edge surface 2226. It is particularly seen that a curved cut-out 2230 is formed in wall portions 2220 and extends downwardly from upwardly facing edge surface 2226.

A needle penetration actuation pin seat portion 2240 is disposed at the junction of forward edge surface 2206 and first side edge surface 2210 and extends upwardly from base wall portion 2200. Seat portion 2240 defines an inner partially circular surface 2242, an outer surface 2244 and an upwardly facing edge 2246. A central aperture 2250 is formed in base wall portion 2200 and disposed interiorly of seat portion 2240. Aperture 2250 defines an interior circumferential surface 2252 and is adapted for insertion of needle penetration actuation pin 1624 therethrough.

A generally longitudinal cut-out groove 2256 is formed in base wall portion 2200 and is disposed between wall portions 2220 and seat portion 2240 and extends from a location adjacent first side edge surface 2210 toward second side edge surface 2212. A side cut-out 2258 is formed in base wall portion 2200 and extends forwardly from cut-out groove 2256 and into the interior volume defined by seat portion 2240.

An additional cut-out 2260 is formed in seat portion 2240 and is disposed upwardly with respect to base wall portion 2200.

A cut-out 2262 is formed in the seat portion 2240 and extends generally downwardly from upwardly facing edge surface 2246 thereof. Cut-out 2262 defines an upwardly facing edge surface 2264, which is disposed lower than upwardly facing edge 2246.

A side protrusion 2270 extends upwardly from base wall portion 2200 and radially outwardly from outer surface 2244 of seat portion 2240. Side protrusion 2270 is a generally planar wall portion defining side surfaces 2272 and 2274, a downwardly facing edge surface having an upwardly extending curved surface 2276 disposed above cut-out groove 2256 and an upwardly facing edge surface 2278, which joins upwardly facing edge surface 2264 of cut-out 2262.

Two parallel side protrusions 2280 extend upwardly from base wall portion 2200 and radially outwardly from outer surface 2244 of seat portion 2240 toward second side edge surface 2212. A generally L-shaped protrusion 2290 extends upwardly from base wall portion 2200 and rearwardly of two parallel side protrusions 2280 and having a wall portion 2292, binding one side of cut-out groove 2256.

A generally L-shaped protrusion 2300 extends upwardly from wall base portion 2200. Protrusion 2300 is disposed adjacent and rearwardly of cut-out groove 2256 and is generally parallel to wall portion 2292.

It is particularly seen in FIGS. 33A-33G that a spike 2310 is formed on base wall portion 2200 and extends upwardly therefrom. Spike 2310 has a sharp upward end 2312 and two generally longitudinally extending grooves 2314 and 2316 are formed within spike 2310. It is seen that groove 2316 is fluidly coupled with medicament conduit 1622 mounted in a longitudinal cut-out 2320 formed in base wall portion 2200, which extends from spike 2310 toward forward edge surface 2206. It is appreciated that groove 2316 provides for fluid flow passage from medicament vial via medicament conduit 1622 and end 1640 thereof into medicament reservoir 660 of disposable base portion 130.

It is further seen that a generally hollow cylindrical protrusion 2322 is formed on base wall portion 2200 adjacent rearward edge surface 2208 and extends upwardly therefrom. Groove 2314 communicates with the atmosphere through conduit 2330, which extends from groove 2314 into the interior of protrusion 2322. It is appreciated that groove 2314 provides for air venting from the medicament reservoir 660 out to the atmosphere through conduit 2330.

It is particularly seen in FIGS. 33A-33G that two generally longitudinal cut-outs 2340 are formed adjacent first side edge surface 2210 and second side edge surface 2212 of base wall portion 2200, disposed rearwardly of wall portions 2220. A lever portion 2350 is formed within each of cut-outs 2340 and is connected to base wall portion 2200 by means of an integral hinge 2352. Each lever portion 2350 preferably includes an upward portion 2354 and a downward portion 2356. It is appreciated that the upward portion 2354 defines an outwardly facing surface 2358, an inwardly facing surface 2360 and a tapered upwardmost edge surface 2362. An inwardly directed protrusion 2364 extends from inwardly facing surface 2360 of each of lever portions 2350. Protrusion 2364 is disposed adjacent upwardmost edge surface 2362. It is also appreciated that protrusion 2364 defines an inwardly facing surface 2366, a forwardly facing edge surface 2370 and a downwardly facing edge surface 2372.

The downward portion 2356 protrudes downwardly from base wall portion 2200 and defines an inwardly facing surface 2380, an outwardly facing surface 2382, a generally rearwardly tapered edge 2384, a planar edge 2386 and a generally forwardly tapered edge 2388.

A lateral cut-out 2390 is formed in base wall portion 2200 and extends from cut-out 2340 to first side edge surface 2210.

It is further seen in FIGS. 33A-33G that a protrusion 2400 is formed on base wall portion 2200 and extends upwardly therefrom. Protrusion 2400 is disposed rearwardly of cut-out 2340, at the junction of first side edge surface 2210 and rearward edge surface 2208.

Additionally, an elongate protrusion 2402 is formed on base wall portion 2200 and extending upwardly therefrom. Protrusion 2402 is disposed adjacent rearward edge surface 2208, generally in an intermediate location between first side edge surface 2210 and second side edge surface 2212.

It is seen particularly on the underside of base element 1620 that a preferably circular protrusion 2410 is formed on base wall portion 2202 and protrudes slightly downwardly from downwardly facing surface 2204, encircling central aperture 2250.

It is further seen that two undercut protrusions 2412 are formed at each side of cut-out groove 2256 and extend slightly downwardly from downwardly facing surface 2204. Undercut protrusions 2412 are adapted for retaining needle penetration prevention element 1626 therewithin.

It is further particularly seen in FIGS. 33A-33F that a medicament conduit seat 2420 is formed on base wall portion 2202 and protrudes slightly downwardly from downwardly facing surface 2204. Seat 2420 is disposed adjacent junction of forwardly facing edge 2206 and second side edge surface 2212. Seat 2420 receives a portion of medicament conduit 1622, which extends through longitudinal cut-out 2320 and extends transversely with respect to base wall portion 2200 at the location defined by seat 2420.

It is appreciated that aperture 2430 is provided in the first end 1640 of medicament conduit 1622.

Reference is now made to FIGS. 34A-34D, which are simplified illustrations of the assembled reusable portion 110 of the patch pump assembly 100 of FIG. 1. FIGS. 34A-34D are respective simplified pictorial view, section views taken along respective lines B-B, C-C and D-D in FIG. 34A of the assembled reusable portion 110.

It is seen particularly in FIGS. 34A-34D that main housing portion 210 is fixedly attached to bottom housing portion 230 by means of heat welding, such that downwardly facing circumferential edge 318 of main housing portion 210 engages arm portions 402 and 404 of bottom housing portion 230, as seen in FIG. 34D. It is appreciated that manually actuable buttons 260 are either operatively attached or integrally made with the main housing portion 210. It is also seen particularly in FIG. 34C that circumferential edge 318 of main housing portion 210 engages upwardly facing rim 408 of bottom housing portion 230 and is fixedly attached thereto.

It is particularly seen in FIGS. 34B & 34D that plunger assembly 240 is fixedly mounted onto main housing portion 210. It is seen that magnetic element 442 of plunger assembly 240 is inserted through cut-out 316 of main housing and through bore 342 of internal subassembly 220. It is further seen that outwardly extending flange 436 of plunger assembly 240 is supported behind wall 314 of main housing portion 210 and thus plunger assembly 240 is retained mounted within base portion 280 of main housing portion 210, between wall 314 and wall 312 thereof.

It is specifically seen in FIG. 34B that container element 430 that gear 438 and electric motor 440 operatively connected thereto, are enclosed within container element 430. Magnetic element 442 is operatively coupled to motor 440 at its forward end for cooperation with hall effect sensor 344. As noted above, protrusion 448 of gear 438 protrudes through opening 435 of the container element 430 and drive element 450 is mounted onto protrusion 448. It is seen that drive element 450 defines rearwardly facing surface 452 and plurality of mutually azimuthally spaced teeth 456 formed thereon and are adapted to operative engage a portion of the disposable base portion 130.

It is particularly seen in FIG. 34C that internal subassembly 220 is inserted into inner volume 285 of main housing portion 210 and is retained between main housing portion 210 and bottom housing portion 230, such that base PCB portion 340 is retained within base portion 280 of main housing portion 210, side PCB portion 346 is retained within arm portion 284 of main housing portion 210 and battery 350 and USB connector 352 are retained within arm portion 282 of main housing portion 210.

It is seen that vial microswitch 378 of internal subassembly 220 is disposed below aperture 302 formed in main housing portion 210 and is aligned therewith. On/Off microswitch 374 of internal subassembly 220 is disposed below aperture 300 formed in main housing portion 210 and is aligned therewith.

It is further seen that sealing element 250 is mounted within inner volume 285 of arm portion 284 of main housing portion 210 and is retained between main housing portion 210 and internal subassembly 220, and is adapted to sealingly cover side PCB portion 340 and particularly microswitches 378 and 374. Particularly, it is seen that upper engagement surface 480 of sealing element 250 is fitted into aperture 302 and once upper engagement surface 480 is pressed, bottom engagement surface 482 of sealing element 250 is adapted to activate vial mnicroswitch 378, which lies underneath. Upper rearwardly tapered engagement surface 488 of sealing element 250 is fitted into aperture 300 and once engagement surface 488 is pressed, bottom engagement surface 490 of sealing element 250 is adapted to activate On/Off microswitch 374 of internal subassembly 220.

Reference is now made to FIGS. 35A-35J, which are simplified illustrations of an assembled disposable base portion 130 of the patch pump assembly 100 of FIG. 1. FIGS. 35A-35J are respective simplified pictorial view and section views taken along respective lines B-B, C-C, D-D, E-E, F-F, G-G, H-H, I-I and J-J in FIG. 35A of the assembled disposable base portion 130. It is seen particularly in FIG. 35B that top housing portion 510 (FIGS. 11A-11E) is fixedly attached to bottom housing portion 520 (FIGS. 23A-23D), preferably by means of welding. Adhesive sticker 670 is fixedly attached to bottom housing portion 520. Medicament reservoir 660 is enclosed between top housing portion 510 and bottom housing portion 520 and piston assembly 620 is partially inserted into medicament reservoir 660, such that piston base element 622 is sealingly disposed with respect to inner surface 778 of medicament reservoir 660. The piston assembly 620 is described in detail hereinabove with respect to FIGS. 16A-16E.

It is a particular feature of an embodiment of the present invention that piston assembly 620 is stationary relative to top housing portion 510 and bottom housing portion 520, whereas the medicament reservoir 660 along with the linear displacer 640 are axially displaceable relative to top housing portion 510 and bottom housing portion 520.

It is specifically seen in FIG. 35B that two upper arm portions 806 of linear displacer 640 (FIGS. 13A-13D) are slidably guided by guiding channels 744 of top housing portion 510 and two bottom arm portions 806 of linear displacer 640 are slidably guided by guiding channels 1494 of bottom housing portion 520.

It is further noted with respect to FIG. 35B that longitudinal slots 730 and 732 formed in top housing portion 510 are adapted for insertion of downward portions 2356 of lever portions 2350 of base portion 1620 (FIGS. 33A-33G) therethrough and lateral extension slot 734 is adapted for insertion of switch actuating protrusion 1900 of vial adaptor portion 1632 (FIGS. 28A-28F) therethrough. Inwardly extending protrusion 750 formed on top housing portion 510 is configured to operatively engage On/Off switch 374 of reusable portion 110.

It is specifically seen in FIG. 35C that in medicament reservoir 660 is initially spaced from curved portion 706 of top housing portion 510 and is disposed forwardly therefrom, such that piston assembly 620 abuts rearward end wall 772 and interior volume 774 of the medicament reservoir 660 is substantially eliminated.

It is further seen that infusion needle assembly 612 is inserted into needle assembly location bore 1030 of housing element 610 and needle hub 1280 of infusion needle assembly 612 is retained from upward displacement by engagement with forward bottom surface 762 of top housing portion 510. It is seen that needle hub 1280 of infusion needle assembly 612 is aligned with aperture 722 of top housing portion 510 and upward edge 1308 of needle hub 1280 is substantially coplanar with upper surface 702 of top housing portion 510 and is disposed within aperture 722.

It is seen in FIG. 35C that 616 is disposed in its first operative orientation, whereas needle biasing and sealing element 616 is in a non-stressed position, such as shown in FIGS. 21A & 21B. It is further noted that needle biasing and sealing element 616 is sealingly disposed over needle hub 1280, such that fluid flow passage outside of througoing bore 1420 of needle biasing and sealing element 616 is prevented.

It is specifically seen that upper circumferential flange 1404 of needle biasing and sealing element 616 is upwardly supported by needle hub 1280, such that upwardly facing surface 1406 of needle biasing and sealing element 616 engages downwardly facing surface 1378 of infusion needle assembly 612. It is appreciated that inner surface 1426 of needle biasing and sealing element 616 engages the needle hub 1280 of infusion needle assembly 612.

It is further seen that radially extending portion 1410 of needle biasing and sealing element 616 is upwardly supported within housing element 610 and downwardly facing surface 1415 of needle biasing and sealing element 616 is supported against upper surface 1472 of bottom housing portion 520, such that cylindrical portion 1419 of needle biasing and sealing element 616 downwardly protrudes into central aperture 1497 of bottom housing portion 520.

It is seen additionally in FIG. 35C that lever portions 1330 of infusion needle assembly 612 are upwardly spaced from protrusions 1045 and 1065 formed within needle assembly location bore 1030 of housing element 610 and thus infusion needle assembly 612 is disposed in a needle retracted operative orientation.

It is appreciated that needle 1290 is aligned with bottom bore portion 1444 of needle biasing and sealing element 616 and with central aperture 1497 of bottom housing portion 520.

It is further specifically seen in FIG. 35C that injection site engagement element 680 is partially inserted through bottom housing portion 520 and through housing element 610. In this operative orientation, the engagement surface defining ring 684 is downwardly spaced from adhesive sticker 670 and is retained from being released out of the housing element 610. Shaft 686 of injection site engagement element 680 extends upwardly into housing element 610 through aperture 692 of bottom housing portion 520 and shaft 688 of injection site engagement element 680 extends upwardly into housing element 610 through aperture 1498 of bottom housing portion 520. It is seen that upwardly facing edge 1506 of shafts 686 and 688 are downwardly spaced from lever portions 1330 of infusion needle assembly 612.

Figure 35D:
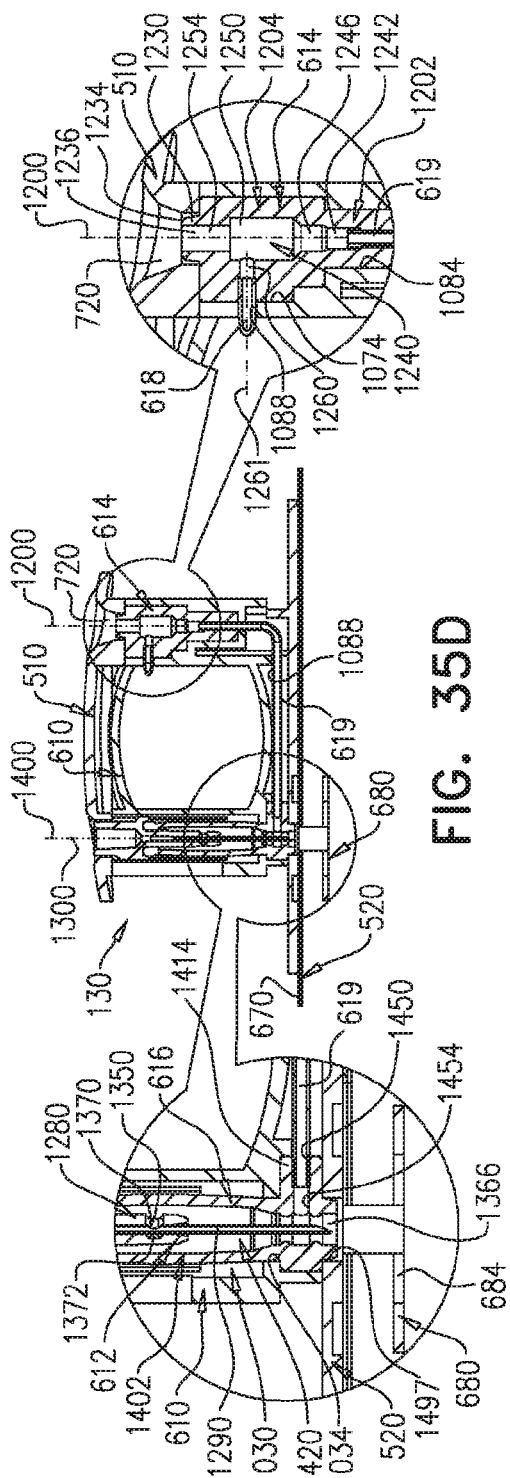
Figure 35E:
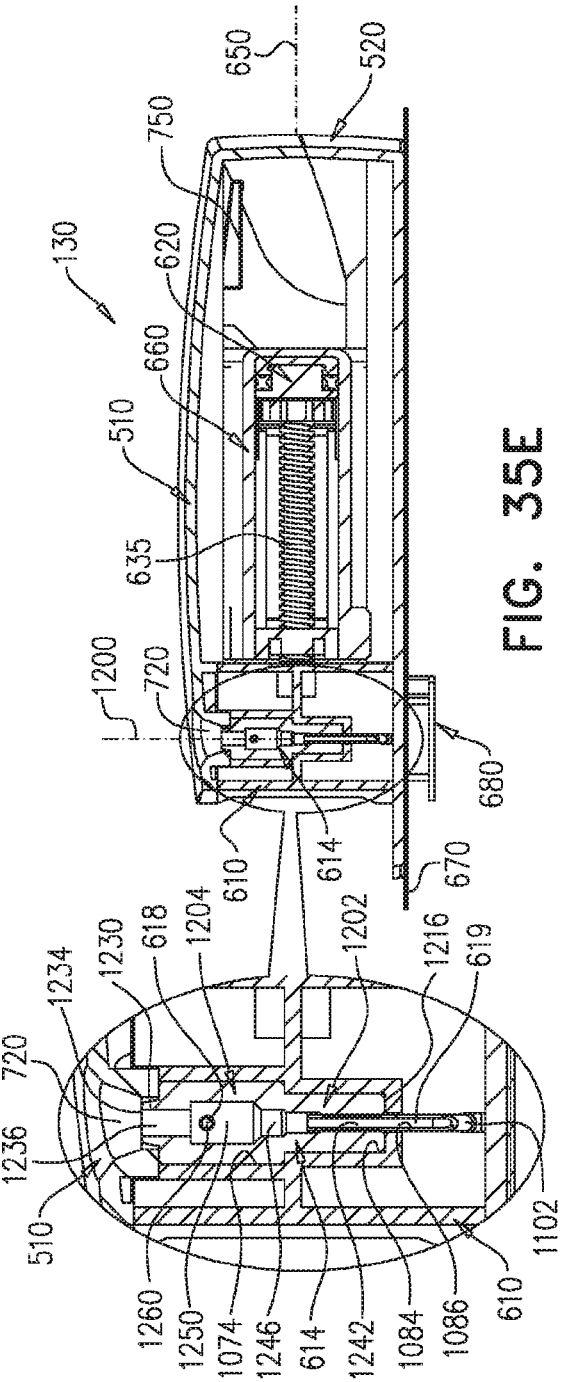

It is seen in FIGS. 35D & 35E that filling septum 614 is inserted into central bore 1074 and bore 1084 of housing element 610. The selectively openable slit 1236 of the filling septum 614 is closed in this operative orientation and planar portion 1234 of filling septum 614 is exposed through aperture 720 of top housing portion 510 of disposable base portion 130. It is particularly seen in FIGS. 35D & 35E that cylindrical bottom portion 1202 of filling septum 614 is seated within bore 1084 of housing element 610, enlarged upper portion 1204 of filling septum 614 is seated within central bore 1074 of housing element 610 and protrusion 1230 of filling septum 614 is seated within aperture 720 of top housing portion 510. Filling septum 614 is fixedly retained between top housing portion 510 and housing element 610 of the disposable base portion 130.

It is a particular feature of an embodiment of the present invention that filling septum 614 provides for two alternative fluid flow paths in different operative orientations of the patch pump assembly 100. The first path fluidly couples the medicament reservoir 660 with a medicament vial by means of medicament coupling filling conduit 618 for aspiration of medication into the medicament reservoir 660. Second path fluidly couples the medicament reservoir 660 with needle 1290 by means of medicament coupling injection conduit 619 for injection of the medicament into the body of a patient.

It is particularly seen in FIGS. 35D and 35E that medicament coupling filling conduit 618 is partially inserted into side fluid conduit 1260 of filling septum 614 through bore 1088 formed in housing element 610. It is noted that medicament coupling filling conduit 618 is adapted to fluidly communicate with varying diameter fluid conduit 1240 of the filling septum 614, containing upper portion 1254, intermediate enlarged portion 1250, intermediate narrow portion 1246 and bottom conduit portion 1242. It is noted that medicament coupling filling conduit 618 extends from filling septum 614 into piston assembly 620 and then into the medicament reservoir 660.

It is further seen that medicament coupling injection conduit 619 is partially inserted into bottom conduit portion 1242 of filling septum 614 through bottom aperture 1086 and bottom recess 1102 formed in housing element 610. It is noted that medicament coupling injection conduit 619 is adapted to fluidly communicate with 1240 of the filling septum 614, containing upper portion 1254, intermediate enlarged portion 1250, intermediate narrow portion 1246 and bottom conduit portion 1242. It is noted that medicament coupling injection conduit 619 extends from filling septum 614 into bore 1454 of needle biasing and sealing element 616 and then into the needle 1290.

It is further noted that in this operative orientation both fluid flow paths, provided by medicament coupling filling conduit 618 and medicament coupling injection conduit 619, are closed and fluid communication is thereby prevented.

It is further seen in FIG. 35D that the infusion needle assembly 612 is positioned in the needle retracted operative orientation when the needle 1290 does not protrude through central aperture 1497 in bottom housing portion 520 and the needle biasing and sealing element 616 is positioned in its first operative orientation, as seen in FIGS. 21A and 21B. It is additionally seen that injection site engagement element 680 is positioned in its first operative orientation whereas injection site surface defining ring 684 is downwardly spaced from adhesive sticker 670.

It is specifically seen in FIGS. 35F and 35G and is a particular feature of an embodiment of the present invention that piston assembly 620 is static relative to top and bottom housing portions 510 and 520, whereas the linear displacer 640 and the medicament reservoir 660, which is fixedly attached thereto, are adapted to be axially displaceable along longitudinal axis 650 relative to top and bottom housing portions 510 and 520, thereby increasing or decreasing the interior volume 774 of medicament reservoir 660.

It is seen in FIGS. 35F and 35G that in this operative orientation the linear displacer 640 abuts back walls 1094 and 1090 of housing element 610 and piston assembly 620 abuts closed rearward end wall 772 of medicament reservoir 660, such that the interior volume 774 of medicament reservoir 660 is eliminated. It is particularly seen that forwardly facing edge 815 of linear displacer 640 abuts back wall 1094 of housing element 610, thus the medicament reservoir 660 is positioned in an empty operative orientation.

It is also seen that lead screws 635 connect the piston assembly 620 and housing element 610. It is particularly seen that forwardly facing surfaces 990 of the forward ends of lead screws 635 engage central protrusions 1098 formed in receiving recesses 1096 of housing element 610. It is appreciated that this engagement substantially reduces friction between the lead screws 635 and housing element 610 during rotation of lead screws 635.

It is particularly seen that the external threading 984 of lead screws 635 engages the inner threading of threaded sockets 636 formed in base element 800 of linear displacer 640 and this engagement is configured for providing axial displacement of linear displacer 640 relative to the rotating leading screws 635.

It is also seen that rearward ends of lead screws 635 are inserted into nuts 980, which in turn engage bearing surface 940 formed in base portion 862 of piston assembly 620. It is appreciated that this engagement substantially reduces friction between the lead screws 635 and the piston assembly 620.

It is seen in FIG. 35F that rearwardly facing surface 872 of piston base element 622 of piston assembly 620 abuts closed rearward end wall 772 of medicament reservoir 660. It is also seen that circumferential edge surface 876, piston seal 624 and outwardly facing edge surface 888 circumferentially engage inner surface 778 of medicament reservoir 660 and thus provide for circumferential sealing engagement between the piston assembly 620 and the medicament reservoir 660.

It is additionally specifically seen in FIG. 35G that medicament coupling filling conduit 618, which extends from filling septum 614, seated in housing element 610 extends into piston assembly 620 and via groove 941 in rearwardly facing surface 872 of piston base element 622 enters into medicament reservoir 660 and provides fluid communication into or out of the interior volume 774 of the medicament reservoir 660.

It is particularly seen in FIG. 35H that medicament coupling filling conduit 618 extends from groove 941 (shown in FIG. 35G) through axially extending aperture 942 formed in piston assembly 620 through aperture 1162 formed in end wall 1142 of housing element 610. Medicament coupling filling conduit 618 further extends through housing element 610 and in turn extends through slit 1072 formed in housing element 610 and finally enters into filling septum 614.

It is particularly seen in FIG. 35I that when injection site surface defining ring 684 of injection site engagement element 680 is downwardly spaced from adhesive sticker 670, shaft 690 of injection site engagement element 680 extends into rectangular recess 1058 formed in housing element 610. It is seen that the upwardly facing edge 691 of shaft 690 does not protrude above rectangular portion 1000 of housing element 610 and does not protrude into slot 724 of top housing portion 510.

Figure 35J:
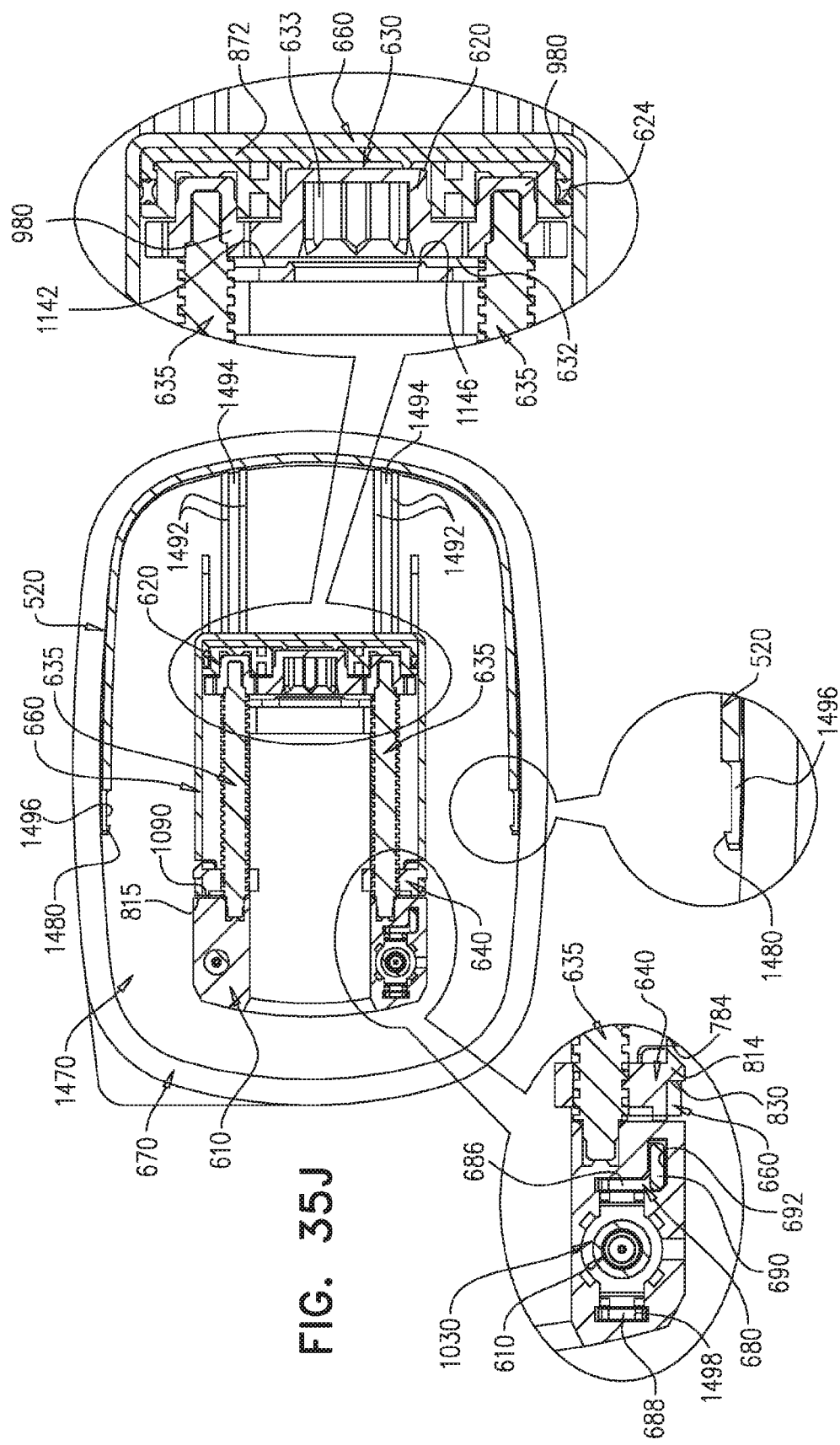

It is specifically seen in FIG. 35J, which is a partially section view along lines J-J in FIG. 35A, where top housing portion 510 is not shown, that bottom housing 520 has recesses 1496 and forwardly facing edges 1480 formed on the sides thereof for operative engagement with manually actuable buttons 260 of reusable portion 110.

It is also seen in FIG. 35J that shafts 690 and 686 of injection site engagement element 680 protrude through aperture 692 formed in floor portion 1470 of bottom housing portion 520 and shaft 688 of injection site engagement element 680 protrudes through aperture 1498 formed in floor portion 1470 of bottom housing portion 520.

It is also seen that radially outwardly extending protrusions 814 of linear displacer 640 is fixedly attached to medicament reservoir 660 by snap-fit engagement within mutually opposed apertures 784 of medicament reservoir 660, such that forwardly facing surfaces 830 of protrusions 814 of the linear displacer 640 lies against a wall defined by the apertures 784 of medicament reservoir 660.

It is a particular feature of an embodiment of the present invention that linear displacer 640 is made of a relatively rigid material and medicament reservoir 660 is made of a less rigid, bio compatible material, since medicament communicates directly with the medicament reservoir 660, which has to preserve the integrity of the medicament. Linear displacer 640 is made of a more rigid material in order to enable motion transfer from the electric motor 440 to the medicament reservoir 660.

Piston assembly 620 is seated within the medicament reservoir 660 and in this operative orientation bearing surface 632 of gear 631 abuts outwardly facing circular protrusion 1146 formed on end wall 1142 of housing element 610 and interior gear teeth 633 are adapted to engage teeth 456 of plunger assembly 240 of the reusable portion 110. Piston assembly 620 circumferentially seals the interior volume 774 of the medicament reservoir 660. Piston assembly 620 is described in detail hereinabove, with reference to FIGS. 16A-16E.

Reference is now made to FIGS. 36A-36I, which are simplified illustrations of the assembled disposable interface and control module 140 of the patch pump assembly 100 of FIG. 1. FIGS. 36A-36I are respective simplified pictorial view and section views taken along respective lines B-B, C-C, D-D, E-E, F-F, G-G, H-H and I-I.

It is seen in FIGS. 36B & 36C that vial seating portion 1822 of vial adaptor 1632 is inserted into well 1604 of housing portion 1600 and vial adaptor retaining portion 1830 of vial adaptor 1632 is disposed within button receiving socket 1760 of housing portion 1600, such that cylindrical rod 1962 of needle actuation penetration pin 1624 is inserted into and slidably guided within central bore 1938 of vial adaptor 1632. Activation rod 1966 of needle actuation penetration pin 1624 protrudes slightly downwardly through central aperture 2250 formed in base portion 1620.

It is further seen that compression spring 1634 is supported at one end on upwardly facing surface 1974 of needle actuation penetration pin 1624 and at another end on downwardly facing edge surface 1924 of vial adaptor retaining portion 1830 of vial adaptor 1632, such that spring seat 1936 of vial adaptor 1632 and ribs 1976 of needle actuation penetration pin 1624 guide the displacement of compression spring 1634.

It is seen in FIG. 36B that undercut portions 1746 are provided within well 1604 and are adapted to engage the medicament vial and fixedly retain it within well 1604 of housing portion 1600.

It is seen that spike 2310 of base portion 1620 protrudes upwardly through central aperture 1842 of vial adaptor 1632 and is adapted to penetrate the seal of medicament vial.

It is further seen in FIGS. 36B & 36C that needle penetration prevention element 1626 is seated within base portion 1620, such that the pivoting rod 2120 thereof is seated within cut-out groove 2256 of base portion 1620 and is supported by side protrusion 2270 of base portion 1620. It is seen that engagement portion 2150 of needle penetration prevention element 1626 protrudes downwardly from base wall portion 2200 of base portion 1620.

It is a particular feature of an embodiment of the present invention that needle penetration prevention element 1626 locks the needle penetration actuation element 1610 and prevents its actuation before connection of reusable portion 110 and disposable portion 120 and attachment of the patch pump assembly 100 to the injection site, as is described in detail hereinbelow.

It is seen in FIG. 36C that first end 1640 of medicament conduit 1622 protrudes downwardly from medicament conduit seat 2420 formed on the underside of base wall portion 2200. It is appreciated that medicament conduit 1622 has side aperture 2430 and a closed downwardmost end.

Figure 36D:
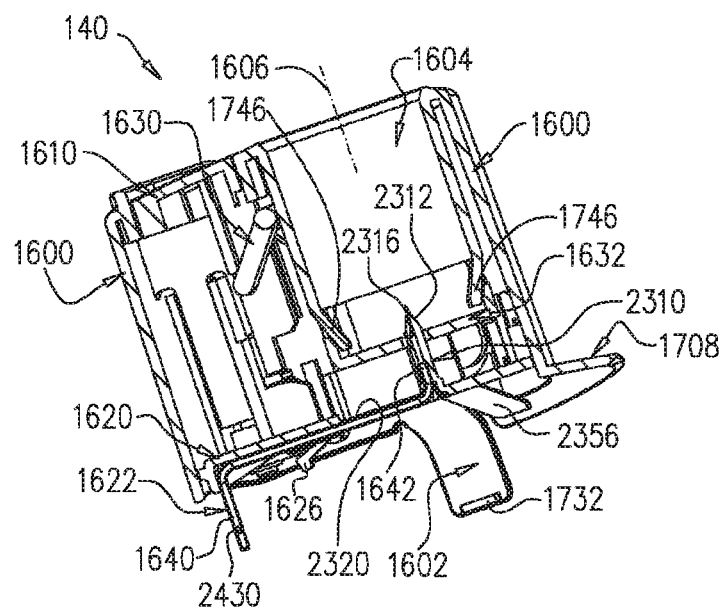
Figure 36E:
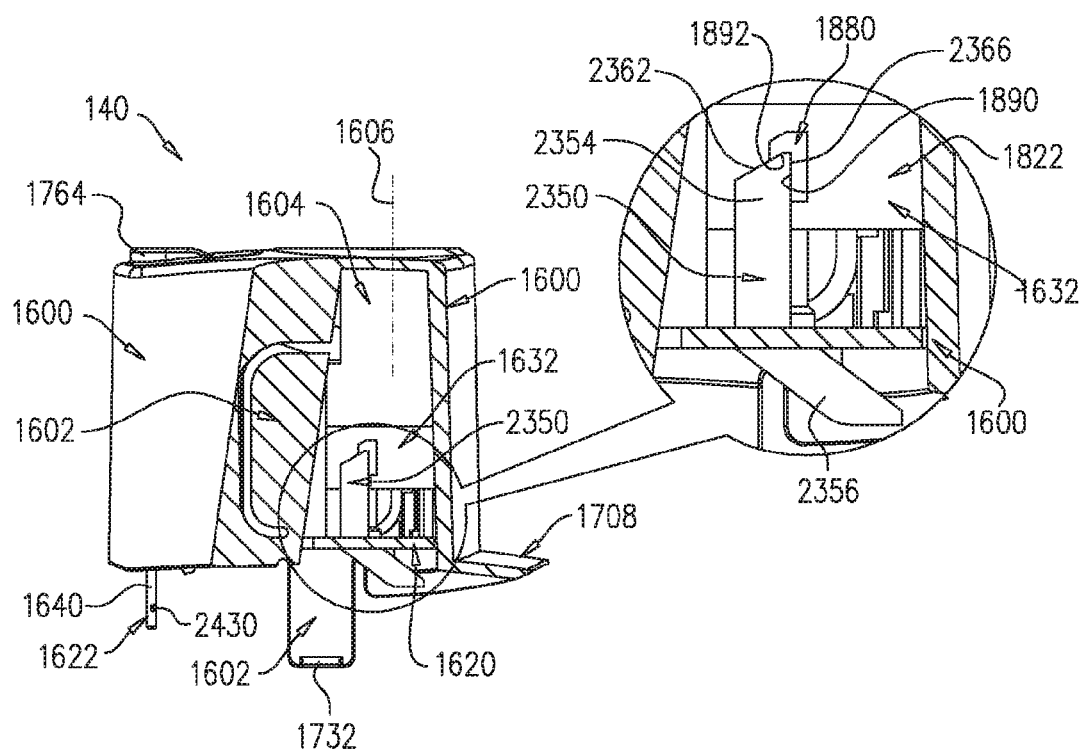

It is particularly seen in FIGS. 36C & 36E and being a particular feature of an embodiment of the present invention that in this operative orientation vial adaptor 1632 is retained from downward displacement relative to housing portion 1600 by means of engagement thereof with base portion 1620. Specifically, it is seen that lever portions 2350 of base portion 1620 are engaged with retaining protrusions 1880 of vial adaptor 1632, such that inner facing edge surfaces 1890 and 1892 of retaining protrusions 1880 engage tapered uppermost edge surface 2362 and inwardly facing surface 2366 of the upward portion 2354 of lever portions 2350, thereby preventing downward displacement of vial adaptor 1632 relative to base portion 1620, and thus preventing piercing of the medicament vial seal by spike 2310.

It is particularly seen in FIG. 36D that first end 1640 of medicament conduit 1622 provides fluid communication between medicament vial adapted to be inserted into well 1604 and between medicament reservoir 660 of disposable base portion 130. Specifically, it is seen that second end 1642 of medicament conduit 1622 is inserted into groove 2316 of spike 2310 and is thus configured to fluidly communicate with a medicament vial, which is adapted to be inserted into well 1604 of housing portion 1600. From spike 2310, medicament conduit 1622 extends through cut-out 2320 into medicament conduit seat 2420 and first end 1640 of medicament conduit 1622, having aperture 2430, is adapted to fluidly communicate with filling septum 1614 of disposable base portion 130.

Figure 36F:
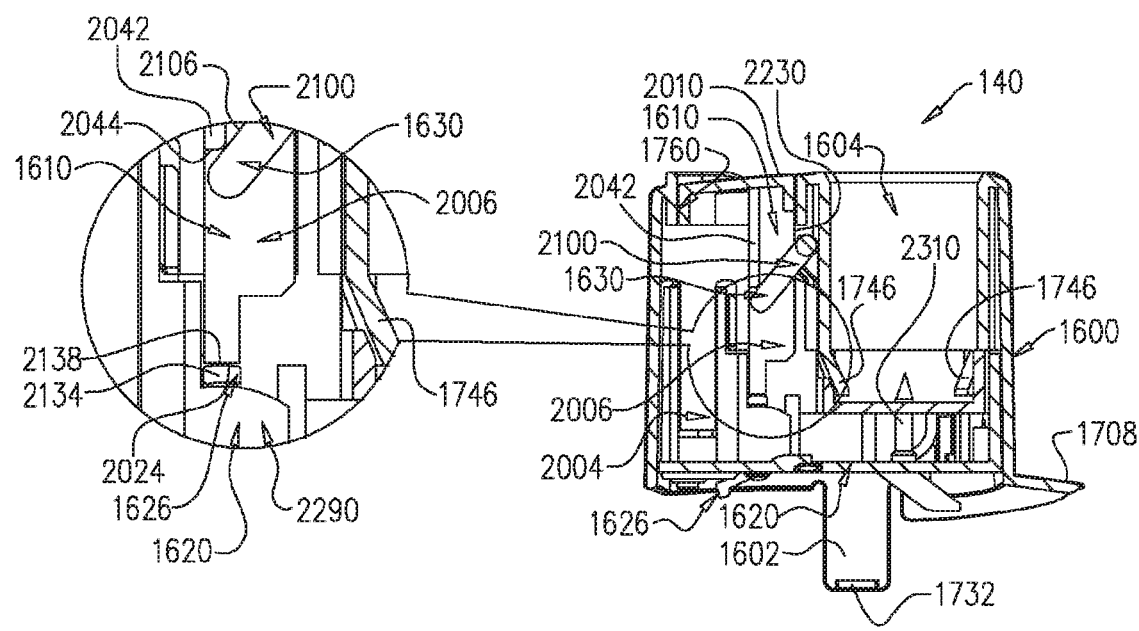
Figure 36G:
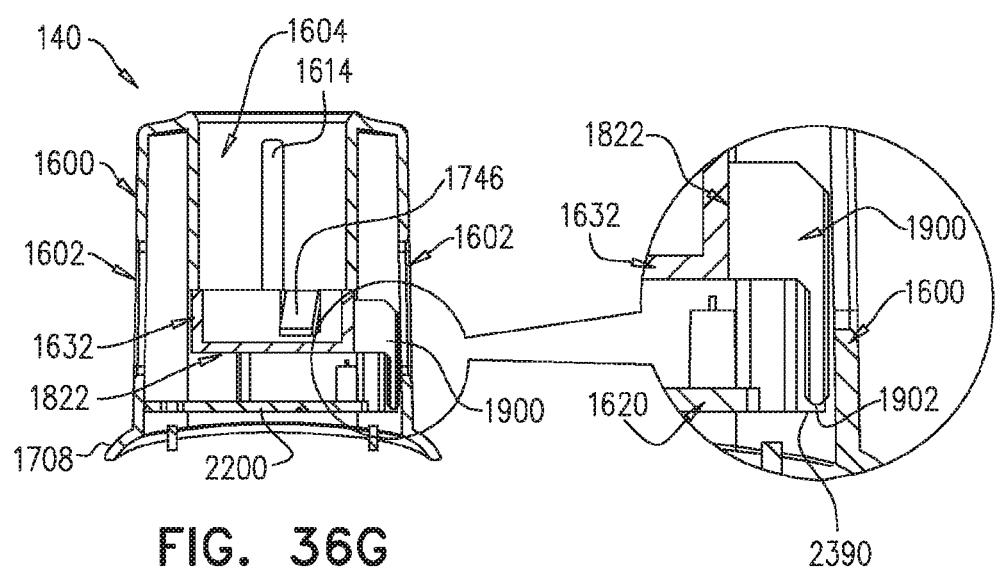

It is seen in FIG. 36G that vial adaptor 1632 is partially inserted into well 1604 of housing portion 1600 and switch actuating protrusion 1900 of vial adaptor 1632 is preferably disposed in lateral cut-out 2390 of base element 1620, such that downwardly facing engaging end 1902 of switch actuating protrusion 1900 does not protrude downwardly from base wall portion 2200 of base element 1620 in this operative orientation.

It is particularly seen in FIG. 36F that needle penetration prevention element 1626 is retained between L-shaped protrusion 2290 of base element 1620 and between retaining shaft 2006 of needle penetration actuation element 1610 in this operative orientation, thereby preventing downward displacement of needle penetration actuation element 1610 by the user. Specifically, it is seen that extension portion 2134 of needle penetration prevention element 1626 is retained between first side surface 2138 of retaining shaft 2006 and upward edge of L-shaped protrusion 2290 of base element 1620, such that first side surface 2138 engages downwardmost edge 2024 of needle penetration actuation element 1610 and thus downward displacement of needle penetration actuation element 1610 is prevented.

It is seen in FIG. 36F that needle penetration actuation element 1610 is inserted into button receiving socket 1760 of housing portion 1600 such that upwardly facing surface 2010 is exposed and adapted for actuation by a finger of a user and activating shaft 2004 and retaining shaft 2006 protrude downwardly into button receiving socket 1760.

It is further seen that inserter decoupling prevention element 1630 is seated within curved cut-outs 2230 of wall portions 2220 of base element 1620 and edge surfaces 2106 of engagement rods 2100 of inserter decoupling prevention element 1630 are disposed below downwardly facing edge surface 2044 of elongate rib 2042 formed on retaining shaft 2006. It is appreciated that elongate rib 2042 of needle penetration actuation element 1610 is adapted to displace engagement rods 2100 downwardly in order to release the below mentioned engagement therebetween and between manually actuable buttons 1602, as will be described in detail hereinbelow.

Figure 36H:
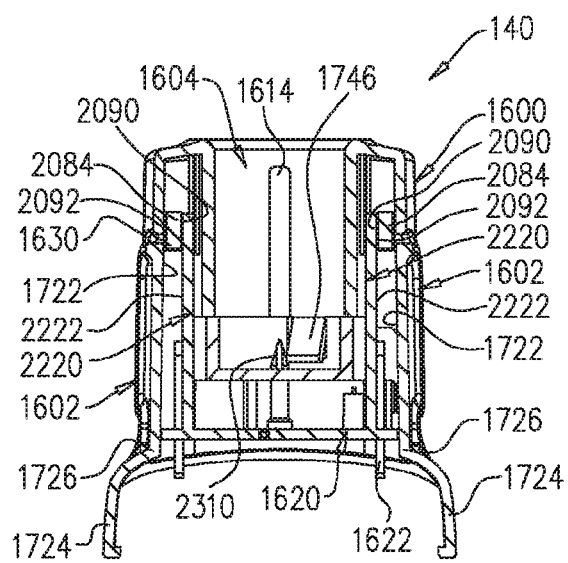

It is seen in FIG. 36H that inserter decoupling prevention element 1630, which is seated between base element 1620 and housing portion 1600 is adapted to prevent actuation of manually actuable buttons 1602 in this operative orientation. It is specifically seen that arm portions 2084 of inserter decoupling prevention element 1630 are seated between wall portions 2220 of base element and manually actuable buttons 1602 of housing portion 1600, such that side edge surfaces 2098 of arm portions 2084 of inserter decoupling prevention element 1630 engage outer surface 1742 of housing portion 1600 and outwardly facing surface 2092 of arm portions 2084 engage planar portions 1722 of manually actuable buttons 1602 of housing portion 1600, thereby preventing inward displacement of manually actuable buttons 1602 upon pivoting thereof around hinge portion 1726.

Figure 36I:
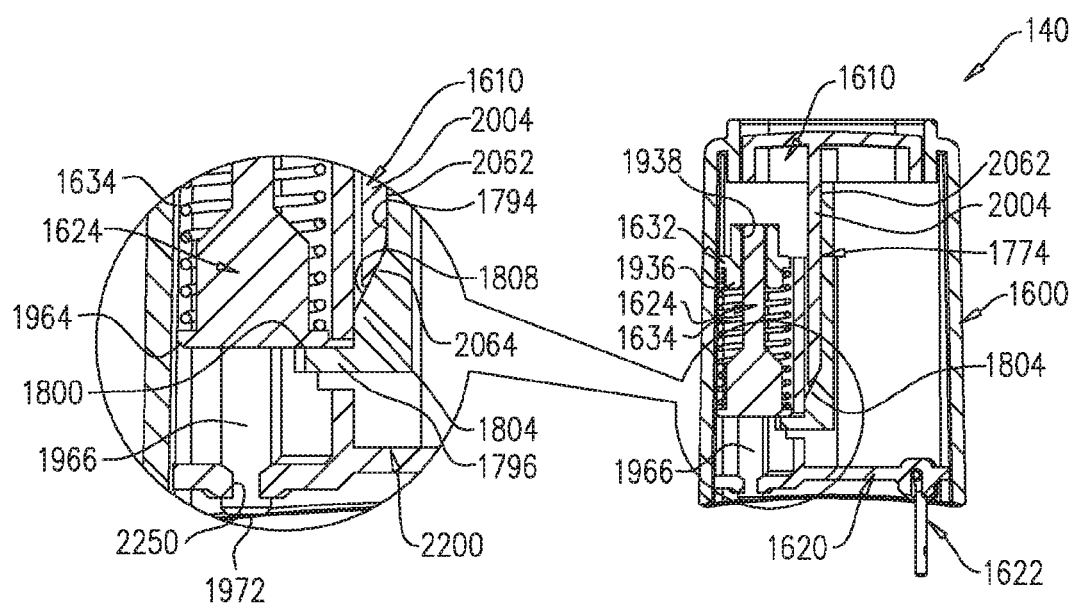

It is particularly seen in FIG. 36I that needle actuation penetration pin 1624 is prevented from being downwardly displaced before needle penetration actuation element 1610 is pressed by the user, thus penetration of needle 1290 into the skin of the user is prevented. It is seen that downward displacement of needle actuation penetration pin 624 is prevented by engagement thereof with housing portion 1600 and with needle penetration actuation element 1610. Specifically, in this operative orientation, activating shaft 2004 of needle penetration actuation element 1610 is supported by forward wall portion 1774 of housing portion 1600, such that inwardly facing surface 2062 of activating shaft 2004 engages second side surface 1794 of forward wall portion 1774 and tapered edge surface 2064 of activating shaft 2004 engages tapered edge surface 1808 of protrusion 1804 formed on forward wall portion 1774.

It is additionally seen that flange portion 1964 of needle actuation penetration pin 1624 engages upwardly facing surface 1800 of transversely disposed wall portion 1796 of housing portion 1600, which protrudes through 2260 of base portion 1620, thus needle actuation penetration pin 1624 is prevented from being downwardly displaced as long as inwardly facing surface 2062 of activating shaft 2004 engages second side surface 1794 of forward wall portion 1774 and tapered edge surface 2064 of activating shaft 2004 engages tapered edge surface 1808 of protrusion 1804 formed on forward wall portion 1774.

It is seen that in this operative orientation, activation rod 1966 of needle actuation penetration pin 1624 slightly protrudes downwardly through central aperture 2250 formed in base wall portion 2200 of base portion 1620.

Reference is now made to FIGS. 37A-37H, which are simplified illustrations of the patch pump assembly 100 of FIGS. 1-36I in a storage operative orientation. FIGS. 37A-37H are respective simplified pictorial view and section views taken along respective lines B-B, C-C, D-D, E-E, F-F and G-G in FIG. 37A, and a partial pictorial view shown without housing portion 1600 of the disposable interface and control module 140 and without top housing portion 510 of the disposable base portion 130, of the patch pump assembly 100.

Patch pump assembly 100 is seen in FIGS. 37A-37H as sold, in storage operative orientation. It is seen that disposable interface and control module 140 and disposable base portion 130 are operatively attached to each other, forming disposable portion 120. The reusable portion 110 is not connected to the disposable portion 120 in this storage operative orientation.

Figure 37B:
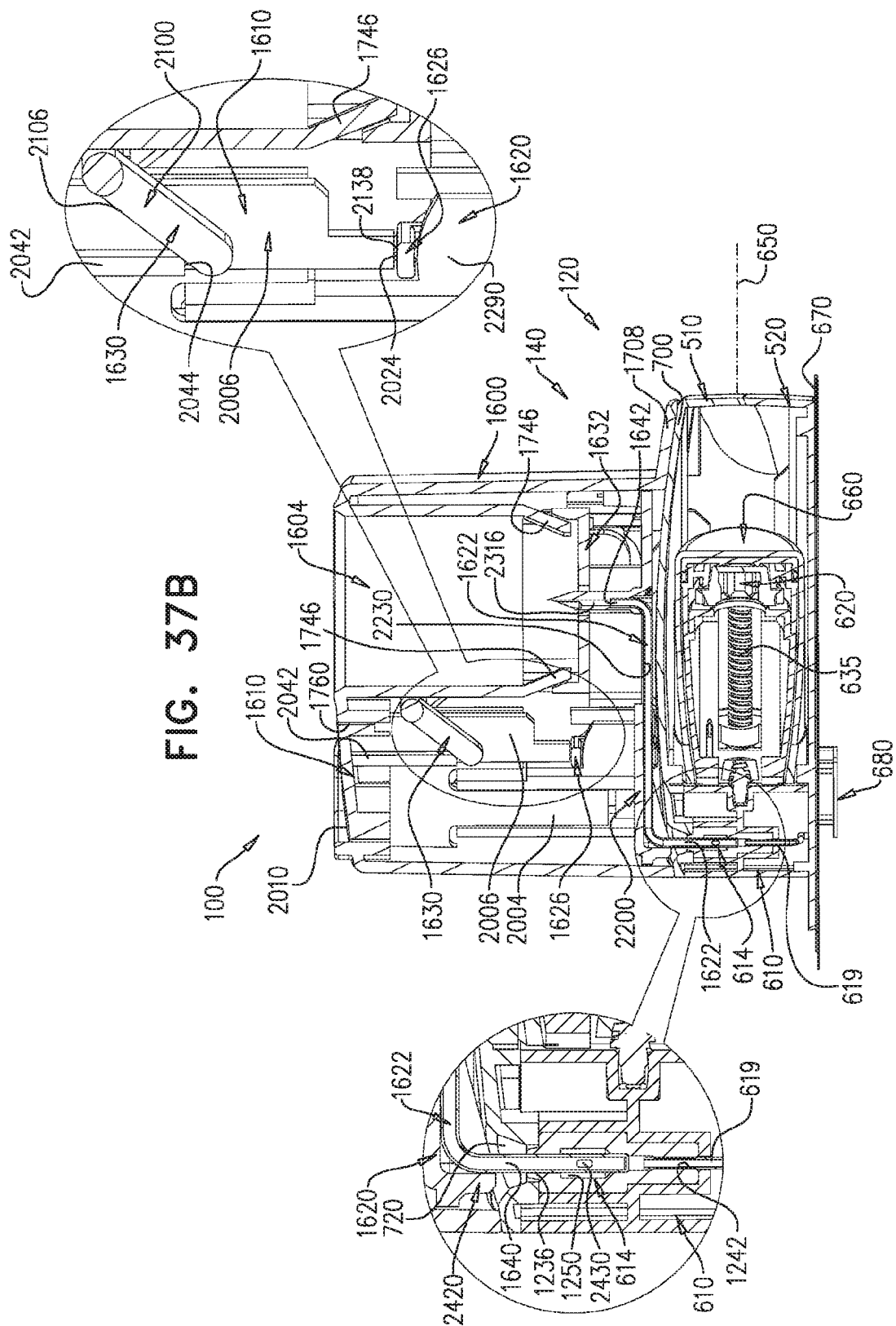

It is seen in FIGS. 37A & 37B that base wall portion 2200 and curved cover extension 1708 of disposable interface and control module 140 engage curved cover portion 700 of top housing portion 510 of disposable base portion 130.

It is particularly seen that in this storage operative orientation that needle penetration prevention element 1626 is retained between L-shaped protrusion 2290 of base element 1620 and between retaining shaft 2006 of needle penetration actuation element 1610 in this operative orientation, thereby preventing downward displacement of needle penetration actuation element 1610 by the user. Specifically, it is seen that extension portion 2134 of needle penetration prevention element 1626 is retained between first side surface 2138 of retaining shaft 2006 and upward edge of L-shaped protrusion 2290 of base element 1620.

It is seen in FIG. 37B that needle penetration actuation element 1610 is inserted into button receiving socket 1760 of housing portion 1600 such that upwardly facing surface 2010 is exposed and adapted for actuation by a finger of a user and activating shaft 2004 and retaining shaft 2006 protrude downwardly into button receiving socket 1760.

It is further seen that inserter decoupling prevention element 1630 is seated within curved cut-outs 2230 of wall portions 2220 of base element 1620 and edge surfaces 2106 of engagement rods 2100 of inserter decoupling prevention element 1630 are disposed below downwardly facing edge surface 2044 of elongate rib 2042 formed on retaining shaft 2006. It is appreciated that elongate rib 2042 of needle penetration actuation element 1610 is adapted to displace engagement rods 2100 downwardly in order to release the below mentioned engagement therebetween and between manually actuable buttons 1602, as will be described in detail hereinbelow.

It is further seen in FIG. 37B that in this storage operative orientation, the first end 1640 of medicament conduit 1622, forming part of disposable interface and control module 140 is inserted through slit 1236 of filling septum 1614, forming part of disposable base portion 130, thus providing fluid communication between medicament vial, which is adapted to be inserted into well 1604 and communicate with groove 2316 of spike 2310, and between medicament reservoir 660.

It is specifically seen that second end 1642 of medicament conduit 1622 is inserted into groove 2316 of spike 2310, medicament conduit 1622 further extends through cut-out 2320 of base portion 1620, through medicament conduit seat 2420 and first end 1640 of medicament conduit 1622 extends through aperture 720 formed in top housing portion 510 of disposable base portion 130. Medicament conduit 1622 further extends through slit 1236 of filling septum 1614, thus providing for fluid communication between groove 2316 of spike 2310 and intermediate enlarged portion 1250 of filling septum 614. It is noted that first end 1640 of medicament conduit 1622 has a closed downwardmost end and aperture 2430, which is configured for fluid communication with the medicament coupling filling conduit 618, which provides for fluid communication between filling septum 1614 and medicament reservoir 660.

It is further noted that fluid flow passage from medicament conduit 1622 to medicament coupling injection conduit 619 is prevented due to closed downwardmost end of medicament conduit 1622 and fluid tight sealing between the downwardmost end of medicament conduit 1622 and between bottom cylindrical portion 1202 of the filling septum 614.

It is particularly seen in FIG. 37C that needle penetration actuation pin 1624 of disposable interface and control module 140 is disposed adjacent infusion needle assembly 612 of disposable base portion 130, however in this storage operative orientation, needle penetration actuation pin 1624 does not exert force on infusion needle assembly 612 and needle biasing and scaling element 616 of disposable base portion 130. It is specifically seen that downwardly facing end surface 1972 of activation rod 1966 of needle penetration actuation pin 1624 protrudes slightly downwardly through aperture 2250 of base portion 2200 of disposable interface and control module 140 and into aperture 722 of top housing portion 510 of disposable base portion 130 up to engagement with upward edge 1308 of needle hub 1280 of infusion needle assembly 612.

It is further seen in FIG. 37C that medicament reservoir 660 is initially spaced from curved portion 706 of top housing portion 510 and is disposed forwardly therefrom, such that piston assembly 620 abuts rearward end wall 772 and interior volume 774 of the medicament reservoir 660 is substantially eliminated.

It is further seen that infusion needle assembly 612 is inserted into needle assembly location bore 1030 of housing element 610 and needle hub 1280 of infusion needle assembly 612 is retained from upward displacement by engagement with forward bottom surface 762 of top housing portion 510. It is seen that needle hub 1280 of infusion needle assembly 612 is aligned with aperture 722 of top housing portion 510 and upward edge 1308 of needle hub 1280 is substantially coplanar with upper surface 702 of top housing portion 510 and is disposed within aperture 722.

It is seen in FIG. 37C that 616 is disposed in its first operative orientation, whereas needle biasing and sealing element 616 is in a non-stressed position, such as shown in FIGS. 21A & 21B. It is further noted that needle biasing and sealing element 616 is disposed over needle hub 1280.

It is seen additionally in FIG. 37C that lever portions 1330 of infusion needle assembly 612 are upwardly spaced from protrusions 1045 and 1065 formed within needle assembly location bore 1030 of housing element 610.

It is appreciated that needle 1290 is aligned with bottom bore portion 1444 of needle biasing and sealing element 616 and with central aperture 1497 of bottom housing portion 520.

It is further specifically seen in FIG. 37C that injection site engagement element 680 is partially inserted through bottom housing portion 520 and through housing element 610. In this operative orientation, the engagement surface defining ring 684 is downwardly spaced from adhesive sticker 670 and is retained from being released out of the housing element 610. Shaft 686 of injection site engagement element 680 extends upwardly into housing element 610 through aperture 692 of bottom housing portion 520 and shaft 688 of injection site engagement element 680 extends upwardly into housing element 610 through aperture 1498 of bottom housing portion 520. It is seen that upwardly facing edge 1506 of shafts 686 and 688 are downwardly spaced from lever portions 1330 of infusion needle assembly 612.

It is also seen in FIG. 37C that vial seating portion 1822 of vial adaptor 1632 is inserted into well 1604 of housing portion 1600 and vial adaptor retaining portion 1830 of vial adaptor 1632 is disposed within button receiving socket 1760 of housing portion 1600, such that cylindrical rod 1962 of needle actuation penetration pin 1624 is inserted into and slidably guided within central bore 1938 of vial adaptor 1632. Activation rod 1966 of needle actuation penetration pin 1624 protrudes slightly downwardly through central aperture 2250 formed in base portion 1620. In this operative orientation, vial adaptor 1632 is disposed in its raised operative orientation, it is particularly seen that wall portion 1824 of vial adaptor 1632 is upwardly spaced from base wall 2200 of base portion 1620 of the disposable interface and control module 140.

It is further seen that compression spring 1634 is supported at one end on upwardly facing surface 1974 of needle actuation penetration pin 1624 and at another end on downwardly facing edge surface 1924 of vial adaptor retaining portion 1830 of vial adaptor 1632, such that spring seat 1936 of vial adaptor 1632 and ribs 1976 of needle actuation penetration pin 1624 guide the displacement of compression spring 1634. It is seen that in this operative orientation, compression spring 1634 is disposed at its released position.

It is seen in FIG. 37C that undercut portions 1746 are provided within well 1604 and are adapted to engage the medicament vial and fixedly retain it within well 1604 of housing portion 1600.

It is seen that spike 2310 of base portion 1620 protrudes upwardly through central aperture 1842 of vial adaptor 1632 and is adapted to penetrate the seal of medicament vial.

Figure 37D:
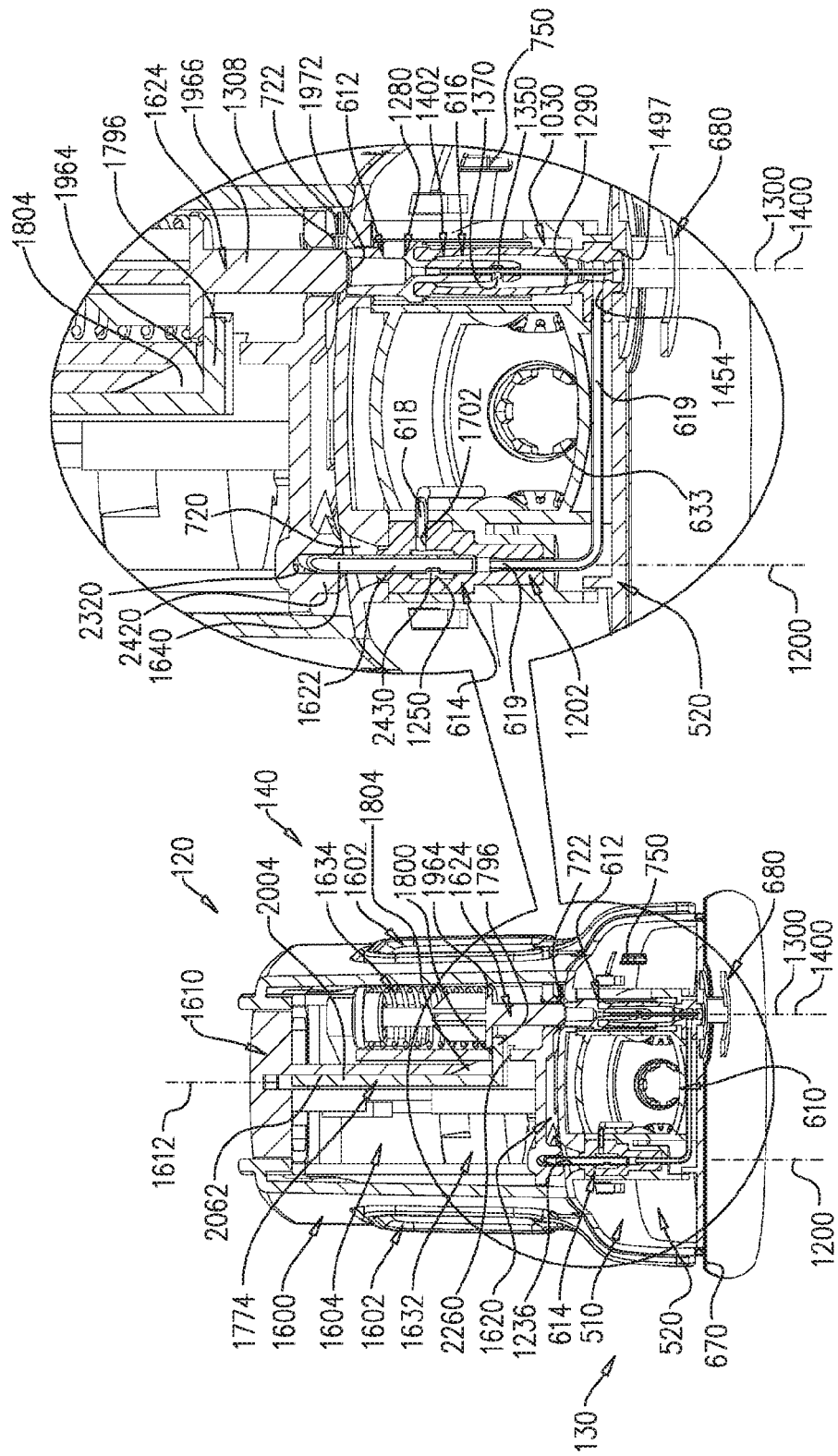

It is seen in FIG. 37D that in this storage operative orientation, the first end 1640 of medicament conduit 1622, forming part of disposable interface and control module 140 is inserted through slit 1236 of filling septum 1614, forming part of disposable base portion 130, thus providing fluid communication between medicament vial, which is adapted to be inserted into well 1604 and communicate with groove 2316 of spike 2310, and between medicament reservoir 660.

It is specifically seen that second end 1642 of medicament conduit 1622 is inserted into groove 2316 of spike 2310, medicament conduit 1622 further extends through cut-out 2320 of base portion 1620, through medicament conduit seat 2420 and first end 1640 of medicament conduit 1622 extends through aperture 720 formed in top housing portion 510 of disposable base portion 130. Medicament conduit 1622 further extends through slit 1236 of filling septum 1614, thus providing for fluid communication between groove 2316 of spike 2310 and intermediate enlarged portion 1250 of filling septum 614. It is noted that first end 1640 of medicament conduit 1622 has a closed downwardmost end and aperture 2430, which is configured for fluid communication with the medicament coupling filling conduit 618 extending through 1072 of 610 and providing for fluid communication between filling septum 1614 and medicament reservoir 660.

It is further noted that fluid flow passage from medicament conduit 1622 to medicament coupling injection conduit 619 is prevented due to closed downwardmost end of medicament conduit 1622 and fluid tight sealing between the downwardmost end of medicament conduit 1622 and between bottom cylindrical portion 1202 of the filling septum 614.

It is further seen that medicament coupling injection conduit 619 extends downwardly from bottom cylindrical portion 1202 of filling septum 614, through bottom aperture 1086 and further through recess 1102 of housing element 610 into bore 1454 of needle biasing and sealing element 616.

It is appreciated that in this storage operative orientation no fluid flow communication is provided between filling septum 614 and needle 1290 since fluid flow passage from filling septum 614 to medicament coupling injection conduit 619 is prevented due to the closed downwardmost end of medicament conduit 1622, which blocks passage of fluid into medicament coupling injection conduit 619 as long as disposable interface and control module 140 is connected to disposable base portion 130.

It is particularly seen in FIG. 37D that needle actuation penetration pin 1624 is prevented from being downwardly displaced before needle penetration actuation element 1610 is pressed by the user, thus penetration of needle 1290 into the skin of the user is prevented. It is seen that downward displacement of needle actuation penetration pin 624 is prevented by engagement thereof with housing portion 1600 and with needle penetration actuation element 1610. Specifically, in this operative orientation, activating shaft 2004 of needle penetration actuation element 1610 is supported by forward wall portion 1774 of housing portion 1600, such that inwardly facing surface 2062 of activating shaft 2004 engages second side surface 1794 of forward wall portion 1774 and tapered edge surface 2064 of activating shaft 2004 engages tapered edge surface 1808 of protrusion 1804 formed on forward wall portion 1774.

It is additionally seen, as previously described with regards to FIG. 36I, that flange portion 1964 of needle actuation penetration pin 1624 engages upwardly facing surface 1800 of transversely disposed wall portion 1796 of housing portion 1600, which protrudes through 2260 of base portion 1620, thus needle actuation penetration pin 1624 is prevented from being downwardly displaced as long as inwardly facing surface 2062 of activating shaft 2004 engages second side surface 1794 of forward wall portion 1774 and tapered edge surface 2064 of activating shaft 2004 engages tapered edge surface 1808 of protrusion 1804 formed on forward wall portion 1774.

It is also seen that downward portions 2356 of lever portions 2350 of base portion 1620 of disposable interface and control module 140 protrude into top housing portion 510 of disposable base portion 130.

It is noted that all spatial relationships described with reference to FIG. 37C regarding infusion needle assembly 612 and regarding needle penetration actuation pin 1624 remain and are also seen in FIG. 37D.

Figure 37E:
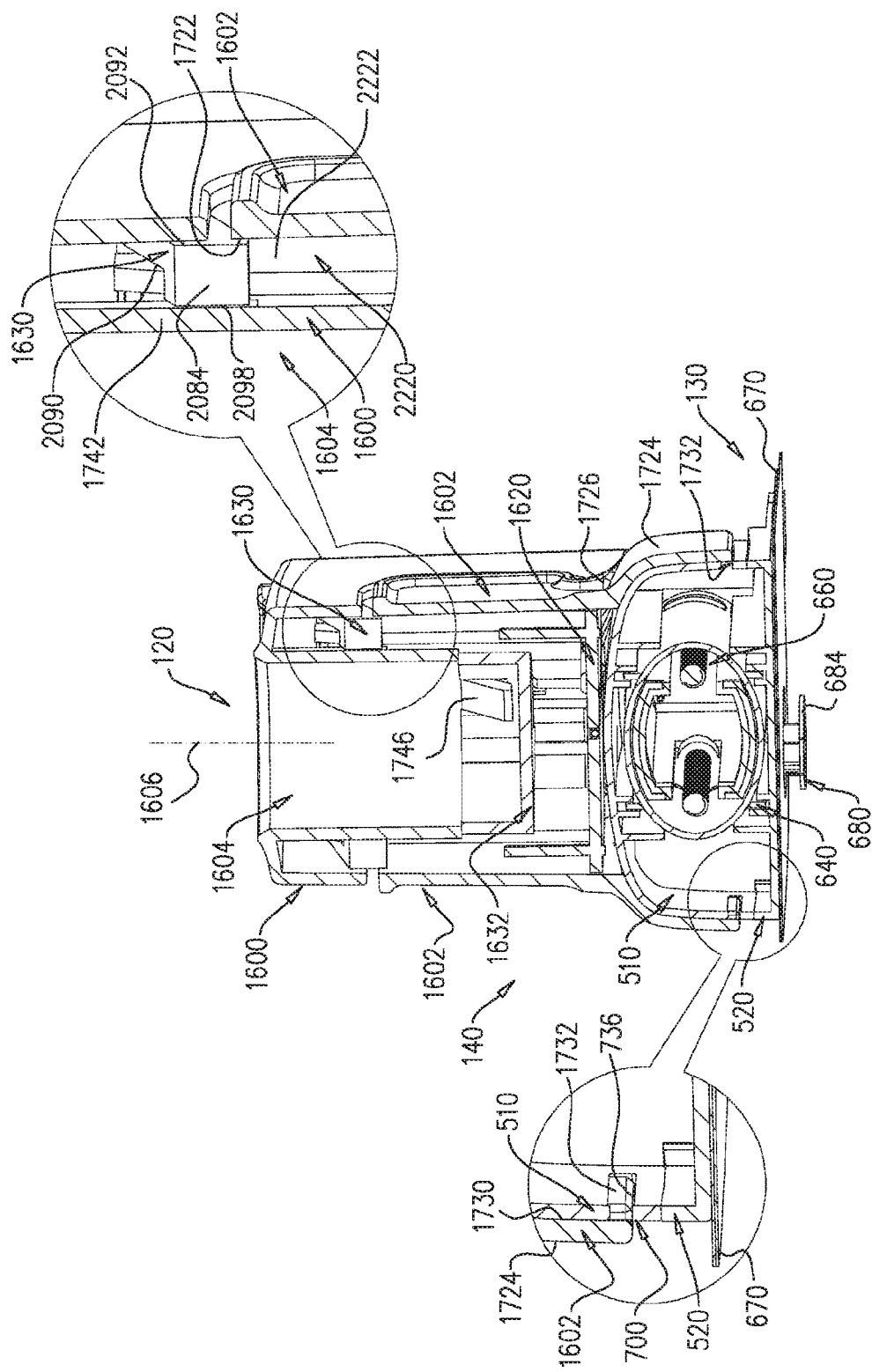

It is seen in FIG. 37E that inserter decoupling prevention element 1630, which is seated between base element 1620 and housing portion 1600 is adapted to prevent actuation of manually actuable buttons 1602 in this operative orientation. It is specifically seen that arm portions 2084 of inserter decoupling prevention element 1630 are seated between wall portions 2220 of base element and manually actuable buttons 1602 of housing portion 1600, such that side edge surfaces 2098 of arm portions 2084 of inserter decoupling prevention element 1630 engage outer surface 1742 of housing portion 1600 inwardly facing surface 2090 of arm portions 2084 of inserter decoupling prevention element 1630 engage inwardly facing surface 2222 of flat walls 2220 of base element 1620 and outwardly facing surface 2092 of arm portions 2084 engage planar portions 1722 of manually actuable buttons 1602 of housing portion 1600, thereby preventing inward displacement of manually actuable buttons 1602 upon pivoting thereof around hinge portion 1726.

It is a particular feature of an embodiment of the present invention that disposable interface and control module 140 is selectively releasably connected to disposable base portion 130, as long as arm portions 2084 of inserter decoupling prevention element 1630 are seated between wall portions 2220 of base element and manually actuable buttons 1602 of housing portion 1600.

It is seen in FIG. 37E that manually actuable buttons 1602 of disposable interface and control module 140 are engaged with top housing portion 510 of disposable base portion 130, such that inwardly retaining protrusions 1732 formed on curved portions 1724 of manually actuable buttons 1602 are inserted into slots 736 formed in curved cover portion 700 of top housing portion 510 of disposable base portion 130.

Figure 37F:
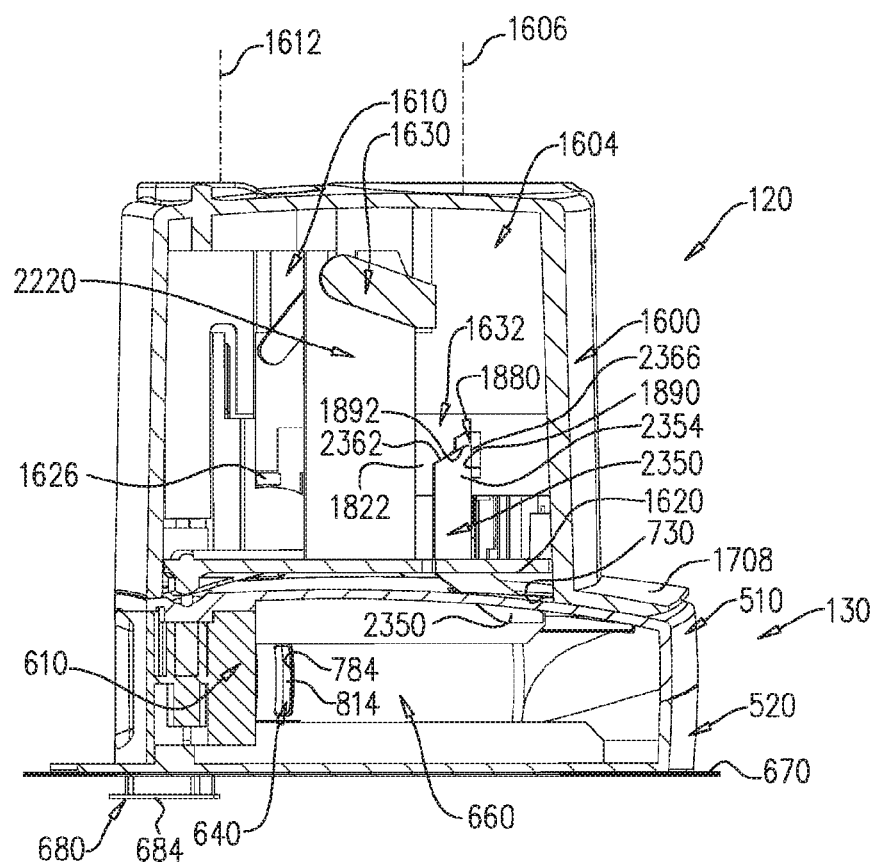

It is seen in FIG. 37F that downward portions 2356 of lever portions 2350 of base portion 1620 of disposable interface and control module 140 protrude into slots 730 and 732 of top housing portion 510 of disposable base portion 130.

It is further seen that radially outwardly extending protrusions 814 of linear displacer 640 are fixedly attached to medicament reservoir 660 by snap-fit engagement within mutually opposed apertures 784 of medicament reservoir 660, such that forwardly facing surfaces 830 of protrusions 814 of the linear displacer 640 lie against a wall defined by the apertures 784 of medicament reservoir 660.

It is particularly seen in FIG. 37F and being a particular feature of an embodiment of the present invention that in this operative orientation vial adaptor 1632 is retained from downward displacement relative to housing portion 1600 by means of engagement thereof with base portion 1620. Specifically, it is seen that lever portions 2350 of base portion 1620 are engaged with retaining protrusions 1880 of vial adaptor 1632, such that inner facing edge surfaces 1890 and 1892 of retaining protrusions 1880 engage tapered upwardmost edge surface 2362 and inwardly facing surface 2366 of the upward portion 2354 of lever portions 2350, thereby retaining the vial adaptor 1632 in its raised operative orientation, such that medicament vial seal cannot be pierced.

It is appreciated that the remaining spatial relationships seen in FIG. 37F are substantially the same as seen and described with reference to FIG. 37B.

It is seen in FIG. 37G that vial adaptor 1632 is partially inserted into well 1604 of housing portion 1600 and switch actuating protrusion 1900 of vial adaptor 1632 is preferably disposed in lateral cut-out 2390 of base element 1620, such that downwardly facing engaging end 1902 of switch actuating protrusion 1900 does not protrude downwardly from base wall portion 2200 of base element 1620 into extension slot 734 of top housing portion 510 of disposable base portion 130.

It is seen that all spatial relations between the components of the reusable portion 110 remain substantially the same as shown and described with reference to FIG. 34C.

Figure 37H:
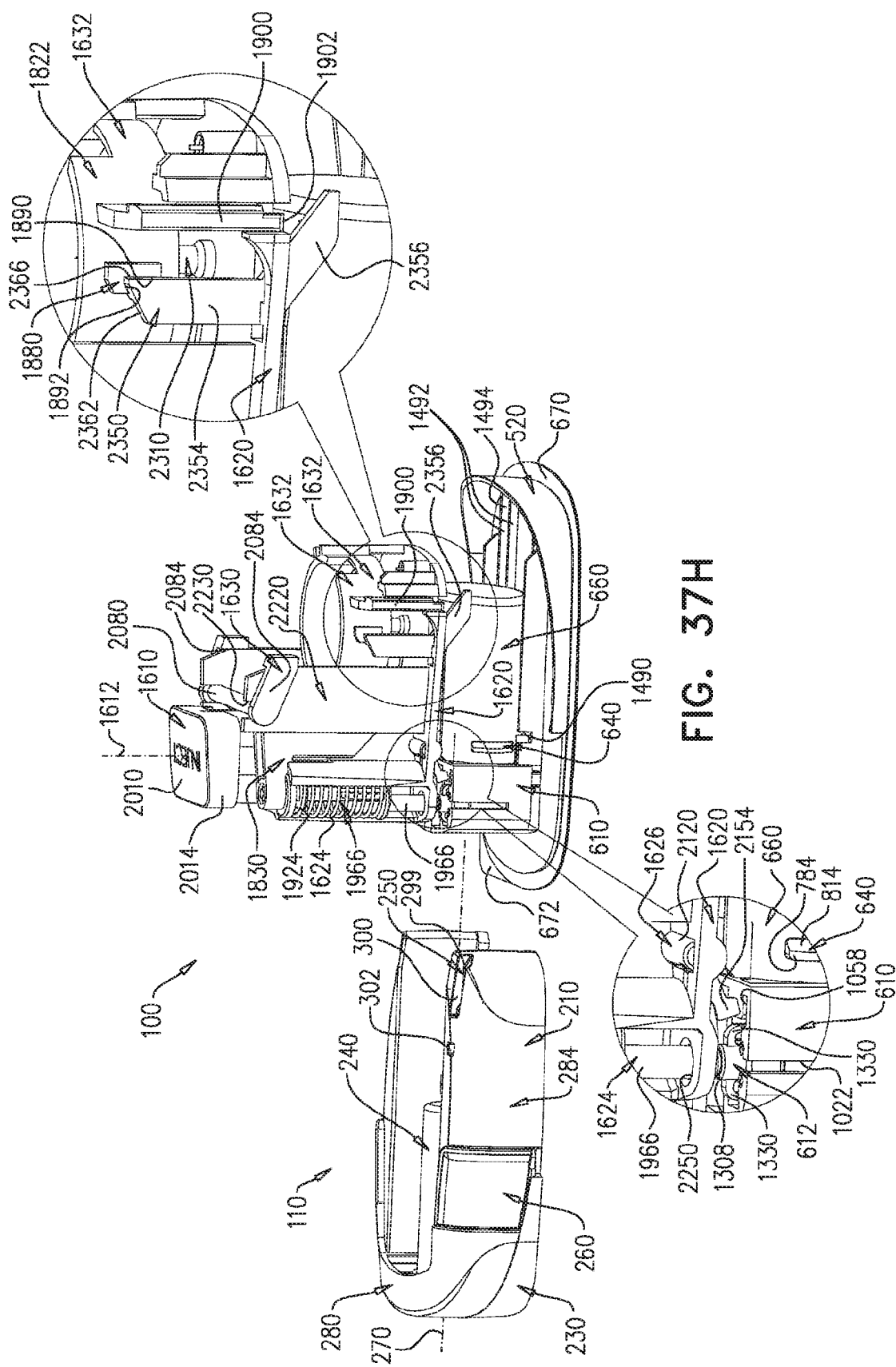

It is seen in FIG. 37H and being a particular feature of an embodiment of the present invention that in this operative orientation vial adaptor 1632 is retained from downward displacement relative to housing portion 1600 by means of engagement thereof with base portion 1620. Specifically, it is seen that lever portions 2350 of base portion 1620 are engaged with retaining protrusions 1880 of vial adaptor 1632, such that inner facing edge surfaces 1890 and 1892 of retaining protrusions 1880 engage tapered upwardmost edge surface 2362 and inwardly facing surface 2366 of the upward portion 2354 of lever portions 2350, thereby preventing downward displacement of the vial adaptor 1632 and thus prevents piercing of the medicament vial seal.

It is further seen in FIG. 37H that vial adaptor 1632 is partially inserted into well 1604 of housing portion 1600 and switch actuating protrusion 1900 of vial adaptor 1632 is preferably disposed in lateral cut-out 2390 of base element 1620, such that downwardly facing engaging end 1902 of switch actuating protrusion 1900 does not protrude downwardly from base wall portion 2200 of base element 1620 into extension slot 734 of top housing portion 510 of disposable base portion 130.

Downward portions 2356 of lever portions 2350 of base portion 1620 of disposable interface and control module 140 are adapted to protrude into slots 730 and 732 of top housing portion 510 of disposable base portion 130.

It is further seen in FIG. 37H that needle penetration prevention element 1626 is seated within base portion 1620, such that the pivoting rod 2120 thereof is seated within cut-out groove 2256 of base portion 1620 and is supported by side protrusion 2270 of base portion 1620. It is seen that engagement portion 2150 of needle penetration prevention element 1626 protrudes downwardly from base wall portion 2200 of base portion 1620.

It is a particular feature of an embodiment of the present invention that needle penetration prevention element 1626 locks the needle penetration actuation element 1610 and prevents its actuation before connection of reusable portion 110 and disposable portion 120 and pressing the patch pump assembly 100 against the injection site, as is described in detail hereinbelow.

It is particularly seen in FIG. 37H that needle penetration actuation pin 1624 of disposable interface and control module 140 is disposed adjacent infusion needle assembly 612 of disposable base portion 130, however in this storage operative orientation, needle penetration actuation pin 1624 does not exert force on infusion needle assembly 612 and needle biasing and sealing element 616 of disposable base portion 130. It is specifically seen that downwardly facing end surface 1972 of activation rod 1966 of needle penetration actuation pin 1624 protrudes slightly downwardly through aperture 2250 of base portion 2200 of disposable interface and control module 140 and into aperture 722 of top housing portion 510 of disposable base portion 130 up to engagement with upward edge 1308 of needle hub 1280 of infusion needle assembly 612.

It is further seen that inserter decoupling prevention element 1630 is seated within curved cut-outs 2230 of wall portions 2220 of base element 1620.

Radially outwardly extending protrusions 814 of linear displacer 640 are fixedly attached to medicament reservoir 660 by snap-fit engagement within mutually opposed apertures 784 of medicament reservoir 660, such that forwardly facing surfaces 830 of protrusions 814 of the linear displacer 640 lie against a wall defined by the apertures 784 of medicament reservoir 660.

It is specifically seen in FIG. 37H that two bottom arm portions 806 of linear displacer 640 are slidably guided by guiding channels 1494 of bottom housing portion 520.

Reference is now made to FIGS. 38A-38F, which are simplified illustrations of the patch pump assembly 100 of FIGS. 1-36I in a pre-vial insertion operative orientation. FIGS. 38A-38F are respective simplified pictorial view, planar side view, section views taken along respective lines C-C and D-D in FIG. 38A, and a partial pictorial view shown without housing portion 1600 of the disposable interface and control module 140 and without top housing portion 510 of the disposable base portion 130, of the patch pump assembly 100.

Patch pump assembly 100 is seen in FIGS. 38A-38F, in a pre-vial insertion operative orientation. It is seen that the reusable portion 110 is now operatively attached to the disposable portion 120 of FIGS. 37A-37H.

It is also seen that a medical vial 2900 containing a medicament 2950 is not yet inserted into well 1604 of disposable interface and control module 140.

Figure 38A:
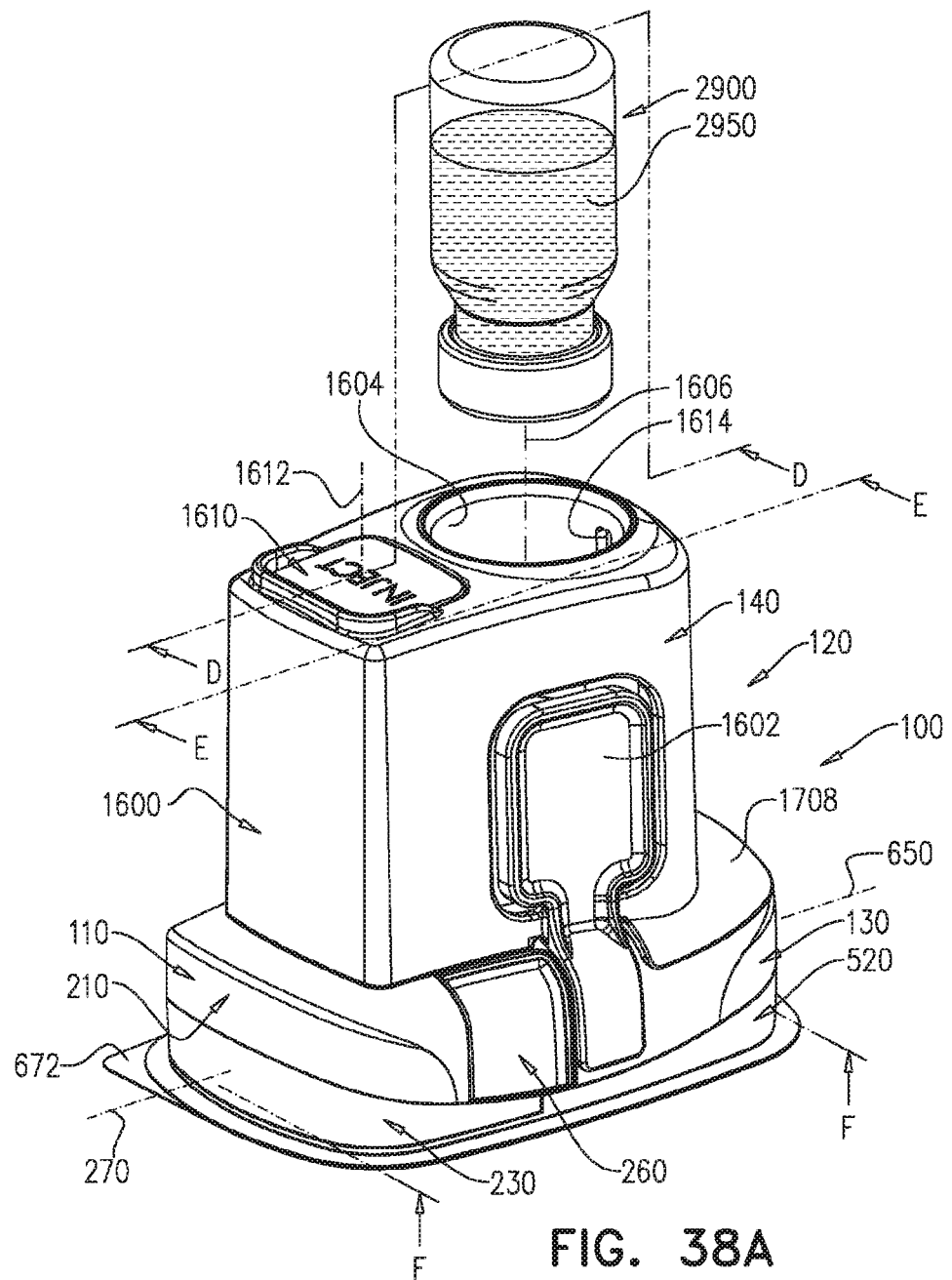
Figure 38B:
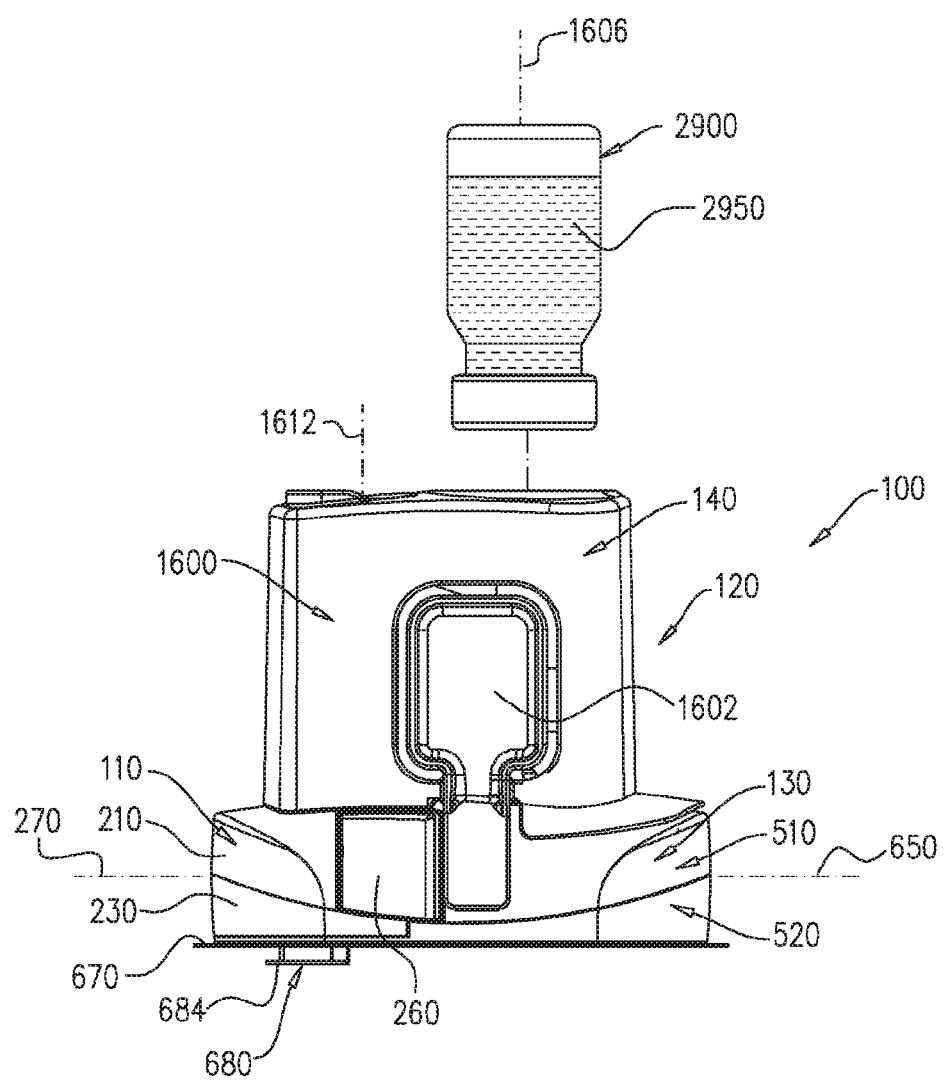
Figure 38C:
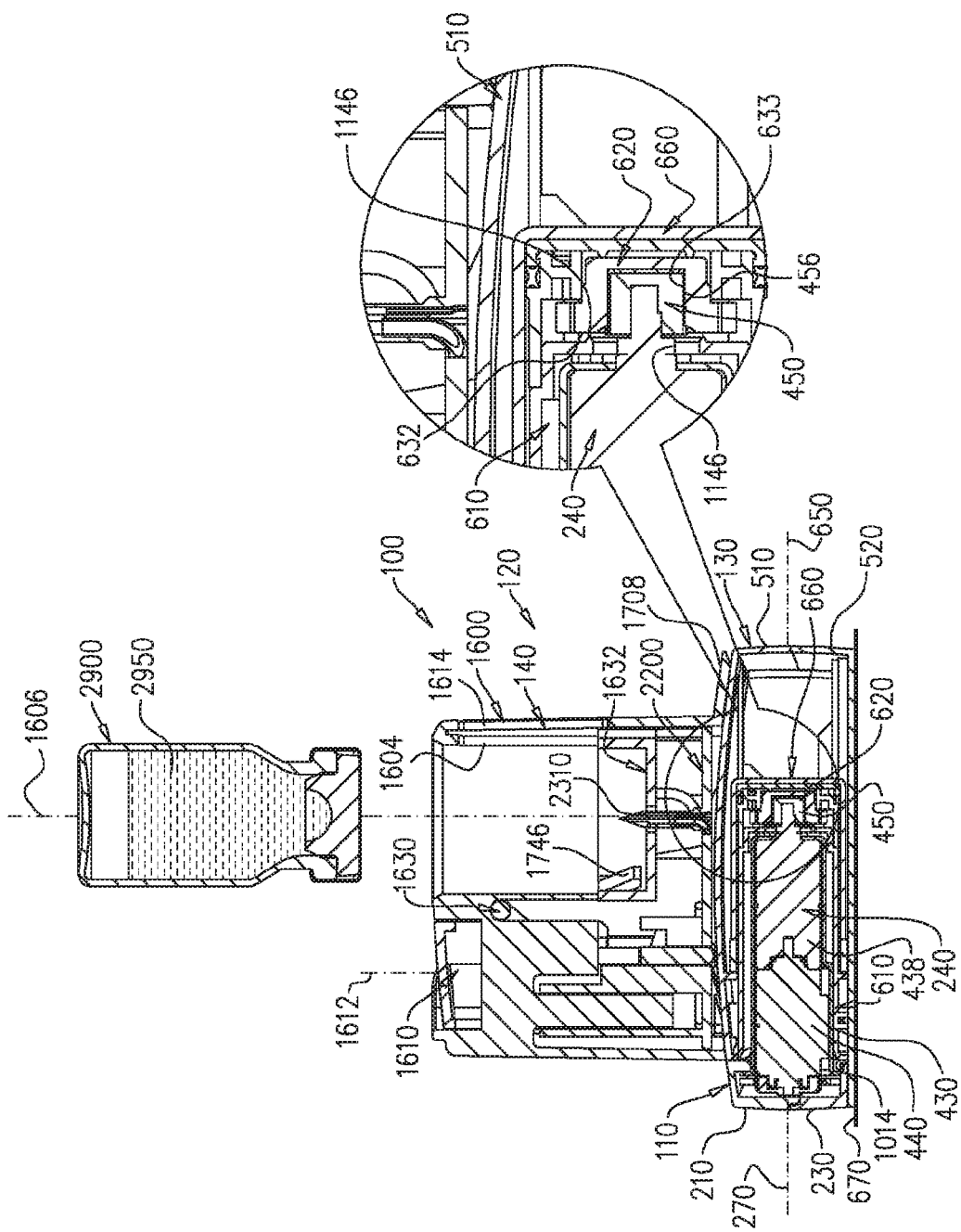

It is specifically seen in FIG. 38C that plunger assembly 240 of reusable portion 110 is inserted into housing element 610 of disposable base portion 130 through central aperture 1014 of housing element 610. It is also seen that drive element 450 of plunger assembly 240 protrudes through aperture 1144 of housing element 610 and extend into piston assembly 620, such that teeth 456 of drive element 450 interconnect with interior gear teeth 633 of piston assembly 620 and bearing surface 632 of piston assembly 620 engages protrusion 1146 of housing element 610.

It is specifically seen in FIG. 38D that upon connecting the reusable portion 110 to disposable portion 120, end surface 292 of main housing portion 210 engages inwardly extending protrusion 750 formed on top housing portion 510 of disposable base portion 130. Protrusion 750 thereby slides through cut-out 298 formed in main housing portion 210 of reusable portion 110, into aperture 300, thereby pushing engagement surface 488 of sealing element 250, causing bottom engagement surface 490 of sealing element 250 to be downwardly displaced into recess 370 and thereby activate on/off microswitch 374, which turns on the patch pump assembly 100. It is appreciated that vial microswitch 378 is not activated in this operative orientation since the vial adaptor 1632 is still disposed in its raised position, where vial seating portion 1822 of vial adaptor 1632 is upwardly spaced from base wall portion 2200 of base portion 1620 of disposable interface and control module 140.

Figure 38E:
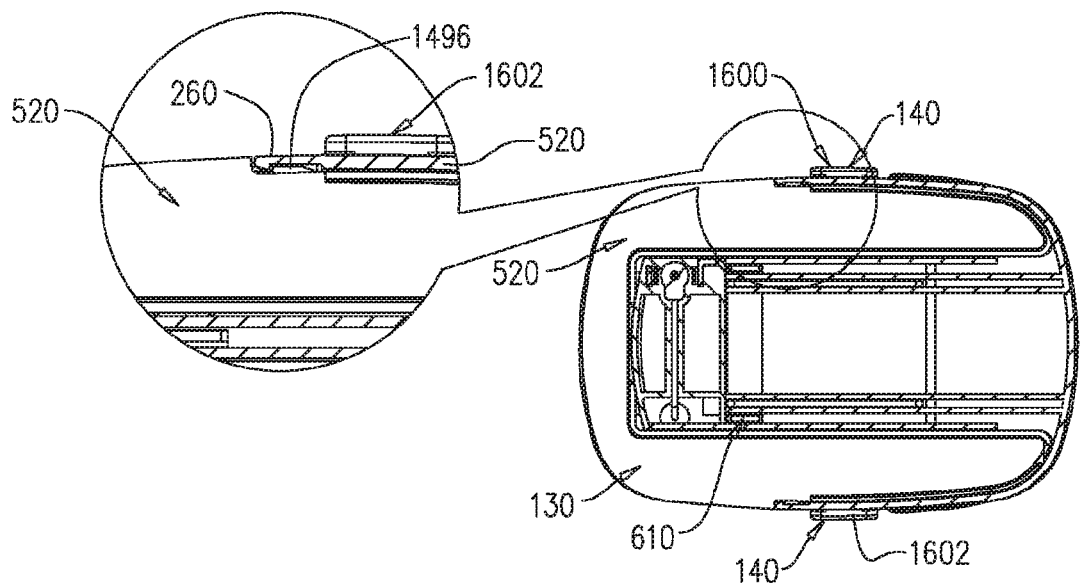

It is specifically seen in FIG. 38E that reusable portion 110 is engaged to disposable base portion 130 by a snap fit engagement between manually actuable buttons 260 of main housing portion 210 of reusable portion 110 with recesses 1496 of bottom housing portion 520 of disposable base portion 130.

Figure 38F:
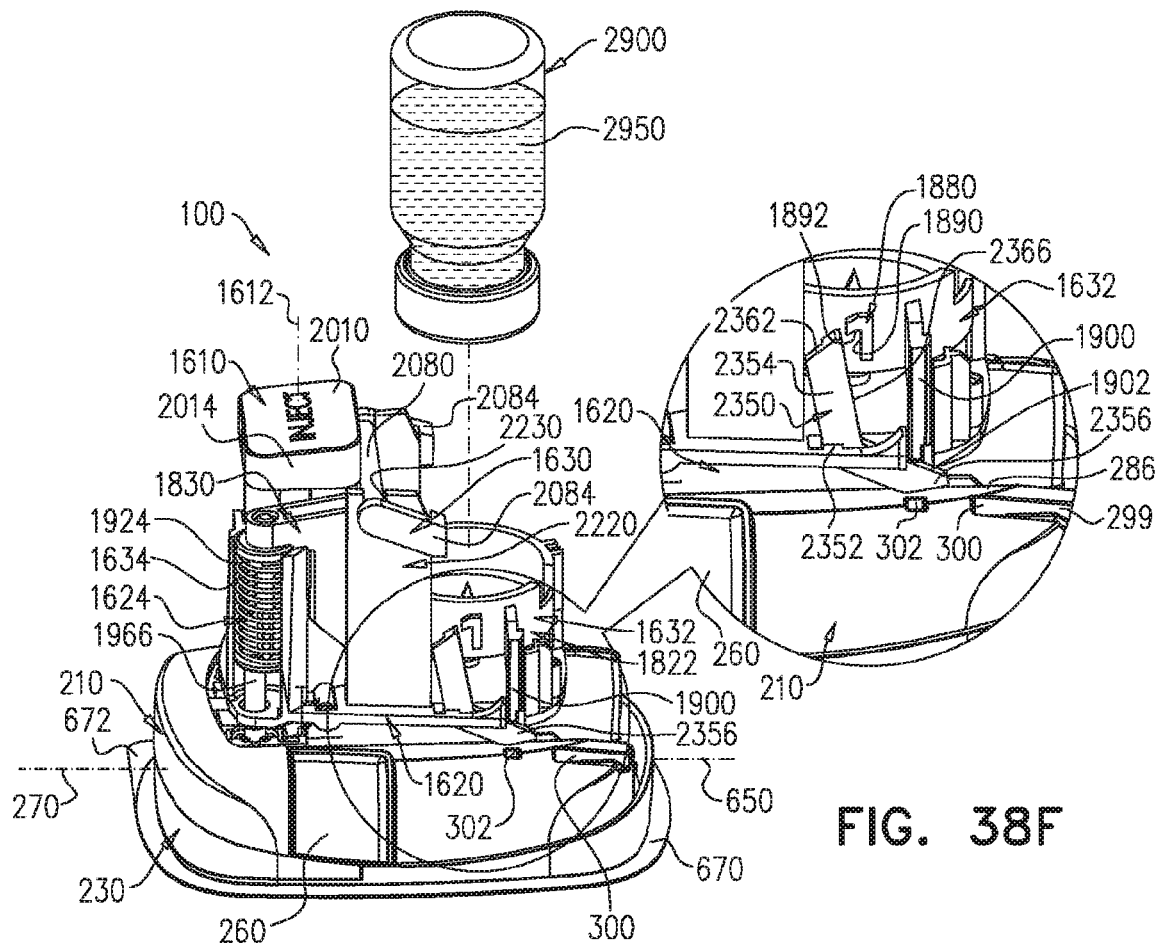

It is specifically seen in FIG. 38F that upon slidable insertion of reusable portion 110 into disposable base portion 130, downward portions 2356 of lever portions 2350 are pushed rearwardly by planar surfaces 286 of main housing portion 210 of reusable portion 110, thus lever portions 2350 pivot around integral hinges 2352 thereof and upward portions 2354 are displaced forwardly, thereby disengaging from retaining protrusions 1880 formed on vial adaptor 1632.

Vial adaptor 1632 is not retained anymore from downward displacement relative to housing portion 1600 since it is not engaged with base portion 1620 anymore. Specifically, tapered upwardmost edge surface 2362 and inwardly facing surface 2366 of the upward portion 2354 of lever portions 2350 disengage from inner facing edge surfaces 1890 and 1892 of retaining protrusions 1880 thus permitting downward displacement of vial seating portion 1822 of vial adaptor 1632 downwardly towards base wall portion 2200 of base portion 1620.

It is appreciated that all the remaining spatial relationships in FIGS. 38A-38F remain substantially the same as described with reference to FIG. 37A-37H.

Reference is now made to FIGS. 39A-39D, which are simplified illustrations of the patch pump assembly 100 of FIGS. 1-36I in a vial insertion operative orientation. FIGS. 39A-39D are respective simplified pictorial view, section views taken along respective lines B-B and C-C in FIG. 39A, and a partial pictorial view shown without housing portion 1600 of the disposable interface and control module 140 and without top housing portion 510 of the disposable base portion 130, of the patch pump assembly 100.

Patch pump assembly 100 is seen in FIGS. 39A-39D, in a vial insertion operative orientation. It is seen that the medical vial 2900 is now operatively inserted into the well 1604 of housing portion 1600 of disposable interface and control module 140.

Figure 39A:
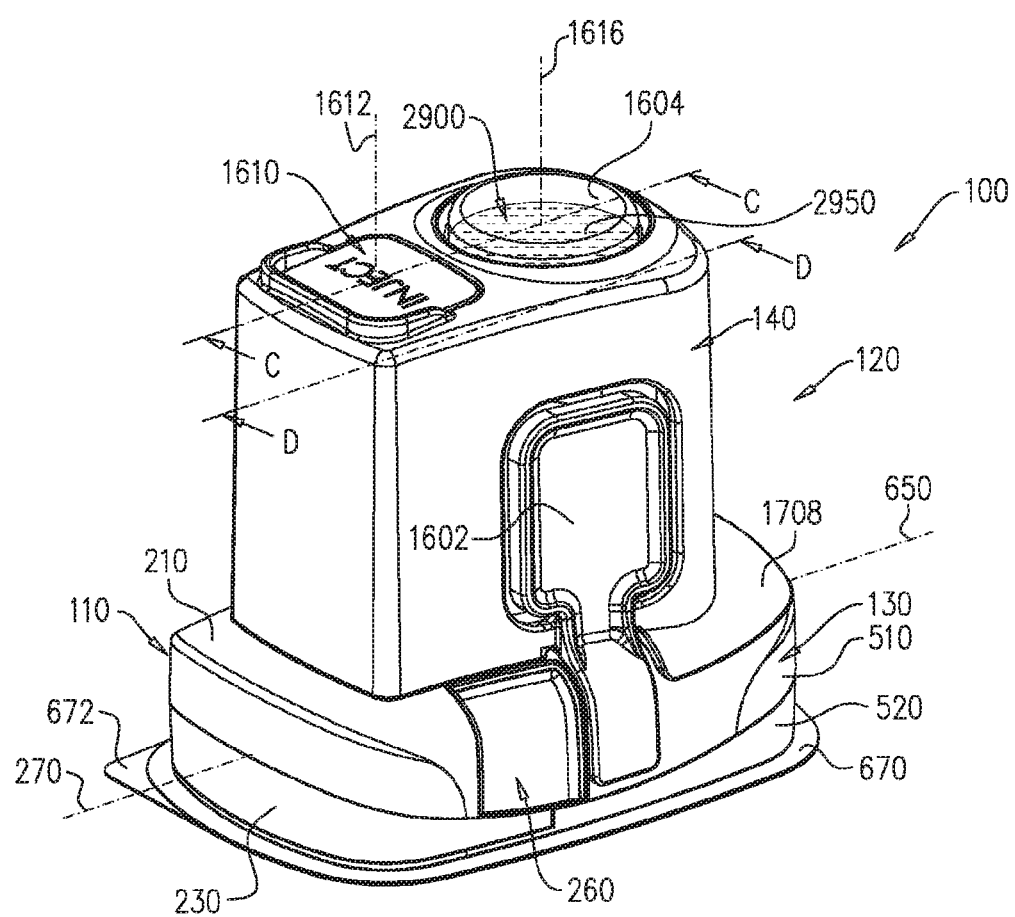
FIGS. 39A-39D are simplified illustrations of the patch pump assembly of FIGS. 1-36I in a vial insertion operative orientation.
Figure 39B:
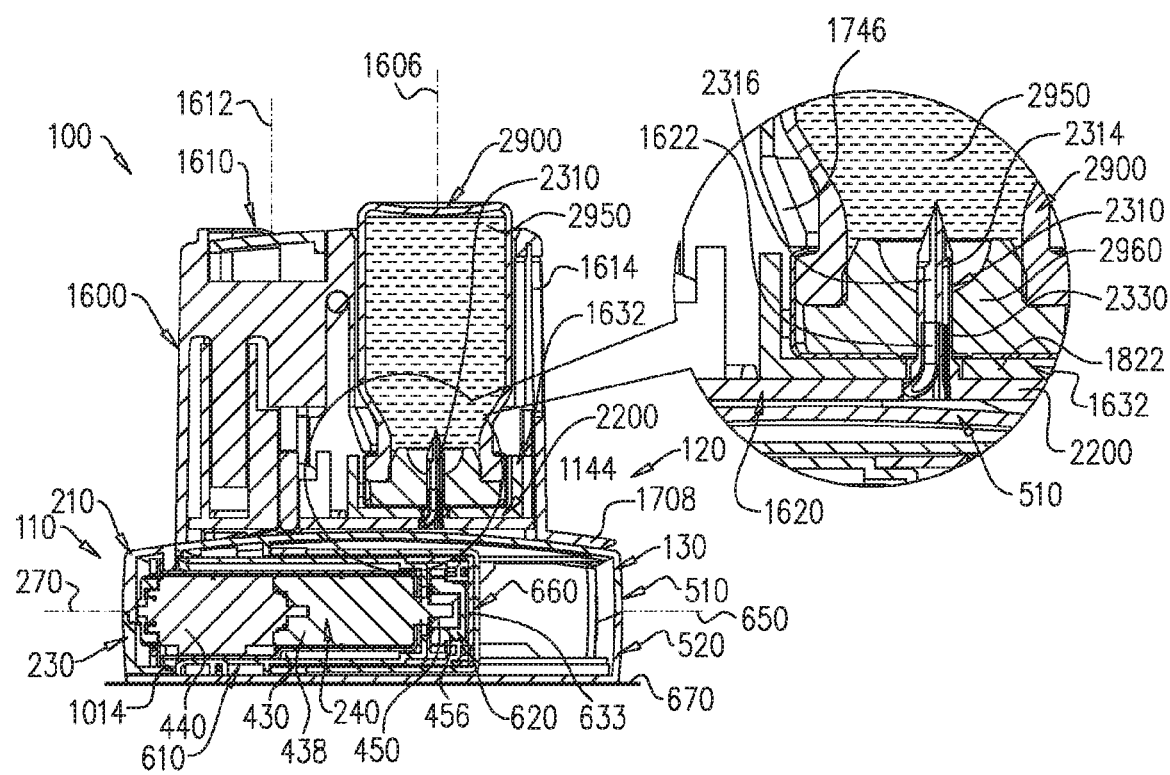

It is specifically seen in FIG. 39B and being a particular feature of an embodiment of the present invention that once vial adaptor 1632 is displaced downwardly such that vial seating portion 1822 abuts base wall portion 2200 of base portion 1620 of disposable interface and control module 140, spike 2310 penetrates a seal 2960 of medical vial 2900 thus fulfilling a first requirement for permitting fluid flow communication between medicament 2950 contained within medical vial 2900 and medical reservoir 660. Fluid flow passage is enabled through medicament conduit 1622, which is disposed within groove 2316 in spike 2310 and through medicament coupling filling conduit 618, as seen specifically in FIG. 37D. Another requirement has to be fulfilled in order to activate aspiration of the medicament 2950 from medical vial 2900 into medical reservoir 660, as will be described in detail hereinbelow, with reference to FIG. 39C.

It is further seen that vial adaptor 1632 along with the medical vial 2900 inserted thereinto is fixedly and non-removably retained within well 1604 of housing portion 1600 of disposable interface and control module 140 by means of undercut portions 1746 formed on housing portion 1600 and engaged with the neck portion of the medical vial 2900.

It is a particular feature of an embodiment of the present invention that the disposable interface and control module 140 is adapted to be disposed along with medical vial 2900 post-usage thereof.

Figure 39C:
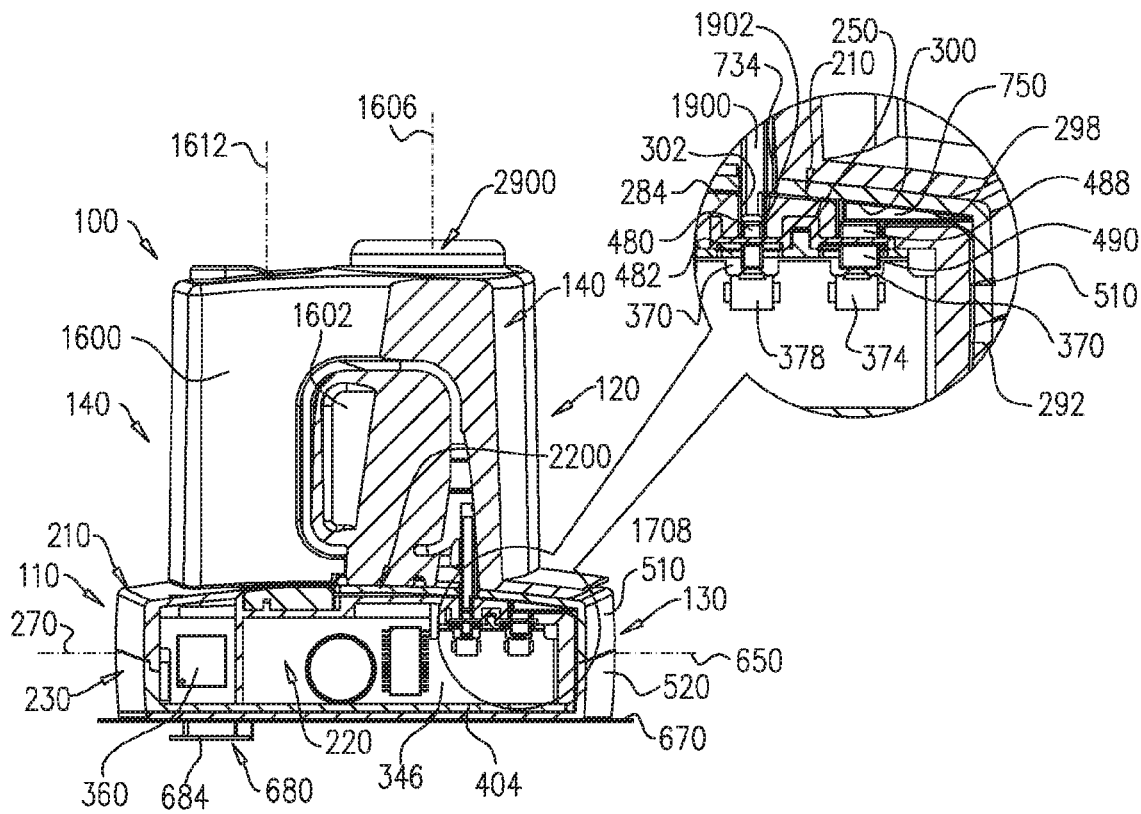

It is specifically seen in FIG. 39C that upon downward displacement of vial adaptor 1632 downwardly with respect to base portion 1620 of disposable interface and control module 140, the vial adaptor 1632 activates vial microswitch 378 in the reusable portion 110. Particularly, it is seen that upon inserting the medical vial 2900 into the vial adaptor 1632, downwardly facing engaging end 1902 of switch actuating protrusion 1900 formed on vial adaptor 1632, extends through slot 734 in top housing portion 510 and protrudes into aperture 302 formed in main housing portion 210 of reusable portion 110, thereby pushing engagement surface 480 of sealing element 250, causing bottom engagement surface 482 of sealing element 250 to be downwardly displaced into recess 370 and thereby activate vial microswitch 378.

It is a particular feature of an embodiment of the present invention that activation of vial microswitch 378 fulfills the second requirement for activating aspiration of the medicament 2950 from medical vial 2900 into medical reservoir 660.

It is a particular feature of an embodiment of the present invention that aspiration of medication from medical vial 2900 to medicament reservoir 660 is initiated automatically upon insertion of medicament vial 2900 into well 1604 of disposable interface and control module 140, without any further manipulation performed by the user.

Upon activation of both On/Off microswitch 374 and vial microswitch 378, a signal is transferred to the control system, which enables activation of the electric motor 440 in a first rotational direction, thereby initiating aspiration of medicament 2950 from medical vial 2900 into medical reservoir 660 of disposable base portion 130.

Figure 39D:
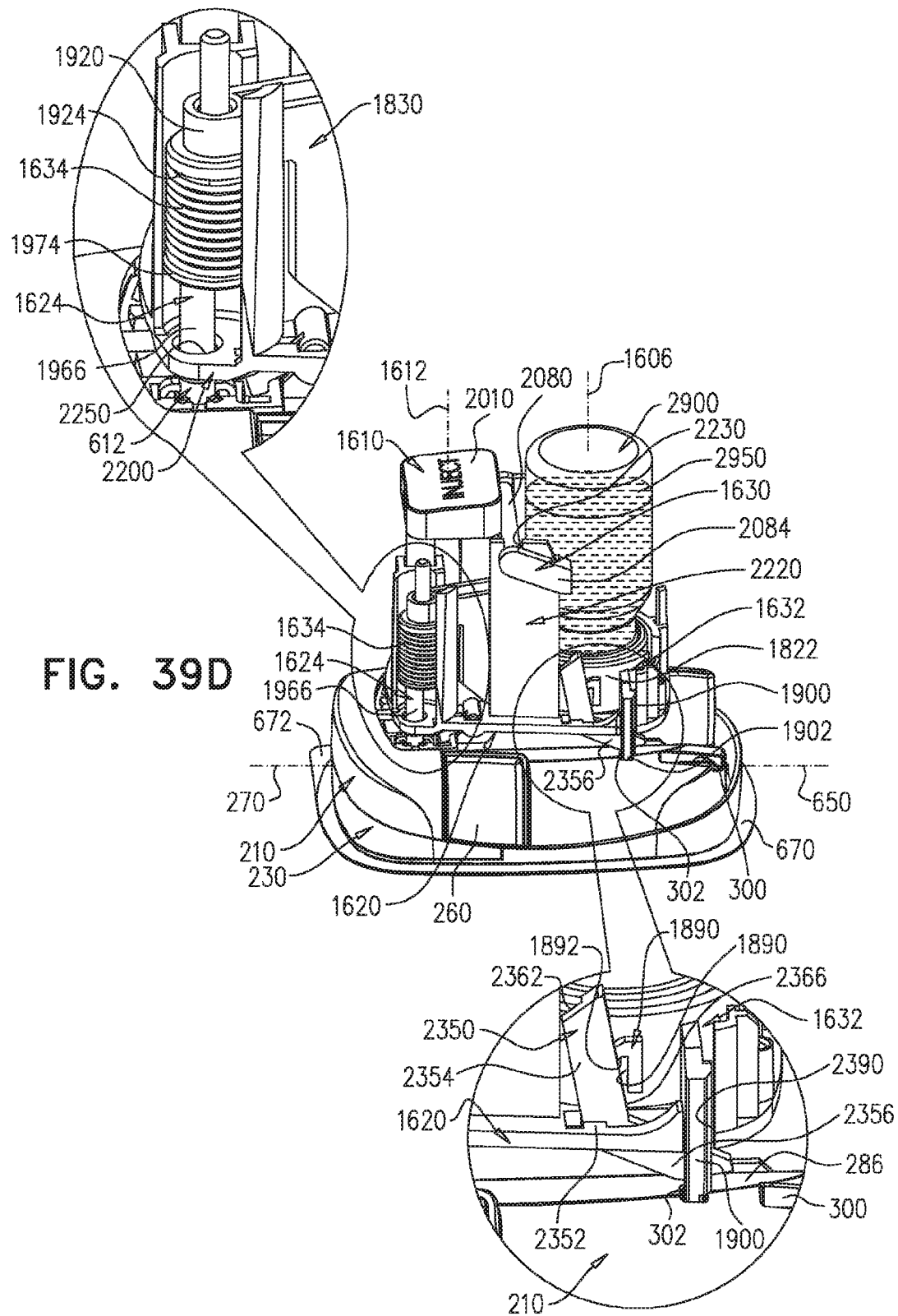

It is specifically seen in FIG. 39D that compression spring 1634 is compressed between downwardly facing edge surface 1924 of vial adaptor 1632 and upwardly facing surface 1974 of needle penetration actuation pin 1624 upon insertion of medical vial 2900 into well 1604 and downward displacement of vial adaptor 1632. It is appreciated that compression spring 1634 cannot be released in this operative orientation since the vial adaptor 1632 is fixedly retained in its lowered position by means of engagement of medical vial 2900 with undercut portions 1746 of housing portion 1600.

It is seen that needle penetration actuation pin 1624 extends slightly into central aperture 2250 of base wall portion 2200 of base portion 1620.

It is further seen in FIG. 39D that upward portions 2354 of lever portions 2350 remain pivoted forwardly and 2356 protrude into top housing portion 510.

It is also seen in FIG. 39D that upon insertion of the medical vial 2900 into the vial adaptor 1632, downwardly facing engaging end 1902 of switch actuating protrusion 1900 formed on vial adaptor 1632, extends through slot 2390 in base portion 1620 of disposable interface and control module 140 and through slot 734 in top housing portion 510 (not shown) and protrudes into aperture 302 formed in main housing portion 210 of reusable portion 110 to activate vial microswitch 378.

It is appreciated that all the remaining spatial relationships in FIGS. 39A-39D remain substantially the same as described with reference to FIG. 38A-38F.

Reference is now made to FIGS. 40A-40E, which are simplified illustrations of the patch pump assembly 100 of FIGS. 1-36I in a medicament reservoir filling operative orientation. FIGS. 40A-40E are respective simplified pictorial view, section views taken along respective lines B-B and C-C. D-D and E-E in FIG. 40A.

Patch pump assembly 100 is seen in FIGS. 40A-40E, in a medicament reservoir filling operative orientation. It is seen that the medicament 2950 is aspirated from medicament vial 2900 to medicament reservoir 660 in this operative orientation, thus the medicament vial 2900 is empty and the interior volume 774 of medicament reservoir 660 is increased, such that rearward end wall 772 of medicament reservoir 660 is now rearwardly spaced from rearwardly facing surface 872 of piston assembly 620 to accommodate medicament 2950 therebetween.

It is appreciated that each of FIGS. 40B-40E shows a portion of the fluid flow path of the medicament 2950 starting from medicament vial 2900 and flowing into medicament reservoir 660.

Figure 40A:
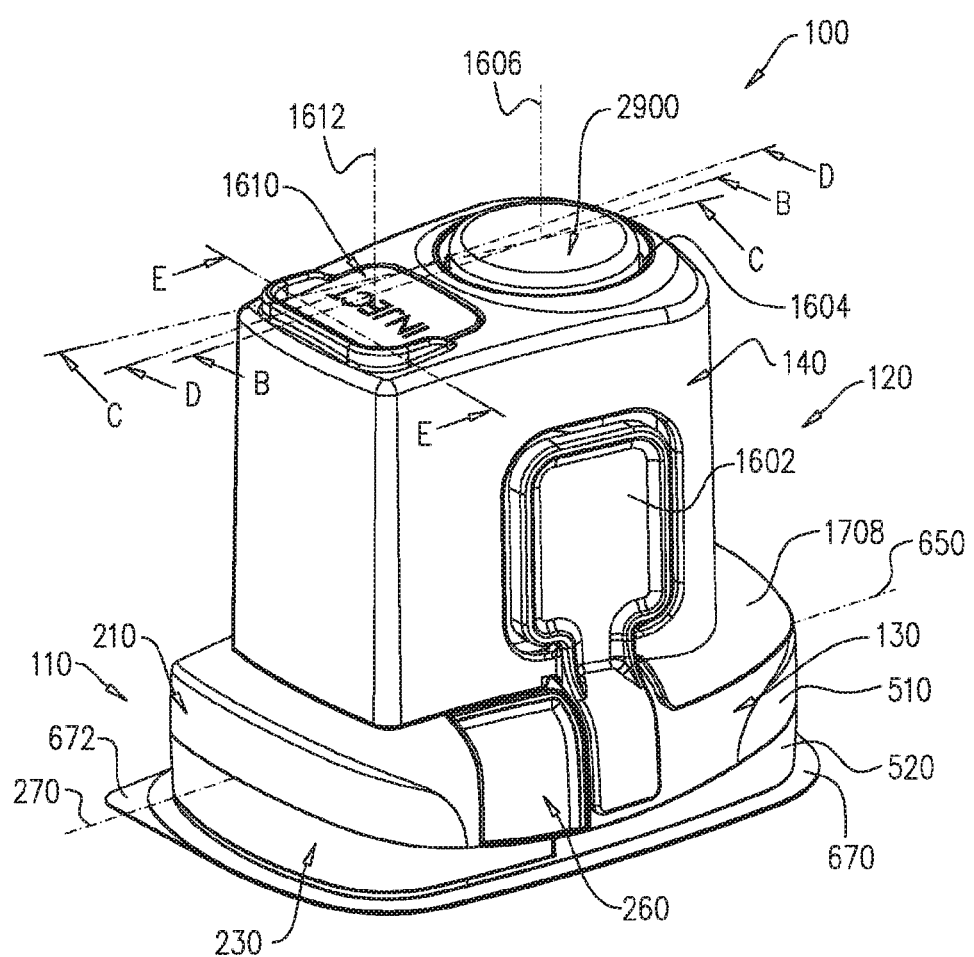
FIGS. 40A-40E are simplified illustrations of the patch pump assembly of FIGS. 1-36I in a medicament reservoir filling operative orientation.
Figure 40B:
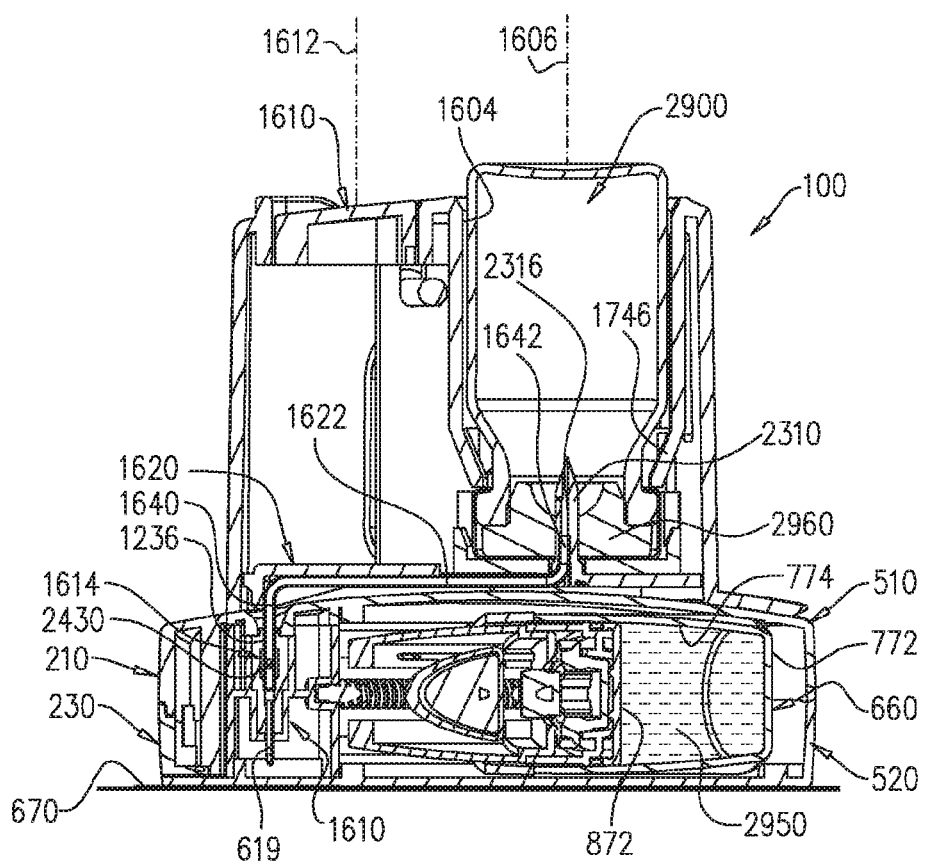

It is specifically seen in FIG. 40B that second end 1642 of medicament conduit 1622 is inserted into groove 2316 of spike 2310, medicament conduit 1622 further extends through cut-out 2320 of base portion 1620, through medicament conduit seat 2420 and first end 1640 of medicament conduit 1622 extends through aperture 720 formed in top housing portion 510 of disposable base portion 130. Medicament conduit 1622 further extends through slit 1236 of filling septum 1614, thus enabling passage of medicament 2950 from medicament vial 2900 through groove 2316 of spike 2310 and intermediate enlarged portion 1250 of filling septum 614. It is noted that first end 1640 of medicament conduit 1622 has a closed downwardmost end and aperture 2430, which is configured for fluid communication with the medicament coupling filling conduit 618, which provides for fluid communication between filling septum 1614 and medicament reservoir 660.

It is further noted that fluid flow passage from medicament conduit 1622 to medicament coupling injection conduit 619 is prevented due to closed downwardmost end of medicament conduit 1622 and fluid tight sealing between the downwardmost end of medicament conduit 1622 and between bottom cylindrical portion 1202 of the filling septum 614.

Figure 40C:
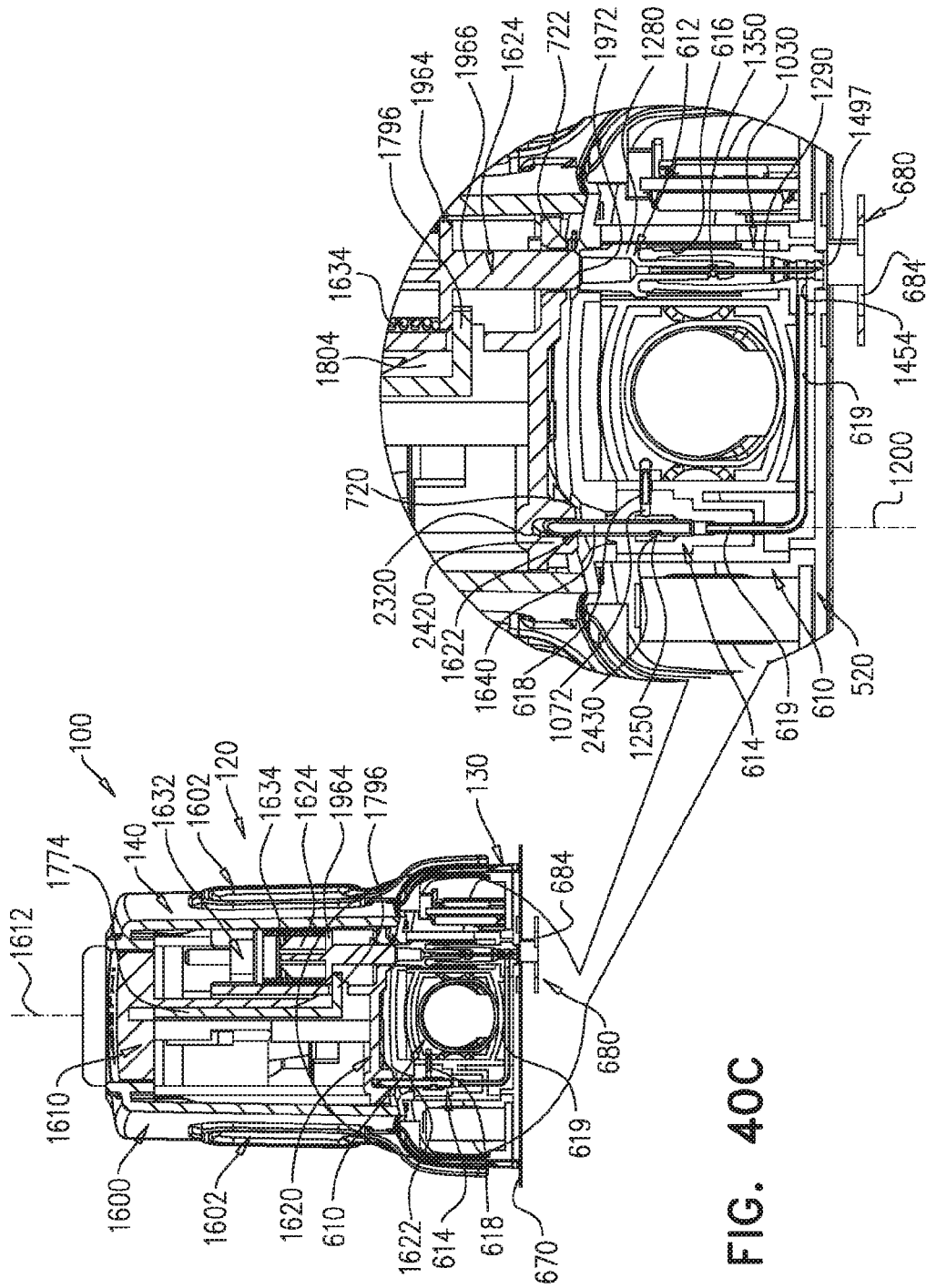

It is further specifically seen in FIG. 40C that the first end 1640 of medicament conduit 1622, forming part of disposable interface and control module 140 is inserted through slit 1236 of filling septum 1614, forming part of disposable base portion 130, thus providing fluid communication between medicament vial 2900, which is inserted into well 1604 and communicates with groove 2316 of spike 2310, and between medicament reservoir 660.

It is specifically seen that second end 1642 of medicament conduit 1622 is inserted into groove 2316 of spike 2310, medicament conduit 1622 further extends through cut-out 2320 of base portion 1620, through medicament conduit seat 2420 and first end 1640 of medicament conduit 1622 extends through aperture 720 formed in top housing portion 510 of disposable base portion 130. Medicament conduit 1622 further extends through slit 1236 of filling septum 1614, thus providing for fluid communication between groove 2316 of spike 2310 and intermediate enlarged portion 1250 of filling septum 614. It is noted that first end 1640 of medicament conduit 1622 has a closed downwardmost end and aperture 2430, which is configured for fluid communication with the medicament coupling filling conduit 618 extending through 1072 of housing element 610 and providing for fluid communication between filling septum 1614 and medicament reservoir 660.

It is particularly seen in FIG. 40C that needle actuation penetration pin 1624 is prevented from being downwardly displaced before needle penetration actuation element 1610 is pressed by the user, thus penetration of needle 1290 into the skin of the user is prevented. It is seen that downward displacement of needle actuation penetration pin 624 is prevented by engagement thereof with housing portion 1600 and with needle penetration actuation element 1610. Specifically, in this operative orientation, activating shaft 2004 of needle penetration actuation element 1610 is supported by forward wall portion 1774 of housing portion 1600, such that inwardly facing surface 2062 of activating shaft 2004 engages second side surface 1794 of forward wall portion 1774 and tapered edge surface 2064 of activating shaft 2004 engages tapered edge surface 1808 of protrusion 1804 formed on forward wall portion 1774.

It is additionally seen, that flange portion 1964 of needle actuation penetration pin 1624 engages upwardly facing surface 1800 of transversely disposed wall portion 1796 of housing portion 1600, which protrudes through 2260 of base portion 1620, thus needle actuation penetration pin 1624 is prevented from being downwardly displaced as long as inwardly facing surface 2062 of activating shaft 2004 engages second side surface 1794 of forward wall portion 1774 and tapered edge surface 2064 of activating shaft 2004 engages tapered edge surface 1808 of protrusion 1804 formed on forward wall portion 1774.

Figure 40E:
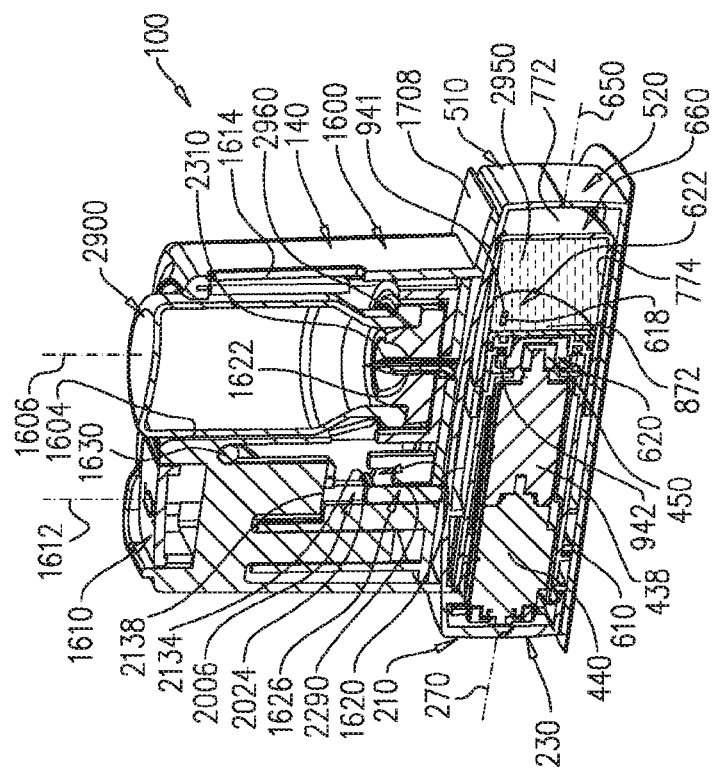
Figure 40D:
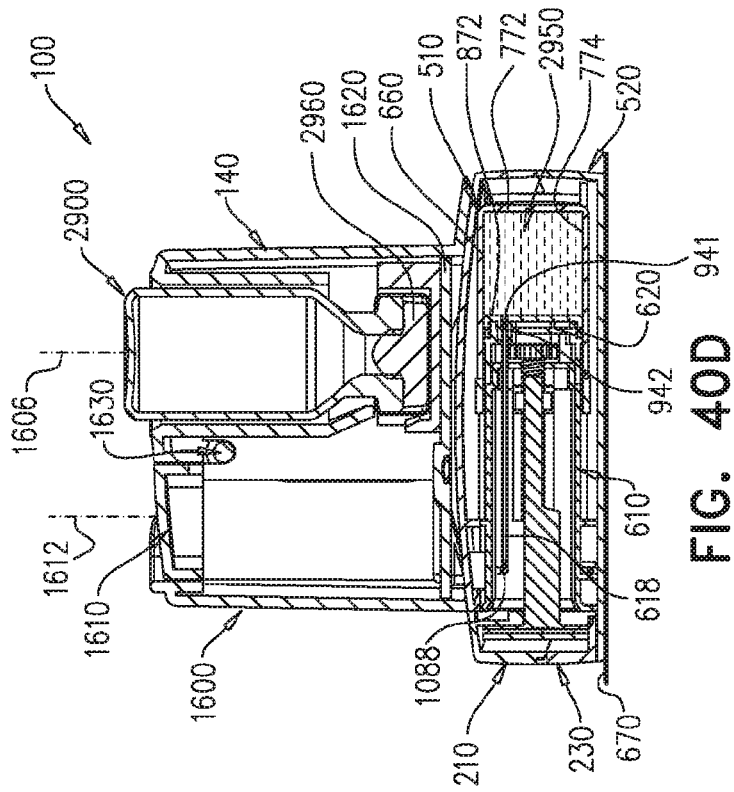

It is specifically seen in FIG. 40D that medicament coupling filling conduit 618 extends from filling septum 614 through slit 1072 formed in housing element 610, longitudinally extends through housing element 610 and further through aperture 1162 formed in end wall 1142 of housing element 610 into aperture 942 formed in piston assembly 620 and thereafter through groove 941 in rearwardly facing surface 872 into the interior volume 774 of medicament reservoir 660.

It is further seen in FIG. 40E that medicament coupling filling conduit 618, which extends from filling septum 614, seated in housing element 610 extends into piston assembly 620 and via groove 941 in rearwardly facing surface 872 of piston base element 622 enters into medicament reservoir 660 and provides fluid communication into or out of the interior volume 774 of the medicament reservoir 660.

It is additionally seen in FIG. 40E that needle penetration prevention element 1626 is retained between L-shaped protrusion 2290 of base element 1620 and between retaining shaft 2006 of needle penetration actuation element 1610 in this operative orientation, thereby preventing downward displacement of needle penetration actuation element 1610 by the user.

It is a particular feature of an embodiment of the present invention that once electric motor 440 is activated, motion is transferred from drive element 450, which is operatively connected to electric motor 440, to rotary-to-longitudinal drive converter 630 of piston assembly 620, by means of interconnection of teeth 456 with interior gear teeth 633. Rotary-to-longitudinal drive converter 630 in turn, transfers motion to nuts 980, which are operatively connected to lead screws 635 and cause rotation movement thereof, and thus urge linear displacement of linear displacer 640 along with medicament reservoir 660, relative to static piston assembly 620 along axis 650, thereby changing the interior volume 774 of medicament reservoir 660.

It is a particular feature of an embodiment of the present invention that automatic priming of the fluid flow passage provided through medicament conduit 1622 is enabled due to the fact that the aspiration of medicament 2950 from medical vial 2900 to medicament reservoir 660 occurs while patch pump assembly 100 is positioned on a horizontal surface and the seal 2960 of medicament vial 2900 is directed downwardly, thus the spike 2310 is fully disposed within medicament 2950 for the entire aspiration process. It is appreciated that groove 2314 of spike 2310 compensates for the vacuum created during the aspiration process due to air passage formed through groove 2314, conduit 2330, protrusion 2322 provided on base portion 1620 and the atmosphere.

It is appreciated that all the remaining spatial relationships in FIGS. 40A-40E remain substantially the same as described with reference to FIG. 39A-39D.

Reference is now made to FIG. 41, which is a simplified pictorial illustration of the patch pump assembly 100 of FIGS. 1-36I in a pre-injection site engagement operative orientation.

It is seen in this operative orientation in FIG. 41 that following aspiration of medicament from medical vial 2900 into medicament reservoir 660 of disposable portion 120, the user holds the disposable interface and control module 140 in one hand and removes release sheet 672 from disposable base element 130 with another hand, thereby exposing the injection site adhesive sticker 670. In this stage, the patch pump assembly 100 is ready to be attached to the injection site by a user.

Figure 42A:
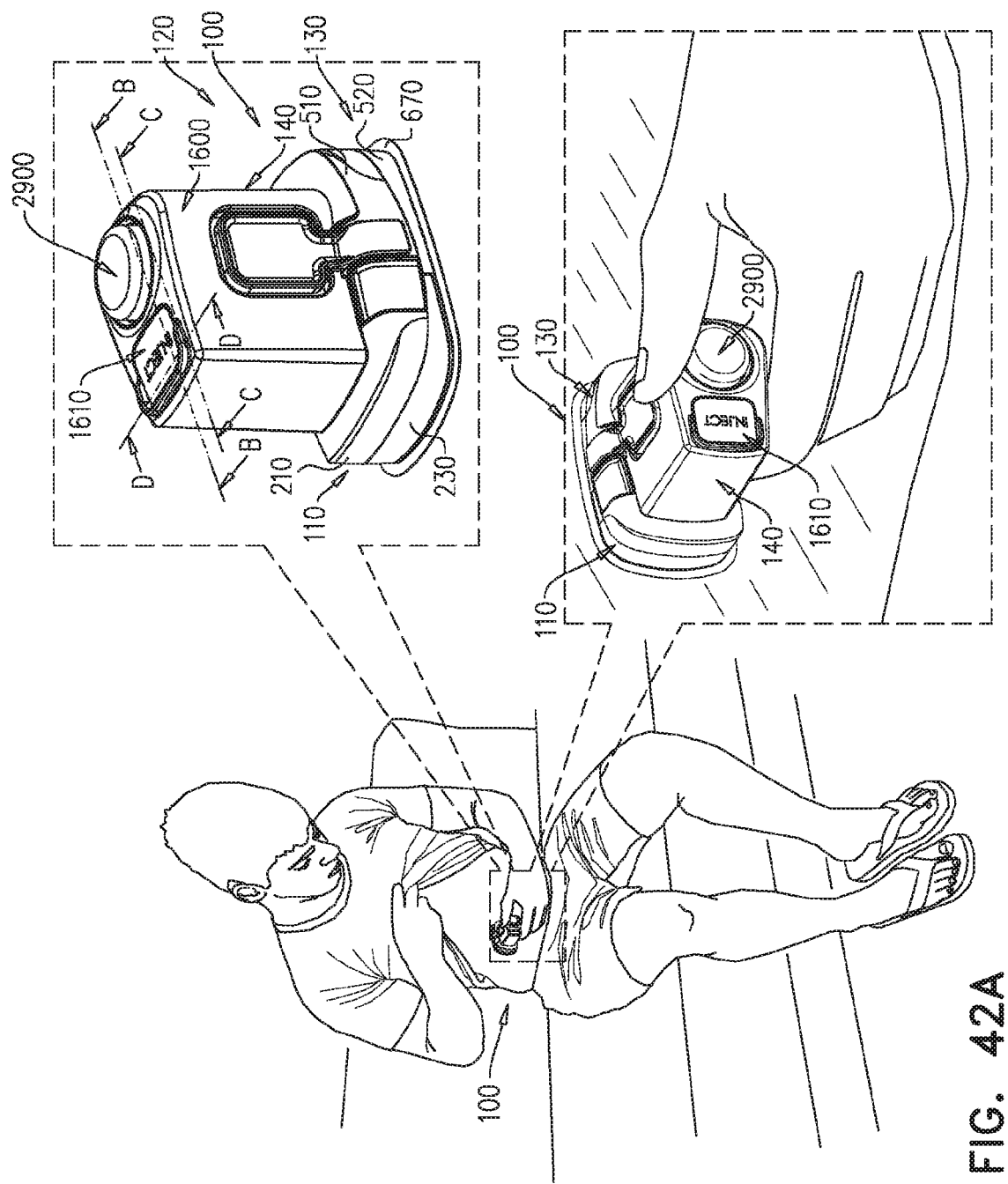
Figure 42E:
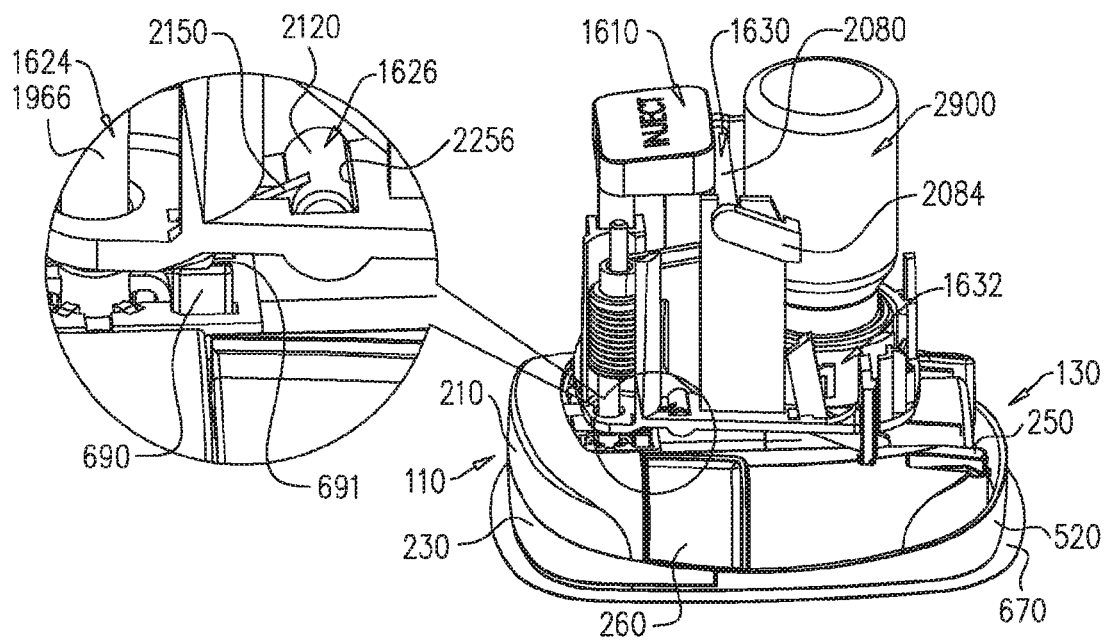
Figure 42F:
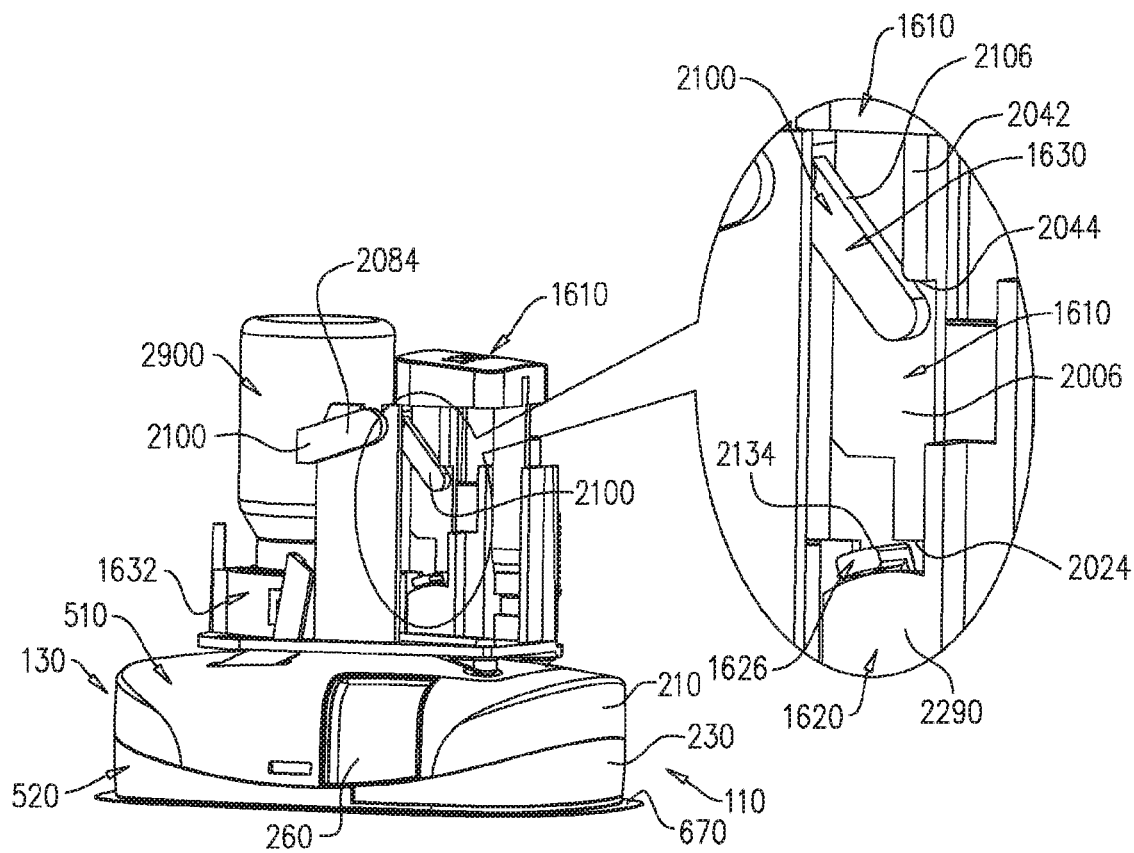

Reference is now made to FIGS. 42A-42F, which are simplified illustrations of the patch pump assembly 100 of FIGS. 1-36I in an injection site engagement operative orientation. FIGS. 42A-42F are respective simplified pictorial view, section views taken along respective lines B-B and C-C and D-D in FIG. 42A and partial pictorial views taken from two different perspectives, FIG. 42E is shown without both the housing portion 1600 of disposable interface and control element 140 and top housing portion 510 of disposable base portion 130 and FIG. 42F is shown without housing portion 1600.

Patch pump assembly 100 is seen in FIGS. 42A-42F, in an injection site engagement operative orientation. It is seen that in this operative orientation the user presses the patch pump assembly 100 against the skin, as particularly seen in FIG. 42A, such that injection site engagement element 680 is inserted inwardly into needle assembly location bore 1030 of housing element 610 of the disposable base portion 130 and the adhesive sticker 670 is adhesively attached to the skin of the user, thereby fixedly retaining the patch pump assembly 100 against the injection site.

It is specifically seen in FIG. 42B that injection site engagement element 680 is pushed upwardly into needle assembly location bore 1030 by the user, such that upwardly facing surface 1516 of injection site engagement surface defining ring 684 of injection site engagement element 680 engages recess 1500 of bottom housing portion 520. Shaft 688 of injection site engagement element 680 extends through aperture 1498 of bottom housing portion 520 upwardly into needle assembly location bore 1030 of housing element 610 and shafts 686 and 690 of injection site engagement element 680 extend through aperture 692 of bottom housing portion 520 upwardly into needle assembly location bore 1030 of housing element 610.

It is seen that shafts 686 and 688 extend up to a location adjacent downwardly tapered protrusions 1045 and 1065 located in needle assembly location bore 1030 of housing element 610. It is specifically seen that upwardly facing edges 1506 of shafts 686 and 688 are disposed slightly above downwardly facing tapered surfaces 1047 and 1067 of downwardly tapered protrusions 1045 and 1065 respectively and slightly radially outwardly with respect to longitudinal axis 1502.

It is appreciated that in this operative orientation needle penetration actuation pin 1624 is disposed in its initial orientation, such that downwardly facing end surface 1972 of activation rod 1966 thereof extends up to aperture 722 of top housing portion 510 and engages the needle hub 1280, upward edge 1308 of which is disposed within aperture 722 of top housing portion 510.

Lever portions 1330 of infusion needle assembly 612 are upwardly spaced from downwardly tapered protrusions 1045 and 1065 formed in housing element 610 in this operative orientation, thus needle 1290 does not protrude through central aperture 1497 of bottom housing portion 520 and is disposed in needle retracted operative orientation.

It is specifically seen in FIGS. 42C & 42E that needle penetration prevention element 1626 is deactivated by needle injection site engagement element 680 in this operative orientation, thus needle penetration actuation element 1610 is released and permitted to be displaced downwardly upon exertion of force on upwardly facing surface 2010 thereof.

It is specifically seen that needle penetration prevention element 1626 is seated within base portion 1620, such that the pivoting rod 2120 thereof is seated within cut-out groove 2256 of base portion 1620 and is supported by side protrusion 2270 of base portion 1620. It is seen that engagement portion 2150 of needle penetration prevention element 1626 which previously protruded downwardly from base wall portion 2200 of base portion 1620, as seen in FIG. 36C, is now pushed upwardly by the upwardly facing edge 691 of shaft 690 of injection site engagement element 680, thus causing needle penetration prevention element 1626 to pivot around the axis of pivoting rod 2120 and thereby displace extension portion 2134 of needle penetration prevention element 1626 rearwardly as described in detail hereinbelow with reference to FIG. 42F.

This engagement of upwardly facing edge 691 of shaft 690 of injection site engagement element 680 with engagement portion 2150 of needle penetration prevention element 1626 is urged by attachment of the patch pump assembly 100 to the skin of the user, which in turn causes insertion of injection site engagement element 680 into disposable base portion 130, such that shaft 690 protrudes upwardly from rectangular portion 1000 of housing element 610 and engages engagement portion 2150 of needle penetration prevention element 1626.

It is specifically seen in FIG. 42D that needle actuation penetration pin 624 is prevented from downward displacement relative to housing portion 1600 of disposable interface and control module 140 as long as needle penetration actuation element 1610 is not pressed downwardly by the user, thus penetration of needle 1290 into the skin of the user is prevented, as described in detail hereinabove with reference to FIG. 37D.

It is further seen that communication between filling septum 614 and medicament coupling injecting conduit 619 is closed as long as medicament conduit 1622 is inserted into filling septum 614. Additionally, infusion needle assembly 612 is still disposed in its retracted operative orientation, thus aperture 1350 of infusion needle assembly 612 is not aligned with medicament coupling injecting conduit 619, which is inserted into bore 1454 of needle biasing and sealing element 616, and thus there is no fluid communication between the filling septum 614 and the needle 1290.

It is specifically seen in FIG. 42F that inserter decoupling prevention element 1630 is seated within curved cut-outs 2230 of wall portions 2220 of base element 1620 and edge surfaces 2106 of engagement rods 2100 of inserter decoupling prevention element 1630 are disposed below downwardly facing edge surface 2044 of elongate rib 2042 formed on retaining shaft 2006.

It is a particular feature of an embodiment of the present invention that following pivoting of needle penetration prevention element 1626, which is pushed by upwardly facing edge 691 of shaft 690 of injection site engagement element 680, extension portion 2134 of needle penetration prevention element 1626 is displaced rearwardly and disengages from downwardmost edge 2024 of retaining shaft 2006 of the needle penetration actuation element 1610, thus permitting downward displacement of needle penetration actuation element 1610.

It is appreciated that elongate rib 2042 of needle penetration actuation element 1610 is now permitted to displace engagement rods 2100 downwardly in order to release the engagement between inserter decoupling prevention element 1630 and between manually actuable buttons 1602.

It is appreciated that all the remaining spatial relationships in FIGS. 42A-42F remain substantially the same as described with reference to FIG. 40A-40E.

Figure 43A:
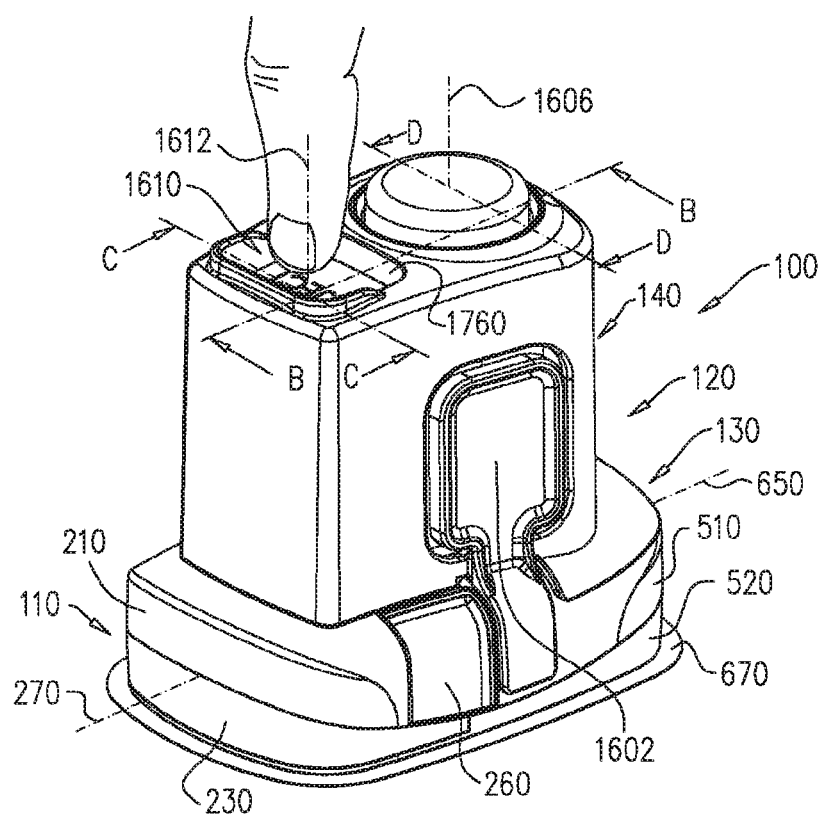
FIGS. 43A-43F are simplified illustrations of the patch pump assembly of FIGS. 1-36I in a needle penetration operative orientation.
Figure 43B:
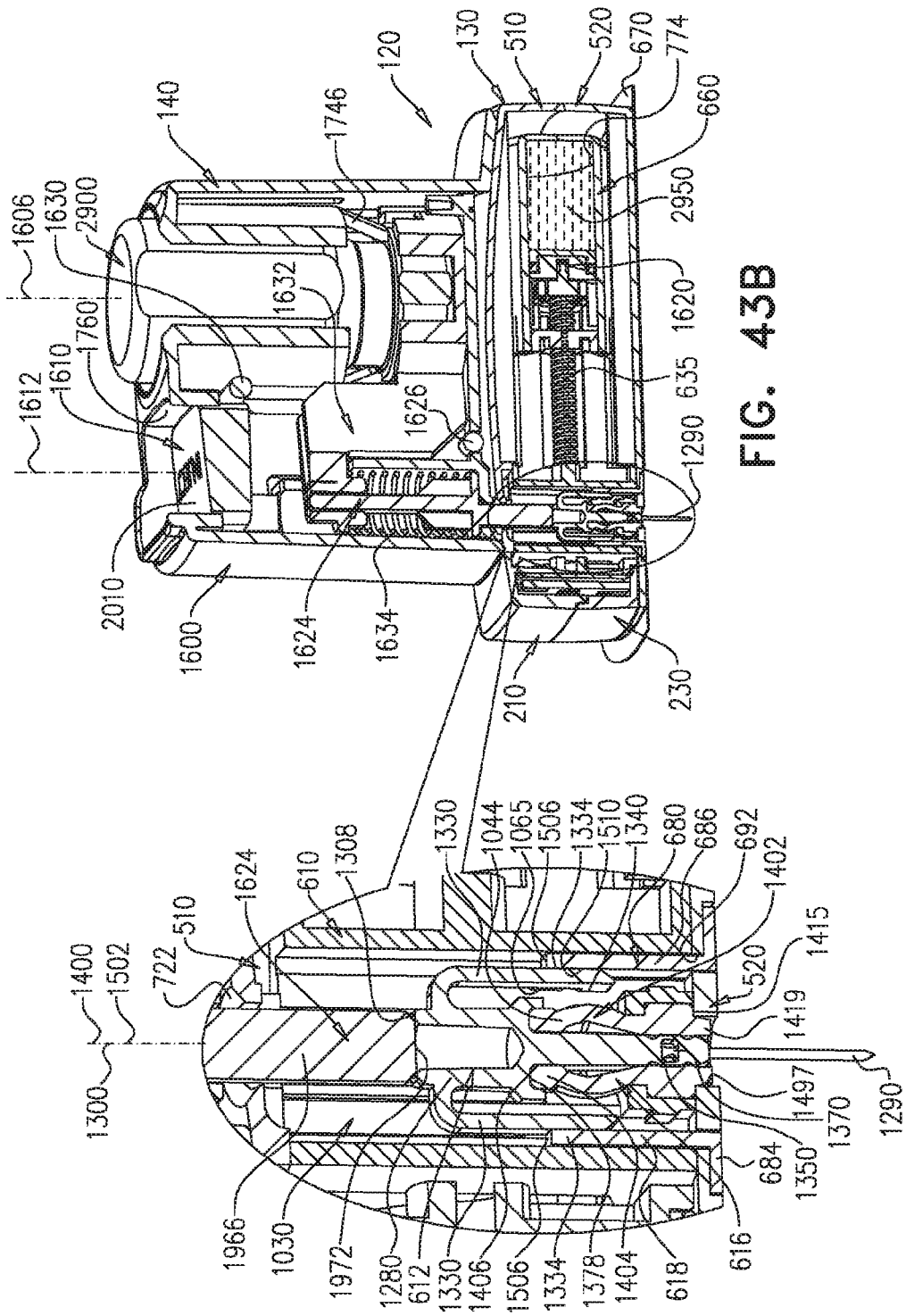
Figure 43C:
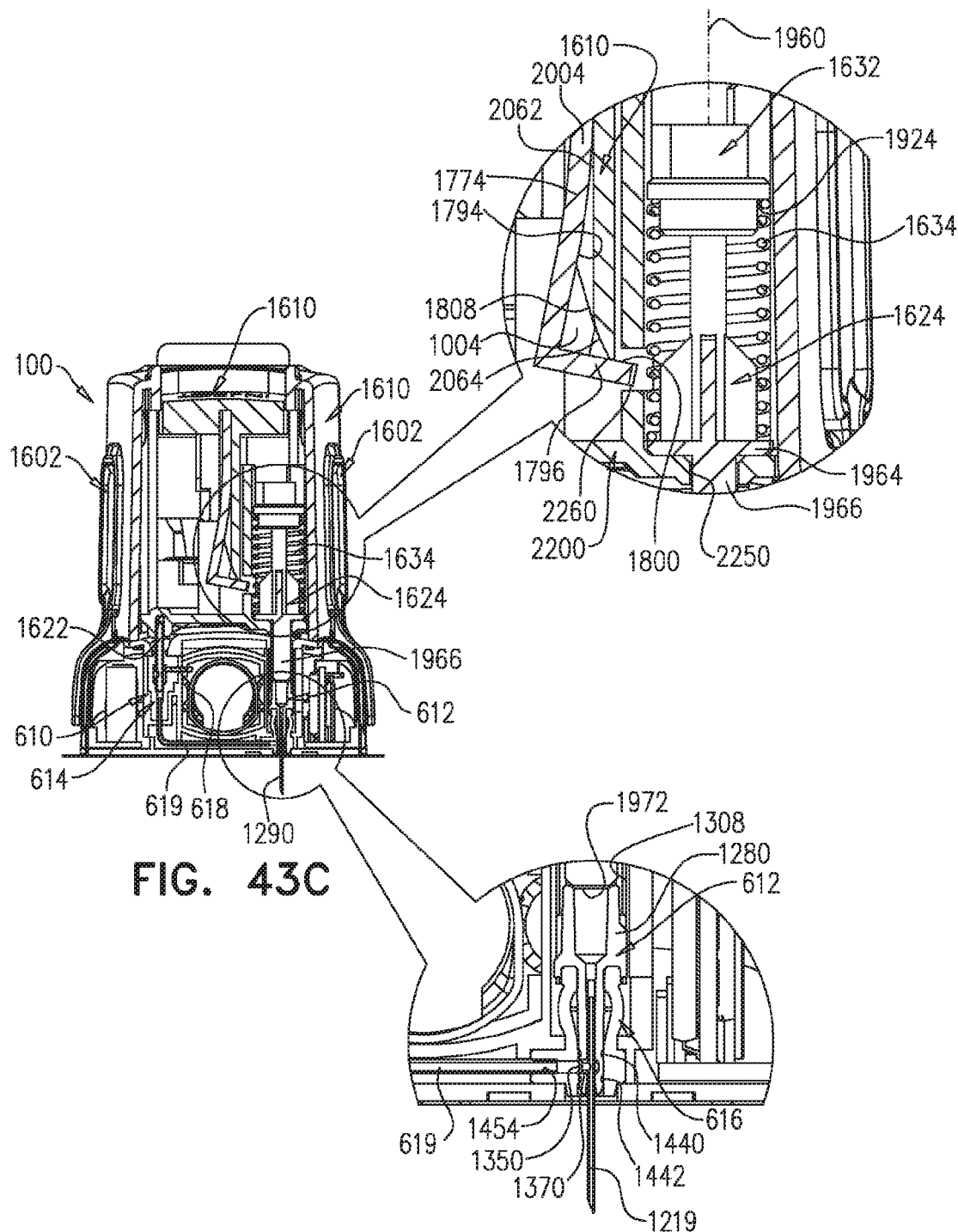
Figure 43D:
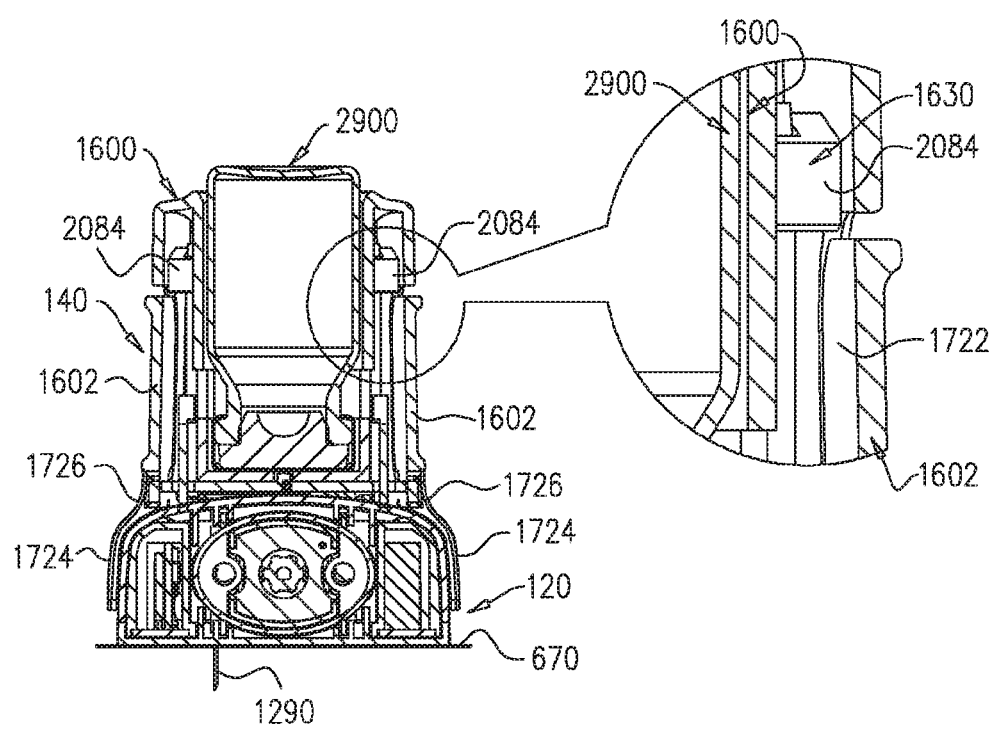
Figure 43E:
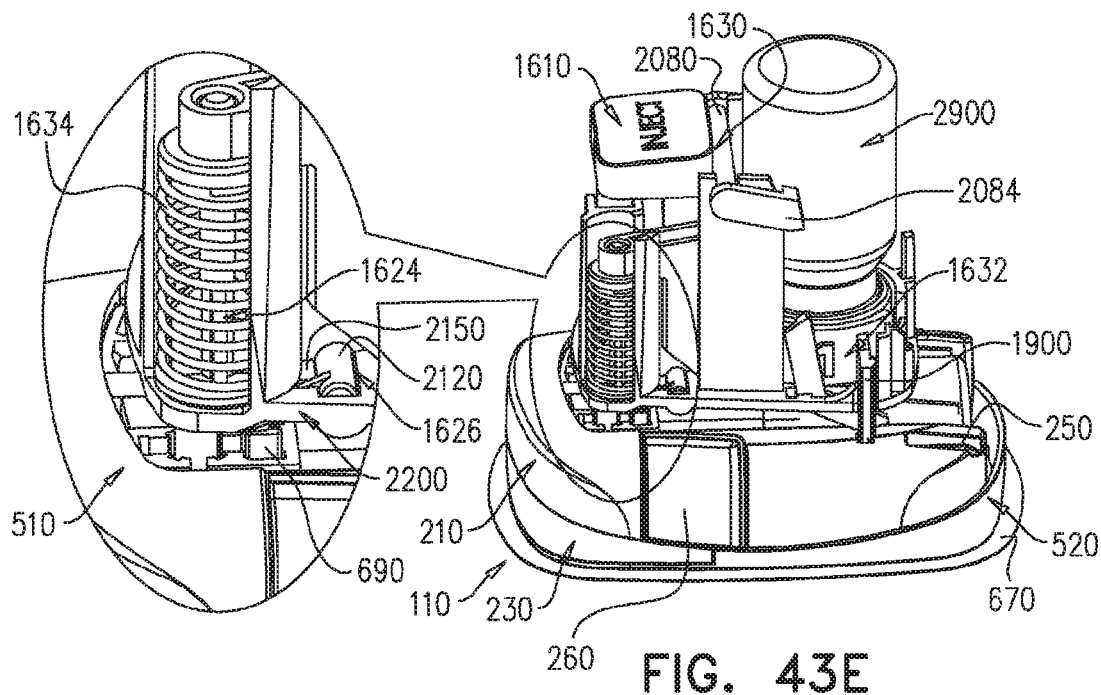
Figure 43F:
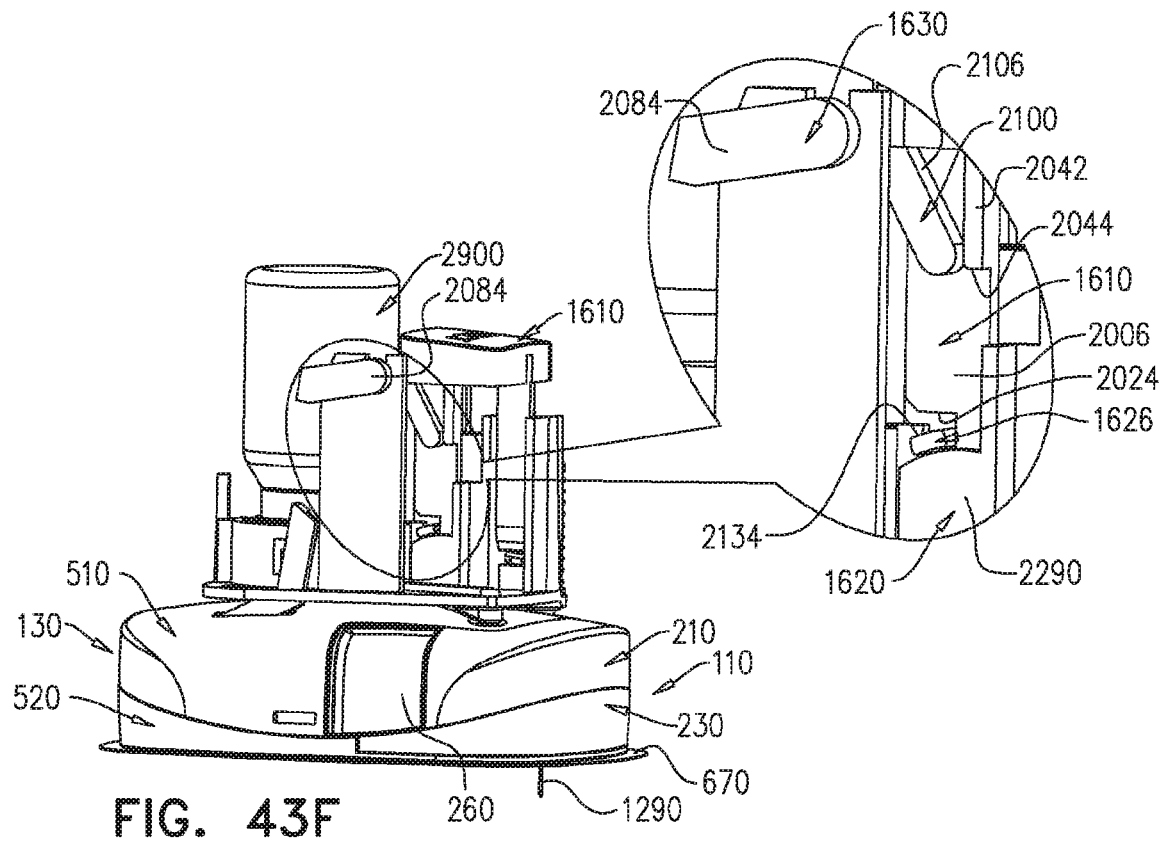

Reference is now made to FIGS. 43A-43F, which are simplified illustrations of the patch pump assembly 100 of FIGS. 1-36I in a needle penetration operative orientation. FIGS. 43A-43F are respective simplified pictorial view, section views taken along respective lines B-B and C-C and D-D in FIG. 43A and partial pictorial views taken from two different perspectives. FIG. 43E is shown without both the housing portion 1600 of disposable interface and control element 140 and top housing portion 510 of disposable base portion 130 and FIG. 43F is shown without housing portion 1600.

Patch pump assembly 100 is seen in FIGS. 43A-43F, in a needle penetration operative orientation. It is seen that in this operative orientation the user presses the needle penetration actuation element 1610, thus causing penetration of needle 1290 into the injection site.

The user depresses needle penetration actuation element 1610 downwardly within button receiving socket 1760, by means of pressing on upwardly facing surface 2010 thereof. It is a particular feature of an embodiment of the present invention that downward displacement of needle penetration actuation element 1610 urges disengagement between needle penetration actuation pin 1624 and housing portion 1600 (shown in FIG. 43C), thus needle penetration actuation pin 1624 is momentarily displaced downwardly under the force of spring 1634, and causes penetration of needle 1290 into the injection site.

It is a further particular feature of an embodiment of the present invention that upon depressing of needle penetration actuation element 1610 by the user, inserter decoupling prevention element 1630 is pivoted and thus is disengaged from planar portions 1722 of manually actuable buttons 1602 of housing portion 1600 of disposable interface and control module 140, thus permitting detaching disposable interface and control module 140 from disposable base portion 130.

It is seen specifically in FIG. 43B that upon downward displacement of needle penetration actuation pin 1624, activation rod 1966 of needle penetration actuation pin 1624 extends downwardly through aperture 722 of top housing portion 510 and by means of engagement between downwardly facing end surface 1972 of needle penetration actuation pin 1624 and upward edge 1308 of infusion needle assembly 612, infusion needle assembly 612 is displaced downwardly from the needle retracted operative orientation to the needle penetration operative orientation, against the force of biasing portion 1411 of needle biasing and sealing element 616, such that needle 1290 protrudes through central aperture 1497 of bottom housing portion 520 and is inserted into the skin of the user.

It is seen that in this operative orientation needle biasing and sealing element 616 is disposed in its stressed operative orientation, such as shown in FIGS. 22A & 22B.

It is a particular feature of an embodiment of the present invention that needle biasing and sealing element 616 sealingly engages needle hub 1280 in this needle penetration operative orientation of the infusion needle assembly 612, such that medicament 2950 passing through medicament coupling injecting conduit 619 passes through apertures 1350 and 1370 of infusion needle assembly 612 and is prevented from passing between needle biasing and sealing element 616 and needle hub 1280 by means of sealing engagement between sealing protrusions 1440 of needle biasing and sealing element 616 and the needle hub 1280.

It is a particular feature of an embodiment of the present invention that following downward displacement of infusion needle assembly 612, lever portions 1330 retain the infusion needle assembly 612 in its needle penetration operative orientation as long as the patch pump assembly 100 is attached to the skin of the user.

It is seen that lever portions 1330 of needle hub 1280 are retained from upward displacement in the needle penetration operative orientation due to the following:

T-shaped extensions 1340 of lever portions 1330 are snapped under downwardly tapered protrusions 1045 and 1065 formed in needle assembly location bore 1030 of housing element 610.

Further, lever portions 1330 of infusion needle assembly 612 are retained from being outwardly radially deflected in order to overcome snap engagement with downwardly tapered protrusions 1045 and 1065 of housing element 610 by means of engagement between outer surfaces 1334 of lever portions 1330 and inwardly facing surfaces 1510 of shafts 686 and 688 of needle penetration actuation pin 680.

It is a particular feature of an embodiment of the present invention that optical sensor 362, which forms part of the reusable portion 110 is a home position sensor, which is adapted to detect outwardly facing surface 788 of protrusion 786 of the medicament reservoir 660, when the medicament reservoir 660 is nearly empty of medicament 2950. Optical sensor 362 is adapted to provide a signal to the control system of the patch pump assembly 100 providing a referenced origin of the medicament reservoir 660. The control system of the patch pump assembly 100 is enabled to calculate and control aspiration/injection volume and rate based on signals provided by optical sensor 362 and hall effect sensor 344. It is specifically seen that optical sensor 362 detects outwardly facing surface 788 of protrusion 786 of the medicament reservoir 660 through cut-out 1490 of bottom housing portion 520 of disposable base portion 130.

It is a further particular feature of an embodiment of the present invention that an additional optical sensor (not shown) may be provided on internal assembly 220, which is adapted to detect the operative orientation of infusion needle assembly 612 and to provide a signal to the control system of the patch pump assembly 100 indicating proper positioning of the needle 1290 during injection. Specifically, additional optical sensor of internal subassembly 220 is adapted to detect the needle 1290 when it is disposed in needle penetration operative orientation through slit 1022 of housing element 610. In the event that on/off microswitch 374 is activated and additional optical sensor does not detect the needle 1290 in needle penetration operative orientation, an error signal is transferred to the control unit of the patch pump assembly 100.

It is specifically seen in FIG. 43C that upon pressing the needle penetration actuation element 1610, downward displacement of needle actuation penetration pin 624 is permitted. Specifically, in this operative orientation, activating shaft 2004 of needle penetration actuation element 1610 is downwardly displaced, thus tapered edge surface 2064 of activating shaft 2004 pushes tapered edge surface 1808 of protrusion 1804 formed on forward wall portion 1774, causing wall portion 1774 to be deflected outwardly with respect to longitudinal axis 1960 and thus urging transversely disposed wall portion 1796 of forward wall portion 1794 to move out of cut-out 2260, thus disengaging from flange portion 1964 of needle penetration actuation pin 1624, and in turn releasing the needle penetration actuation pin 1624 to be displaced downwardly under the force of spring 1634.

It is further seen that communication between filling septum 614 and medicament coupling injecting conduit 619 is closed as long as medicament conduit 1622 is inserted into filling septum 614. It is specifically seen in FIG. 43C, that infusion needle assembly 612 is disposed in needle penetration operative orientation, thus aperture 1350 of infusion needle assembly 612 is now aligned with medicament coupling injecting conduit 619, which is inserted into bore 1454 of needle biasing and sealing element 616.

It is specifically seen in FIG. 43D that upon depressing of needle penetration actuation element 1610 by the user, inserter decoupling prevention element 1630 is pivoted such that arm portions 2084 of inserter decoupling prevention element 1630 are disengaged from planar portions 1722 of manually actuable buttons 1602 of housing portion 1600 of disposable interface and control module 140, thus permitting the user to press on both manually actuable buttons 1602, which are adapted to pivot around hinge portions 1726 in order to release curved portions 1724 from top housing portion 510 and thus detaching disposable interface and control module 140 from disposable base portion 130.

It is specifically seen in FIGS. 43E & 43F that inserter decoupling prevention element 1630 is seated within curved cut-outs 2230 of wall portions 2220 of base element 1620 and edge surfaces 2106 of engagement rods 2100 of inserter decoupling prevention element 1630 is pivoted by downward displacement of elongate rib 2042 of needle penetration actuation element 1610.

It is a particular feature of an embodiment of the present invention that following pivoting of needle penetration prevention element 1626, downward displacement of needle penetration actuation element 1610 is permitted, as specifically described hereinabove with reference to FIG. 42F.

It is appreciated that elongate rib 2042 of needle penetration actuation element 1610 is now displacing engagement rod 2100 downwardly in order to release the engagement between inserter decoupling prevention element 1630 and between manually actuable buttons 1602. It is specifically seen that once engagement rod 2100 pivots around pivoting rod 2080 of inserter decoupling prevention element 1630, arm portions 2084 are urged to pivot upwardly around pivoting rod 2080 and disengage from planar portions 1722 of manually actuable buttons 1602, thus permitting manually actuable buttons 1602 to pivot around hinge portion 1726 in order to decouple disposable interface and control module 140 from disposable base portion 130.

It is appreciated that all the remaining spatial relationships in FIGS. 43A-43F remain substantially the same as described with reference to FIG. 42A-42F.

Figure 44A:
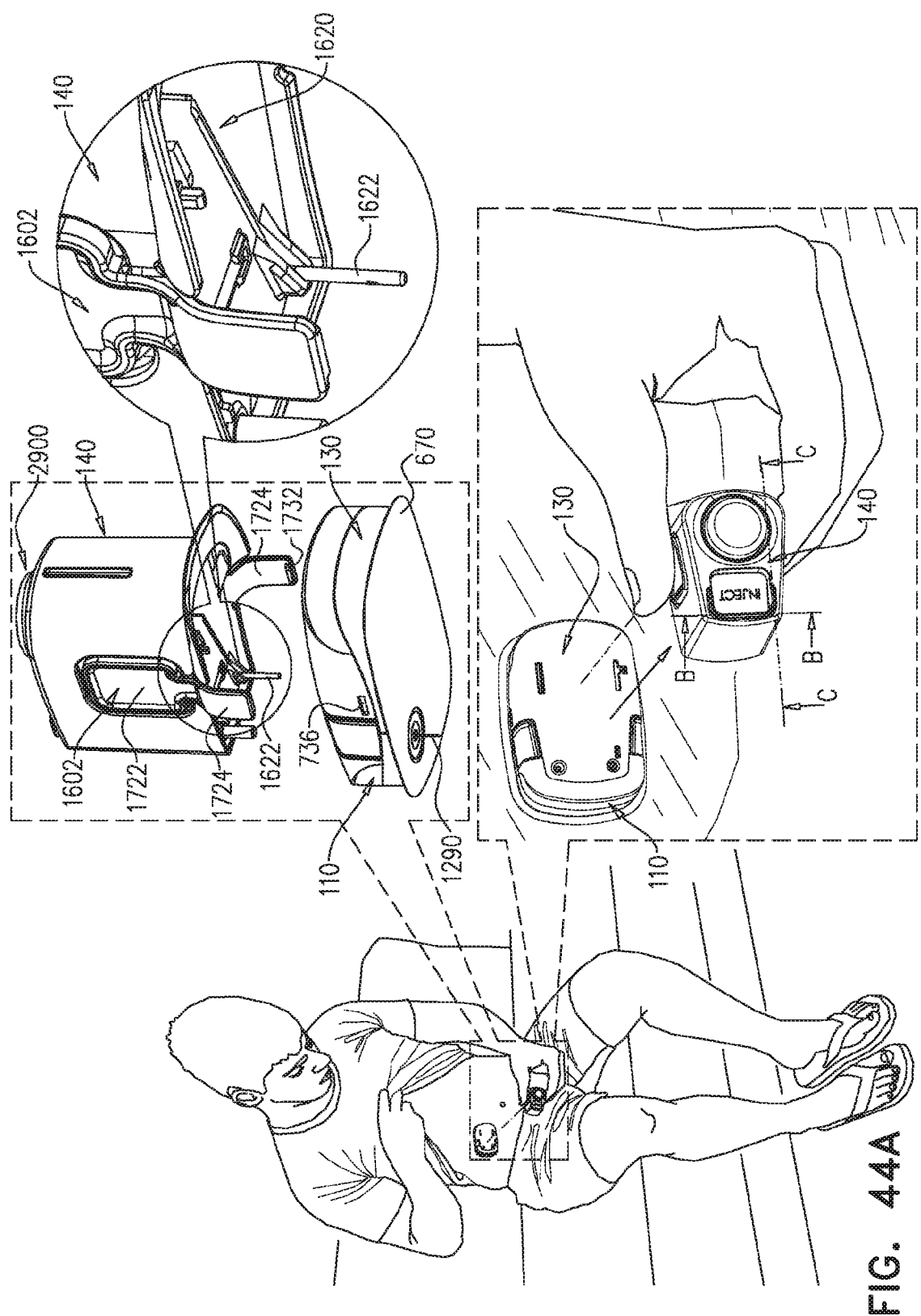
FIGS. 44A-44C are simplified illustrations of the patch pump assembly of FIGS. 1-36I in a disposable interface and control module disengagement operative orientation.
Figure 44B:
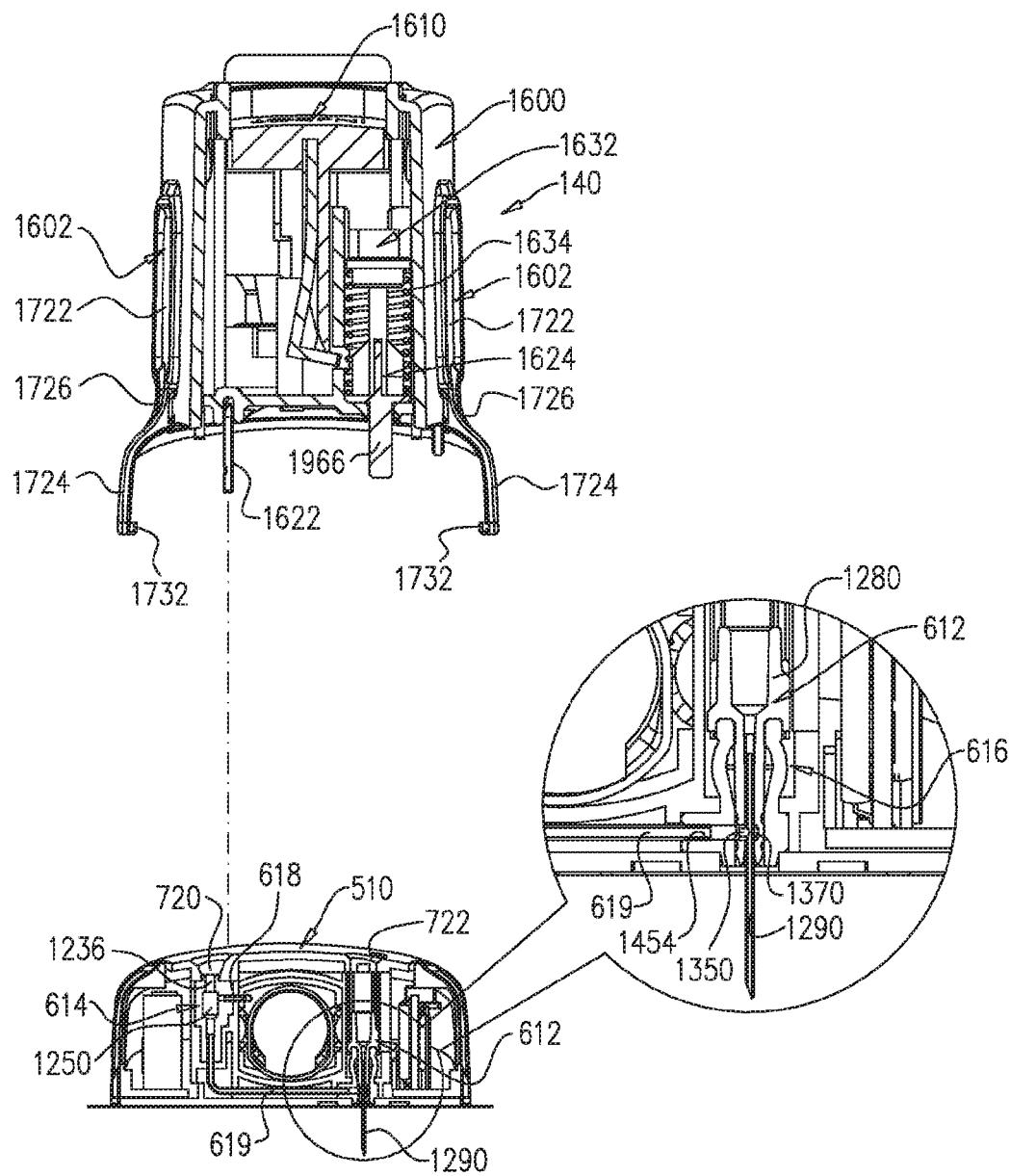
Figure 44C:
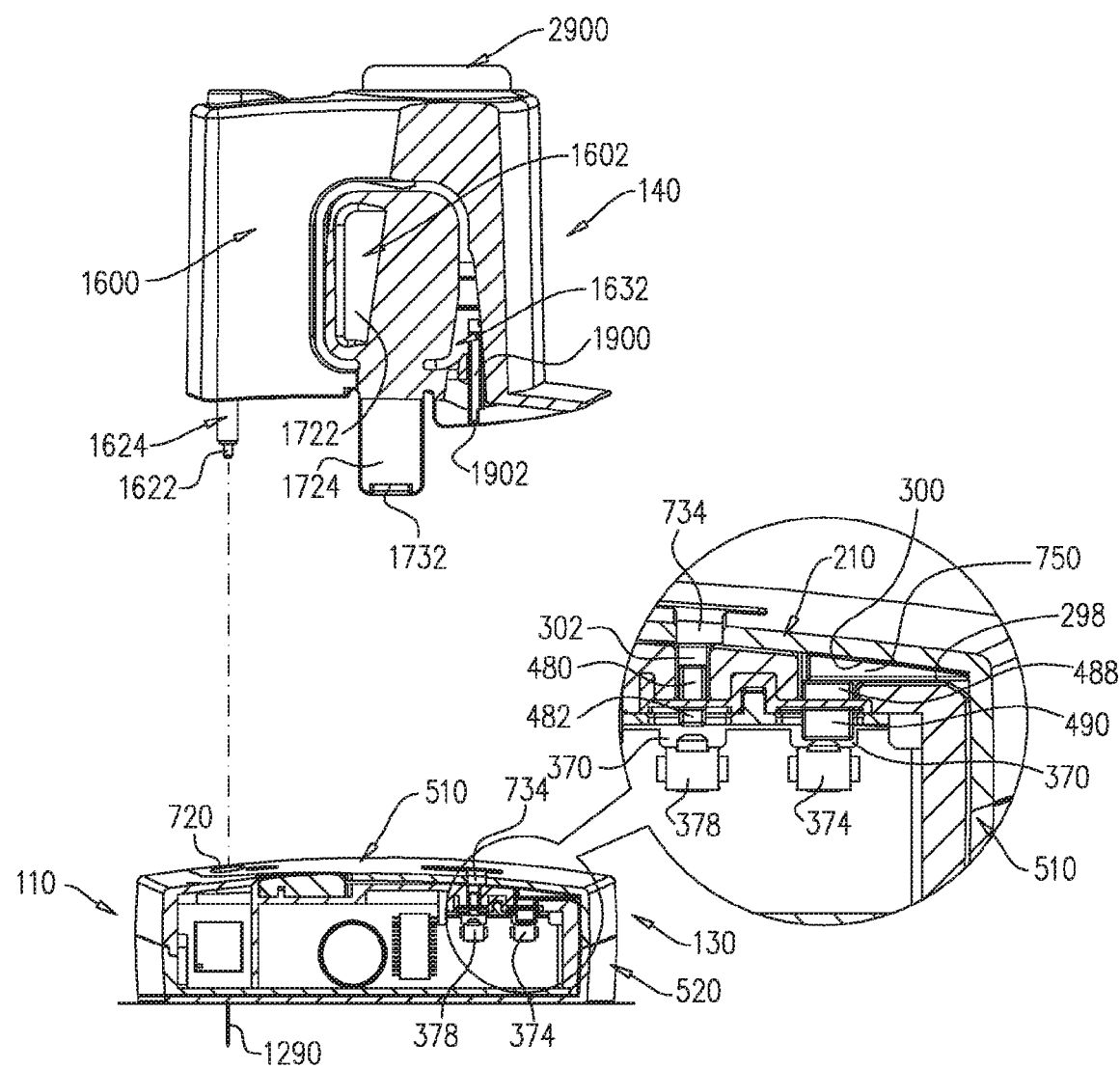

Reference is now made to FIGS. 44A-44C, which are simplified illustrations of the patch pump assembly 100 of FIGS. 1-36I in a disposable interface and control module 140 disengagement operative orientation. FIGS. 44A-44C are respective simplified pictorial view and section views taken along respective lines B-B and C-C in FIG. 44A.

Patch pump assembly 100 is seen in FIGS. 44A-44C, in a disposable interface and control module 140 disengagement operative orientation. It is seen that in this operative orientation the user decouples the disposable interface and control module 140 from disposable base portion 130, thus leaving only the disposable base portion 130 and reusable portion 110, which are mutually attached, adhesively attached to the skin of the user for the period of time required for injection of the medicament 2950.

It is specifically seen in FIGS. 44A & 44B that following deactivation of inserter decoupling prevention element 1630, as described in detail hereinabove with reference to FIGS. 43A-43F, the user can depress manually actuable buttons 1602 of disposable interface and control module 140 and decouple the disposable interface and control module 140 from disposable base portion 130. It is specifically seen that this removal is permitted by means of pressing on planar portions 1722 of manually actuable buttons 1602, resulting in pivotal displacement of curved portions 1724 around hinge portions 1726, thus causing disengagement of retaining protrusions 1732 of manually actuable buttons 1602 of disposable interface and control module 140 from slots 736 of top housing portion 510 of disposable base portion 130.

It is seen that during this decoupling of disposable interface and control module 140 from disposable base portion 130, medicament conduit 1622 is removed from filling septum 614 through aperture 720 in top housing portion 510, thus causing slit 1236 of filling septum 614 to assume its closed orientation. It is a particular feature of an embodiment of the present invention that upon this decoupling fluid flow communication is permitted between the medicament reservoir 660 and the needle 1290 through medicament coupling injecting conduit 619.

It is further seen that needle penetration actuation pin 1624 is removed from top housing portion 510 through aperture 722, thus disengages infusion needle assembly 612. It is a particular feature of an embodiment of the present invention that infusion needle assembly 612 remains retained in its needle penetration operative orientation due to engagement thereof with injection site engagement element 680, as described in detail hereinabove with respect to FIG. 43B.

It is specifically seen that upon decoupling disposable interface and control module 140 from disposable base portion 130, fluid flow passage is permitted from medicament reservoir 660 through medicament coupling filling conduit 618 into enlarged portion 1250 of filling septum 614 and from there into medicament coupling injecting conduit 619, which is adapted to fluidly communicate with apertures 1350 and 1370 of needle 1290, which in turn is adapted to transfer the medicament 2950 into the body of the user.

It is specifically seen in FIG. 44C that an additional requirement has to be fulfilled in order to initiate activation of electric motor 440 and rotation thereof in a second direction, opposite to the rotation direction while aspirating fluid from the medicament vial 2900 into medicament reservoir 660, in order to enable fluid flow passage from the medicament reservoir 660 to needle 1290 of infusion needle assembly 612.

It is specifically seen that once disposable interface and control module 140 is decoupled from disposable base portion 130, switch actuating protrusion 1900 of vial adaptor 1632 of disposable interface and control module 140 disengages from vial microswitch 378, thereby deactivating the vial microswitch 378. This deactivation results from removal of switch actuating protrusion 1900 through aperture 302 in main housing portion 210 and slot 734 in top housing portion 510 and disengagement of engaging edge 1902 of switch actuating protrusion 1900 from protrusion 480 of sealing element 250. It is appreciated that On/Off microswitch 374 remains activated in this operative orientation since the reusable portion 110 and the disposable base portion 130 are mutually attached.

It is a particular feature of an embodiment of the present invention that the control unit of the patch pump assembly 100 causes initiation of rotation of the electric motor 440, which effectuates initiation of the injection process of medicament 2950 into the body of the user through needle 1290, upon receiving the two following signals: Deactivated vial microswitch 378, indicating that the disposable interface and control module 140 is decoupled from disposable base portion 130 and activated On/Off microswitch 374, indicating that reusable portion 110 is coupled with disposable base portion 130.

It is appreciated that all the remaining spatial relationships in FIGS. 44A-44C remain substantially the same as described with reference to FIG. 43A-43F.

Figure 45B:
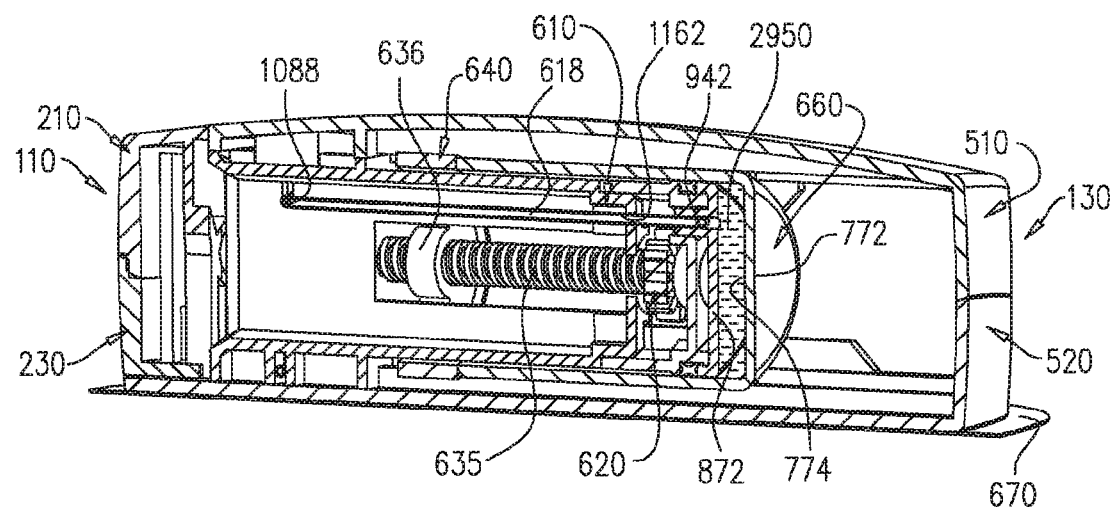
Figure 45C:
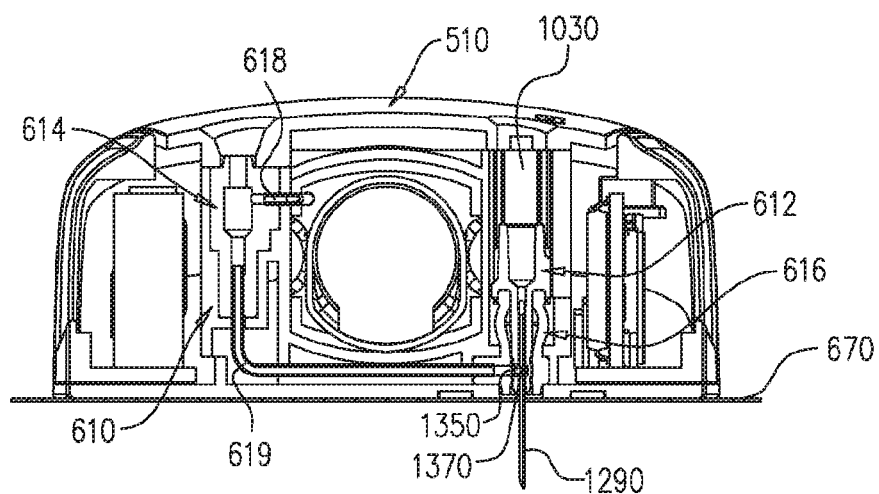

Reference is now made to FIGS. 45A-45C, which are simplified illustrations of the patch pump assembly 100 of FIGS. 1-36I in an intermediate injection operative orientation. FIGS. 45A-45C are respective simplified pictorial view and section views taken along respective lines B-B and C-C in FIG. 45A.

Patch pump assembly 100 is seen in FIGS. 45A-45C, in an intermediate injection operative orientation. It is seen that in this operative orientation the medicament 2950 is ejected from medicament reservoir 660 of disposable base portion 130 through needle 1290 into the body of the user.

It specifically seen in FIG. 45B that linear displacer 640 along with medicament reservoir 660 is almost entirely displaced forwardly with respect to housing element 610, such that only a small amount of medicament 2950 is remained in medicament reservoir 660 in this operative orientation, such that rearward end wall 772 of medicament reservoir 660 is positioned adjacent rearwardly facing surface 872 of the piston assembly 620 and the interior volume 774 of the medicament reservoir 660 is substantially decreased. It is appreciated that medicament 2950 passes through aperture 942 in piston assembly 620 into medicament coupling filling conduit 618, which passes through aperture 1162 in housing element 610, further through bore 1088 in housing element 610 and into the filling septum 614.

It is specifically seen in FIG. 45C that from filling septum 614, the medicament 2950 passes into medicament coupling injecting conduit 619 and in turn through apertures 1350 and 1370 in infusion needle assembly 612, into needle 1290 and into the body of the user.

It is a particular feature of an embodiment of the present invention that due to the particular design of engagement between drive element 450 of plunger assembly 240 and rotary-to-longitudinal drive converter 630 of piston assembly 620, the reusable portion 110 can be decoupled from the disposable base portion 130 at any point of time. Specifically, due to the fact that both drive element 450 and rotary-to-longitudinal drive converter 630 have respective teeth 456 and 633 which extend in parallel to longitudinal axes 270 and 650, the user can press manually actuable buttons 260 of reusable portion 110 and decouple reusable portion 110 and disposable base portion 130 at any point of time, notwithstanding the axial longitudinal location of the linear displacer 640. This may be beneficial for example in emergency situations when the user wants to momentarily stop the injection process or in an event that there is insufficient amount of energy in battery 350 and the user needs to recharge the reusable portion 110 in order to proceed with the injection process.

It is appreciated that all the remaining spatial relationships in FIGS. 45A-45C remain substantially the same as described with reference to FIG. 44A-44C.

Figure 46A:
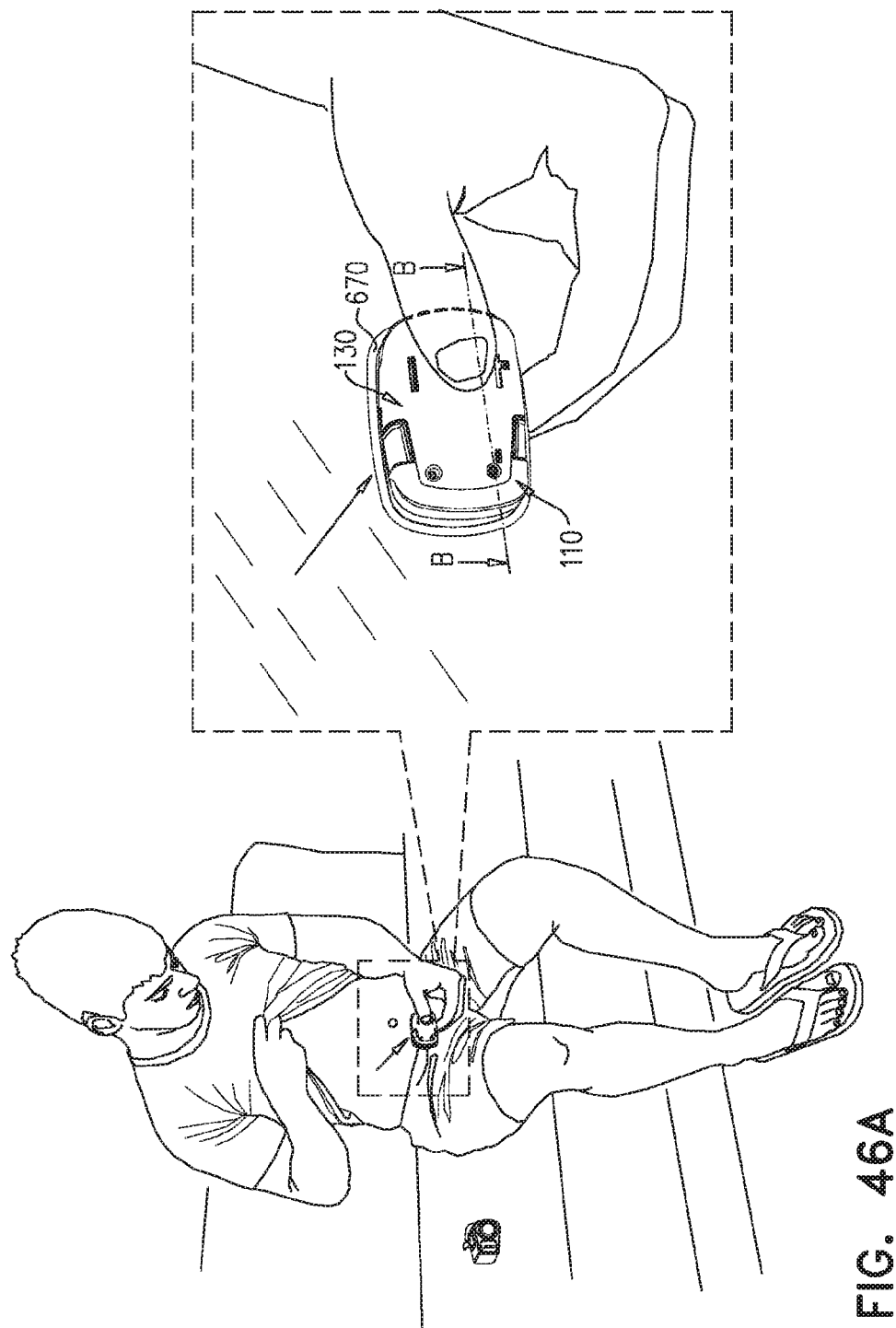
FIGS. 46A-46B are simplified illustrations of the patch pump assembly of FIGS. 1-36I in a patch pump assembly removal operative orientation.
Figure 46B:
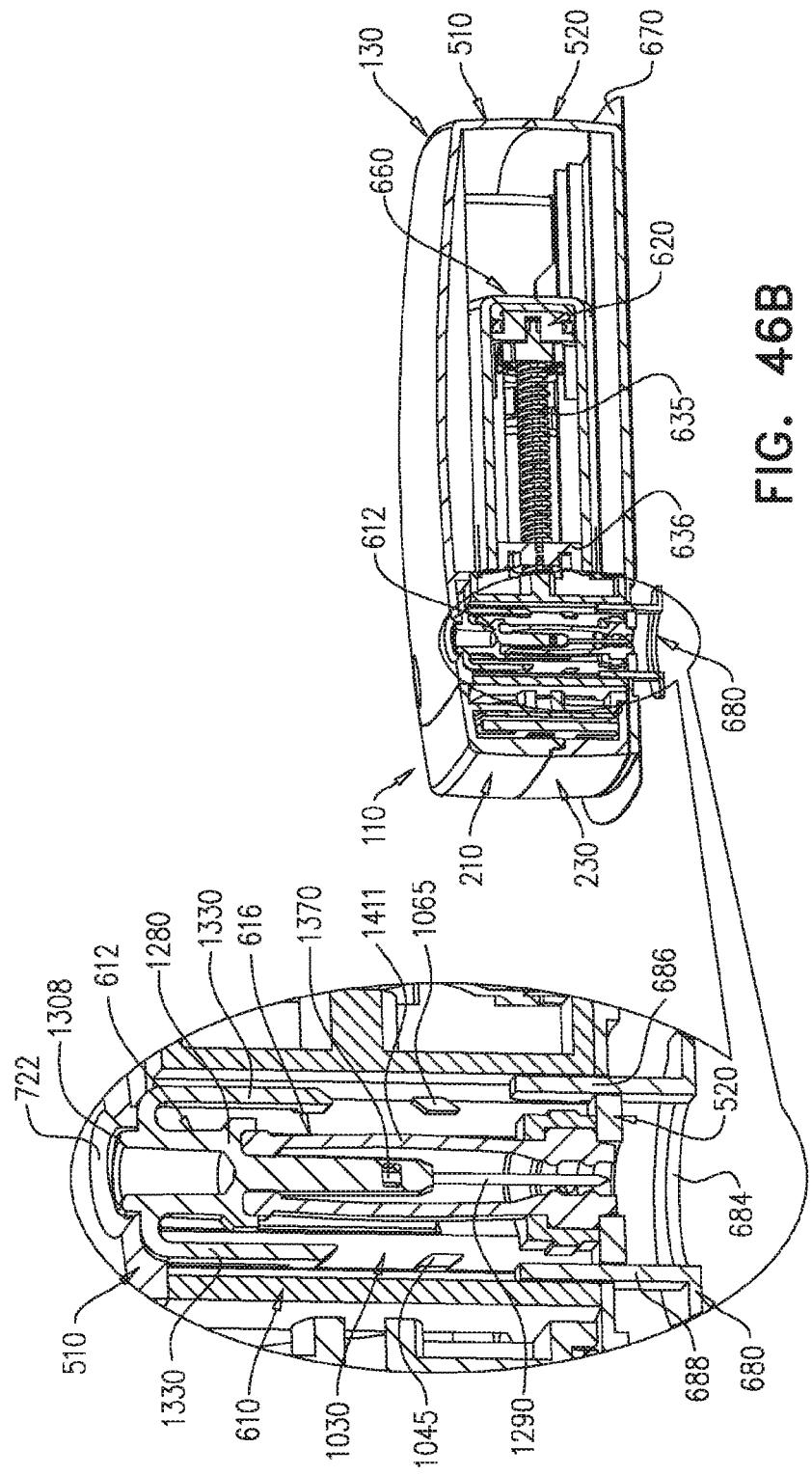

Reference is now made to FIGS. 46A & 46B, which are simplified illustrations of the patch pump assembly 100 of FIGS. 1-36I in a patch pump assembly removal operative orientation. FIGS. 46A & 46B are respective simplified pictorial view and section view taken along respective lines B-B in FIG. 46A.

Patch pump assembly 100 is seen in FIGS. 46A & 46B, in a patch pump assembly removal operative orientation. It is seen that in this operative orientation the user detaches the patch pump assembly 100 from the skin.

It is specifically seen in FIGS. 46A & 46B that once the user detaches the patch pump assembly 100 from the skin, the injection site engagement element 680 is displaced downwardly relative to bottom housing portion 520 of disposable base portion 130, such that injection site engagement surface defining ring 684 is now downwardly spaced from 520.

It is a particular feature of an embodiment of the present invention that infusion needle assembly 612 is retracted back into housing element 610 upon downward displacement of injection site engagement element 680 and thus is now positioned in the needle retracted operative orientation. It is specifically seen that once injection site engagement element 680 is displaced downwardly, lever portions 1330 of needle hub 1280 are not retained by shafts 686 and 688 anymore and thus are allowed to be outwardly deflected and retract upwardly under the force of biasing portion 1411 of needle biasing and scaling element 616, such that upward edge 1308 of needle hub 1280 is again disposed adjacent aperture 722 of top housing portion 510.

Figure 47C:
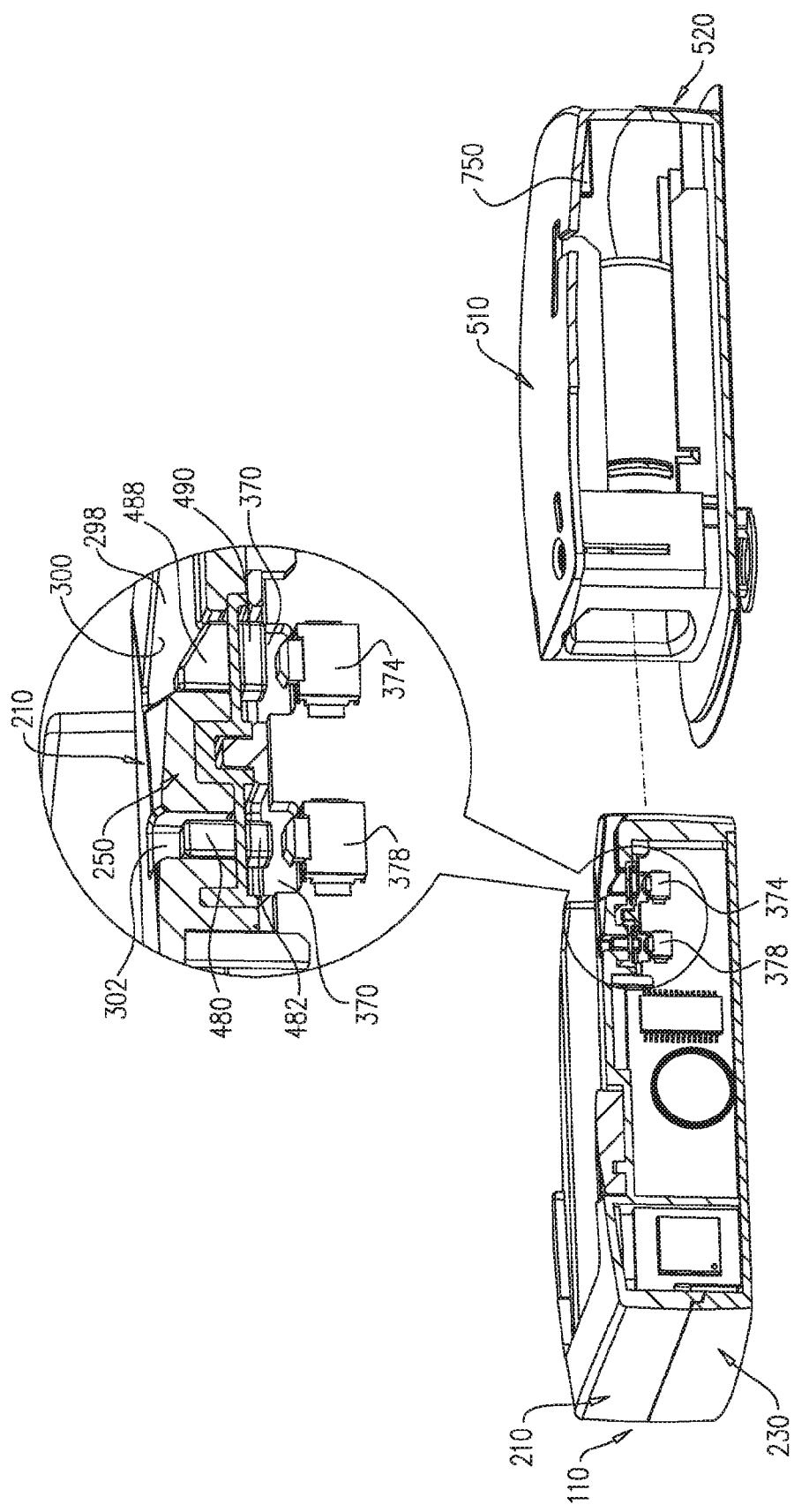

Reference is now made to FIGS. 47A-47C, which are simplified illustrations of the patch pump assembly 100 of FIGS. 1-36I in a reusable portion/disposable portion disengagement operative orientation. FIGS. 47A-47C are respective simplified two pictorial views shown in an assembled and disassembled orientation and a section view taken along lines C-C in FIG. 47B.

Patch pump assembly 100 is seen in FIG. 47A before disassembling the reusable portion 110 from disposable base portion 130 and in FIGS. 47B & 47C following disassembly of reusable portion 110 from disposable base portion 130 after completion of medicament injection.

It is specifically seen in FIG. 47B that the user presses manually actuable buttons 260 of main housing portion 210 of reusable portion 110 and detaches the reusable portion 110 from disposable base portion 130.

It is specifically seen in FIG. 47C that upon disengagement of reusable portion 110 and disposable base portion 130, protrusion 750 of top housing portion 510 slides out of cut-out 298 and aperture 300 of main housing 210 of reusable portion 110 and thus on/off microswitch 374 is deactivated. It is specifically seen that disengagement of protrusion 750 from engagement surface 488 of sealing element 250, results in disengagement of bottom engagement surface 490 from on/off microswitch 374.

It is appreciated that both on/off microswitch 374 and vial microswitch 378 are deactivated when reusable portion 110 is snot attached to disposable base portion 130.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

The invention claimed is:

1. A patch pump comprising:
 a medicament reservoir having an inner surface defining an elongate piston engagement pathway;
 an electric motor having a rotary drive element;
 a piston replaceably axially fixed to said electric motor, said piston having an outer surface arranged for sealing engagement with said inner surface of said medicament reservoir, said piston also comprising a rotary to longitudinal drive converter receiving a rotary drive input from said rotary drive element of said electric motor and providing a longitudinal drive to said medicament reservoir, thereby driving said medicament reservoir in longitudinal motion relative to said piston in which said elongate piston engagement pathway defined by said inner surface of said medicament reservoir is displaced axially and in sealing engagement with said outer surface of said piston.

2. The patch pump according to claim 1 and wherein said piston defines at least one medicament passageway.

3. The patch pump according to claim 2 and wherein said electric motor is operative in a first mode of operation in a first rotational direction to draw a medicament into said medicament reservoir via said medicament passageway and is operative in a second mode of operation in a second rotational direction to force medicament out of said medicament reservoir via said medicament passageway.

4. The patch pump according to claim 1 and wherein said patch pump includes a disposable portion and a reusable portion, which are adapted to be selectably operatively coupled to each other.

5. The patch pump according to claim 3 and wherein said electric motor is operative in said first mode of operation automatically in response to operative engagement of a medicament containing vial therewith.

6. The patch pump according to claim 4 and also comprising a plunger assembly, which is adapted to be part of said reusable portion and to replaceably engage said piston, wherein said piston and said medicament reservoir are adapted to be part of said disposable portion.

7. The patch pump according to claim 1 and wherein said rotary to longitudinal drive converter includes a gear, having interior gear teeth and exterior gear teeth, which exterior gear teeth drive a pair of linear driving screws.

8. The patch pump according to claim 1, and wherein an optical sensor is provided to detect a reference position of said medicament reservoir.

9. A patch pump comprising:
 a medicament reservoir; and
 an electric motor having a rotary drive element and being operative in a first mode of operation in a first rotational direction to draw a medicament into said medicament reservoir and in a second mode of operation in a second rotational direction to dispense medicament from said medicament reservoir, said electric motor being operative in said first mode of operation automatically in response to operative engagement of a medicament-containing vial therewith.

10. The patch pump according to claim 9 and also comprising a piston, which is fixed with respect to said electric motor, and which cooperates with said medicament reservoir, whereby linear displacement of said medicament reservoir relative to said electric motor and to said piston causes medicament to be forced out of said medicament reservoir.

11. The patch pump according to claim 10 and wherein said piston includes a medicament passageway, said patch pump also comprising an infusion needle assembly which is coupled to said medicament passageway.

12. The patch pump according to claim 9 and wherein said electric motor is adapted to be reusable and said medicament reservoir is adapted to be replaceably coupled to said drive element.

13. The patch pump according to claim 9 and wherein said patch pump includes a disposable portion and a reusable portion, which are adapted to be selectably operatively coupled to each other.

14. The patch pump according to claim 9 and wherein said medicament reservoir includes a portion that is adapted to be detected by an optical sensor, which is adapted to provide a signal to a control system of said patch pump indicating a position reference point of said medicament reservoir.

* * * * *